US010422009B2

(12) United States Patent
Davicioni et al.

(10) Patent No.: US 10,422,009 B2
(45) Date of Patent: *Sep. 24, 2019

(54) COMPOSITIONS AND METHODS FOR CLASSIFYING THYROID NODULE DISEASE

(71) Applicant: GenomeDx Biosciences Inc., Vancouver (CA)

(72) Inventors: Elai Davicioni, Vancouver (CA); Sam Michael Wiseman, Vancouver (CA)

(73) Assignee: GenomeDx Biosciences Inc., Vancouver, BC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/626,401

(22) Filed: Jun. 19, 2017

(65) Prior Publication Data

US 2018/0112275 A1 Apr. 26, 2018

Related U.S. Application Data

(63) Continuation of application No. 14/727,801, filed on Jun. 1, 2015, now Pat. No. 9,714,452, which is a continuation of application No. 13/254,571, filed as application No. PCT/CA2010/000266 on Mar. 3, 2010, now Pat. No. 9,074,258.

(60) Provisional application No. 61/157,552, filed on Mar. 4, 2009.

(51) Int. Cl.

*C12Q 1/68* (2018.01)
*C12Q 1/6886* (2018.01)
*C40B 60/12* (2006.01)

(52) U.S. Cl.

CPC ............ *C12Q 1/6886* (2013.01); *C40B 60/12* (2013.01); *C12Q 2600/112* (2013.01); *C12Q 2600/158* (2013.01)

(58) Field of Classification Search

CPC .. C12Q 1/68; C12Q 1/6886; C12Q 2600/112; C12Q 2600/158; C40B 60/04; C40B 60/12

USPC .............. 435/6.1, 6.11, 6.12; 506/16, 17, 35

See application file for complete search history.

(56) References Cited

U.S. PATENT DOCUMENTS

| | | | |
|---|---|---|---|
| 3,645,691 | A | 2/1972 | Knapp et al. |
| 3,687,808 | A | 8/1972 | Thomas, Jr. et al. |
| 5,130,238 | A | 7/1992 | Malek et al. |
| 5,143,854 | A | 9/1992 | Pirrung et al. |
| 5,288,514 | A | 2/1994 | Ellman |
| 5,384,261 | A | 1/1995 | Winkler et al. |
| 5,399,491 | A | 3/1995 | Kacian et al. |
| 5,455,166 | A | 10/1995 | Walker |
| 5,494,810 | A | 2/1996 | Barany et al. |
| 5,538,848 | A | 7/1996 | Livak et al. |
| 5,677,195 | A | 10/1997 | Winkler et al. |
| 5,705,365 | A | 1/1998 | Ryder et al. |
| 5,710,029 | A | 1/1998 | Ryder et al. |
| 5,830,711 | A | 11/1998 | Barany et al. |
| 5,846,717 | A | 12/1998 | Brow et al. |
| 5,854,033 | A | 12/1998 | Lizardi |
| 5,888,779 | A | 3/1999 | Kacian et al. |
| 5,965,360 | A | 10/1999 | Zain et al. |
| 5,985,557 | A | 11/1999 | Prudent et al. |
| 5,989,815 | A | 11/1999 | Skolnick et al. |
| 5,994,069 | A | 11/1999 | Hall et al. |
| 6,001,567 | A | 12/1999 | Brow et al. |
| 6,022,692 | A | 2/2000 | Coulie et al. |
| 6,027,887 | A | 2/2000 | Zavada et al. |
| 6,090,543 | A | 7/2000 | Prudent et al. |
| 6,136,182 | A | 10/2000 | Dolan et al. |
| 6,225,051 | B1 | 5/2001 | Sugiyama et al. |
| 6,251,639 | B1 | 6/2001 | Kurn |
| 6,268,142 | B1 | 7/2001 | Duff et al. |
| 6,410,278 | B1 | 6/2002 | Notomi et al. |
| 6,436,642 | B1 | 8/2002 | Gould-Rothberg et al. |
| 6,723,506 | B2 | 4/2004 | Fletcher et al. |
| 7,186,514 | B2 | 3/2007 | Zavada et al. |
| 7,211,390 | B2 | 5/2007 | Rothberg et al. |
| 7,244,559 | B2 | 7/2007 | Rothberg et al. |
| 7,264,929 | B2 | 9/2007 | Rothberg et al. |
| 7,280,922 | B2 | 10/2007 | Mei et al. |

(Continued)

FOREIGN PATENT DOCUMENTS

| | | | |
|---|---|---|---|
| CA | 2712773 | A1 | 7/2009 |
| CN | 101501214 | A | 8/2009 |

(Continued)

OTHER PUBLICATIONS

US 5,962,233 A, 10/1999, Livak et al. (withdrawn)

(Continued)

*Primary Examiner* — Antonio Galisteo Gonzalez

(74) *Attorney, Agent, or Firm* — Wilson, Sonsini, Goodrich & Rosati

(57) ABSTRACT

A system for classifying thyroid nodule tissue as malignant or benign is provided that is based on the identification of sets of gene transcripts, which are characterized in that changes in expression of each gene transcript within a set of gene transcripts can be correlated to with either malignant or benign thyroid nodule disease. The thyroid classification system provides for sets of "thyroid classifying" target sequences and further provides for combinations of polynucleotide probes and primers derived there from. These combinations of polynucleotide probes can be provided in solution or as an array. The combination of probes and the arrays can be used for diagnosis. The invention further provides further methods of classifying thyroid nodule tissue.

18 Claims, 5 Drawing Sheets

Specification includes a Sequence Listing.

(56) References Cited

U.S. PATENT DOCUMENTS 7,300,788 B2 11/2007 Matsuzaki et al.
7,319,011 B2 1/2008 Riggins et al.
7,323,305 B2 1/2008 Leamon et al.
7,335,762 B2 2/2008 Rothberg et al.
7,358,061 B2 4/2008 Yamamoto et al.
7,361,488 B2 4/2008 Fan et al.
7,378,233 B2 5/2008 Sidransky et al.
7,407,755 B2 8/2008 Lubinski et al.
7,541,169 B2 6/2009 Freimuth et al.
7,598,052 B2 10/2009 Giordano et al.
7,662,553 B2 2/2010 Lenz
7,767,391 B2 8/2010 Scott et al.
7,901,881 B2 3/2011 Libutti et al.
7,901,888 B2 3/2011 Kebebew
7,927,826 B2 4/2011 Riggins et al.
8,008,009 B2 8/2011 Choquet-Kastylevsky et al.
8,202,692 B2 6/2012 Giordano et al.
8,293,880 B2 10/2012 Cote et al.
8,354,228 B2 1/2013 Ron
8,465,914 B2 6/2013 Brown et al.
8,541,170 B2 9/2013 Kennedy et al.
8,568,971 B2 10/2013 Brown et al.
8,669,057 B2 3/2014 Kennedy et al.
8,802,599 B2 8/2014 Aharonov et al.
8,828,656 B2 9/2014 Bullerdiek et al.
8,877,445 B2 11/2014 Shackney
8,945,829 B2 2/2015 Keutgen et al.
9,040,286 B2 5/2015 Zon et al.
9,074,258 B2 7/2015 Davicioni et al.
9,096,906 B2 8/2015 Aharonov et al.
9,157,123 B2 10/2015 Xing
9,175,352 B2 11/2015 Keutgen et al.
9,206,482 B2 12/2015 Davicioni et al.
9,234,244 B2 1/2016 Zeiger et al.
9,495,515 B1 11/2016 Kennedy et al.
9,587,279 B2 3/2017 Fahey, III et al.
9,617,604 B2 4/2017 Davicioni et al.
9,708,667 B2 7/2017 Barnett-Itzhaki et al.
9,714,452 B2 7/2017 Davicioni et al.
9,856,537 B2 1/2018 Kennedy et al.
10,114,924 B2 10/2018 Kennedy et al.
10,236,078 B2 3/2019 Kennedy et al.
2001/0051344 A1 12/2001 Shalon et al.
2002/0076735 A1 6/2002 Williams et al.
2002/0169137 A1 11/2002 Reiner et al.
2003/0186248 A1 10/2003 Erlander et al.
2003/0190602 A1 10/2003 Pressman et al.
2003/0194734 A1 10/2003 Jatkoe
2004/0019466 A1 1/2004 Minor et al.
2004/0058378 A1 3/2004 Kong et al.
2005/0042222 A1 2/2005 Yamamoto et al.
2005/0048533 A1 3/2005 Sidransky et al.
2005/0137805 A1 6/2005 Lewin et al.
2005/0240357 A1 10/2005 Minor
2005/0250125 A1 11/2005 Novakoff
2005/0266443 A1 12/2005 Croce et al.
2006/0019256 A1 1/2006 Clarke et al.
2006/0019615 A1 1/2006 Ditmer
2006/0035244 A1 2/2006 Riggins et al.
2006/0083744 A1 4/2006 Chen et al.
2006/0088851 A1 4/2006 Erlander et al.
2006/0094061 A1 5/2006 Brys et al.
2006/0105360 A1 5/2006 Croce et al.
2006/0127907 A1 6/2006 Matsubara et al.
2007/0020657 A1 1/2007 Grebe et al.
2007/0031873 A1 2/2007 Wang et al.
2007/0037186 A1 2/2007 Jiang et al.
2007/0048738 A1 3/2007 Donkena et al.
2007/0065833 A1 3/2007 Gupta
2007/0099209 A1 5/2007 Clarke et al.
2007/0105133 A1 5/2007 Clarke et al.
2007/0148667 A1 6/2007 Williams et al.
2007/0148687 A1 6/2007 Bedingham et al.
2007/0161004 A1 7/2007 Brown et al.
2007/0172844 A1 7/2007 Lancaster et al.
2007/0220621 A1 9/2007 Clarke et al.
2007/0238119 A1 10/2007 Yu et al.
2008/0028302 A1 1/2008 Meschkat
2008/0044824 A1 2/2008 Giordano et al.
2008/0124344 A1 5/2008 Combs et al.
2008/0131892 A1 6/2008 Becker et al.
2008/0145841 A1 6/2008 Libutti et al.
2008/0254470 A1 10/2008 Berlin
2008/0274457 A1 11/2008 Eng et al.
2008/0280302 A1 11/2008 Kebebew et al.
2008/0281568 A1 11/2008 Kao et al.
2009/0020433 A1 1/2009 Cohen et al.
2009/0191535 A1 7/2009 Connelly et al.
2009/0204333 A1 8/2009 Friend et al.
2009/0280490 A1 11/2009 Baker et al.
2010/0055704 A1 3/2010 Giordano et al.
2010/0075384 A1 3/2010 Kong et al.
2010/0099093 A1 4/2010 Weaver et al.
2010/0131286 A1 5/2010 Houlgatte et al.
2010/0131432 A1 5/2010 Kennedy et al.
2010/0178653 A1 7/2010 Aharonov et al.
2010/0285979 A1 11/2010 Zeiger et al.
2011/0092375 A1 4/2011 Zamore et al.
2011/0152110 A1 6/2011 Vierlinger et al.
2011/0212855 A1 9/2011 Rafnar et al.
2011/0229894 A1 9/2011 Levy et al.
2011/0230372 A1 9/2011 Willman et al.
2011/0287946 A1 11/2011 Gudmundsson et al.
2011/0312520 A1 12/2011 Kennedy et al.
2012/0015839 A1 1/2012 Chinnaiyan
2012/0015843 A1 1/2012 Von Hoff et al.
2012/0115743 A1 5/2012 Davicioni et al.
2012/0122698 A1 5/2012 Stacey et al.
2012/0122718 A1 5/2012 Reisman
2012/0157334 A1 6/2012 Beaudenon-Huibregtse et al.
2012/0172243 A1 7/2012 Davicioni et al.
2012/0214165 A1 8/2012 Walfish et al.
2012/0220474 A1 8/2012 Kennedy et al.
2013/0023434 A1 1/2013 Van Laar
2013/0142728 A1 6/2013 Beaudenon-Huibregtse et al.
2013/0150257 A1 6/2013 Abdueva et al.
2013/0172203 A1 7/2013 Yeatman et al.
2013/0184999 A1 7/2013 Ding
2013/0225662 A1 8/2013 Kennedy et al.
2013/0231258 A1 9/2013 Wilde et al.
2013/0273543 A1 10/2013 Gudmundsson et al.
2013/0302810 A1 11/2013 Latham et al.
2013/0303826 A1 11/2013 Jurisica et al.
2014/0030714 A1 1/2014 Paschke et al.
2014/0080731 A1 3/2014 Davicioni et al.
2014/0087961 A1 3/2014 Sulem et al.
2014/0099261 A1 4/2014 Keutgen et al.
2014/0121126 A1 5/2014 Bivona et al.
2014/0143188 A1 5/2014 Mackey et al.
2014/0228237 A1 8/2014 Kennedy et al.
2014/0243240 A1 8/2014 Soldin et al.
2014/0302042 A1 10/2014 Chin et al.
2014/0315199 A1 10/2014 Rhodes et al.
2014/0315739 A1 10/2014 Aharonov et al.
2014/0349856 A1 11/2014 Schnabel et al.
2014/0349864 A1 11/2014 Kennedy et al.
2014/0371096 A1 12/2014 Umbricht et al.
2015/0038376 A1 2/2015 Tian et al.
2015/0099665 A1 4/2015 Rosenfeld et al.
2015/0141470 A1 5/2015 Garraway et al.
2015/0275306 A1 10/2015 Bernards et al.
2015/0299808 A1 10/2015 Gonzalez Diaz et al.
2015/0307947 A1 10/2015 Basu et al.
2015/0329915 A1 11/2015 Davicioni et al.
2015/0368724 A1 12/2015 Aharonov et al.
2016/0024586 A1 1/2016 Delfour et al.
2016/0032400 A1 2/2016 Gomis et al.
2016/0068915 A1 3/2016 Kennedy et al.
2016/0115546 A1 4/2016 Rosenfeld et al.
2016/0120832 A1 5/2016 Rabinowitz et al.
2016/0312305 A1 10/2016 Kennedy et al.
2016/0312306 A1 10/2016 Kennedy et al.
2016/0312307 A1 10/2016 Kennedy et al.
2016/0312308 A1 10/2016 Kennedy et al.

(56) References Cited

U.S. PATENT DOCUMENTS

| | | | |
|---|---|---|---|
| 2017/0016076 | A1 | 1/2017 | Barnett-Itzhaki et al. |
| 2017/0145513 | A1 | 5/2017 | Kennedy et al. |
| 2017/0166980 | A1 | 6/2017 | Fahey, III et al. |
| 2017/0329894 | A1 | 11/2017 | Kennedy et al. |
| 2018/0016642 | A1 | 1/2018 | Kennedy et al. |
| 2018/0068058 | A1 | 3/2018 | Abdueva et al. |
| 2018/0122508 | A1 | 5/2018 | Wilde et al. |
| 2018/0127832 | A1 | 5/2018 | Kennedy et al. |
| 2019/0080047 | A1 | 3/2019 | Kennedy et al. |
| 2019/0100809 | A1 | 4/2019 | Kennedy et al. |

FOREIGN PATENT DOCUMENTS

| | | | |
|---|---|---|---|
| EP | 0684315 | A1 | 11/1995 |
| EP | 1975245 | A1 | 10/2008 |
| EP | 1975252 | A1 | 10/2008 |
| EP | 2231874 | A2 | 9/2010 |
| EP | 2366800 | A1 | 9/2011 |
| EP | 3360978 | A2 | 8/2018 |
| JP | 2004526154 | A | 8/2004 |
| JP | 2005168432 | A | 6/2005 |
| JP | 2005304497 | A | 11/2005 |
| JP | 2007513635 | A | 5/2007 |
| JP | 2008545400 | A | 12/2008 |
| JP | 2008545431 | A | 12/2008 |
| WO | WO-9015070 | A1 | 12/1990 |
| WO | WO-9210092 | A1 | 6/1992 |
| WO | WO-9309668 | A1 | 5/1993 |
| WO | WO-9322684 | A1 | 11/1993 |
| WO | WO-9515331 | A1 | 6/1995 |
| WO | WO-0120035 | A2 | 3/2001 |
| WO | WO-2005005601 | A2 | 1/2005 |
| WO | WO-2005085471 | A2 | 9/2005 |
| WO | WO-2005100608 | A2 | 10/2005 |
| WO | WO-2005005601 | A3 | 4/2006 |
| WO | WO-2006047484 | A2 | 5/2006 |
| WO | WO-2006062118 | A1 | 6/2006 |
| WO | WO-2006127537 | A2 | 11/2006 |
| WO | WO-2007038792 | A2 | 4/2007 |
| WO | WO-2007038792 | A3 | 11/2007 |
| WO | WO-2007126882 | A2 | 11/2007 |
| WO | WO-2008104380 | A2 | 9/2008 |
| WO | WO-2008119776 | A1 | 10/2008 |
| WO | WO-2008104380 | A3 | 11/2008 |
| WO | WO-2009020905 | A2 | 2/2009 |
| WO | WO-2009026605 | A2 | 3/2009 |
| WO | WO-2009029266 | A2 | 3/2009 |
| WO | WO-2009037337 | A1 | 3/2009 |
| WO | WO-2006127537 | A3 | 4/2009 |
| WO | WO-2009042728 | A1 | 4/2009 |
| WO | WO-2009068591 | A2 | 6/2009 |
| WO | WO-2009079450 | A2 | 6/2009 |
| WO | WO-2009126271 | A1 | 10/2009 |
| WO | WO-2009143603 | A1 | 12/2009 |
| WO | WO-2010018601 | A2 | 2/2010 |
| WO | WO-2010056374 | A2 | 5/2010 |
| WO | WO-2010073248 | A2 | 7/2010 |
| WO | WO-2010056374 | A3 | 9/2010 |
| WO | WO-2010073248 | A3 | 9/2010 |
| WO | WO-2010099598 | A1 | 9/2010 |
| WO | WO-2010123626 | A1 | 10/2010 |
| WO | WO-2010124372 | A1 | 11/2010 |
| WO | WO-2010127322 | A1 | 11/2010 |
| WO | WO-2010129934 | A2 | 11/2010 |
| WO | WO-2011079846 | A2 | 7/2011 |
| WO | WO-2011143361 | A2 | 11/2011 |
| WO | WO-2013063544 | A1 | 5/2013 |
| WO | WO-2013086429 | A2 | 6/2013 |
| WO | WO-2013086522 | A1 | 6/2013 |
| WO | WO-2013088457 | A1 | 6/2013 |
| WO | WO-2014043803 | A1 | 3/2014 |
| WO | WO-2014151764 | A2 | 9/2014 |
| WO | WO-2015071876 | A2 | 5/2015 |
| WO | WO-2016141127 | A1 | 9/2016 |
| WO | WO-2019023517 | A2 | 1/2019 |

OTHER PUBLICATIONS

Finley et al.; Discrimination of Benign and Malignant Thyroid Nodules by Molecular Profiling; Annals of Surgery; vol. 240, No. 3, Sep. 2004, pp. 425-437 (Year: 2004).*

Aldred et al. Papillary and follicular thyroid carcinomas show distinctly different microarray expression profiles and can be distinguished by a minimum of five genes. J Clin Oncol. 2004;22(17):3531-9.

Ausubel, et al. Current Protocols in Molecular Biology. Wiley & Sons, New York, 1995.

Cerutti et al. Diagnosis of suspicious thyroid nodules using four protein biomarkers. Clin Cancer Res. 2006;12(11 Pt 1):3311-8.

Cibas, et al. The Bethesda System for Reporting Thyroid Cytopathology. Am J Clin Pathol. Nov. 2009;132(5):658-65. doi: 10.1309/AJCPPHLWMI3JV4LA.

Co-pending U.S. Appl. No. 15/440,575, filed Feb. 23, 2017.

Dougherty. The fundamental role of pattern recognition for gene-expression/microarray data in bioinformatics. Pattern recognition. 2005; 38:2226-2228.

Endocrine website. http://www.endocrineweb.com/noduleus.html.

Englisch, et al. Chemically Modified Oligonucleotides as Probes and Inhibitors. Angew. Chem. Int. Ed. Eng. 1991; 30:613-629.

Finley et al. Advancing the molecular diagnosis of thyroid nodules: defining benign lesions by molecular profiling. Thyroid. 2005;15(6):562-8.

Finley et al. Discrimination of benign and malignant thyroid nodules by molecular profiling. Ann Surg. 2004;240(3):425-36; discussion 436-7.

Fodor, et al. Light-directed, spatially addressable parallel chemical synthesis. Science. Feb. 15, 1991;251(4995):767-73.

Fontaine, et al. Increasing the number of thyroid lesions classes in microarray analysis improves the relevance of diagnostic markers. PLoS One. Oct. 29, 2009;4(10):e7632. doi: 10.1371/journal.pone.0007632.

Fryknas et al. Molecular markers for discrimination of benign and malignant follicular thyroid tumors. Tumour Biol. 2006;27(4):211-20.

Fujarewicz, et al. A multi-gene approach to differentiate papillary thyroid carcinoma from benign lesions: gene selection using support vector machines with bootstrapping. Endocr Relat Cancer. Sep. 2007;14(3):809-26.

Gait. Chapter 16: Oligoribonucleotides. Antisense Research and Applications, Crookeand Lebleu Eds., CRC Press (pp. 289-302) (1993).

Griffith, et al. Biomarker panel diagnosis of thyroid cancer: a critical review. Expert Rev Anticancer Ther. Sep. 2008;8(9):1399-413. doi: 10.1586/14737140.8.9.1399.

Griffith et al. Meta-analysis and meta-review of thyroid cancer gene expression profiling studies identifies important diagnostic biomarkers. J Clin Oncol. 2006;24(31):5043-51.

Hamada, et al. Diagnostic usefulness of PCR profiling of the differentially expressed marker genes in thyroid papillary carcinomas. Cancer Lett. Jun. 28, 2005;224(2):289-301. Epub Nov. 18, 2004.

International Search Report for PCT/CA2010/000621, completed Jul. 14, 2010.

International Search Report for PCT/CA2010/000266, dated Jul. 12, 2010.

Kanehisa. Use of statistical criteria for screening potential homologies in nucleic acid sequences. Nucleic Acids Res. Jan. 11, 1984;12(1 Pt 1):203-13.

Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.

Kebebew et al. Diagnostic and extent of disease multigene assay for malignant thyroid neoplasms. Cancer. 2006;106(12):2592-7.

Koshkin et al. LNA (locked nucleic acids): An RNA mimic forming exceedingly stable Lna: Lna duplexes. J Am Chem Soc 120:13252-13253 (1998).

(56) References Cited

OTHER PUBLICATIONS

Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kroschwitz. The Concise Encyclopedia of Polymer Science and Engineering. (pp. 858-859) (1990).
Kumar, et al. The first analogues of LNA (locked nucleic acids): phosphorothioate-LNA and 2'- thio-LNA. Bioorg Med Chem Lett. Aug. 18, 1998;8(16):2219-22.
Martin. A New Access to 2'-O-Alkylated Ribonucleosides and Properties of 2'-O-Alkylated Oligoribonucleotides. Helv. Chim. Acta. 1995; 78:486-504. (in German with English abstract).
Mazzanti, et al. Using gene expression profiling to differentiate benign versus malignant thyroid tumors. Cancer Res. Apr. 15, 2004;64(8):2898-903.
Mineva, et al. Differential expression of alphaB-crystallin and Hsp27-1 in anaplastic thyroid carcinomas because of tumor-specific alphaB-crystallin gene (CRYAB) silencing. Cell Stress Chaperones. 2005 Autumn;10(3):171-84.
Nielsen et al. Sequence-selective recognition of DNA by strand displacement with a thymine-substituted polyamide. Science 254:1497-1500 (1991).
Notice of allowance dated Mar. 27, 2015 for U.S. Appl. No. 13/254,571.
Notice of Allowance dated Mar. 30, 2017 for U.S. Appl. No. 14/727,801.
Notice of allowance dated Jul. 30, 2015 for U.S. Appl. No. 13/258,429.
Notice of allowance dated Nov. 28, 2016 for U.S. Appl. No. 14/926,349.
Office action dated Jan. 16, 2015 for U.S. Appl. No. 13/258,429.
Office action dated Feb. 26, 2016 for U.S. Appl. No. 14/926,349.
Office action dated Mar. 11, 2014 for U.S. Appl. No. 13/254,571.
Office action dated Apr. 8, 2014 for U.S. Appl. No. 13/258,429.
Office action dated Sep. 7, 2016 for U.S. Appl. No. 14/727,801.
Office action dated Sep. 11, 2013 for U.S. Appl. No. 13/258,429.
Office action dated Dec. 4, 2014 for U.S. Appl. No. 13/254,571.
Prasad et al. Identification of genes differentially expressed in benign versus malignant thyroid tumors. Clin Cancer Res. 2008;14(11):3327-37.
Puskas, et al. Gene profiling identifies genes specific for well-differentiated epithelial thyroid tumors. Cell Mol Biol (Noisy-le-grand). Sep. 5, 2005;51(2):177-86.
Robinson, et al. A comparison of Affymetrix gene expression arrays. BMC Bioinformatics. Nov. 15, 2007;8:449.
Sanghvi. Heterocyclic base modifications in nucleic acids and their applications in antisense oligonucleotides. In Antisense Research and Applications. Crooke, S. T. and Lebleu, B., ed., CRC Press. 1993; Ch 15 274-285.
Shibru, et al. Does the 3-gene diagnostic assay accurately distinguish benign from malignant thyroid neoplasms? Cancer. Sep. 1, 2008;113(5):930-5. doi: 10.1002/cncr.23703.
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Written Opinion of the International Searching Authority for PCT/CA2010/000621, dated Aug. 11, 2010.
Yukinawa, et al. A multi-class predictor based on a probabilistic model: application to gene expression profiling-based diagnosis of thyroid tumors. BMC Genomics. Jul. 27, 2006;7:190.
Extended European Search Report dated Apr. 22, 2016 for European Patent Application No. 13838743.6.
International Search Report and Written Opinion dated Nov. 18, 2013 for International PCT Patent Application No. PCT/CA2013/050686.
Office Action dated May 5, 2017 for U.S. Appl. No. 14/020,183.
Abratani, Hiroyuki. Characteristic Diagnosis of Cancer by Gene Expression Profiling. Personalized Diagnosis of Cancer by Gene Expression Profiling. English Translation. Journal of Clinical and Experimental Medicine (Igaku No Ayumi), Jun. 1, 2002, vol. 201, No. 9, p. 687-692.
Abrosimov et al. The cytoplasmic expression of MUC1 in papillary thyroid carcinoma of different histological variants and its correlation with cyclin D1 overexpression. Endocr Pathol. 2007;18(2):68-75.
Abubaker et al. Clinicopathological analysis of papillary thyroid cancer with PIK3CA alterations in a Middle Eastern population. J Clin Endocrinol Metab. 2008;93(2):611-8.
Adapt, The Peterson Institute for Cancer Research, probesets for ARSG, printed Jan. 10, 2013.
Adapt, The Peterson Institute for Cancer Research, probesets for FREM2, printed Jan. 10, 2013.
Adapt, The Peterson Institute for Cancer Research, probesets for GIMAP2, printed Jan. 10, 2013.
Adapt, The Peterson Institute for Cancer Research, probesets for HRASLS3, printed Jan. 10, 2013.
Adapt, The Peterson Institute for Cancer Research, probesets for PIGN, printed Jan. 10, 2013.
Adapt website. Paterson Institute for Cancer Research. Probesets for AUTS2. Printed Jul. 1, 2014. 2 pages.
Adapt website. Paterson Institute for Cancer Research. Probesets for FXYD6. Printed Jul. 1, 2014. 1 page.
Affymetrix: "Data Sheet Affymetrix(R) Genome-Wide Human SNP Array 6.0", 2007, pp. 1-4, XP002525407. Retrieved from the Internet: URL:http://www.affymetrix.com/support/technical/datasheets/genomewide_snp6_datasheet.pdf.
Affymetrix Technical Note: GeneChip® Gene 1.0 ST Array Design (created Sep. 5, 2007; downloaded from http://media.affymetrix.com/support/technical/technotes/gene_1_0_st_technote.pdf).
Affymetrix website for HG-U133A probe set list version 2004, Archived NetAffx Annotation Files (http://www.affymetrix.com/estore/catalog/131537/AFFY/Human+Genome+U133A+2.0+Array#1_3) printed Mar. 2015.
Afink, et al. Molecular characterization of iodotyrosine dehalogenase deficiency in patients with hypothyroidism. J Clin Endocrinol Metab. Dec. 2008;93(12):4894-901.
Aggarwal et al. Thyroid carcinoma-associated genetic mutations also occur in thyroid lymphomas. Mod Pathol. vol. 25 No. 9. May 11, 2012. pp. 1203-1211.
Agrawal, et al. Cancer Genome Atlas Research Network. Integrated genomic characterization of papillary thyroid carcinoma. Cell. Oct. 23, 2014;159(3):676-90. doi: 10.1016/j.cell.2014.09.050.
Akester et al. Cancer in the thyroid is not always thyroid cancer. Hormones-Athens- 2 (2003): 250-255.
Aldred et al. Caveolin-1 and caveolin-2, together with three bone morphogenetic protein-related genes, may encode novel tumor suppressors down-regulated in sporadic follicular thyroid carcinogenesis. Cancer Res. 2003;63(11):2864-71.
Alexander et al. Preoperative diagnosis of benign thyroid nodules with indeterminate cytology. N Engl J Med. Aug. 23, 2012;367(8):705-15.
Ali et al. Use of the Afirma® Gene Expression Classifier for Preoperative Identification of Benign Thyroid Nodules with Indeterminate Fine Needle Aspiration Cytopathology. PLoS Currents 5:pp. 1-7 (2013).
Arnesen et al. Expression of N-acetyl transferase human and human Arrest defective 1 proteins in thyroid neoplasms. Thyroid. 2005;15(10):1131-6.
Ashley. Towards precision medicine. Nature Reviews Genetics 17.9 (2016): 507.
Asseroshn et al. The feasibility of using fine needle aspiration from primary breast cancers for cDNA microarray analyses. Clinical Cancer Research 8.3 (2002): 794-801.
Auton et al. 1000 Genomes Project Consortium. A global reference for human genetic variation. Nature 526, 7571 (2015): 68.
Bai et al. Mutational analysis of thyroid transcription factor-1 gene (TTF-1) in lung carcinomas. In Vitro Cell Dev Biol Anim. 2008;44(1-2):17-25.
Baloch, et al. Our approach to follicular-patterned lesions of the thyroid. J Clin Pathol. Mar. 2007;60(3):244-50. Epub Jun. 23, 2006.

(56) References Cited

OTHER PUBLICATIONS

Banito et al. Aneuploidy and RAS mutations are mutually exclusive events in the development of well-differentiated thyroid follicular tumours. Clin Endocrinol (Oxf). 2007;67(5):706-11.
Barden et al. Classification of follicular thyroid tumors by molecular signature: results of gene profiling. Clin Cancer Res. 2003;9(5):1792-800.
Baris et al. Transcriptional profiling reveals coordinated up-regulation of oxidative metabolism genes in thyroid oncocytic tumors. J Clin Endocrinol Metab. 2004;89(2):994-1005.
Beaudenon-Huibregtse, et al. Centralized molecular testing for oncogenic gene mutations complements the local cytopathologic diagnosis of thyroid nodules. Thyroid. Oct. 2014;24(10):1479-87. Epub Jun. 18, 2014.
Bessarabova, et al. Bimodal gene expression patterns in breast cancer. BMC Genomics. Feb. 10, 2010;11 Suppl 1:S8. doi: 10.1186/1471-2164-11-S1-S8.
Bolstad, et al. A comparison of normalization methods for high density oligonucleotide array data based on variance and bias. Bioinformatics. Jan. 22, 2003;19(2):185-93.
Bonora et al. Novel germline variants identified in the inner mitochondrial membrane transporter TIMM44 and their role in predisposition to oncocytic thyroid carcinomas. Br J Cancer. 2006;95(11):1529-36.
Boulesteix, et al. Evaluating microarray-based classifiers: an overview. Cancer Inform. 2008;6:77-97. Epub Feb. 29, 2008.
Brasseur et al. Papillary thyroid carcinoma in a 9-year-old girl with ataxia-telangiectasia. Pediatr Blood Cancer. 2008;50(5):1058-60.
Brozek et al. Thyroid cancer in two siblings with FAP syndrome and APC mutation. Int J Colorectal Dis. 2008;23(3):331-2.
Bugalho et al. Mutation analysis of the RET proto-oncogene and early thyroidectomy: results of a Portuguese cancer centre. Surgery. 2007;141(1):90-5.
Byron et al. Translating RNA sequencing into clinical diagnostics: opportunities and challenges. Nature Reviews Genetics 17.5 (2016): 257.
Cameselle-Teijeiro et al. Follicular thyroid carcinoma with an unusual glomeruloid pattern of growth. Hum Pathol. 2008;39(10):1540-7.
Carda et al. Anaplastic carcinoma of the thyroid with rhabdomyosarcomatous differentiation: a report of two cases. Virchows Arch. 2005;446(1):46-51.
Carroll et al. Promising Molecular Techniques for Discriminating Among Follicuar Thyroid Neoplasms. Surgical Oncology, Blackwell Scientific Publ., Oxford, GB, vol. 15, No. 2, Aug. 1, 2006, pp. 59-64.
Castro et al. Adenomas and follicular carcinomas of the thyroid display two major patterns of chromosomal changes. J Pathol. 2005;206(3):305-11.
Castro et al.PAX8-PPARgamma rearrangement is frequently detected in the follicular variant of papillary thyroid carcinoma. J Clin Endocrinol Metab. 2006;91(1):213-20.
Centeno et al. Classification of human tumors using gene expression profiles obtained after microarray analysis of fine-needle aspiration biopsy samples. Cancer Cytopathology: Interdisciplinary International Journal of the American Cancer Society 105.2 (2005): 101-109.
Cerutti et al. A preoperative diagnostic test that distinguishes benign from malignant thyroid carcinoma based on gene expression. J Clin Invest. 2004;113(8):1234-42.
Chan, et al. Integrating Transcriptomics and Proteomics. Drug Discovery and Development. Apr. 1, 2006. 4 pages. Published in G&P magazine 2006 vol. 6 No. 3 pp. 20-26.
Chen et al. Restricted kappa/lambda light chain ratio by flow cytometry in germinal center B cells in Hashimoto thyroiditis. Am J Clin Pathol. 2006;125(1):42-8.
Cheng et al. A Multi-Cancer Mesenchymal Transition Gene Expression Signature Is Associated with Prolonged Time to Recurrence in Glioblastoma. Plos One 7(4):e34705 (2012).
Cheung, et al. Immunohistochemical diagnosis of papillary thyroid carcinoma. Mod Pathol. Apr. 2001;14(4):338-42.
Chevillard et al. Gene expression profiling of differentiated thyroid neoplasms: diagnostic and clinical implications. Clin Cancer Res. 2004;10(19):6586-97.
Chiappetta et al. The antiapoptotic protein BAG3 is expressed in thyroid carcinomas and modulates apoptosis mediated by tumor necrosis factor-related apoptosis-inducing ligand. J Clin Endocrinol Metab. 2007;92(3):1159-63.
Choi et al. Case-control association testing in the presence of unknown relationships. Genetic epidemiology 33.8 (2009): 668-678.
Chudova, et al. Molecular classification of thyroid nodules using high-dimensionality genomic data. J Clin Endocrinol Metab. Dec. 2010;95(12):5296-304. doi: 10.1210/jc.2010-1087. Epub Sep. 8, 2010.
Chung et al. Detection of BRAFV600E mutation on fine needle aspiration specimens of thyroid nodule refines cyto-pathology diagnosis, especially in BRAF600E mutation-prevalent area. Clin Endocrinol (Oxf). 2006;65(5):660-6.
Ciampi et al. BRAF copy number gains in thyroid tumors detected by fluorescence in situ hybridization. Endocr Pathol. 2005;16(2):99-105.
Cirulli Uncovering the roles of rare variants in common disease through whole-genome sequencing. Nature Reviews Genetics 11.6 (2010): 415.
Clark et al. Discovery of tissue-specific exons using comprehensive human exon microarrays. Genome Biol. 2007;8(4):R64.
Cohen et al. Mutational Analysis of BRAF in Fine Needle Aspiration Biopsies of the Thyroid: A Potential Application for the Preoperative Assessment of Thyroid Nodules. Clinical Cancer Research 10:2761-2765 (Apr. 2004).
Combined search report and examination report dated Oct. 1, 2013 for GB Application No. 1315760.7.
Cooper, et al. Management guidelines for patients with thyroid nodules and differentiated thyroid cancer. Thyroid. Feb. 2006;16(2):109-42.
Co-pending U.S. Appl. No. 15/096,739, filed Apr. 12, 2016.
Co-pending U.S. Appl. No. 15/934,666, filed Mar. 23, 2018.
Co-pending U.S. Appl. No. 16/017,899, filed Jun. 25, 2018.
Costa et al. New somatic mutations and WNK1-B4GALNT3 gene fusion in papillary thyroid carcinoma. Oncotarget 6:11242-11251 (2015).
Crescioli et al. Methimazole inhibits CXC chemokine ligand 10 secretion in human thyrocytes. J Endocrinol. 2007;195(1):145-55.
Cross et al. The promise of molecular profiling for cancer identification and treatment. Clinical medicine & research 2.3 (2004): 147-150.
De Lellis et al. The pathobiology of the human calcitonin (C)-cell: a review. Pathol Annu. 1981;16(Pt 2):25-52.
Del Senno et al. c-myc oncogene alterations in human thyroid carcinomas. Cancer Detect Prev. 1987;10(3-4):159-66.
Delellis et al. C-cell hyperplasia. An ultrastructural analysis. Lab Invest. 1977;36(3):237-48.
Derringer, et al. Malignant lymphoma of the thyroid gland: a clinicopathologic study of 108 cases. Am J Surg Pathol. May 2000;24(5):623-39.
Dettori et al. Aneuploidy in oncocytic lesions of the thyroid gland: diffuse accumulation of mitochondria within the cell is associated with trisomy 7 and progressive numerical chromosomal alterations. Genes Chromosomes Cancer. 2003;38(1):22-31.
Diaz-Uriarte et al. Gene selection and classification of microarray data using random forest. BMC Bioinformatics. 2006;7:3.
Druckenthaner et al. Evidence for Somatostatin receptor 2 in thyroid tissue. Regul Pept. 2007;138(1):32-9.
Durand et al. Evaluation of gene expression profiles in thyroid nodule biopsy material to diagnose thyroid cancer. J Clin Endocrinol Metab. 2008;93(4):1195-202.
Durante, et al. BRAF mutations in papillary thyroid carcinomas inhibit genes involved in iodine metabolism. J Clin Endocrinol Metab. Jul. 2007;92(7):2840-3. Epub May 8, 2007.

(56) References Cited

OTHER PUBLICATIONS

Elisei et al. RET genetic screening in patients with medullary thyroid cancer and their relatives: experience with 807 individuals at one center. J Clin Endocrinol Metab. 2007;92(12):4725-9.
Engstrom et al. Systematic evaluation of spliced alignment programs for RNA-seq data. Nature methods 10.12 (2013): 1185.
EP16759458.9 European Search Report dated Sep. 6, 2018.
Erdogan et al. The prevalence of RET/PTC mutations in papillary thyroid cancers in Turkish population and its relation between tumor histopathology and prognostic factors. Exp Clin Endocrinol Diabetes. 2008;116(4):225-30.
Erkkila et al. Probabilistic analysis of gene expression measurements from heterogeneous tissues. Bioinformatics 26(20):2571-2577 (2010).
Esperante, et al. Identification and characterization of four PAX8 rare sequence variants (p. T225M, p. L233L, p. G336S and p. A439A) in patients with congenital hypothyroidism and dysgenetic thyroid glands. Clin Endocrinol (Oxf). May 2008;68(5):828-35.
Eszlinger et al. Gene expression analysis reveals evidence for inactivation of the TGF-beta signaling cascade in autonomously functioning thyroid nodules. Oncogene. 2004;23(3):795-804.
Eszlinger et al. Meta- and reanalysis of gene expression profiles of hot and cold thyroid nodules and papillary thyroid carcinoma for gene groups. J Clin Endocrinol Metab. 2006;91(5):1934-42.
Eszlinger et al. Perspectives and limitations of microarray-based gene expression profiling of thyroid tumors. Endocr Rev. 2007;28(3):322-38.
Eszlinger, et al. Perspectives for Improved and More Accurate Classification of Thyroid Epithelial Tumors. J Clin Endocrinol Metab. Sep. 2008;93(9):3286-94. Epub Jul. 1, 2008.
European Search Report dated Jan. 10, 2018 for EP3265588.
European Search Report dated May 25, 2018 for EP172108505.
European search report and opinion dated Mar. 5, 2014 for EP Application No. 11781242.0.
European search report and opinion dated Apr. 28, 2016 for EP 16153243.7.
European search report and search opinion dated Jan. 28, 2013 for Application No. 10772919.6.
European search report and search opinion dated Nov. 27, 2012 for Application No. 09826462.5.
Ferrari, et al. An approach to estimate between- and within-group correlation coefficients in multicenter studies: plasma carotenoids as biomarkers of intake of fruits and vegetables. Am J Epidemiol. Sep. 15, 2005;162(6):591-8. Epub Aug. 10, 2005.
Filicori, et al. Risk stratification of indeterminate thyroid fine-needle aspiration biopsy specimens based on mutation analysis. Surgery. Dec. 2011;150(6):1085-91.
Final Office action dated Aug. 28, 2018 for U.S. Appl. No. 13/105,756.
Final Office action dated Sep. 10, 2018 for U.S. Appl. No. 15/694,157.
Finley et al. Discrimination of benign and malignant thyroid nodules by molecular profiling. Annals of surgery 240.3 (2004): 425.
Finley et al. Molecular analysis of Hurthle cell neoplasms by gene profiling. Surgery. 2004;136(6):1160-8.
Finley et al. Molecular profiling distinguishes papillary carcinoma from benign thyroid nodules. J Clin Endocrinol Metab. 2004;89(7):3214-23.
Finn, et al. Expression microarray analysis of papillary thyroid carcinoma and benign thyroid tissue: emphasis on the follicular variant and potential markers of malignancy. Virchows Arch. Mar. 2007;450(3):249-60.
Fishel, et al. Meta-analysis of gene expression data: a predictor-based approach. Bioinformatics. Jul. 1, 2007;23(13):1599-606. Epub Apr. 26, 2007.
Fontaine et al. Microarray analysis refines classification of non-medullary thyroid tumours of uncertain malignancy. Oncogene. 2008;27(15):2228-36.
Foppiani et al. Uncommon association of germline mutations of RET proto-oncogene and CDKN2A gene. Eur J Endocrinol. 2008;158(3):417-22.
Frampton, et al. Development and validation of a clinical cancer genomic profiling test based on massively parallel DNA sequencing. Nat Biotechnol. Nov. 2013;31(11):1023-31. Epub Oct. 20, 2013.
Frattini, et al. Alternative mutations of BRAF, RET and NTRK1 are associated with similar but distinct gene expression patterns in papillary thyroid cancer. Oncogene. Sep. 23, 2004;23(44):7436-40.
Fujarewicz et al. A multi-gene approach to differentiate papillary thyroid carcinoma from benign lesions: gene selection using support vector machines with bootstrapping. Endocrine-Related Cancer 14.3 (2007): 809-826.
Garcia-Lopez et al. Thyrocytes from autoimmune thyroid disorders produce the chemokines IP-10 and Mig and attract CXCR3+ lymphocytes. J Clin Endocrinol Metab. 2001;86(10):5008-16.
Gardina et al. Alternative splicing and differential gene expression in colon cancer detected by a whole genome exon array. BMC Genomics. 2006;7:325.
Gasparre et al. Disruptive mitochondrial DNA mutations in complex I subunits are markers of oncocytic phenotype in thyroid tumors. Proc Natl Acad Sci USA. 2007;104(21):9001-6.
Gene Annot Website. Array Probesets for HOMER2, printed Jan. 2016.
Gene Annot website. Probesets for ALDH1B1. Printed Feb. 2018.
Gene Annot website. Probesets for AUTS2. Printed Feb. 2018.
Gene Annot website. Probesets for CFHR1. Printed Feb. 2018.
Gene Annot website. Probesets for CPE. Printed Feb. 2018.
Gene Annot website. Probesets for FN1. Printed Feb. 2018.
Gene Annot website. Probesets for GABRB2. Printed Feb. 2018.
Gene Annot website. Probesets for PLCB1. Printed Feb. 2018.
Gene Annot website. Probesets for PYGL. Printed Feb. 2018.
Gene Annot website. Probesets for ROS1. Printed Feb. 2018.
GeneAnnot website. Probesets for AKT1. Printed Aug. 30, 2016. 1 page.
GeneAnnot website. Probesets for ALK. Printed Aug. 30, 2016. 1 page.
GeneAnnot website. Probesets for BRAF. Printed Aug. 30, 2016. 1 page.
GeneAnnot website. Probesets for CALCA. Printed Aug. 30, 2016. 1 page.
GeneAnnot website. Probesets for CTNNB1. Printed Aug. 30, 2016. 1 page.
GeneAnnot website. Probesets for EIF1AY. Printed Aug. 30, 2016. 1 page.
GeneAnnot website. Probesets for IGF2BP2. Printed Aug. 30, 2016. 1 page.
GeneAnnot website. Probesets for KRAS. Printed Feb. 7, 2017. 2 pages.
GeneAnnot website. Probesets for KRT7. Printed Aug. 30, 2016. 1 page.
GeneAnnot website. Probesets for MET. Printed Aug. 30, 2016. 1 page.
GeneAnnot website. Probesets for NTRK2. Printed Aug. 30, 2016. 1 page.
GeneAnnot website. Probesets for NTRK3. Printed Aug. 30, 2016. 2 pages.
GeneAnnot website. Probesets for PIK3CA. Printed Aug. 30, 2016. 1 page.
GeneAnnot website. Probesets for PPARGC1A. Printed Aug. 30, 2016. 1 page.
GeneAnnot website. Probesets for PROS1. Printed Nov. 8, 2016. 1 page.
GeneAnnot website. Probesets for PTEN. Printed Aug. 30, 2016. 2 pages.
GeneAnnot website. Probesets for PTH. Printed Aug. 30, 2016. 1 page.
GeneAnnot website. Probesets for RASA1. Printed Aug. 30, 2016. 1 page.
GeneAnnot website. Probesets for RET. Printed Aug. 30, 2016. 1 page.
GeneAnnot website. Probesets for RXRG. Printed Nov. 8, 2016. 1 page.
GeneAnnot website. Probesets for TP53. Printed Aug. 30, 2016. 1 page.

(56) References Cited

OTHER PUBLICATIONS

GeneAnnot website. Probesets for TSHR. Printed Aug. 30, 2016. 1 page.
GeneAnnot website. Probesets for TTF1. Printed Aug. 30, 2016. 1 page.
Gereben et al. Pretranslational regulation of type 2 deiodinase. Thyroid. 2005;15(8):855-64.
Gerstung, et al. Combining gene mutation with gene expression data improves outcome prediction in myelodysplastic syndromes. Nat Commun. Jan. 9, 2015;6:5901.
Gill, et al. Nucleic acid isothermal amplification technologies: a review. Nucleosides Nucleotides Nucleic Acids. Mar. 2008;27(3):224-43.
Giordano et al. Delineation, functional validation, and bioinformatic evaluation of gene expression in thyroid follicular carcinomas with the PAX8-PPARG translocation. Clin Cancer Res. 2006;12(7 Pt 1):1983-93.
Giordano et al. Distinct transcriptional profiles of adrenocortical tumors uncovered by DNA microarray analysis. Am J Pathol. 2003;162(2):521-31.
Giordano et al. Molecular Classification of Papillary Thyroid Carcinoma; distinct BRAF, RAS and RET/PTC mutation-specific gene expression profiles discovered by DNA microarray Analysis Oncogene. Oncogene 24:6646-6656 (2005).
Giordano et al. Organ-specific molecular classification of primary lung, colon, and ovarian adenocarcinomas using gene expression profiles. Am J Pathol. 2001;159(4):1231-8.
Giordano. Genome-wide studies in thyroid neoplasia. Endocrinol Metab Clin North Am. 2008;37(2):311-31, vii-viii.
Gombos, et al. Characterization of microarray gene expression profiles of early stage thyroid tumours. Cancer Genomics Proteomics. Nov.-Dec. 2007;4(6):403-9.
Gonzalez-Campora et al. Blood group antigens in differentiated thyroid neoplasms. Arch Pathol Lab Med. 1998;122(11):957-65.
Gould et al. (1987). Synaptophysin expression in neuroendocrine neoplasms as determined by immunocytochemistry. Am J Pathol. 126(2):243-57.
Greenbaum, et al. Comparing protein abundance and mRNA expression levels on a genomic scale. Genome Biol. 2003;4(9):117. Epub Aug. 29, 2003.
Greenbaum, et al. Interrelating different types of genomic data, from proteome to secretome: foming in on function. Genome Res. Sep. 2001;11(9):1463-8.
Ha et al. Localized non-Hodgkin lymphoma involving the thyroid gland. Cancer91.4 (2001): 629-635.
Hadd, et al. Targeted, high-depth, next-generation sequencing of cancer genes in formalin-fixed, paraffin-embedded and fine-needle aspiration tumor specimens. J Mol Diagn. Mar. 2013;15(2):234-47. doi: 10.1016/j.jmoldx.2012.11.006. Epub Jan. 13, 2013.
Harach et al. Histology of familial thyroid tumours linked to a gene mapping to chromosome 19p13.2. J Pathol. 1999;189(3):387-93.
Hartigan, et al. The dip test of unimodality. Annals of Statistics. 1985; 13(1):70-84.
Haugen, et al. Development of a novel molecular classifier to accurately identify benign thyroid nodules in patients with indeterminate FNA cytology. Abstract presented at 14th International Thyroid Congress. Sep. 15, 2010.
Haugen et al. Increased expression of genes encoding mitochondrial proteins in papillary thyroid carcinomas. Thyroid. 2003;13(7):613-20.
Hawthorn, et al. TIMP1 and SERPIN-A overexpression and TFF3 and CRABP1 underexpression as biomarkers for papillary thyroid carcinoma. Head Neck. Dec. 2004;26(12):1069-83.
He, et al. A susceptibility locus for papillary thyroid carcinoma on chromosome 8q24. Cancer Res. Jan. 15, 2009;69(2):625-31.
He et al. The role of microRNA genes in papillary thyroid carcinoma. Proc Natl Acad Sci USA. 2005;102(52):19075-80.
Hellwig, et al. Comparison of scores for bimodality of gene expression distributions and genome-wide evaluation of the prognostic relevance of high-scoring genes. BMC Bioinformatics. May 25, 2010;11:276. doi: 10.1186/1471-2105-11-276.
Hemmer et al. Comparison of benign and malignant follicular thyroid tumours by comparative genomic hybridization. Br J Cancer. 1998;78(8):1012-7.
Hemmer, et al. DNA copy number changes in thyroid carcinoma. Am J Pathol. May 1999;154(5):1539-47.
Heuer et al. Different cytokine mRNA profiles in Graves' disease, Hashimoto's thyroiditis, and nonautoimmune thyroid disorders determined by quantitative reverse transcriptase polymerase chain reaction (RT-PCR). Thyroid. 1996;6(2):97-106.
Holden et al. Tyrosine kinase activating mutations in human malignancies: implications for diagnostic pathology. Exp Mol Pathol. 2008; 85(1):68-75.
Hoshikawa, et al. Hypoxia induces different genes in the lungs of rats compared with mice. Physiol Genomics. Feb. 6, 2003;12(3):209-19.
Hou et al. Genetic alterations and their relationship in the phosphatidylinositol 3-kinase/Akt pathway in thyroid cancer. Clin Cancer Res. 2007;13(4):1161-70.
Hsu et al. Characterization of a novel tripartite nuclear localization sequence in the EGFR family. J Biol Chem. 2007;282(14):10432-40.
Huang et al. A genome-wide approach to identify genetic variants that contribute to etoposide-induced cytotoxicity. Proc Natl Acad Sci USA. 2007;104(23):9758-63.
Huang et al. A tool for RNA sequencing sample identity check. Bioinformatics 29.11 (2013): 1463-1464.
Huang et al. Gene expression in papillary thyroid carcinoma reveals highly consistent profiles. Proc Natl Acad Sci USA. 2001;98(26):15044-9.
Hunt, et al. A microdissection and molecular genotyping assay to confirm the identity of tissue floaters in paraffin-embedded tissue blocks Arch Pathol Lab Med. 2003; 127(2):213-217.
Inaji et al. Demonstration and diagnostic significance of pro-gastrin-releasing peptide in medullary thyroid carcinoma. Oncology. 2000;59(2):122-5.
International search report and written opinion dated Jan. 19, 2012 for PCT Application No. US2011/36143.
International search report and written opinion dated Feb. 25, 2011 for PCT Application No. US2010/034140.
International search report and written opinion dated Feb. 25, 2013 for PCT Application No. US2012/068804.
International Search Report and Written Opinion dated Apr. 4, 2017 for International PCT Patent Application No. PCT/US2016/053578.
International search report and written opinion dated Apr. 17, 2015 for PCT/US2014/026411.
International search report and written opinion dated May 8, 2013 for PCT Application No. US2012/068587.
International Search Report and Written Opinion dated Jun. 2, 2016 for International PCT Patent Application No. PCT/US2016/020583.
International search report dated Jul. 29, 2010 for PCT Application No. US2009/06162.
Irizarry, et al. Exploration, normalization, and summaries of high density oligonucleotide array probe level data. Biostatistics. Apr. 2003;4(2):249-64.
Ito, et al. Distant and lymph node metastases of thyroid nodules with no pathological evidence of malignancy: a limitation of pathological examination. Endocr J. Oct. 2008;55(5):889-94. Epub Jun. 14, 2008.
Ito et al. Simultaneous expression of keratan sulphate epitope (a sulphated poly-N-acetyllactosamine) and blood group ABH antigens in papillary carcinomas of the human thyroid gland. Histochem J. 1996;28(9):613-23.
Jacques et al. Two-step differential expression analysis reveals a new set of genes involved in thyroid oncocytic tumors. J Clin Endocrinol Metab. 2005;90(4):2314-20.
Jarzab et al. Gene Expression Profile of Papillary Thyroid Cancer: Sources of Variability and Diagnostic Implications. Cancer Res. 2005;65(4):1587-1597.
Jazdzewski et al. Common SNP in pre-miR-146a decreases mature miR expression and predisposes to papillary thyroid carcinoma. Proc Natl Acad Sci USA. 2008;105(20):7269-74.

(56) References Cited

OTHER PUBLICATIONS

Jo, et al. Influence of the BRAF V600E mutation on expression of vascular endothelial growth factor in papillary thyroid cancer. J Clin Endocrinol Metab. Sep. 2006;91(9):3667-70. Epub Jun. 13, 2006.
Johansson, et al. Confirmation of a BRAF mutation-associated gene expression signature in melanoma. Pigment Cell Res. Jun. 2007;20(3):216-21.
Joseph et al. Lack of mutations in the thyroid hormone receptor (TR) alpha and beta genes but frequent hypermethylation of the TRbeta gene in differentiated thyroid tumors. J Clin Endocrinol Metab. 2007;92(12):4766-70.
Jovanovic et al. Most multifocal papillary thyroid carcinomas acquire genetic and morphotype diversity through subclonal evolution following the intra-glandular spread of the initial neoplastic clone. J Pathol. 2008;215(2):145-54.
Jun et al. Detecting and estimating contamination of human DNA samples in sequencing and array-based genotype data. The American Journal of Human Genetics 91.5 (2012): 839-848.
Kakudo et al. Immunohistochemical study of substance P-like immunoreactivity in human thyroid and medullary carcinoma of the thyroid. J Submicrosc Cytol. 1983;15(2):563-8.
Kang et al. High prevalence of RET, RAS, and ERK expression in Hashimoto's thyroiditis and in papillary thyroid carcinoma in the Korean population. Thyroid. 2007;17(11):1031-8.
Kannengiesser, et al. Gene expression signature associated with BRAF mutations in human primary cutaneous melanomas. Mol Oncol. Apr. 2008;1(4):425-30. doi: 10.1016/j.molonc.2008.01.002. Epub Jan. 12, 2008.
Kapadia, et al. Malignant lymphoma of the thyroid gland: a clinicopathologic study. Head Neck Surg. Mar.-Apr. 1982;4(4):270-80.
Katoh et al. Thyroid transcription factor-1 in normal, hyperplastic, and neoplastic follicular thyroid cells examined by immunohistochemistry and nonradioactive in situ hybridization. Mod Pathol. 2000;13(5):570-6.
Kawai, et al. Recent Advances of DNA chip application. Latest Situation in DNA Chip Applications. English Translation. Protein Nucleic Acid and Enzyme, Aug. 1, 2000, vol. 45, No. 11, p. 47-53.
Kebebew et al. Diagnostic and prognostic value of angiogenesis-modulating genes in malignant thyroid neoplasms. Surgery. Dec. 2005;138(6):1102-9; discussion 1109-10.
Kebebew, et al. The prevalence and prognostic value of BRAF mutation in thyroid cancer. Ann Surg. Sep. 2007;246(3):466-70; discussion 470-1.
Krause, et al. Characterisation of DEHAL1 expression in thyroid pathologies. Eur Endocrinol. Mar. 2007;156(3):295-301.
Krawczak, et al. The mutational spectrum of single base-pair substitutions in mRNA splice junctions of human genes: causes and consequences. Hum Genet. Sep.-Oct. 1992;90(1-2):41-54.
Kreula, et al. Sample size in fine needle aspiration biopsy. Br J Surg. Dec. 1989;76(12):1270-2.
Kristensen, et al. Genetic variation in putative regulatory loci controlling gene expression in breast cancer. Proc Natl Acad Sci U S A. May 16, 2006;103(20):7735-40. Epub May 9, 2006.
Kroese et al. Genetic tests and their evaluation: Can we answer the key questions? Genetics in Medicine 6:475-480 (2004).
Kwan, et al. Heritability of alternative splicing in the human genome. Genome Res. Aug. 2007;17(8):1210-8.
Lacroix, et al. PAX8 and peroxisome proliferator-activated receptor gamma 1 gene expression status in benign and malignant thyroid tissues. Eur J Endocrinol. Sep. 2004;151(3):367-74.
Lau et al. Thyroid transcription factor-1: a review. Appl Immunohistochem Mol Morphol. 2002;10(2):97-102.
Lauter et al. Mutational analysis of CDKN1B, a candidate tumor-suppressor gene, in refractory secondary/tertiary hyperparathyroidism. Kidney Int. 2008;73(10):1137-40.
Lee et al. NGSCheckMate: software for validating sample identity in next-generation sequencing studies within and across data types. Nucleic acids research 45.11 (2017).
Lima et al. Thyroid Peroxidase and Thyroglobulin Expression in Normal Human Thyroid Glands. Endocr Pathol. 1998;9(1):333-338.
Lin et al. Expression of sodium iodide symporter in benign and malignant human thyroid tissues. Endocr Pathol. 2001;12(1):15-21.
Lin, et al. Thyroid ultrasonography with fine-needle aspiration cytology for the diagnosis of thyroid cancer. J Clin Ultrasound. Mar.-Apr. 1997;25(3):111-8.
Liu et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab. 2008;93(8):3106-16.
Love, et al. Moderated estimation of fold change and dispersion for RNA-seq data with DESeq2. Genome Biol. Dec. 5, 2014;15(12):550.
Lubitz et al. 2006;Microarray analysis of thyroid nodule fine-needle aspirates accurately classifies benign and malignant lesions. J Mol Diagn. 8(4):490-8; quiz 528.
Lubitz et al. Molecular analysis of minimally invasive follicular carcinomas by gene profiling. Surgery. 2005;138(6):1042-8; discussion 1048-9.
Lucentini. Gene Association Studies Typically Wrong. The Scientist, 18(24):20 (2004).
Lui et al. 2008;CREB3L2-PPARgamma fusion mutation identifies a thyroid signaling pathway regulated by intramembrane proteolysis. Cancer Res. 68(17):7156-64.
Machens et al. Genotype-phenotype based surgical concept of hereditary medullary thyroid carcinoma. World J Surg. 2007;31(5):957-68.
Manichaikul, et al. Robust relationship inference in genome-wide association studies. Bioinformatics. Nov. 15, 2010;26(22):2867-73. Epub Oct. 5, 2010.
Marsh, et al. Genome-wide copy number imbalances identified in familial and sporadic medullary thyroid carcinoma. J Clin Endocrinol Metab. Apr. 2003;88(4):1866-72.
Masini-Repiso et al. Ultrastructural localization of thyroid peroxidase, hydrogen peroxide-generating sites, and monoamine oxidase in benign and malignant thyroid diseases. Hum Pathol. 2004; 35(4):436-46.
Mason, et al. Bimodal distribution of RNA expression levels in human skeletal muscle tissue. BMC Genomics. Feb. 7, 2011;12:98. doi: 10.1186/1471-2164-12-98.
Matsubayashi et al. Gastrin-releasing peptide immunoreactivity in medullary thyroid carcinoma. Cancer. 1984;53(11):2472-7.
Maximo et al. Somatic and germline mutation in GRIM-19, a dual function gene involved in mitochondrial metabolism and cell death, is linked to mitochondrion-rich (Hurthle cell) tumours of the thyroid. Br J Cancer. 2005;92(10):1892-8.
McCarroll, et al. Integrated detection and population-genetic analysis of SNPs and copy number variation. Nature Genetics 40, 1166-1174 (2008).
Mitomo et al. Downregulation of miR-138 is associated with overexpression of human telomerase reverse transcriptase protein in human anaplastic thyroid carcinoma cell lines. Cancer Sci. 2008;99(2):280-6.
Miyamoto et al. Potential Marker of Oral Squamous Cell Carcinoma Aggressiveness Detected by Fluorescence in Situ Hybridization in Fine-Needle Aspiration Biopsies. Cancer American Cancer Society 95(10):2152-2159 (Jun. 6, 2002).
Mizukami, et al. Late bone metastasis from an encapsulated follicular carcinoma of the thyroid without capsular and vascular invasion. Pathol Int. Jun. 1996;46(6):457-61.
Montero-Conde et al. Molecular profiling related to poor prognosis in thyroid carcinoma. Combining gene expression data and biological information. Oncogene. 2008;27(11):1554-61.
Moreno, et al. Mutations in the iodotyrosine deiodinase gene and hypothyroidism. N Engl J Med. Apr. 24, 2008;358(17):1811-8. doi: 10.1056/NEJMoa0706819.
Murphy et al. Identification of immunohistochemical biomarkers for papillary thyroid carcinoma using gene expression profiling. Hum Pathol. 2008;39(3):420-6.
Nakano et al. Apoptosis-induced decrease of intrathyroidal CD4(+)CD25(+) regulatory T cells in autoimmune thyroid diseases. Thyroid. 2007;17(1):25-31.

(56) References Cited

OTHER PUBLICATIONS

Nakashima et al. Foci formation of P53-binding protein 1 in thyroid tumors: activation of genomic instability during thyroid carcinogenesis. Int J Cancer. 2008;122(5):1082-8.
Nakashima et al. RET oncogene amplification in thyroid cancer: correlations with radiation-associated and high-grade malignancy. Hum Pathol. 2007;38(4):621-8.
Nakayama et al. High molecular weight caldesmon positive stromal cells in the capsule of thyroid follicular tumours and tumour-like lesions. J Clin Pathol. 2002;55(12):917-20.
Nam, et al. BRAF V600E mutation analysis of thyroid nodules needle aspirates in relation to their ultrasongraphic classification: a potential guide for selection of samples for molecular analysis. Thyroid. Mar. 2010;20(3):273-9. doi: 10.1089/thy.2009.0226.
National Cancer Institute web page: "Common Cancer Types", captured by WayBack machine on Dec. 4, 2011, http://www.cancer.gov/cancertopics/types/commoncancers.
NCBI gene report for LOC100131599. Printed Feb. 2018.
Neonakis et al. Expression of calcitonin and somatostatin peptide and mRNA in medullary thyroid carcinoma. World J Surg. 1994;18(4):588-93.
Nikiforova, et al. Highly accurate diagnosis of cancer in thyroid nodules with follicular neoplasm/suspicious for a follicular neoplasm cytology by ThyroSeq v2 next-generation sequencing assay. Cancer. Dec. 1, 2014;120(23):3627-34. Epub Sep. 10, 2014.
Nikiforova et al. MicroRNA expression profiling of thyroid tumors: biological significance and diagnostic utility. J Clin Endocrinol Metab. 2008;93(5):1600-8.
Nikiforova, et al. Molecular diagnostics and predictors in thyroid cancer. Thyroid. Dec. 2009;19(12):1351-61.
Nikiforova, et al. Targeted Next-Generation Sequencing Panel (ThyroSeq) for Detection of Mutations in Thyroid Cancer. J Clin Endocrinol Metab. Nov. 2013; 98(11): E1852-E1860.
Nikolova et al. Genome-wide gene expression profiles of thyroid carcinoma: Identification of molecular targets for treatment of thyroid carcinoma. 2008;Oncol Rep. 20(1):105-21.
Notice of allowance dated Jun. 13, 2013 for U.S. Appl. No. 12/592,065.
Notice of Allowance dated Aug. 21, 2017 for U.S. Appl. No. 15/274,492.
Notice of allowance dated Sep. 13, 2016 for U.S. Appl. No. 12/964,666.
Notice of allowance dated Oct. 18, 2013 for U.S. Appl. No. 13/318,751.
Notice of allowance dated Oct. 24, 2018 for U.S. Appl. No. 15/661,496.
Notice of allowance dated Sep. 13, 2018 for U.S. Appl. No. 15/851,377.
Nucera, et al. BRAF(V600E) mutation and the biology of papillary thyroid cancer. Endocr Relat Cancer. Mar. 2008;15(1):191-205. doi: 10.1677/ERC-07-0212.
Oerntoft, et al. Genome-wide study of gene copy numbers, transcripts, and protein levels in pairs of non-invasive and invasive human transitional cell carcinomas. Mol Cell Proteomics. Jan. 2002;1(1):37-45.
Office action dated Jan. 5, 2015 for U.S. Appl. No. 14/086,716.
Office Action dated Jan. 12, 2018 for U.S. Appl. No. 13/589,022.
Office action dated Jan. 16, 2013 for U.S. Appl. No. 12/592,065.
Office action dated Jan. 16, 2018 for U.S. Appl. No. 13/105,756.
Office action dated Jan. 22, 2016 for U.S. Appl. No. 13/708,439.
Office action dated Feb. 4, 2014 for U.S. Appl. No. 13/708,439.
Office Action dated Feb. 13, 2017 for U.S. Appl. No. 15/164,241.
Office action dated Feb. 27, 2015 for U.S. Appl. No. 13/710,134.
Office Action dated Mar. 2, 2018 for U.S. Appl. No. 13/589,022.
Office action dated Mar. 9, 2016 for U.S. Appl. No. 13/589,022.
Office Action dated Mar. 9, 2017 for U.S. Appl. No. 13/710,134.
Office Action dated Mar. 21, 2017 for U.S. Appl. No. 15/164,217.
Office Action dated Mar. 21, 2017 for U.S. Appl. No. 15/164,230.
Office action dated Mar. 23, 2015 for U.S. Appl. No. 13/589,022.
Office Action dated Mar. 23, 2017 for U.S. Appl. No. 15/164,220.
Office Action dated Mar. 23, 2017 for U.S. Appl. No. 15/274,492.
Office action dated Mar. 27, 2018 for U.S. Appl. No. 114/153,219.
Office action dated Mar. 29, 2018 for U.S. Appl. No. 14/086,716.
Office action dated Apr. 6, 2012 for U.S. Appl. No. 12/964,666.
Office action dated Apr. 18, 2013 for U.S. Appl. No. 13/318,751.
Office action dated Apr. 27, 2015 for U.S. Appl. No. 12/964,666.
Office action dated May 8, 2014 for U.S. Appl. No. 13/105,756.
Office action dated May 9, 2016 for U.S. Appl. No. 12/964,666.
Office action dated May 16, 2016 for U.S. Appl. No. 14/153,219.
Office action dated May 27, 2015 for U.S. Appl. No. 13/105,756.
Office action dated Jun. 6, 2012 for U.S. Appl. No. 12/592,065.
Office action dated Jun. 10, 2014 for U.S. Appl. No. 13/708,439.
Office Action dated Jun. 12, 2017 for U.S. Appl. No. 13/105,756.
Office action dated Jun. 15, 2018 for U.S. Appl. No. 15/661,496.
Office action dated Jun. 15, 2018 for U.S. Appl. No. 15/851,377.
Office action dated Jun. 20, 2014 for U.S. Appl. No. 12/964,666.
Office Action dated Jun. 23, 2017 for U.S. Appl. No. 14/153,219.
Office action dated Jun. 29, 2018 for U.S. Appl. No. 15/702,126.
Office Action dated Jul. 5, 2017 for U.S. Appl. No. 14/086,716.
Office action dated Jul. 6, 2011 for U.S. Appl. No. 12/964,666.
Office action dated Jul. 10, 2014 for U.S. Appl. No. 13/589,022.
Office action dated Jul. 26, 2016 for U.S. Appl. No. 13/710,134.
Office action dated Jul. 30, 2014 for U.S. Appl. No. 13/710,134.
Office action dated Aug. 10, 2016 for U.S. Appl. No. 14/086,716.
Office Action dated Aug. 29, 2017 for U.S. Appl. No. 15/185,960.
Office action dated Sep. 2, 2015 for U.S. Appl. No. 14/086,716.
Office action dated Sep. 8, 2016 for U.S. Appl. No. 15/164,241.
Office action dated Sep. 10, 2018 for U.S. Appl. No. 15/702,217.
Office action dated Sep. 11, 2012 for U.S. Appl. No. 13/318,751.
Office action dated Sep. 19, 2016 for U.S. Appl. No. 15/164,217.
Office action dated Sep. 19, 2016 for U.S. Appl. No. 15/164,220.
Office action dated Sep. 19, 2016 for U.S. Appl. No. 15/164,230.
Office action dated Sep. 19, 2018 for U.S. Appl. No. 15/096,739.
Office Action dated Oct. 12, 2017 for U.S. Appl. No. 13/589,022.
Office action dated Oct. 17, 2013 for U.S. Appl. No. 13/105,756.
Office action dated Nov. 7, 2016 for U.S. Appl. No. 13/105,756.
Office action dated Nov. 17, 2016 for U.S. Appl. No. 13/589,022.
Office action dated Nov. 18, 2016 for U.S. Appl. No. 14/153,219.
Office action dated Nov. 19, 2015 for U.S. Appl. No. 13/710,134.
Office action dated Nov. 29, 2013 for U.S. Appl. No. 13/710,134.
Office action dated Nov. 30, 2016 for U.S. Appl. No. 13/708,439.
Office action dated Dec. 17, 2015 for U.S. Appl. No. 13/105,756.
Office Action dated Dec. 26, 2017 for U.S. Appl. No. 15/185,960.
Oler, et al. Gene expression profiling of papillary thyroid carcinoma identifies transcripts correlated with BRAF mutational status and lymph node metastasis. Clin Cancer Res. Aug. 1, 2008;14(15):4735-42. doi: 10.1158/1078-0432.CCR-07-4372.
Owens, et al. Metastatic breast carcinoma involving the thyroid gland diagnosed by fine-needle aspiration: a case report. Diagn Cytopathol. Aug. 2005;33(2):110-5.
Pallante et al. MicroRNA deregulation in human thyroid papillary carcinomas. Endocr Relat Cancer. 2006;13(2):497-508.
Panicker et al. A common variation in deiodinase 1 gene DIO1 is associated with the relative levels of free thyroxine and triiodothyronine. J Clin Endocrinol Metab. 2008;93(8):3075-81.
Pankratz et al. Usual interstitial pneumonia can be detected in transbronchial biopsies using machine learning. Annals of the American Thoracic Society 14.11 (2017): 1646-1654.
Pavelic, et al. Molecular genetic alterations of FHIT and p53 genes in benign and malignant thyroid gland lesions. Mutat Res. Jul. 25, 2006;599(1-2):45-57. Epub May 15, 2006.
Pavey, et al. Microarray expression profiling in melanoma reveals a BRAF mutation signature. Oncogene. May 20, 2004;23(23):4060-7.
Penland, et al. RNA expression analysis of formalin-fixed paraffin-embedded tumors. Lab Invest. Apr. 2007;87(4):383-91.
Phenekos et al. Th1 and Th2 serum cytokine profiles characterize patients with Hashimoto's thyroiditis (Th1) and Graves' disease (Th2). Neuroimmunomodulation. 2004;11(4):209-13.
Pinto et al. mRNA expression of tachykinins and tachykinin receptors in different human tissues. EurJ Pharmacol. 2004;494(2-3):233-9.

(56) References Cited

OTHER PUBLICATIONS

Pita et al. Gene expression profiling associated with the progression to poorly differentiated thyroid carcinomas. Br J Cancer. 2009;101(10):1782-1791.
Prasad et al. Identification of genes differentially expressed in benign versus malignant thyroid tumors. Clinical Cancer Research 14.11 (2008): 3327-3337.
Qian, et al. Renal cell carcinoma metastatic to Hurthle cell adenoma of thyroid. Ann Diagn Pathol. Oct. 2004;8(5):305-8.
Reyes, et al. Identification of kallikrein 7, kallikrein 10 and secreted frizzled-related protein 2 as candidate molecular markers for papillary thyroid carcinoma using microarray analysis. Proc Amer Assoc Cancer Res. 2005, vol. 46, Abstract #38.
Ringel et al. Expression of the sodium iodide symporter and thyroglobulin genes are reduced in papillary thyroid cancer. Mod Pathol. 2001;14(4):289-96.
Robinson et al. A dynamic programming approach for the alignment of signal peaks in multiple gas chromatography-mass spectrometry experiments. BMC bioinformatics 8.1 (2007): 419.
Rodrigues-Serpa, et al. Loss of heterozygosity in follicular and papillary thyroid carcinomas. Cancer Genet Cytogenet. Feb. 2003;141(1):26-31.
Roque, et al. Chromosome imbalances in thyroid follicular neoplasms: a comparison between follicular adenomas and carcinomas. Genes Chromosomes Cancer. Mar. 2003;36(3):292-302.
Ros et al. Thyroid-specific Gene Expression in the Multi-Step Process of Thyroid Carcinogenesis, Biochimie, Masson, Paris, FR, vol. 81, No. 4, Apr. 1, 1999, pp. 389-396.
Rosai et al. Pitfalls in the diagnosis of thyroid neoplasms. Pathol Res Pract. 1987;182(2):169-79.
Rosen et al. A six-gene model for differentiating benign from malignant thyroid tumors on the basis of gene expression. Surgery. 2005;138(6):1050-6; discussion 1056-7.
Roura-Mir et al. Single-cell analysis of intrathyroidal lymphocytes shows differential cytokine expression in Hashimoto's and Graves' disease. Eur J Immunol. 1997;27(12):3290-302.
Rowe et al. Utility of BRAF V600E Mutation Detection in Cytologically Indeterminate Thyroid Nodules. CytoJoural 3(10):1-10 (Apr. 2006).
Saeys, et al. A review of feature selection techniques in bioinformatics. Bioinformatics. Oct. 1, 2007;23(19):2507-17. Epub Aug. 24, 2007.
Saiz et al. Immunohistochemical expression of cyclin D1, E2F-1, and Ki-67 in benign and malignant thyroid lesions. J Pathol. 2002;198(2):157-62.
Salvatore et al. A cell proliferation and chromosomal instability signature in anaplastic thyroid carcinoma. Cancer Res. 2007;67(21):10148-58.
Santarpia et al. Phosphatidylinositol 3-kinase/akt and ras/raf-mitogen-activated protein kinase pathway mutations in anaplastic thyroid cancer. J Clin Endocrinol Metab. 2008;93(1):278-84.
Sapio, et al., Detection of RETIPTC, TRK and BRAF mutations in preoperative diagnosis of thyroid nodules with indeterminate cytological findings, C]Jnica1 Endocrjnology, 2007, 66: 678-683.
Satake et al. Overview of the primary structure, tissue-distribution, and functions of tachykinins and their receptors. Curr Drug Targets. 2006;7(8):963-74.
Savagner et al. Defective mitochondrial ATP synthesis in oxyphilic thyroid tumors. J Clin Endocrinol Metab. 2001;86(10):4920-5.
Savagner et al. PGC-1-related coactivator and targets are upregulated in thyroid oncocytoma. Biochem Biophys Res Commun. 2003;310(3):779-84.
Schiff, et al. Epidermal growth factor receptor (EGFR) is overexpressed in anaplastic thyroid cancer, and the EGFR inhibitor gefitinib inhibits the growth of anaplastic thyroid cancer. Clin Cancer Res. Dec. 15, 2004;10(24):8594-602.
Schroeder, et al. The RIN: an RNA integrity number for assigning integrity values to RNA measurements. BMC Mol Biol. Jan. 31, 2006;7:3.
Sheu et al. The C allele of the GNB3 C825T polymorphism of the G protein beta3-subunit is associated with an increased risk for the development of oncocytic thyroid tumours. J Pathol. 2007;211(1):60-6.
Shi, et al. Combined analysis of gene expression, DNA copy number, and mutation profiling data to display biological process anomalies in individual breast cancers. Breast Cancer Res Treat. Apr. 2014;144(3):561-8. Epub Mar. 12, 2014.
Shirasawa, S. Susceptibility genes for the development of autoimmune thyroid disease. Nippon Rinsho. Dec. 2006;64(12):2208-14. (Abstract only).
Shvero et al. Immunohistochemical profile and treatment of uncommon types of thyroid carcinomas. Oncol Rep. 2003;10(6):2075-8.
Singh et al. Screening for genetic aberrations in papillary thyroid cancer by using comparative genomic hybridization. Surgery. 2000;128(6):888-93;discussion 893-4.
Siragusa et al. MUC1 oncoprotein promotes refractoriness to chemotherapy in thyroid cancer cells. Cancer Res. 2007;67(11):5522-30.
Smith et al. Methylation status of genes in papillary thyroid carcinoma. Arch Otolaryngol Head Neck Surg. 2007;133(10):1006-11.
Smyth. Limma: Linear Models for Microarray Data. In: Bioinformatics and Computational Biology Solutions using R and Bioconductor, R. Gentleman, V. Carey, S. Dudoit, R. Irizarry, W. Huber (eds.), Springer, New York. 2005; pp. 397-420.
Smyth. Linear models and empirical bayes methods for assessing differential expression in microarray experiments. Stat Appl Genet Mol Biol. 2004;3:Article3. Epub Feb. 12, 2004.
Spargo, et al. Detection of M. tuberculosis DNA using thermophilic strand displacement amplification. Mol Cell Probes. Aug. 1996;10(4):247-56.
Stanta et al. The biochemical and immunohistochemical profile of thyroid neoplasia. Pathol Annu. 1988;23 Pt 1: 129-57.
Subramaniam et al. Clonal characterization of sporadic cribriform-morular variant of papillary thyroid carcinoma by laser microdissection-based APC mutation analysis. Am J Clin Pathol. 2007;128(6):994-1001.
Supplementary European search report and opinion dated Oct. 12, 2016 for EP Application No. 14770813.
Symmans, et al. Total RNA Yield and Microarray Gene Expression Profiles from Fine-Needle Aspiration Biopsy and Core-Needle Biopsy Samples of Breast Carcinoma. 2003; Cancer 97(12): 2960-2971.
Takakura et al. Oncogenic role of miR-17-92 cluster in anaplastic thyroid cancer cells. Cancer Sci. 2008;99(6):1147-54.
Takano et al. Expression of oncofetal fibronectin messenger ribonucleic acid in fibroblasts in the thyroid: a possible cause of false positive results in molecular-based diagnosis of thyroid carcinomas. J Clin Endocrinol Metab. 2000;85(2):765-8.
Takano et al. Preoperative diagnosis of thyroid papillary and anaplastic carcinomas by real-time quantitative reverse transcription-polymerase chain reaction of oncofetal fibronectin messenger RNA. Cancer Res. 1999;59(18):4542-5.
Tamir et al. Expression and development of a functional plasmalemmal 5-hydroxytryptamine transporter by thyroid follicular cells. Endocrinology. 1996;137(10):4475-86.
Taniguchi et al. Differentiation of follicular thyroid adenoma from carcinoma by means of gene expression profiling with adapter-tagged competitive polymerase chain reaction. Oncology. 2005;69(5):428-35.
Terada. Brain metastasis from thyroid adenomatous nodules or an encapsulated thyroid follicular tumor without capsular and vascular invasion: a case report. Cases J. Jul. 17, 2009;2:7180. doi: 10.4076/1757-1626-2-7180.
Tetzlaff et al. Differential expression of miRNAs in papillary thyroid carcinoma compared to multinodular goiter using formalin fixed paraffin embedded tissues. Endocr Pathol. 2007;18(3):163-73.
Thompson et al. Primary smooth muscle tumors of the thyroid gland. Cancer. 1997;79(3):579-87.
Thornton et al. Estimating kinship in admixed populations. The American Journal of Human Genetics 91.1 (2012): 122-138.
Tian, et al. A combined oncogenic pathway signature of BRAF, KRAS and PI3KCA mutation improves colorectal cancer classifi-

(56) References Cited

OTHER PUBLICATIONS cation and cetuximab treatment prediction. Gut. Apr. 2013;62(4):540-9. doi: 10.1136/gutjnl-2012-302423. Epub Jul. 14, 2012.
Tian, et al. Effects of Gender on Gene Expression in the Blood of Ischemic Stroke Patients. Journal of Cerebral Blood Flow & Metabolism. J Cereb Blood Flow Metab. May 2012;32(5):780- 91. doi: 10.1038/jcbfm.2011.179. Epub Dec. 14, 2011.
Todaro et al. Autocrine production of interleukin-4 and interleukin-10 is required for survival and growth of thyroid cancer cells. Cancer Res. 2006;66(3):1491-9.
Trovisco et al. Molecular Genetics of Papillary Thyroid Carcinoma—Great Expectations . . . Arq Bras Endocrinol Metab, Jul. 1, 2007, pp. 643-653.
Tukey. Exploratory Data Analysis: Past, Present, and Future. Technical Report No. 302. Department of Statistics, Princeton University. 1971-1977. 1993.
Tzen, et al. Is atypical follicular adenoma of the thyroid a preinvasive malignancy? Hum Pathol. Jul. 2003;34(7):666-9.
Ueda, et al. Analysis of PAX8 Gene in Congenital Hypothyroidism Mass Screening Positive Subjects. Folia Endocrinologica Japonica. Mar. 30, 2007, vol. 82, No. 4, p. 859. (in Japanese with English translation).
Ullmannova, et al. The use of housekeeping genes (HKG) as an internal control for the detection of gene expression by quantitative real-time RT-PCR. Folia Biol (Praha). 2003;49(6):211-6.
Unger et al. Array CGH demonstrates characteristic aberration signatures in human papillary thyroid carcinomas governed by RET/PTC. Oncogene. 2008;27(33):4592-602.
U.S. Appl. No. 14/020,183 Notice of Allowance dated Apr. 3, 2018.
U.S. Appl. No. 14/851,864 Office Action dated Nov. 9, 2018.
Van Allen et al. Whole-exome sequencing and clinical interpretation of formalin-fixed, paraffin-embedded tumor samples to guide precision cancer medicine. Nature medicine 20.6 (2014): 682.
Van Der Laan, et al. A new algorithm for hybrid hierarchical clustering with visualization and the bootstrap. Journal of Statistical Planning and Inference. Dec. 2003. 117(2):275-303.
Vasko, et al. Gene expression and functional evidence of epithelial-to-mesenchymal transition in papillary thyroid carcinoma invasion. Proc Natl Acad Sci U S A. Feb. 20, 2007;104(8):2803-8. Epub Feb. 12, 2007.
Viale et al. Coexpression of cytokeratins and vimentin in normal and diseased thyroid glands. Lack of diagnostic utility of vimentin immunostaining. Am J Surg Pathol. 1989;13(12):1034-40.
Viney et al. Regulation of the cell-specific calcitonin/calcitonin gene-related peptide enhancer by USF and the Foxa2 forkhead protein. J Biol Chem. 2004;279(48):49948-55.
Visone et al. MicroRNAs (miR)-221 and miR-222, both overexpressed in human thyroid papillary carcinomas, regulate p27Kip1 protein levels and cell cycle. Endocr Relat Cancer. 2007;14(3):791-8.
Visone et al. Specific microRNAs are downregulated in human thyroid anaplastic carcinomas. Oncogene. 2007;26(54):7590-5.
Wang et al. Association of the T1799A BRAF mutation with tumor extrathyroidal invasion, higher peripheral platelet counts, and over-expression of platelet-derived growth factor-B in papillary thyroid cancer. Endocr Relat Cancer. 2008;15(1):183-90.
Wang et al. RNA-seq: a revolutionary tool for transcriptomics. Nature Reviews Genetics 10:57-63 (2009).
Wang et al. The expression analysis of ICOS-L on activated T cells and immature dendritic cells as well as malignant B cells and Grave's-disease-derived thyroid tissues by two novel mAbs against human ICOS-L. Tissue Antigens. 2007;69(1):62-72.
Watanabe et al. Decrease of intrathyroidal CD161+Valpha24+ Vbeta11+ NKT cells in Graves' disease. Endocr J. 2008; 55(1):199-203.
Wattel, et al. Gene expression in thyroid autonomous adenomas provides insight into their physiopathology. Oncogene. Oct. 20, 2005;24(46):6902-16.
Weber et al. A limited set of human MicroRNA is deregulated in follicular thyroid carcinoma. J Clin Endocrinol Metab. 2006;91(9):3584-91. Epub Jul. 5, 2006.
Weber et al. Genetic classification of benign and malignant thyroid follicular neoplasia based on a three-gene combination. J Clin Endocrinol Metab. 2005;90(5):2512-21.
Weber et al. Silencing of the maternally imprinted tumor suppressor Arhi contributes to follicular thyroid carcinogenesis. J Clin Endocrinol Metab. 2005;90(2):1149-55.
Wessagowit, et al. Normal and abnormal mechanisms of gene splicing and relevance to inherited skin diseases. J Dermatol Sci. Nov. 2005;40(2):73-84. Epub Jul. 27, 2005.
Wessels, et al., A protocol for building and evaluating predictors of disease state based on microarray data, Bioinformatics, 2005, 21:3755-3762).
Wharam, et al. Specific detection of DNA and RNA targets using a novel isothermal nucleic acid amplification assay based on the formation of a three-way junction structure. Nucleic Acids Res. Jun. 1, 2001;29(11):E54-4.
Whitehead, et al. Variation in tissue-specific gene expression among natural populations. Genome Biol. 2005;6(2):R13. Epub Jan. 26, 2005.
Wiseman et al. Molecular phenotyping of thyroid tumors identifies a Marker panel for differentiated thyroid cancer diagnosis. Ann Surg Oncol. 2008;15(10):2811-26.
Wreesmann et al. Genome-wide profiling of papillary thyroid cancer identifies MUC1 as an independent prognostic marker. Cancer Res. 2004;64(11):3780-9.
Wu, et al. A comparative study of 200 fine needle aspiration biopsies performed by clinicians and cytopathologists. Laryngoscope. Jul. 2006;116(7):1212-5.
Wu et al. Uncommon mutation, but common amplifications, of the PIK3CA gene in thyroid tumors. J Clin Endocrinol Metab. 2005;90(8):4688-93.
Xu et al. Differential expression of galectin-1 and galectin-3 in thyroid tumors. Potential diagnostic implications. Am J Pathol. 1995;147(3):815-22.
Yan, et al. Isothermal amplified detection of DNA and RNA. Mol Biosyst. May 2014;10(5):970-1003.
Yang et al. C-myc, N-myc, N-ras, and c-erb-B: lack of amplification or rearrangement in human medullary thyroid carcinoma and a derivative cell line. Anticancer Res. 1990;10(1):189-92.
Yano et al. Gene expression profiling identifies platelet-derived growth factor as a diagnostic molecular marker for papillary thyroid carcinoma. Clin Cancer Res. 2004;10(6):2035-43.
Yatabe et al. Epidermal growth factor receptor gene amplification is acquired in association with tumor progression of EGFR-mutated lung cancer. Cancer Res. 2008;68(7):2106-11.
Yeh et al. Differentiated thyroid cancer cell invasion is regulated through epidermal growth factor receptor-dependent activation of matrix metalloproteinase (MMP)-2/gelatinase A. Endocr Relat Cancer. 2006;13(4):1173-83.
Yeh et al. Somatic mitochondrial DNA (mtDNA) mutations in papillary thyroid carcinomas and differential mtDNA sequence variants in cases with thyroid tumours. Oncogene. 2000;19(16):2060-6.
Yoon et al. Identification of a novel noncoding RNA gene, NAMA, that is downregulated in papillary thyroid carcinoma with BRAF mutation and associated with growth arrest. Int J Cancer. 2007;121(4):767-75.
Yousefi et al. A SNP panel for identification of DNA and RNA specimens. BMC genomics 19.1 (2018): 90.
Zabel et al. S-100 protein and neuron-specific enolase in parathyroid glands and C-cells of the thyroid. Histochemistry. 1987;86(4):389-92.
Zanna et al. Trop-1 are conserved growth stimulatory molecules that mark early stages of tumor progression. Cancer. 2007;110(2):452-64.
Zeng et al. The contributions of oestrogen receptor isoforms to the development of papillary and anaplastic thyroid carcinomas. J Pathol. 2008;214(4):425-33.
Zhang, et al. Association between single-nucleotide polymorphisms of BRAF and papillary thyroid carcinoma in a Chinese population. Thyroid. Jan. 2013;23(1):38-44. doi: 10.1089/thy.2012.0228.

(56) References Cited

OTHER PUBLICATIONS

Zhang, et al. CDC23 Regulates Cancer Cell Phenotype and is Overexpressed in Papillary Thyroid Cancer. Endocr Relat Cancer. Endocr Relat Cancer. 2011 Nov 28;18(6):731-42. doi: 10.1530/ERC-11-0181. Print 2011.

Zhang et al. Regulation of tumor necrosis factor-related apoptosis-inducing ligand-induced apoptosis by DJ-1 in thyroid cancer cells. Endocr Relat Cancer. 2008;15(2):535-44.

Zhou et al. RET proto-oncogene mutations are restricted to codons 634 and 918 in mainland Chinese families with MEN2A and MEN2B. Clin Endocrinol (Oxf). 2007;67(4):570-6.

Zhu et al. U1 snRNP-dependent function of TIAR in the regulation of alternative RNA processing of the human calcitonin/CGRP pre-mRNA. Mol Cell Biol. 2003;23(17):5959-71.

Adams, J.U., The Human Genome project set out to sequence all of the 3 billion nucleotides in the human genome. Exactly how was this daunting task done with such incredible speed and accuracy? DNA sequencing technologies. Nature Education, 2008; 1(1):193, pp. 1-6.

Co-pending U.S. Appl. No. 16/248,074, filed Jan. 15, 2019.

Co-pending U.S. Appl. No. 16/279,252, filed Feb. 19, 2019.

Co-pending U.S. Appl. No. 16/353,248, filed Mar. 14, 2019.

Delibasis, et al., "Computer-Aided Diagnosis of Thyroid Malignancy Using an Artificial Immune System Classification Algorithm," IEEE Transactions on Information Technology in Biomedicine, vol. 13, No. 5, pp. 680-686, Sep. 2009.

Frohman on Beyond Classic RACE (Rapid Amplification of eDNA Ends) PCR Methods and Applications vol. 4, pp. S40-S58 (Year: 1994).

GeneAnnot Search for Affymetrix HG-U 133A microarray pro besets for TIMP1, printed Dec. 2018.

GeneAnnot Search for Affymetrix HG-U 133A microarray probesets for SLCA4, printed Dec. 2018.

Nikiforov et al. Impact of Mutational Testing on the Diagnosis and Management of Patients with Cytologically Indeterminate Thyroid Nodules: A Prospective Analysis of 1056 FNA Samples Journal of Clinical Endocrinology and Metabolism vol. 96, pp. 3390-3397 (Year: 2011).

Office Action dated Nov. 20, 2018 for U.S. Appl. No. 13/589,022.

Oshlack et al. FRom RNA-seq reads to differential expression results Genome Biology vol. 11, article 220 (Year: 201 0).

PCT/US2018/043984 International Search Report and Written Opinion dated Jan. 21, 2019.

Office Action dated Dec. 12, 2018 for U.S. Appl. No. 14/086,716.

Office action dated Dec. 13, 2018 for U.S. Appl. No. 14/153,219.

Ramaswamy, et al. "Multiclass cancer diagnosis using tumor gene expression signatures" Proceedings of the National Academy of Sciences Dec. 2001, 98 (26) 15149-15154.

U.S. Appl. No. 15/185,960 Office Action dated Dec. 21, 2018.

U.S. Appl. No. 15/440,575 Office Action dated Apr. 9, 2019.

U.S. Appl. No. 15/661,496 Notice of Allowance dated Feb. 11, 2019.

U.S. Appl. No. 15/694,157 Office Action dated Mar. 7, 2019.

Xing et al. BRAF V600E and TERT Promoter Mutations Cooperatively Identify the Most Aggressive Papillary Thyroid Cancer With Highest Recurrence Journal of Clinical Oncology vol. 32, pp. 2718-2726 (Year: 2014).

U.S. Appl. No. 15/702,126 Office Action dated Apr. 19, 2019

* cited by examiner

COMPOSITIONS AND METHODS FOR CLASSIFYING THYROID NODULE DISEASE

CROSS-REFERENCE

This application is a continuation application of U.S. patent application Ser. No. 14/727,801, filed Jun. 1, 2015 and now issued as U.S. Pat. No. 9,714,452, which is a continuation application of U.S. patent application Ser. No. 13/254,571, filed Nov. 28, 2011, and now issued as U.S. Pat. No. 9,074 258, which is a National Stage Entry of International Application No. PCT/CA 2010/000266, filed Mar. 3, 2010, which claims the benefit of U.S. Provisional Patent Application No. 61/157,552 filed Mar. 4, 2009, each of which is entirely incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 1, 2011, is named 1004001U.txt and is 290,717 bytes in size.

FIELD OF THE INVENTION

This invention relates to the field of diagnostics and in particular to systems and methods for diagnosis of thyroid cancer.

BACKGROUND

Thyroid nodule disease is a common clinical problem, found in 4-7% of the living adult population in North America. The occurrence of thyroid nodules increases with age; autopsies reveal the presence of thyroid nodules in 50% of the population. It is estimated that, at 80 years old, 90% of the population will have at least one thyroid nodule. However, the vast majority of solitary thyroid nodules are benign in nature, and would require no further treatment if a correct diagnosis could be obtained without surgery.

A number of techniques can be used to diagnose thyroid conditions, including radioactive thyroid scans, ultrasound, thyroid hormone level and thyroglobulin measurements, and fine needle aspiration biopsy (FNAB). Thyroid scans do not effectively distinguish benign and malignant conditions, however, and are typically used in conjunction with other techniques. Similarly, ultrasound may provide information suggestive of either benign or malignant conditions, but cannot definitively diagnose thyroid status. Measurements of thyroid hormone level and thyroglobulin can be informative, but are nondiagnostic by themselves.

Thyroid FNAB is the only non-surgical method which can by itself differentiate malignant and benign nodules. More than 300,000 fine needle aspiration biopsies (FNAB) of the thyroid are performed annually in the US and evaluated using cytology. The primary purpose of FNAB is to distinguish thyroid nodules that require immediate surgical intervention (e.g., total thyroidectomy in the case of a diagnosis of malignant disease) from nodules that can be treated effectively with less aggressive clinical approaches.

In FNAB, samples of thyroid cells are obtained by inserting a needle into the thyroid and aspirating cells into a syringe. Usually, 2 to 4 aspirations are made from different sites in each nodule. The cells are mounted on a slide (for each aspiration, 2 to 4 slides are prepared), stained, and examined. The sample is then classified as nondiagnostic (indeterminate), benign, suspicious or malignant. Most samples are categorized as benign.

FNAB can be used to successfully diagnose papillary carcinoma, medullary carcinoma, anaplastic carcinoma, thyroid lymphoma and metastases to the thyroid from other sites. Papillary carcinoma accounts for ~60-70% and the follicular variant of papillary carcinoma accounts for ~6% of thyroid cancers. These well differentiated thyroid cancers are usually curable, but they must be found first.

Especially problematic are cases considered ‘suspicious’, ‘inadequate’ or ‘indeterminate’ by cytological diagnosis of FNAB samples. These patients are invariably triaged by invasive surgery, which has a significant morbidity. Overtreatment with total-thyroidectomy frequently occurs as a result; it is estimated that less than 25% of patients with such diagnoses in fact have cancer that warrants removal of the thyroid gland. Approximately 5-10% of samples are classified as nondiagnostic by FNAB. In those cases, FNAB can be repeated; however, only half of repeat biopsies yield a diagnostic result. For the remaining patients, further testing and surgery may be required. Due to the fear of cancer, invasive surgery is chosen, but in most cases is unnecessary. Approximately 10-20% of samples are classified as suspicious by FNAB. Of these, approximately 25% will ultimately prove to be malignant after surgery, typically exhibiting follicular or Hurthle cell cancers, which cannot be diagnosed by FNAB. Follicular carcinoma, which accounts for ~12-15% of all thyroid cancers and the less prevalent Hurthle cell carcinoma cannot be distinguished cytologically from benign follicular or Hurthle cell adenomas. Therefore, most patients with suspicious biopsies are typically subjected to surgery, when in fact ~75% of these patients do not have malignant disease.

A contributing factor to the difficulties with current FNAB cytology-based diagnoses is the variability between different pathologists and cytopathologists in diagnostic agreement between cytological analysis and final histological review, ranging from 40%-90%. The overall accuracy of diagnoses using only FNAB ranges from 60% to >90%, and is dependent on the expertise of the cytologist and whether or not ‘suspicious’ or ‘indeterminate’ diagnostic categories are included in the reported accuracy of the study. When factoring the cytology diagnostic categories of ‘suspicious’ or ‘indeterminate’, the literature shows that the overall specificity of FNAB cytology for diagnosis of malignant disease decreases dramatically to <60% with false-positive rates of ~40%. Patients with malignant thyroid disease are invariably treated by total removal of the tumor and all of the thyroid gland followed by radioactive iodine treatment, whereas benign thyroid disease can be treated less aggressively with a near-total thyroidectomy, partial thyroidectomy (e.g., ‘lobectomy’) or a watchful-waiting approach (e.g., observation without surgical intervention). As FNAB and cytology cannot reliably distinguish malignant from benign disease in cases with ‘suspicious’ cytological findings, such as occurs in the case of follicular and Hurthle cell lesions, these patients are typically all treated as if they were diagnosed with malignant disease (i.e., with aggressive surgery). Since only a small fraction of these patients in fact have malignant disease, over-treatment of thyroid nodule disease patients occurs frequently, with significant consequences for patients. As such, many unnecessary thyroidectomies are therefore performed in patients with what ultimately proves to be benign or non-neoplastic thyroid nodule disease when an FNAB sample is deemed as ‘suspicious’ or 'indeterminate.' These deficiencies negatively impact patient outcomes, long-term well-being and healthcare efficiencies.

Use of molecular analyses has the potential to increase the sensitivity, specificity and/or overall accuracy of thyroid diagnoses as compared to FNAB cytology alone. In the pre-operative setting, such a result would likely reduce the number of unnecessary surgeries for patients without malignant disease and avoid inadvertent undertreatment of highly curable thyroid cancers resulting from misdiagnoses. In addition, an accurate molecular based diagnosis as an adjunct assay to established pathological review diagnosis of thyroidectomy specimens in the post-operative setting could be beneficial by increasing the confidence of pathologists in establishing a definitive diagnosis for cancer that would likely influence the course of treatment and management of definitive malignant disease. However, prior attempts at using gene expression profiling to develop diagnostic gene expression signatures and identify mRNA biomarkers useful for the differential diagnosis of thyroid nodule disease have not yet yielded new clinical tools to improve the diagnosis of malignant from benign thyroid nodule disease from clinical specimens. Most of these efforts and those of protein immunohistochemistry studies focused on the protein-encoding genome. However, the transcriptome is inherently more complex than this, given that <2% of the genome encodes for protein and recent studies that have shown that more than 90% of the genome undergoes transcription yielding millions of non-coding RNA transcripts that serve regulatory roles over the protein-endcoding transcriptome. So, gene-level analysis may provide only a rough estimate of diagnosis as it cannot capture the full differences between the genomes of malignant and benign thyroid nodule disease (e.g., alternative gene splicing, non-coding and functional RNA expression). Recent efforts to validate a 3-gene signature for diagnosis of thyroid nodule disease FNAB with a QRT-PCR approach report a low diagnostic accuracy in a large validation study (see Sibru et al., citation #14). Other prior attempts using gene-biased microarrays showed similar performance characteristics with low diagnostic accuracy for gene-based signatures (see Jiang et al., US 2007/0037186 A1). For example, Jiang et al., (US 2007/0037186 A1) disclosed a 4-gene QRT-PCR panel with a sensitivity of 92% but a specificity of just 61%. As a result, diagnoses using these provide results little better than FNAB cytology. In addition, other prior attempts utilize samples which are generally not available in the clinical setting. In particular, in the majority of clinical settings fresh tissue is unavailable. Formalin fixation is an essential part of the routine processing of tissue samples because this fixative best preserves the architecture of the tissue and cellular morphology, allowing pathologists enough definition to ascertain a diagnosis. Fresh or frozen unfixed tissue is suboptimal for viewing key details that pathologists use to differentially diagnose disease (e.g., benign vs cancer). For example, US 2008/0145841 and WO2006/127537 describes a thyroid fine needle aspiration molecular assay using fresh frozen samples. WO 2006/127537 showed a best result of 92% specificity and 76% sensitivity (see Table 12, page 98) and VS 2008/0145841 showed an accuracy of 87.1% (sec para [0127]).

Another possible reason why previous efforts aimed to developing molecular based classification schemes for thyroid nodule disease have not led to routine clinical assays relates to the technical feasibility of administering a molecular test. Typically, thyroid nodule fine-needle aspirate biopsies provide only a small amount of cells and therefore only minute yields of extractable nucleic acids or proteins that may be insufficient for standard molecular assays. In addition, many FNABs are further processed to prepare cell blocks or cell pellets made by centrifuging a fine-needle aspirate, followed by fixation similar to an FFPE block. After surgical resection, standard pathology practices require detailed post-operative evaluation of thyroidectomy specimens; this is especially important to establish a definitive diagnosis of cancer in cases where the FNAB cytology results were only 'suspicious' or indeterminate for the presence of cancer. Both of these procedures involve formalin-fixation and paraffin embedding, as this procedure best preserves the morphology and definition of the cells (in comparison to fresh or frozen preparates) favored by pathologists for microscopic evaluation but problematic for many nucleic acid molecular assays due to fragmentation of nucleic acids by formalin-fixation and paraffin embedding. Therefore, small amounts of sample and the use of fixatives are two additional technical impediments that must be overcome in order to apply molecular analyses of nucleic acids in routine clinical settings.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide systems and methods for expression-based classification of thyroid nodule disease from patient specimens. In accordance with one aspect of the present invention, there is provided a system for expression-based classification of thyroid tissue as malignant or benign, said system comprising one or more polynucleotides, each of said polynucleotides capable of specifically hybridizing to a RNA transcript comprising the sequence as set forth in any one of SEQ ID NOs: 1 to 584 or the complement thereof.

In accordance with another aspect of the present invention, there is provided a nucleic acid array for expression-based classification of thyroid tissue as malignant or benign, said array comprising at least ten probes immobilized on a solid support, each of said probes being between about 15 and about 500 nucleotides in length, each of said probes being derived from a sequence corresponding to, or complementary to, a RNA transcript comprising the sequence as set forth in any one of SEQ ID NOs: 1 to 584, or a portion of said transcript.

In accordance with another aspect of the present invention, there is provided a method of classifying a thyroid nodule in a subject as malignant or benign, said method comprising: (a) determining the expression level of one or more transcripts in a test sample obtained from said subject to provide an expression pattern profile, each of said transcripts comprising a sequence as set forth in any one of SEQ ID NOs: 1 to 584, and (c) comparing said expression pattern profile with a reference expression pattern profile.

In accordance with another aspect of the present invention, there is provided a kit for characterizing the expression of one or more nucleic acid sequences depicted in SEQ ID NOs: 1-584 comprising one or more nucleic acids selected from:

(a) a nucleic acid depicted in any of SEQ ID NOs: 1-584;

(b) an RNA form of any of the nucleic acids depicted in SEQ ID NOs: 1-584;

(c) a peptide nucleic acid form of any of the nucleic acids depicted in SEQ ID NOs: 1-584;

(d) a nucleic acid comprising at least 20 consecutive bases of any of (a-c);

(e) a nucleic acid comprising at least 25 consecutive bases having at least 90% sequence identity to any of (a-c); or (f) a complement to any of (a-e); and optionally instructions for correlating the expression level of said one or more nucleic acid sequences with the disease state of thyroid tissue.

In accordance with another aspect of the present invention, there is provided an array of probe nucleic acids certified for use in classifying thyroid disease status, wherein said array comprises at least two different probe nucleic acids that specifically hybridize to corresponding different target nucleic acids depicted in any one of SEQ ID NOs: 1-584, an RNA form thereof, or a complement to either thereof.

In accordance with another aspect of the present invention, there is provided an array of probe nucleic acids certified for use in classifying thyroid disease status, wherein said array comprises at least two different probe nucleic acids that specifically hybridize to corresponding different target nucleic acids depicted in any one of SEQ ID NOs: 1, 2, 3, 4, 5, 6, 7, 8, 9, and 10, an RNA form thereof, or a complement to either thereof.

In accordance with another aspect of the present invention, there is provided an array of probe nucleic acids certified for use in classifying thyroid disease status, wherein said array comprises at least two different probe nucleic acids that specifically hybridize to corresponding different target nucleic acids depicted in any one of SEQ ID NOs: 1, 10, 11, 12, 13, 14, and 15, an RNA form thereof, or a complement to either thereof.

In accordance with another aspect of the present invention, there is provided a device for classifying a biological sample from a thyroid gland as malignant or benign, the device comprising means for measuring the expression level of one or more transcripts, each of said transcripts comprising a sequence as set forth in any one of SEQ ID NOs: 1 to 584; means for correlating the expression level with a classification of thyroid disease status; and means for outputting the thyroid disease status.

In accordance with another aspect of the present invention, there is provided a computer-readable medium comprising one or more digitally-encoded expression pattern profiles representative of the level of expression of one or more transcripts, each of said transcripts comprising a sequence as set forth in any one of SEQ ID NOs: 1 to 584, each of said one or more expression pattern profiles being associated with a value wherein each of said values is correlated with the presence of malignant or benign tissue in a thyroid gland sample.

In accordance with another aspect of the present invention, there is provided a system for expression-based classification of thyroid tissue as malignant or benign, said system comprising one or more polynucleotides, each of said polynucleotides capable of specifically hybridizing to a RNA transcript comprising the non-coding sequence as set forth in any one of SEQ ID NOs: 1-4, 6-15, 17-31, 33-43, 47, 49-55, 57-62, 64, 65, 67-71, 73-78, 80, 84, 85, 88, 90-95, 101, 102, 104, 105, 107, 108, 111-113, 116-118, 122-125, 128, 129, 131-133, 135-137, 139, 140-144, 148-150, 152-156, 158, 162-164, 166-171, 173, 175, 176, 177, 179, 185-187, 189, 191-195, 197, 201, 204, 208-217, 220, 221, 224-229, 231-233, 235-241, 245, 247, 250-254, 256-259, 261, 263-267, 269-273, 276, 279, 283-293, 299, 301, 303, 304-306, 308, 309, 312, 313, 315-323, 325, 327, 328, 329, 331-335, 337, 343, 345-353, 355, 358, 360-363, 365, 367, 370-376, 378, 381-384, 389-392, 396, 399-402, 404, 405, 410-414, 418, 420-424, 426-431, 434, 435, 437, 438, 440, 444-449, 451-456, 458, 459, 460, 462, 463-473, 475, 476, 478, 480, 481, 485-488, 490-498, 500-503, 505, 507, 509, 511, 512, 515, 516, 519, 520, 522, 523, 525, 526, 528-532, 534, 535, 538, 541, 542, 544, 547-549, 550-553, 558, 561, 562, 564, 566, 567, 569, 571-573, 575, 576, 579 and 581-584.

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
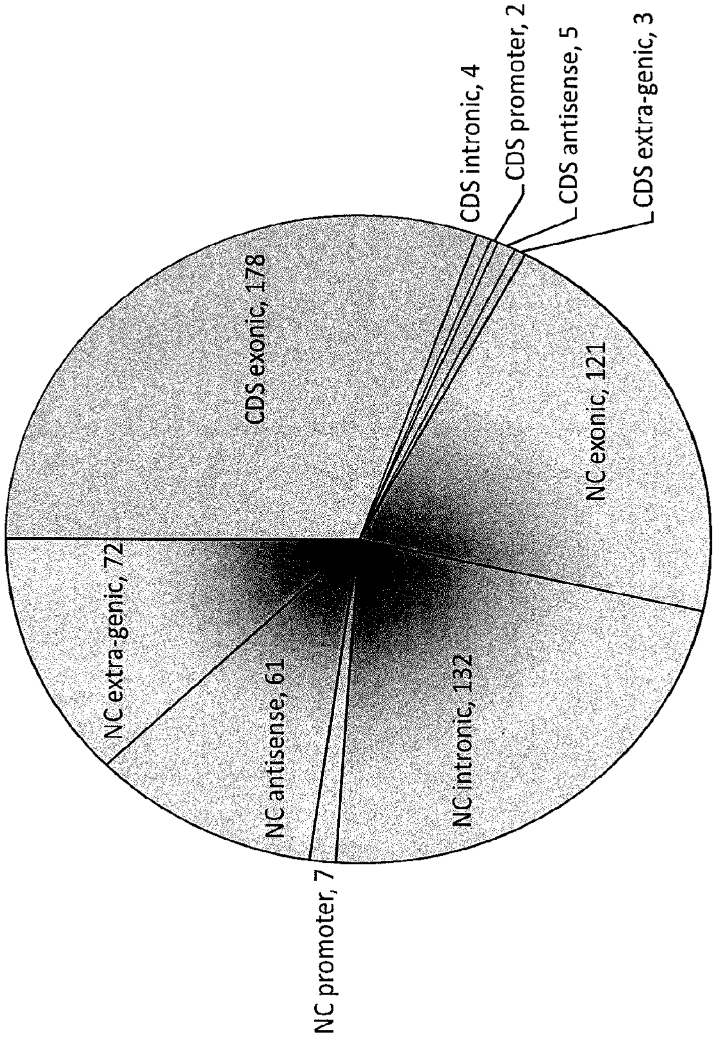
FIG. 1 is a pie chart that depicts the annotations of the 584 selected RNAs identified as differentially expressed in the training subset. Note that only 30% correspond to canonical exons of that overlap the translated coding sequences of genes while more than 67% correspond to non-canonical expressed transcripts (i.e., intronic, antisense, promoter and extra-genic RNA sequences) that are largely the non-coding sequences of the transcriptome. The labels in the pie chart indicate the position of the differentially expressed probes relative to the nearest annotated gene. CDS-RNA overlaps with the coding sequence translations of mRNAs in RefSeq or GenBank databases, NC-'non-coding' RNA does not overlap with the CDS.
Figure 2A:
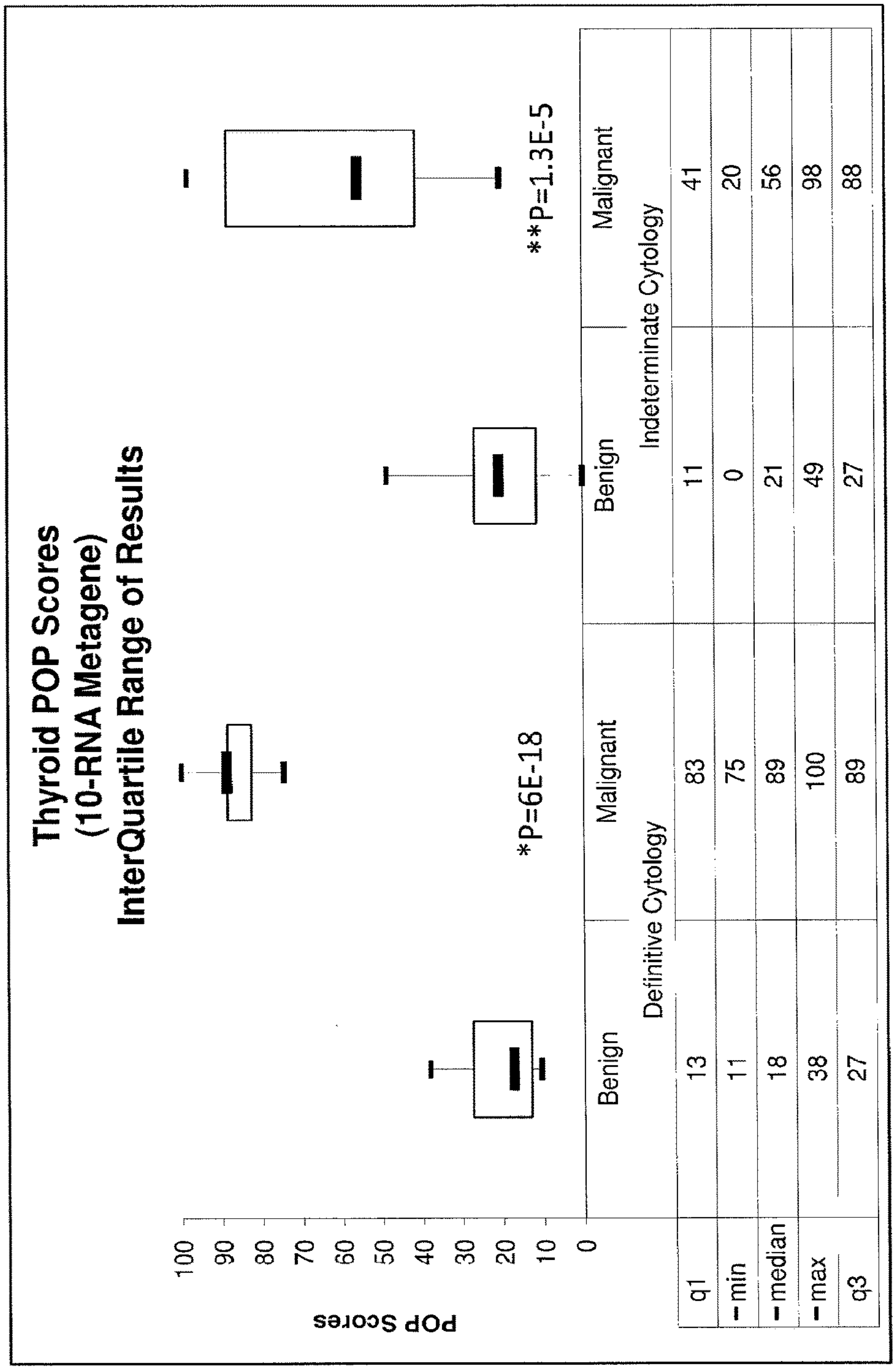
FIG. 2A depicts box plots showing interquartile range and distribution of 'POP' scores for thyroid nodule disease benign and malignant sample groups using a 10-RNA metagene to derive patient outcome predictor scores normalized on a data range of 0-100 points.
Figure 2B:
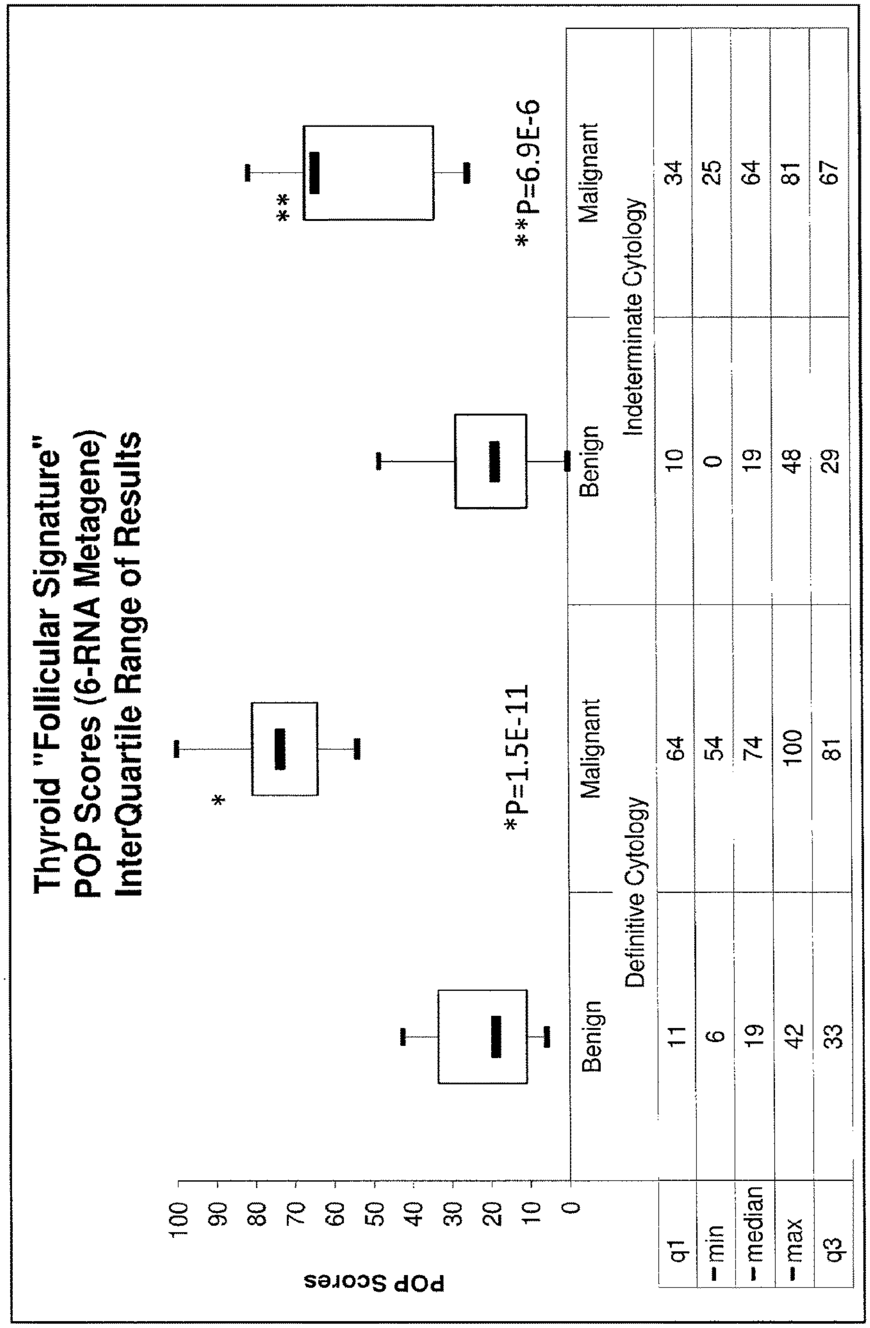
FIG. 2B depicts box plots showing interquartile range and distribution of 'POP' scores for thyroid nodule disease benign and malignant sample groups using a 6-RNA metagene to derive patient outcome predictor scores normalized on a data range of 0-100 points. Box plots for specimens definitively diagnosed by original FNAB cytology and those where FNAB cytology was indeterminate are depicted separately. Differences in POP scores between pathology review diagnosed benign and malignant thyroid nodule disease groups were highly significant as evaluated by t-tests for significance as indicated.

The present invention provides systems and methods for classifying thyroid tissue from a subject as malignant or benign, which allows for the diagnosis of thyroid cancer in the subject. The systems and methods are based on the identification of expressed transcripts that are differentially expressed in malignant thyroid nodule disease (i.e., cancer) relative to benign thyroid nodule disease conditions. These expressed transcripts can be considered as a library which can be used as a resource for the identification of sets of specific target sequences ("thyroid classification sets"), which may represent the entire library of expressed transcripts or a subset of the library and the detection of which is indicative of the status of the thyroid tissue (for example, malignant or benign). The invention further provides for probes capable of detecting these target sequences and primers that are capable of amplifying the target sequences.

In accordance with one embodiment of the invention, the target sequences comprised by the thyroid classification set are sequences based on or derived from the gene transcripts from the library, or a subset thereof. Such sequences are occasionally referred to herein as "probe selection regions" or "PSRs." In another embodiment of the invention, the target sequences comprised by the thyroid classification set are sequences based on the gene transcripts from the library, or a subset thereof, and include both coding and non-coding sequences.

The methods employ molecular analysis of the expression levels of one or more transcripts corresponding to SEQ ID NOs:1 to 584. Increased relative expression of one or more transcripts in Group I corresponding to the expression products SEQ ID NOs:1-6, 11-13, 16-248 and/or decreased relative expression of one or more transcripts in Group II corresponding to the expression products of SEQ ID NOs: 7-10, 14, 15, 249-584 can be correlated with increased likelihood of malignant thyroid nodule disease. Conversely, increased relative expression of one or more transcripts in Group II and/or decreased relative expression of one or more transcripts in Group 1 can be correlated with an increased likelihood of benign thyroid nodule disease. Subsets and combinations of these transcripts may be used as described herein. In one embodiment, the systems and methods provide for the molecular analysis of the expression levels of one or more of the target sequences as set forth in SEQ ID NOs: 1-584. Subsets and combinations of these target sequences or probes complementary thereto may be used as described herein.

In one embodiment of the invention, the subset includes non-canonical expressed transcripts.

In one embodiment of the invention, the subset includes a plurality of transcripts, each of the transcripts comprising a non-coding sequence as set forth in any one of SEQ ID NOs: 1-4, 6-15, 17-31, 33-43, 47, 49-55, 57-62, 64, 65, 67-71, 73-78, 80, 84, 85, 88, 90-95, 101, 102, 104, 105, 107, 108, 111-113, 116-118, 122-125, 128, 129, 131-133, 135-137, 139, 140-144, 148-150, 152-156, 158, 162-164, 166-171, 173, 175, 176, 177, 179, 185-187, 189, 191-195, 197, 201, 204, 208-217, 220, 221, 224-229, 231-233, 235-241, 245, 247, 250-254, 256-259, 261, 263-267, 269-273, 276, 279, 283-293, 299, 301, 303, 304-306, 308, 309, 312, 313, 315-323, 325, 327, 328, 329, 331-335, 337, 343, 345-353, 355, 358, 360-363, 365, 367, 370-376, 378, 381-384, 389-392, 396, 399-402, 404, 405, 410-414, 418, 420-424, 426-431, 434, 435, 437, 438, 440, 444-449, 451-456, 458, 459, 460, 462, 463-473, 475, 476, 478, 480, 481, 485-488, 490-498, 500-503, 505, 507, 509, 511, 512, 515, 516, 519, 520, 522, 523, 525, 526, 528-532, 534, 535, 538, 541, 542, 544, 547-549, 550-553, 558, 561, 562, 564, 566, 567, 569, 571-573, 575, 576, 579 and 581-584.

In one embodiment of the invention, the subset includes intronic sequences.

In one embodiment of the invention, the systems and methods provide for the molecular analysis of the expression levels of one or more of the target sequences as set forth in SEQ ID NOs 1 to 10.

In one embodiment of the invention, the systems and methods provide for the molecular analysis of the expression levels of one or more of the target sequences as set forth in SEQ ID NOs: 1, 11, 12, 13, 14 and 15.

Before the present invention is described in further detail, it is to be understood that this invention is not limited to the particular methodology, compositions, articles or machines described, as such methods, compositions, articles or machines can, of course, vary. It is also to be understood that the terminology used herein is for the purpose of describing particular embodiments only, and is not intended to limit the scope of the present invention.

Definitions

Unless defined otherwise or the context clearly dictates otherwise, all technical and scientific terms used herein have the same meaning as commonly understood by one of ordinary skill in the art to which this invention belongs. In describing the present invention, the following terms will be employed, and are intended to be defined as indicated below.

The term "polynucleotide" as used herein refers to a polymer of greater than one nucleotide in length of ribonucleic acid (RNA), deoxyribonucleic acid (DNA), hybrid RNA/DNA, modified RNA or DNA, or RNA or DNA mimetics, including peptide nucleic acids (PNAs). The polynucleotides may be single- or double-stranded. The term includes polynucleotides composed of naturally-occurring nucleobases, sugars and covalent internucleoside (backbone) linkages as well as polynucleotides having non-naturally-occurring portions which function similarly. Such modified or substituted polynucleotides are well-known in the art and for the purposes of the present invention, are referred to as "analogues."

"Complementary" or "substantially complementary" refers to the ability to hybridize or base pair between nucleotides or nucleic acids, such as, for instance, between a sensor peptide nucleic acid or polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide will hybridize under selective hybridization conditions to its complement. Typically, selective hybridization will occur when there is at least about 65% complementarity over a stretch of at least 14 to 25 bases, for example at least about 75%, or at least about 90% complementarity. See, M. Kanehisa Nucleic Acids Res. 12:203 (1984).

"Preferential binding" or "preferential hybridization" refers to the increased propensity of one polynucleotide to bind to its complement in a sample as compared to a noncomplementary polymer in the sample.

Hybridization conditions will typically include salt concentrations of less than about 1M, more usually less than about 500 mM, for example less than about 200 mM. In the case of hybridization between a peptide nucleic acid and a polynucleotide, the hybridization can be done in solutions containing little or no salt. Hybridization temperatures can be as low as 5° C., but are typically greater than 22° C., and more typically greater than about 30° C., for example in excess of about 37° C. Longer fragments may require higher hybridization temperatures for specific hybridization as is known in the art. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

“Multiplexing” herein refers to an assay or other analytical method in which multiple analytes can be assayed simultaneously.

A “target sequence” as used herein (also occasionally referred to as a “PSR” or “probe selection region”) refers to a region of the genome against which one or more probes can be designed. As used herein, a probe is any polynucleotide capable of selectively hybridizing to a target sequence or its complement, or to an RNA version of either. A probe may comprise ribonucleotides, deoxyribonucleotides, peptide nucleic acids, and combinations thereof. A probe may optionally comprise one or more labels. In some embodiments, a probe may be used to amplify one or both strands of a target sequence or an RNA form thereof, acting as a sole primer in an amplification reaction or as a member of a set of primers.

“Having” is an open ended phrase like “comprising” and “including,” and includes circumstances where additional elements are included and circumstances where they are not.

“Optional” or “optionally” means that the subsequently described event or circumstance may or may not occur, and that the description includes instances where the event or circumstance occurs and instances in which it does not.

The term “suspected of comprising thyroid cancer,” as used in reference to biological samples or purified fractions or components thereof or products derived therefrom, refers to any sample or product that is to analyzed for the expression of the target sequences described herein, and includes samples comprising normal thyroid tissue, as well as samples comprising thyroid tumors, whether benign or malignant. Such tissue may be obtained from the thyroid itself, from another location within a patient that is a suspected metastases, or from a known sample of malignant thyroid cancer or from a known thyroid cancer cell line. Samples known to be malignant can function as positive controls, while samples known to be noncancerous (or of non-thyroid origin) can function as negative controls, but are “suspected” of comprising thyroid cancer in that they are tested to determine whether the assay being performed produces false positives or other abnormal results, indicating a problem with a given assay.

As used herein, the term “about” refers to approximately a +/−10% variation from a given value. It is to be understood that such a variation is always included in any given value provided herein, whether or not it is specifically referred to.

Use of the singular forms “a,” “an,” and “the” include plural references unless the context clearly dictates otherwise. Thus, for example, reference to “a polynucleotide” includes a plurality of polynucleotides, reference to “a target” includes a plurality of such targets, reference to “a normalization method” includes a plurality of such methods, and the like.

Additionally, use of specific plural references, such as “two,” “three,” etc., read on larger numbers of the same subject, unless the context clearly dictates otherwise.

Terms such as “connected,” “attached,” “linked” and “conjugated” are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Thyroid Classification System

The system of the present invention is based on the identification of a library of gene transcripts that are differentially expressed in thyroid cancer relative to benign thyroid nodule disease and thus may be diagnostic for thyroid cancer. For example, relative over and/or under expression of one or more of the gene transcripts in a thyroid nodule sample compared to a reference sample or expression profile or signature there from may be indicative of a malignant condition. The reference sample can be, for example, from one or more benign thyroid nodules from one or more references subject(s). The reference expression profile or signature may optionally be normalized to one or more appropriate reference gene transcripts. Alternatively or in addition to, expression of one or more of the gene transcripts in a thyroid nodule sample may be compared to an expression profile or signature from one or more known thyroid cancer samples such that a substantially similar expression profile or signature may be used to validate a finding of cancer or may be compared to the expression profile or signature from normal thyroid tissue.

Expression profiles or signatures from diagnostic samples may be normalized to one or more house keeping gene transcripts such that normalized over and/or under expression of one or more of the gene transcripts in a thyroid nodule sample may be indicative of a malignant condition.

Thyroid Classification Library

The Thyroid Classification Library in accordance with the present invention comprises one or more gene transcripts whose relative and/or normalized expression is indicative of a thyroid malignancy or of benign thyroid nodule disease. Gene transcripts which show differential expression in benign and/or malignant thyroid tissue include transcripts comprising the sequences as set forth in SEQ If) NOs: 1 to 584. In one embodiment of the invention, the library comprises one or more of the gene transcripts, each of the transcripts comprising a sequence as set forth in any one of SEQ ID NOs: 1 to 584.

In one embodiment, the library comprises at least one transcript comprising a sequence as set forth in any one of SEQ ID NOs: 1 to 584. In one embodiment, the library comprises at least five transcripts, each of the at least five transcripts comprising a sequence as set forth in any one of SEQ ID NOs: 1 to 584. In another embodiment, the library comprises at least 10 transcripts, each of the at least 10 transcripts comprising a sequence as set forth in any one of SEQ ID NOs: 1 to 584. In a further embodiment, the library comprises at least 15 transcripts, each of the at least 15 transcripts comprising a sequence as set forth in any one of SEQ ID NOs: 1 to 584. In other embodiments, the library comprises at least 20, at least 25, at least 30, at least 35, at least 40, at least 45, at least 50, at least 55, at least 60 and at least 65 transcripts, each of the at least 20, at least 25, at least 30, at least 35, at least 40, at least 45, at least 50, at least 55, at least 60 and at least 65 transcripts comprising a sequence as set forth in any one of SEQ ID NOs: 1 to 584. In a further embodiment, the library comprises at least 584 transcripts, each of the at least 584 transcripts comprising a sequence as set forth in any one of SEQ ID NOs: 1 to 584.

In one embodiment, the library comprises a plurality of transcripts, each of the transcripts comprising a sequence as set forth in any one of SEQ ID NOs: 1 to 584, wherein the majority (e.g. 70%, 80%, 90%, 95% or 98%) of the target sequences are in non-coding regions.

In one embodiment, the library comprises a plurality of transcripts, each of the transcripts comprising a sequence as set forth in any one of SEQ ID NOs: 1-4, 6-15, 17-31, 33-43, 47, 49-55, 57-62, 64, 65, 67-71, 73-78, 80, 84, 85, 88, 90-95, 101, 102, 104, 105, 107, 108, 111-113, 116-118, 122-125, 128, 129, 131-133, 135-137, 139, 140-144, 148-150, 152-156, 158, 162-164, 166-171, 173, 175, 176, 177, 179, 185-187, 189, 191-195, 197, 201, 204, 208-217, 220, 221, 224-229, 231-233, 235-241, 245, 247, 250-254, 256-259, 261, 263-267, 269-273, 276, 279, 283-293, 299, 301, 303, 304-306, 308, 309, 312, 313, 315-323, 325, 327, 328, 329, 331-335, 337, 343, 345-353, 355, 358, 360-363, 365, 367, 370-376, 378, 381-384, 389-392, 396, 399-402, 404, 405, 410-414, 418, 420-424, 426-431, 434, 435, 437, 438, 440, 444-449, 451-456, 458, 459, 460, 462, 463-473, 475, 476, 478, 480, 481, 485-488, 490-498, 500-503, 505, 507, 509, 511, 512, 515, 516, 519, 520, 522, 523, 525, 526, 528-532, 534, 535, 538, 541, 542, 544, 547-549, 550-553, 558, 561, 562, 564, 566, 567, 569, 571-573, 575, 576, 579 and 581-584.

The invention also contemplates that alternative libraries may be designed that include in addition to transcripts comprising a sequence as set forth in any one of SEQ ID NOs: 1 to 584, additional gene transcripts that are identified as having differential expression in benign and/or malignant thyroid tissue (for example, see Table 2). As is known in the art, the publication and sequence databases can be mined using a variety of search strategies to identify appropriate candidates for inclusion in the library. For example, currently available scientific and medical publication databases such as Medline, Current Contents, OMIM (online Mendelian inheritance in man), various Biological and Chemical Abstracts, Journal indexes, and the like can be searched using term or key-word searches, or by author, title, or other relevant search parameters. Many such databases are publicly available, and strategies and procedures for identifying publications and their contents, for example, genes, other nucleotide sequences, descriptions, indications, expression pattern, etc, are well known to those skilled in the art. Numerous databases are available through the internet for free or by subscription, see, for example, the National Center Biotechnology Information (NCBI), Infotrieve, Thomson ISI, and Science Magazine (published by the AAAS) websites. Additional or alternative publication or citation databases are also available that provide identical or similar types of information, any of which can be employed in the context of the invention. These databases can be searched for publications describing altered gene expression between malignant thyroid nodule disease and benign thyroid nodule disease. Additional potential candidate genes may be identified by searching the above described databases for differentially expressed proteins and by identifying the nucleotide sequence encoding the differentially expressed proteins.

Thyroid Classification Sets

A Thyroid Classification Set comprises one or more target sequences identified within the gene transcripts in the thyroid classification library, or a subset of these gene transcripts. The target sequences may be within the coding and/or non-coding regions of the gene transcripts. The set can comprise one or a plurality of target sequences from each gene transcript in the library, or subset thereof. The relative and/or normalized level of these target sequences in a sample is indicative of the level of expression of the particular gene transcript and thus of a thyroid malignancy or of benign thyroid nodule disease. For example, the relative and/or normalized expression level of one or more of the target sequences may be indicative of a thyroid malignancy while the relative and/or normalized expression level of one or more other target sequences may be indicative of benign thyroid nodule disease.

Accordingly, one embodiment of the present invention provides for a library or catalog of candidate target sequences derived from the transcripts (both coding and non-coding regions) of at least one gene suitable for classifying thyroid nodules as being malignant or benign. In a further embodiment, the library or catalog of candidate target sequences comprise target sequences as set forth in SEQ ID NOs 1 to 584. The library or catalog in affect provides a resource list of transcripts from which target sequences appropriate for inclusion in a thyroid classification set can be derived. In one embodiment, an individual thyroid classification set may comprise target sequences derived from the transcripts of one or more genes exhibiting a positive correlation with thyroid cancer. In one embodiment, an individual thyroid classification set may comprise target sequences derived from the transcripts of one or more genes exhibiting a negative correlation with thyroid cancer. In one embodiment, an individual Thyroid Classification Set may comprise target sequences derived from the transcripts of from two or more genes, wherein at least one gene has a transcript that exhibits a positive correlation with thyroid cancer and at least one gene has a transcript that exhibits a negative correlation.

In one embodiment, the Thyroid Classification Set comprises target sequences derived from the transcripts of at least one gene. In one embodiment, the Thyroid Classification set comprises target sequences derived from the transcripts of at least 5 genes. In another embodiment, the Thyroid Classification set comprises target sequences derived from the transcripts of at least 10 genes. In a further embodiment, the Thyroid Classification set comprises target sequences derived from the transcripts of at least 15 genes. In other embodiments, the Thyroid Classification set comprises target sequences derived from the transcripts of at least 20, at least 25, at least 30, at least 35, at least 40, at least 45, at least 50, at least 55, at least 60 and at least 65 genes.

Following the identification of candidate gene transcripts, appropriate target sequences can be identified by screening for target sequences that have been annotated to be associated with each specific gene locus from a number of annotation sources including GenBank, RefSeq, Ensembl, dbEST, GENSCAN, TWINSCAN, Exoniphy, Vega, microRNAs registry and others (see Affymetrix Exon Array design note).

As part of the target sequence selection process, target sequences can be further evaluated for potential cross-hybridization against other putative transcribed sequences in the design (but not the entire genome) to identify only those target sequences that are predicted to uniquely hybridize to a single target.

The set of target sequences that are predicted to uniquely hybridize to a single target can be further filtered using a variety of criteria including, for example, sequence length, for their mean expression levels across a wide selection of human tissues, as being representative of transcripts expressed either as novel alternative (i.e., non-consensus) exons, alternative retained introns, novel exons 5' or 3' of the gene's transcriptional start site or representing transcripts expressed in a manner antisense to the gene, amongst others.

In one embodiment, the Thyroid Classification Set comprises target sequences derived from the sequences as set forth in SEQ ID NOs: 1, 2, 3, 4, 5, 6, 7, 8, 9, and 10.

In one embodiment, the Thyroid Classification Set comprises target sequences derived from the sequences as set forth in SEQ ID NOs: 1, 11, 12, 13, 14, and 15.

In one embodiment, the potential set of target sequences can be filtered for their expression levels using the multi-tissue expression data made publicly available by Affymetrix such that probes with, for example, expression across numerous tissues or no expression in thyroid tissue can be excluded.

In one embodiment, the thyroid classification set can be specifically designed to be indicative of malignant thyroid cancer in general or alternatively be indicative of one or more individual types of thyroid cancer.

Validation of Target Sequences

Following in silico selection of target sequences, each target sequence suitable for use in the thyroid classification set may be validated to confirm differential relative or normalized expression in thyroid cancer or benign thyroid nodule disease. Validation methods are known in the art and include hybridization techniques such as microarray analysis or Northern blotting using appropriate controls, and may include one or more additional steps, such as reverse transcription, transcription, PCR, RT-PCR and the like. The validation of the target sequences using these methods is well within the abilities of a worker skilled in the art.

Minimal Expression Signature

In one embodiment, individual thyroid classification sets provide for at least a determination of a minimal expression signature, capable of distinguishing malignant from benign thyroid nodule disease. Means for determining the appropriate number of target sequences necessary to obtain a minimal expression signature are known in the art and include the Nearest Shrunken Centroids (NSC) method.

In this method (see US 20070031873), a standardized centroid is computed for each class. This is the average gene expression for each gene in each class divided by the within-class standard deviation for that gene. Nearest centroid classification takes the gene expression profile of a new sample, and compares it to each of these class centroids. The class whose centroid that it is closest to, in squared distance, is the predicted class for that new sample. Nearest shrunken centroid classification "shrinks" each of the class centroids toward the overall centroid for all classes by an amount called the threshold. This shrinkage consists of moving the centroid towards zero by threshold, setting it equal to zero if it hits zero. For example if threshold was 2.0, a centroid of 3.2 would be shrunk to 1.2, a centroid of −3.4 would be shrunk to −1.4, and a centroid of 1.2 would be shrunk to zero. After shrinking the centroids, the new sample is classified by the usual nearest centroid rule, but using the shrunken class centroids. This shrinkage can make the classifier more accurate by reducing the effect of noisy genes and provides an automatic gene selection. In particular, if a gene is shrunk to zero for all classes, then it is eliminated from the prediction rule. Alternatively, it may be set to zero for all classes except one, and it can be learned that the high or low expression for that gene characterizes that class. The user decides on the value to use for threshold. Typically one examines a number of different choices. To guide in this choice, PAM does K-fold cross-validation for a range of threshold values. The samples are divided up at random into K roughly equally sized parts. For each part in turn, the classifier is built on the other K−1 parts then tested on the remaining part. This is done for a range of threshold values, and the cross-validated misclassification error rate is reported for each threshold value. Typically, the user would choose the threshold value giving the minimum cross-validated misclassification error rate.

Alternatively, minimal expression signatures can be established through the use of optimization algorithms such as the mean variance algorithm widely used in establishing stock portfolios. This method is described in detail in US patent publication number 20030194734. Essentially, the method calls for the establishment of a set of inputs (stocks in financial applications, expression as measured by intensity here) that will optimize the return (e.g., signal that is generated) one receives for using it while minimizing the variability of the return. In other words, the method calls for the establishment of a set of inputs (e.g., expression as measured by intensity) that will optimize the signal while minimizing variability. Many commercial software programs are available to conduct such operations. "Wagner Associates Mean-Variance Optimization Application," referred to as "Wagner Software" throughout this specification, is preferred. This software uses functions from the "Wagner Associates Mean-Variance Optimization Library" to determine an efficient frontier and optimal portfolios in the Markowitz sense is preferred. Use of this type of software requires that microarray data be transformed so that it can be treated as an input in the way stock return and risk measurements are used when the software is used for its intended financial analysis purposes.

The process of selecting a minimal expression signature can also include the application of heuristic rules. Preferably, such rules are formulated based on biology and an understanding of the technology used to produce clinical results. More preferably, they are applied to output from the optimization method. For example, the mean variance method of portfolio selection can be applied to microarray data for a number of genes differentially expressed in subjects with cancer. Output from the method would be an optimized set of genes that could include some genes that are expressed in peripheral blood as well as in diseased tissue.

Other heuristic rules can be applied that are not necessarily related to the biology in question. For example, one can apply a rule that only a prescribed percentage of the portfolio can be represented by a particular gene or group of genes. Commercially available software such as the Wagner Software readily accommodates these types of heuristics. This can be useful, for example, when factors other than accuracy and precision (e.g., anticipated licensing fees) have an impact on the desirability of including one or more genes.

In one embodiment, the thyroid classification set for obtaining a minimal expression signature comprises at least one, two, three, four, five, six, eight, 10, 15, 20, 25 or more of target sequences shown to have a positive correlation with malignant thyroid disease, for example those depicted in SEQ ID NOs: 1-6, 11-13, and 16-248 or a subset thereof. In another embodiment, the thyroid classification set for obtaining a minimal expression signature comprises at least one, two, three, four, five, six, eight, 10, 15, 20, 25 or more of those target sequences shown to have a positive correlation with benign thyroid disease, for example those depicted in of SEQ ID NOs: 7-10, 14, 15, and 249-584, or a subset therof. In yet another embodiment, the thyroid classification set for obtaining a minimal expression signature comprises at least one, two, three, four, five, six, eight, 10, 15, 20, 25 or more of target sequences shown to have a positive or negative correlation with malignant thyroid disease, for example those depicted in SEQ ID NOs:1-584 or a subset thereof.

In some embodiments, the thyroid classification set comprises target sequences for detecting expression products of SEQ ID NOs:1-584. In some embodiments, the thyroid classification set comprises probes for detecting expression levels of sequences exhibiting positive and negative correlation with a disease status of interest are employed. For example, a combination useful for identifying a sample as exhibiting malignant or benign disease comprises at least one, two, three, four, five, six, eight, 10, 15, 20, 25 or more of those target sequences shown to have a positive correlation with malignant thyroid disease, for example those depicted in SEQ ID NOs:1-6, 11-13, and 16-248 or a subset thereof; and at least one, two, three, four, five, six, eight, 10, 15, 20. 25 or more of those target sequences shown to have a positive correlation with benign thyroid disease, for example those depicted in of SEQ ID NOs: 7-10, 14, 15, and 249-584, or a subset therof.

Exemplary subsets and combinations of interest also include at least one, two, three, four, five, six, 10, 15, 18, 20, 23, 25, 27, 30, 35, 40, 45, 50, 55, 60, 70, 80, 90, 100, 125, 150, 175, 200, 225, 250, 275, 300, 350, 400, 450, or 500 of the 584 of the target sequences set forth in SEQ ID NOs: 1 to 584; at least one, two, three, four, five, six, or ten of the target sequences set forth in SEQ ID NOs: 1, 2, 3, 4, 5, 6, 7, 8, 9, and 10, or a combination comprising any or all thereof; at least one, two, three, four, five or six of the target sequences set forth in SEQ ID NOs: 1, 11, 12, 13, 14, and 15, or a combination comprising any or all thereof.

Of particular interest are those combinations utilizing at least one sequence exhibiting positive correlation with the trait of interest, as well as those combinations utilizing at least one sequence exhibiting negative correlation with the trait of interest. Also of interest are those combinations utilizing at least two, at least three, at least four, at least five or at least six of those sequences exhibiting such a positive correlation, in combination with at least two, at least three, at least four, at least five, or at least six of those sequences exhibiting such a negative correlation.

It is to be recognized that those sequences shown as having a positive correlation with malignant disease conversely also possess a negative correlation with benign disease. Correspondingly, those sequences shown as having a positive correlation with benign disease also possess a negative correlation with malignant disease.

The thyroid classification set can optionally include one or more target sequences specifically derived from the transcripts of one or more housekeeping genes and/or one or more internal control target sequences and/or one or more negative control target sequences. In one embodiment, these target sequences can, for example, be used to normalize expression data. Housekeeping genes from which target sequences for inclusion in a Thyroid Classification Set can be derived from are known in the art and include those genes in which are expressed at a constant level in normal, benign and malignant thyroid tissue.

The target sequences described herein may be used alone or in combination with each other or with other known or later identified disease markers.

Thyroid Classification Probes/Primers

The system of the present invention provides for combinations of polynucleotide probes that are capable of detecting the target sequences of the Thyroid Classification Sets. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a PSR in the thyroid classification set. Computer programs can also be employed to select probe sequences that will not cross hybridize or will not hybridize non-specifically.

One skilled in the art will understand that the nucleotide sequence of the polynucleotide probe need not be identical to its target sequence in order to specifically hybridise thereto. The polynucleotide probes of the present invention, therefore, comprise a nucleotide sequence that is at least about 75% identical to a region of the target gene or mRNA. In another embodiment, the nucleotide sequence of the polynucleotide probe is at least about 90% identical a region of the target gene or mRNA. In a further embodiment, the nucleotide sequence of the polynucleotide probe is at least about 95% identical to a region of the target gene or mRNA. Methods of determining sequence identity are known in the art and can be determined, for example, by using the BLASTN program of the University of Wisconsin Computer Group (GCG) software or provided on the NCBI website. The nucleotide sequence of the polynucleotide probes of the present invention may exhibit variability by differing (e.g. by nucleotide substitution, including transition or transversion) at one, two, three, four or more nucleotides from the sequence of the target gene.

Other criteria known in the art may be employed in the design of the polynucleotide probes of the present invention. For example, the probes can be designed to have <50% G content and/or between about 25% and about 70% G+C content. Strategies to optimize probe hybridization to the target nucleic acid sequence can also be included in the process of probe selection. Hybridization under particular pH, salt, and temperature conditions can be optimized by taking into account melting temperatures and by using empirical rules that correlate with desired hybridization behaviours. Computer models may be used for predicting the intensity and concentration-dependence of probe hybridization.

As is known in the art, in order to represent a unique sequence in the human genome, a probe should be at least 15 nucleotides in length. Accordingly, the polynucleotide probes of the present invention range in length from about 15 nucleotides to the full length of the PSR or target mRNA. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides in length.

The polynucleotide probes of a thyroid classification set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability.

The system of the present invention further provides for primers and primer pairs capable of amplifying target sequences defined by the thyroid classification set, or fragments or subsequences or complements thereof. The nucleotide sequences of the thyroid classifying set may be provided in computer-readable media for in silico applications and as a basis for the design of appropriate primers for amplification of one or more target sequences of the thyroid classifying set.

Primers based on the nucleotide sequences of target sequences can be designed for use in amplification of the target sequences. For use in amplification reactions such as PCR, a pair of primers will be used. The exact composition of the primer sequences is not critical to the invention, but for most applications the primers will hybridize to specific sequences of the thyroid classification set under stringent conditions, particularly under conditions of high stringency, as known in the art. The pairs of primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays to assess transcript expression levels of RNAs defined by the thyroid classification set. Alternatively, these primers may be used in combination with probes, such as molecular beacons in amplifications using real-time PCR.

In one embodiment, the primers or primer pairs, when used in an amplification reaction, specifically amplify at least a portion of a nucleic acid depicted in one of SEQ ID NOs: 1-584, an RNA form thereof, or a complement to either thereof. Optionally, when amplified, either stand produced by amplification may be provided in purified and/or isolated form.

In one embodiment, the primers or primer pairs, when used in an amplification reaction, specifically amplify at least a portion of a nucleic acid depicted in one of SEQ ID NOs: 1-10, an RNA form thereof, or a complement to either thereof.

In one embodiment, the primers or primer pairs, when used in an amplification reaction, specifically amplify at least a portion of a nucleic acid depicted in one of SEQ ID NOs: 1, 11, 12, 13, 14 and 15, an RNA form thereof, or a complement to either thereof.

As is known in the art, a nucleoside is a base-sugar combination and a nucleotide is a nucleoside that further includes a phosphate group covalently linked to the sugar portion of the nucleoside. In forming oligonucleotides, the phosphate groups covalently link adjacent nucleosides to one another to form a linear polymeric compound, with the normal linkage or backbone of RNA and DNA being a 3' to 5' phosphodiester linkage. Specific examples of polynucleotide probes or primers useful in this invention include oligonucleotides containing modified backbones or non-natural internucleoside linkages. As defined in this specification, oligonucleotides having modified backbones include both those that retain a phosphorus atom in the backbone and those that lack a phosphorus atom in the backbone. For the purposes of the present invention, and as sometimes referenced in the art, modified oligonucleotides that do not have a phosphorus atom in their internucleoside backbone can also be considered to be oligonucleotides.

Exemplary polynucleotide probes or primers having modified oligonucleotide backbones include, for example, those with one or more modified internucleotide linkages that are phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Exemplary modified oligonucleotide backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include morpholino linkages (formed in part from the sugar portion of a nucleoside); siloxane backbones; sulfide, sulfoxide and sulphone backbones; formacetyl and thioformacetyl backbones; methylene formacetyl and thioformacetyl backbones; alkene containing backbones; sulphamate backbones; methyleneimino and methylenehydrazino backbones; sulphonate and sulfonamide backbones; amide backbones; and others having mixed N, O, S and $CH_2$ component parts.

The present invention also contemplates oligonucleotide mimetics in which both the sugar and the internucleoside linkage of the nucleotide units are replaced with novel groups. The base units are maintained for hybridization with an appropriate nucleic acid target compound. An example of such an oligonucleotide mimetic, which has been shown to have excellent hybridization properties, is a peptide nucleic acid (PNA) [Nielsen et al., *Science,* 254:1497-1500 (1991)]. In PNA compounds, the sugar-backbone of an oligonucleotide is replaced with an amide containing backbone, in particular an aminoethylglycine backbone. The nucleobases are retained and are bound directly or indirectly to aza-nitrogen atoms of the amide portion of the backbone.

The present invention also contemplates polynucleotide probes or primers comprising "locked nucleic acids" (LNAs), which are novel conformationally restricted oligonucleotide analogues containing a methylene bridge that connects the 2'-O of ribose with the 4'-C (see, Singh et al., *Chem. Commun.,* 1998, 4:455-456). LNA and LNA analogues display very high duplex thermal stabilities with complementary DNA and RNA, stability towards 3'-exonuclease degradation, and good solubility properties. Synthesis of the LNA analogues of adenine, cytosine, guanine, 5-methylcytosine, thymine and uracil, their oligomerization, and nucleic acid recognition properties have been described (see Koshkin et al., *Tetrahedron,* 1998, 54:3607-3630). Studies of mis-matched sequences show that LNA obey the Watson-Crick base pairing rules with generally improved selectivity compared to the corresponding unmodified reference strands.

LNAs form duplexes with complementary DNA or RNA or with complementary LNA, with high thermal affinities. The universality of LNA-mediated hybridization has been emphasized by the formation of exceedingly stable LNA:LNA duplexes (Koshkin et al., *J. Am. Chem. Soc.,* 1998, 120:13252-13253). LNA:LNA hybridization was shown to be the most thermally stable nucleic acid type duplex system, and the RNA-mimicking character of LNA was established at the duplex level. Introduction of three LNA monomers (T or A) resulted in significantly increased melting points toward DNA complements.

Synthesis of 2'-amino-LNA (Singh et al., J. Org. Chem., 1998, 63, 10035-10039) and 2'-methylamino-LNA has been described and thermal stability of their duplexes with complementary RNA and DNA strands reported. Preparation of phosphorothioate-LNA and 2'-thio-LNA have also been described (Kumar et al., *Bioorg. Med. Chem. Lett.,* 1998, 8:2219-2222).

Modified polynucleotide probes or primers may also contain one or more substituted sugar moieties. For example, oligonucleotides may comprise sugars with one of the following substituents at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Examples of such groups are: $O[CH_2)_n O]_m CH_3$, $O(CH_2)_n OCH_3$, $O(CH_2)_n NH_2$, $O(CH_2)_n CH_3$, $O(CH_2)_n ONH_2$, and $O(CH_2)_n ON[CH_2)_n CH_3)]_2$, where n and m are from 1 to about 10. Alternatively, the oligonucleotides may comprise one of the following substituents at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, ONO2, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Specific examples include 2'-methoxyethoxy (2'-O—$CH_2CH_2OCH_3$, also known as 2'-O-(2-methoxyethyl) or 2'-MOE) [Martin et al., *Helv. Chirp. Acta,* 78:486-504(1995)1, 2'-dimethylaminooxyethoxy ($O(CH_2)_2ON(CH_3)_2$ group, also known as 2'-DMAOE), 2'-methoxy (2'-O—$CH_3$), 2'-aminopropoxy (2'-$OCH_2CH_2CH_2NH_2$) and 2'-fluoro (2'-F).

Similar modifications may also be made at other positions on the polynucleotide probes or primers, particularly the 3' position of the sugar on the 3' terminal nucleotide or in 2'-5' linked oligonucleotides and the 5' position of 5' terminal nucleotide. Polynucleotide probes or primers may also have sugar mimetics such as cyclobutyl moieties in place of the pentofuranosyl sugar.

Polynucleotide probes or primers may also include modifications or substitutions to the nucleobase. As used herein, "unmodified" or "natural" nucleobases include the purine bases adenine (A) and guanine (G), and the pyritnidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808; The Concise Encyclopedia Of Polymer Science And Engineering, (1990) pp 858-859, Kroschwitz, J. I., ed. John Wiley & Sons; Englisch et al., *Angewandte Chemie, Int. Ed.,* 30:613 (1991); and Sanghvi, Y. S., (1993) *Antisense Research and Applications*, pp 289-302, Crooke, S. T. and Lebleu, B., ed., CRC Press. Certain of these nucleobases are particularly useful for increasing the binding affinity of the polynucleotide probes of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi, Y. S., (1993) *Antisense Research and Applications*, pp 276-278, Crooke, S. T. and Lebleu, B., ed., CRC Press, Boca Raton].

One skilled in the art will recognize that it is not necessary for all positions in a given polynucleotide probe or primer to be uniformly modified. The present invention, therefore, contemplates the incorporation of more than one of the aforementioned modifications into a single polynucleotide probe or even at a single nucleoside within the probe or primer.

One skilled in the art will also appreciate that the nucleotide sequence of the entire length of the polynucleotide probe or primer does not need to be derived from the target sequence. Thus, for example, the polynucleotide probe may comprise nucleotide sequences at the 5' and/or 3' to the transcription start and stop sites, respectively that are not derived from the target sequences. Nucleotide sequences which are not derived from the nucleotide sequence of the target sequence may provide additional functionality to the polynucleotide probe. For example, they may provide a restriction enzyme recognition sequence or a "tag" that facilitates detection, isolation, purification or immobilisation onto a solid support. Alternatively, the additional nucleotides may provide a self-complementary sequence that allows the primer/probe to adopt a hairpin configuration. Such configurations are necessary for certain probes, for example, molecular beacon and Scorpion probes, which can be used in solution hybridization techniques.

The polynucleotide probes or primers can incorporate moieties useful in detection, isolation, purification, or immobilisation, if desired. Such moieties are well-known in the art (see, for example, Ausubel et al., (1997 & updates) *Current Protocols in Molecular Biology*, Wiley & Sons, New York) and are chosen such that the ability of the probe to hybridize with its target sequence is not affected.

Examples of suitable moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the invention. A variety of different coding schemes are known in the art, including fluorophores, including SCNCs, deposited metals, and RF tags.

Polynucleotides from the described target sequences may be employed as probes for detecting target sequences expression, for ligation amplification schemes, or may be used as primers for amplification schemes of all or a portion of a target sequences. When amplified, either strand produced by amplification may be provided in purified and/or isolated form.

In one embodiment, polynucleotides of the invention include a nucleic acid depicted in (a) any of SEQ ID NOs: 1-584; (b) an RNA form of any of the nucleic acids depicted in SEQ ID NOs: 1-584; (c) a peptide nucleic acid form of any of the nucleic acids depicted in SEQ ID NOs: 1-584; (d) a nucleic acid comprising, at least 20 consecutive bases of any of (a-c); (e) a nucleic acid comprising at least 25 consecutive bases having at least 90% sequence identity to any of (a-c); and a complement to any of (a-e).

Complements may take any polymeric form capable of base pairing to the species recited in (a)-(e), including nucleic acid such as RNA or DNA, or may be a neutral polymer such as a peptide nucleic acid. Polynucleotides of the invention can be selected from the subsets of the recited nucleic acids described herein, as well as their complements.

In some embodiments, polynucleotides of the invention comprise at least 20 consecutive bases as depicted in SEQ ID NOs:1-584, or a complement thereto. The polynucleotides may comprise at least 21, 22, 23, 24, 25, 27, 30, 32, 35 or more consecutive bases as depicted in SEQ ID NOs: 1-584.

The polynucleotides may be provided in a variety of formats, including as solids, in solution, or in an array. The polynucleotides may optionally comprise one or more labels, which may be chemically and/or enzymatically incorporated into the polynucleotide.

In one embodiment, solutions comprising polynucleotide and a solvent are also provided. In some embodiments, the solvent may be water or may be predominantly aqueous. In some embodiments, the solution may comprise at least two, three, four, five, six, seven, eight, nine, ten, twelve, fifteen, seventeen, twenty or more different polynucleotides, including primers and primer pairs, of the invention. Additional substances may be included in the solution, alone or in combination, including one or more labels, additional solvents, buffers, biomolecules, polynucleotides, and one or more enzymes useful for performing methods described herein, including polymerases and ligases. The solution may further comprise a primer or primer pair capable of amplifying a polynucleotide of the invention present in the solution.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextral' polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Preparation of Probes and Primers

The polynucleotide probes or primers of the present invention can be prepared by conventional techniques well-known to those skilled in the art. For example, the polynucleotide probes can be prepared using solid-phase synthesis using commercially available equipment. As is well-known in the art, modified oligonucleotides can also be readily prepared by similar methods. The polynucleotide probes can also be synthesized directly on a solid support according to methods standard in the art. This method of synthesizing polynucleotides is particularly useful when the polynucleotide probes are part of a nucleic acid array.

Polynucleotide probes or primers can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261. Still further techniques include bead based techniques such as those described in PCT Appl. No. PCT/US93/04145 and pin based methods such as those described in U.S. Pat. No. 5,288,514. Additional flow channel or spotting methods applicable to attachment of sensor polynucleotides to a substrate are described in U.S. patent application Ser. No. 07/980,523, filed Nov. 20, 1992, and U.S. Pat. No. 5,384,261.

Alternatively, the polynucleotide probes of the present invention can be prepared by enzymatic digestion of the naturally occurring target gene, or mRNA or cDNA derived therefrom, by methods known in the art.

Thyroid Classification Methods

The present invention further provides methods for characterizing thyroid samples for the presence of malignant or benign thyroid nodule disease. The methods use the thyroid classification sets, probes and primers described herein to provide expression signatures or profiles from a test sample derived from a subject having or suspected of having thyroid cancer. In some embodiments, such methods involve contacting a test sample with thyroid classifying probes (either in solution or immobilized) under conditions that permit hybridization of the probe(s) to any target nucleic acid(s) present in the test sample and then detecting any probe:target duplexes formed as an indication of the presence of the target nucleic acid in the sample. Expression patterns thus determined are then compared to one or more reference profiles or signatures. Optionally, the expression pattern can be normalized. The methods use the thyroid classification sets, probes and primers described herein to provide expression signatures or profiles from a test sample derived from a subject to classify thyroid nodule tissue as malignant or benign.

The assay/method is capable of discriminating malignant and benign samples with good accuracy even in samples classified as "indeterminate" by FNAB cytology and that can only otherwise be diagnosed by pathology review diagnosis.

In some embodiments, such methods involve the specific amplification of target sequences nucleic acid(s) present in the test sample using methods known in the art to generate an expression profile or signature which is then compared to a reference profile or signature.

In some embodiments, the invention further provides for diagnosing thyroid cancer, for prognosing patient outcome, and/or for designating treatment modalities.

In one embodiment, the methods generate expression profiles or signatures detailing the expression of the 584 target sequences having altered relative expression in malignant and benign thyroid disease disclosed herein. In one embodiment, the methods generate expression profiles or signatures detailing the expression of the subsets of these target sequences having 10 or 6 target sequences as described in the examples.

In some embodiments, the methods detect increased relative expression of one or more target sequences in Group I corresponding to the expression products of SEQ ID NOs: 1-6, 11-13, and 16-248, and/or decreased relative expression of one or more target sequences in Group II corresponding to the expression products of SEQ ID NOs: 7-10, 14, 15, and 249-584, and thereby designate a sample as comprising malignant thyroid nodule disease. In some embodiments, increased relative expression of one or more target sequences in Group II and/or decreased relative expression of one or more target sequences in Group I and thereby designate a sample as comprising benign thyroid nodule disease.

In some embodiments, the methods detect combinations of expression levels of sequences exhibiting positive and negative correlation with a disease status. In one embodiment, the methods detect a minimal expression signature.

Any method of detecting and/or quantitating the expression of the encoded target sequences can in principle be used in the invention. Such methods can include Northern blotting, array or microarray hybridization, by enzymatic cleavage of specific structures (e.g., an Invader® assay, Third Wave Technologies, e.g. as described in U.S. Pat. Nos. 5,846,717, 6,090,543; 6,001,567; 5,985,557; and 5,994,069) and amplification methods, e.g. RT-PCR, including in a TaqMan® assay (PE Biosystems, Foster City, Calif., e.g. as described in U.S. Pat. Nos. 5,962,233 and 5,538,848), and may be quantitative or semi-quantitative, and may vary depending on the origin, amount and condition of the available biological sample. Combinations of these methods may also be used. For example, nucleic acids may be amplified, labeled and subjected to microarray analysis. Single-molecule sequencing Illumina, Helicos, PacBio, ABI SOLID), in situ hybridization, bead-array technologies (e.g., Luminex xMAP, Illumina BeadChips), branched DNA technology (e.g., Panomics, Genisphere).

The expressed target sequences can be directly detected and/or quantitated, or may be copied and/or amplified to allow detection of amplified copies of the expressed target sequences or its complement. In some embodiments, degraded and/or fragmented RNA can be usefully analyzed for expression levels of target sequences, for example RNA having an RNA integrity number of less than 8.

In some embodiments, quantitative RT-PCR assays are used to measure the expression level of target sequences depicted in SEQ ID NOs: 1-584. In other embodiments, a GeneChip or microarray can be used to measure the expression of one or more of the target sequences.

Molecular assays measure the relative expression levels of the target sequences, which can be normalized to the expression levels of one or more control sequences, for example array control sequences and/or one or more housekeeping genes, for example GAPDH. Increased (or decreased) relative expression of the target sequences as described herein, including any of SEQ ID NOs:1-584, may thus be used alone or in any combination with each other in the methods described herein. In addition, negative control probes may be included.

Diagnostic Samples

Diagnostic samples for use with the systems and in the methods of the present invention comprise nucleic acids suitable for providing RNAs expression information. In principle, the biological sample from which the expressed RNA is obtained and analyzed for target sequence expression can be any material suspected of comprising thyroid cancer. The diagnostic sample can be a biological sample used directly in a method of the invention. Alternatively, the diagnostic sample can be a sample prepared from a biological sample.

In one embodiments, the sample or portion of the sample comprising or suspected of comprising thyroid cancer can be any source of biological material, including cells, tissue or fluid, including bodily fluids. Non-limiting examples of the source of the sample include an aspirate, a needle biopsy, a liquid-based preparation (e.g., ThinPrep®) cytology pellet, a bulk tissue preparation or a section thereof obtained for example by surgery or autopsy, lymph fluid, blood, plasma, serum, tumors, and organs. The assay and methods are broadly applicable to FFPE samples.

The samples may be archival samples, having a known and documented medical outcome, or may be samples from current patients whose ultimate medical outcome is not yet known. Samples to be analyzed for thyroid cancer are typically obtained as fine needle aspirates, a cytology smear, a cytology pellet, or as bulk samples obtained, for example, from a thyroidectomy. Where samples of a bodily fluid are obtained, cells or cell types may be isolated and/or purified therefrom. For example, circulating epithelial cells can be obtained from peripheral blood and analyzed as described herein. In some embodiments, magnetic separation can be used to obtain circulating epithelial cells (U.S. Pat. No. 6,136,182).

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Helv solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFM™, Cryo-Gel™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

RNA Extraction

RNA can be extracted and purified from biological samples using any suitable technique. A number of techniques are known in the art, and several are commercially available (e.g., FormaPure™ nucleic acid extraction kit, Agencourt Biosciences, Beverly Mass., High Pure PPPE RNA Micro Kit™, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA concentrations can be made using a Nanodrop ND-1000 spectrophotometer (Nanodrop Technologies, Rockland, Del.). RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a PSR, and may optionally be labeled. A variety of amplification methods are suitable for use, including polymerase-based methods and ligation-based methods. Exemplary amplification techniques include the polymerase chain reaction method (PCR), the ligase chain reaction (LCR), ribozyme-based methods, self sustained sequence replication (3SR), nucleic acid sequence-based amplification (NASBA), the use of Q Beta replicate, reverse transcription, nick translation, and the like.

Asymmetric amplification reactions may be used to preferentially amplify one strand representing the PSR that is used for detection as the target polynucleotide. In some cases, the presence and/or amount of the amplification product itself may be used to determine the expression level of a given PSR. In other instances, the amplification product may be used to hybridize to an array or other substrate comprising sensor polynucleotides which are used to detect and/or quantitate PSR expression.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used. Exemplary enzymes include: DNA polymerases such as DNA Polymerase 1 ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB-D DNA polymerases; RNA polymerases such as *E. soli*, SP6, T3 and T7 RNA polymerases; and reverse transcriptases such as AMV, M-MuLV, MMLV, RNAse $H^-$ MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfx, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, Calif.), including the WT-Ovation™ System, WT-Ovation™ System v2, WT-Ovation™ Pico System, WT-Ovation™ FFPE Exon Module, WT-Ovation™ FFPE Exon Module RiboAmp and RiboAmp$^{Plus}$ RNA Amplification Kits (MDS Analytical Technologies (formerly Arcturus) (Mountain View, Calif.), Genisphere, Inc. (Hatfield, Pa.), including the RampUp Plus™ and SenseAmp™ RNA Amplification kits, alone or in combination. Amplified nucleic acids may be subjected to one or more purification reactions after amplification and labeling, for example using magnetic beads (e.g., RNAClean magnetic beads, Agencourt Biosciences).

Multiple RNA biomarkers can be analyzed using real-time quantitative multiplex RT-PCR platforms and other multiplexing technologies such as GenomeLab GeXP Genetic Analysis System (Beckman Coulter, Foster City, Calif.), SmartCycler® 9600 or GeneXpert® Systems (Cepheid, Sunnyvale, Calif.), ABI 7900 HT Fast Real Time PCR system (Applied Biosystems, Foster City, Calif.), LightCycler® 480 System (Roche Molecular Systems, Pleasanton, Calif.), xMAP 100 System (Luminex, Austin, Tex.) Solexa Genome Analysis System (Illumina, Hayward, Calif.), OpenArray Real Time qPCR (BioTrove, Woburn, Mass.) and BeadXpress System (Illumina, Hayward, Calif.).

Thyroid Classification Arrays

The present invention contemplates that a thyroid classification set or probes derived therefrom may be provided in an array format. In the context of the present invention, an "array" is a spatially or logically organized collection of polynucleotide probes. Any array comprising sensor probes specific for two or more of the target sequences depicted in SEQ ID NOs: 1-584 or a product derived from the target sequences depicted therein can be used. Desirably, an array will be specific for 5, 10, 15, 20, 25, 30, 50, 75, 100, 150, 200, 250, 300, 350, 400, 450, 500, 600, 700 or more of SEQ ID NOs: 1-584. Expression of these sequences may be detected alone or in combination with other transcripts. In some embodiments, an array is used which comprises a wide range of sensor probes for thyroid-specific expression products, along with appropriate control sequences. An array of interest is the Human Exon 1.0 ST Array (HuEx 1.0 ST, Affymetrix, Inc., Santa Clara, Calif.).

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that will be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In one embodiment of the present invention, the thyroid classification array is a chip.

Data Analysis

Array data can be managed and analyzed using techniques known in the art. The Genetrix suite of tools can be used for microarray analysis (Epicenter Software, Pasadena, Calif.). Probe set modeling and data pre-processing can be derived using the Robust Multi-Array (RMA) algorithm or variant GC-RMA, Probe Logarithmic Intensity Error (PLIER) algorithm or variant iterPLIER. Variance or intensity filters can be applied to pre-process data using the RMA algorithm, for example by removing$^{-}$ target sequences with a standard deviation of <10 or a mean intensity of <100 intensity units of a normalized data range, respectively.

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (i.e., an 'expression signature') and converted into a likelihood score. This likelihood score indicates the probability that a biological sample is from malignant thyroid nodule disease or benign disease. The likelihood score can be used to distinguish malignant from benign thyroid nodule disease. The models and/or algorithms can be provided in machine readable format, and may be used to correlate expression levels or an expression profile with a disease state, and/or to designate a treatment modality for a patient or class of patients.

Thus, results of the expression level analysis can be used to correlate increased expression of one or more target sequences in group I (or a subset thereof) and/or decreased expression of one or more target sequences in group II (or a subset thereof) with thyroid cancer, and to designate a treatment modality selected from total thyroidectomy, radioactive iodine treatment, and a combination thereof. Patients with benign disease would be candidates for watchful waiting (careful monitoring at regular intervals), thyroid hormone suppression therapy (treating with levothyroxine or other synthetic forms of thyroxine) to shrink the nodule, radioactive iodine to treat hyperfunctioning adenomas or multinodular goiters and surgery. For benign patients surgical management is much more limited to either cosmetic debulking procedures or only partial thyroidectomy leaving thyroid function largely intact. In contrast, the usual treatment for malignant nodules is surgical removal using more aggressive approaches such as near-total or total thyroidectomy followed by radioactive iodine ablation therapy and permanent thyroid hormone replacement therapy. Results of the expression level analysis can be used to correlate increased expression of one or more target sequences in group II (or a subset thereof) and/or decreased expression of one or more target sequences in group I (or a subset thereof) with benign disease, and to designate a treatment modality selected from near-total thyroidectomy, partial thyroidectomy, or watchful-waiting. The preferred treatment regimen for benign or non-neoplastic disease is observation.

Factors known in the art for diagnosing and/or suggesting, selecting, designating, recommending or otherwise determining a course of treatment for a patient or class of patients suspected of having thyroid disease can be employed in combination with measurements of the target sequence expression. These techniques include FNAB cytology and classification, ultrasound analysis, MRI results, CT scan results, thyroid scans, and measurements of thyroid hormone levels.

For example, factors which may be used to indicate a benign condition include a family history of Hashimoto's thyroiditis, of benign thyroid nodule, or of goiter, symptoms of hyper- or hypothyroidism, pain or tenderness associated with a nodule, a nodule that is soft, smooth and mobile, a multinodular goiter without a predominant nodule, a nodule that is "warm" on a thyroid scan, or an ultrasound indication of a simple cyst structure.

Factors which may be used to indicate a malignant thyroid condition include patient age less than 20 or greater than seventy, male gender, new onset of swallowing difficulties or hoarseness, a history of external neck irradiation, a nodule that is firm, irregular and fixed, cervical lymphadenopathy, a history of thyroid cancer, a nodule that is "cold" on a thyroid scan, and a solid or complex morphology seen on ultrasound.

Certified tests for classifying thyroid disease status and/or designating treatment modalities are also provided. A certified test comprises a means for characterizing the expression levels of one or more of the target sequences of interest, and a certification from a government regulatory agency endorsing use of the test for classifying the thyroid disease status of a biological sample.

In some embodiments, the certified test may comprise reagents for amplification reactions used to detect and/or quantitate expression of the target sequences to be characterized in the test. An array of probe nucleic acids can be used, with or without prior target amplification, for use in measuring target sequence expression.

The test is submitted to an agency having authority to certify the test for use in distinguishing benign from malignant thyroid tissues. Results of detection of expression levels of the target sequences used in the test and correlation with disease status and/or outcome are submitted to the agency. A certification authorizing the diagnostic and/or prognostic use of the test is obtained.

Also provided are portfolios of expression levels comprising a plurality of normalized expression levels of the target sequences described herein, including SEQ ID NOs: 1-584. Such portfolios may be provided by performing the methods described herein to obtain expression levels from an individual patient or from a group of patients. The expression levels can be normalized by any method known in the art; exemplary normalization methods that can be used in various embodiments include Robust Multichip Average (RMA), probe logarithmic intensity error estimation (PLIER), non-linear fit (NLFIT) quantile-based and nonlinear normalization, and combinations thereof. Background correction can also be performed on the expression data; exemplary techniques useful for background correction include mode of intensities, normalized using median polish probe modeling and sketch-normalization.

In some embodiments, portfolios are established such that the combination of genes in the portfolio exhibit improved sensitivity and specificity relative to known methods. In considering a group of genes for inclusion in a portfolio, a small standard deviation in expression measurements correlates with greater specificity. Other measurements of variation such as correlation coefficients can also be used in this capacity. The invention also encompasses the above methods where the specificity is at least about 50% and at least about 60%. The invention also encompasses the above methods where the sensitivity is at least about 90%.

The gene expression profiles of each of the target sequences comprising the portfolio can fixed in a medium such as a computer readable medium. This can take a number of forms. For example, a table can be established into which the range of signals (e.g., intensity measurements) indicative of disease is input. Actual patient data can then be compared to the values in the table to determine whether the patient samples are normal, benign or diseased. In a more sophisticated embodiment, patterns of the expression signals (e.g., fluorescent intensity) are recorded digitally or graphically.

Comparisons can also be used to determine whether the patient is not likely to experience the disease. The expression profiles of the samples are then compared to a control portfolio. If the sample expression patterns are consistent with the expression pattern for cancer then (in the absence of countervailing medical considerations) the patient is treated as one would treat a thyroid cancer patient. If the sample expression patterns are consistent with the expression pattern from the normal/control cell then the patient is diagnosed negative for cancer.

Genes can be grouped so that information obtained about the set of genes in the group can be used to make or assist in making a clinically relevant judgment such as a diagnosis, prognosis, or treatment choice.

A patient report is also provided comprising a representation of measured expression levels of a plurality of target sequences in a biological sample from the patient, wherein the representation comprises expression levels of target sequences corresponding to any one, two, three, four, five, six, eight, ten, twenty, thirty, fifty or more of the target sequences depicted in SEQ ID NOs: 1-584, or of the subsets described herein, or of a combination thereof. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known thyroid status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

Kits

Kits for performing the desired method(s) are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. At least two, three, four or five primers or pairs of primers suitable for selectively amplifying the same number of target sequence-specific polynucleotides can be provided in kit form. In some embodiments, the kit comprises from five to fifty primers or pairs of primers suitable for amplifying the same number of target sequence-representative polynucleotides of interest.

The reagents may independently be in liquid or solid form. The reagents may be provided in mixtures. Control samples and/or nucleic acids may optionally be provided in the kit. Control samples may include tissue and/or nucleic acids obtained from or representative of benign thyroid tissue, as well as tissue and/or nucleic acids obtained from or representative of malignant thyroid tissue.

The nucleic acids may be provided in an array format, and thus an array or microarray may be included in the kit. The kit optionally may be certified by a government agency for use in classifying the disease status of thyroid tissue and/or for designating a treatment modality.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

Devices

Devices useful for performing methods of the invention are also provided. The devices can comprise means for characterizing the expression level of a target sequence of the invention, for example components for performing one or more methods of nucleic acid extraction, amplification, and/or detection. Such components may include one or more of an amplification chamber (for example a thermal cycler), a plate reader, a spectrophotometer, capillary electrophoresis apparatus, a chip reader, and or robotic sample handling components. These components ultimately can obtain data that reflects the expression level of the target sequences used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection components.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

The devices also comprise a means for correlating the expression levels of the target sequences being studied with a classification of thyroid disease. Such means may comprise one or more of a variety of correlative techniques, including lookup tables, algorithms, multivariate models, and linear or nonlinear combinations of expression models or algorithms. The expression levels may be converted to one or more likelihood scores, reflecting the likelihood that the sample comprises malignant tissue and/or the likelihood that the sample comprises benign tissue. The models and/or algorithms can be provided in machine readable format, and can optionally further designate a treatment modality for a patient or class of patients The device also comprises output means for outputting the thyroid disease status and/or a treatment modality. Such output means can take any form which transmits the results to a patient and/or a healthcare provider, and may include a monitor, a printed format, or both. The device may use a computer system for performing one or more of the steps provided.

Citations

1: Griffith O L, et al., “Meta-analysis and meta-review of thyroid cancer gene expression profiling studies identifies important diagnostic biomarkers,” J Clin Oncol. 2006 Nov. 1, 24(31):5043-51.

2: Puskas L G, et al., “Gene profiling identifies genes specific for well-differentiated epithelial thyroid tumors,” Cell Mol Biol (Noisy-le-grand), 2005 Sep. 5, 51(2):177-86.

3: Fujarewicz K, et al., "A multi-gene approach to differentiate papillary thyroid carcinoma from benign lesions: gene selection using support vector machines with bootstrapping," Endocr Relat Cancer. 2007 September, 14(3):809-26.

4: Kebebew E, et al., "Diagnostic and extent of disease multigene assay for malignant thyroid neoplasms," Cancer. 2006 Jun. 15, 106(12):2592-7.

5: Finley D J, et al., "Discrimination of benign and malignant thyroid nodules by molecular profiling," Ann Surg. 2004 September, 240(3):425-36; discussion 436-7.

6: Mazzanti C, et al., "Using gene expression profiling to differentiate benign versus malignant thyroid tumors," Cancer Res. 2004 Apr. 15; 64(8):2898-903. Erratum in: Cancer Res. 2004 Jul. 15, 64(14):5028.

7: Finley D J, et al., "Advancing the molecular diagnosis of thyroid nodules: defining benign lesions by molecular profiling," Thyroid. 2005 June:15(6):562-8.

8: Cerutti J M, et al., "Diagnosis of suspicious thyroid nodules using four protein biomarkers," Clin Cancer Res. 2006 Jun. 1; 12(11 Pt 1):3311-8.

9: Fryknäs M, et al., "Molecular markers for discrimination of benign and malignant follicular thyroid tumors," Tumour Biol. 2006; 27(4):211-20.

10: Hamada A, et al., "Diagnostic usefulness of PCR profiling of the differentially expressed marker genes in thyroid papillary carcinomas," Cancer Lett. 2005 Jun. 28, 224(2):289-301.

11: Yukinawa N, et al., "A multi-class predictor based on a probabilistic model: application to gene expression profiling-based diagnosis of thyroid tumors," BMC Genomics. 2006 Jul. 27, 7:190.

12: Griffiths O L, et al., "Biomarker panel diagnosis of thyroid cancer: a critical review," Expert Rev. Anticancer Therapy. 2008 September, 8(9): 1399-1413.

13: Prasad N B, et al., "Identification of Genes Differentially Expressed in Benign versus Malignant Thyroid Tumors," Clinical Cancer Res. 2008 Jun. 1, 14(11): 3327-37.

14: Shibru D, et al., "Does the 3-gene diagnostic assay accurately distinguish benign from malignant thyroid neoplasms?" Cancer. 2008 Sep. 1; 113(5):930-5.

To gain a better understanding of the invention described herein, the following examples are set forth. It will be understood that these examples are intended to describe illustrative embodiments of the invention and are not intended to limit the scope of the invention in any way. Efforts have been made to ensure accuracy with respect to numbers used (e.g., amounts, temperature, etc.) but some experimental error and deviation should he accounted for. Unless otherwise indicated, parts are parts by weight, temperature is degree centigrade and pressure is at or near atmospheric, and all materials are commercially available.

EXAMPLES

Materials and Methods:

Tissue Samples. Sixty (60) formalin-fixed paraffin embedded (FFPE) surgical specimens of human thyroid nodule disease were collected from patients at the Department of Surgery, St. Paul's Hospital (Vancouver, BC, Canada) according to an institutional review board-approved protocol. For a subset of 13 surgical specimens, fine-needle aspirate cell blocks were also available. For surgical specimens, a tissue microarrayer (Beecher Instruments, Silver Spring, Md.) was used to core each FFPE surgical resected specimen once with either a 0.6 mm or 1.0 diameter cylinder ('FFPE TMA'). Surgical resected samples from 60 patients were evaluated. These samples were divided into three subsets consisting of training (n=30) and testing (n=20) subsets used to select for differentially expressed RNA probe sets and a follicular testing subset (n=10) consisting of difficult to diagnose follicular pattern lesions from patients with an fine needle aspiration biopsy (FNAB) diagnosis of suspicious for cancer.

Extraction of RNA. RNA was extracted and purified from the FFPE TMA cores using a modified protocol for the commercially available Formapure nucleic acid extraction kit (Agencourt Biosciences, Beverly Mass.) adopted to process small amounts of input tissue. Principal modifications to the kit protocol included preheating the lysis buffer to 70° C. before immersing the FFPE sections in a reduced amount of lysis buffer (to increase concentration of lysate) and then subjecting FFPE lysates to incubation at 99° C. for 1 min. In addition, FFPE samples were incubated with Proteinase K (20 ul of 40 mg/mL) for an extended 16 hrs in a water bath at 55° C. RNA was further purified using DNAse I treatment (Ambion, Austin, Tex.) to eliminate any contaminating DNA. RNA was eluted with 300 ul of RNAse-free water and subsequently concentrated and purified using sodium acetate precipitation and a series of ethanol washes and resuspended in 15 ul of water. RNA concentrations were calculated using a Nanodrop ND-1000 spectrophotometer (Nanodrop Technologies, Rockland, Del.). These additional purification steps significantly improved the yield of amplified material in subsequent steps described below. RNA integrity was evaluated by running electropherograms and RNA integrity number, RIN (a correlative measure that indicates intactness of mRNA) was determined using the RNA 6000 PicoAssay for the Bioanalyzer 2100 (Agilent Technologies, Santa Clara, Calif.). Sufficient RNA (75 ng) was obtained using these procedures from all 60 FFPE TMA.

Nucleic Acid Amplification and GeneChip Hybridization. Purified RNA was subjected to whole-transcriptome amplification using the WT-Ovation FFPE system including the WT-Ovation Exon and FL-Ovation Biotin V2 labeling modules, with the following modifications. Seventy-five (75) nanograms of RNA extracted from FFPE TMA cores or FNAB cell blocks was used to generate amplified Ribo-SPIA product. For the WT-Ovation Exon sense-target strand conversion kit 4 ug of Ribo-SPIA product were used. Between 2.5 and 5 micrograms of WT-Ovation Exon product were used to fragment and label using the FL-Ovation Biotin V2 labeling module and labeled product was hybridized to Affymetrix Human Exon 1.0 ST GeneChips following manufacturer's recommendations (Affymetrix, Santa Clara, Calif.).

Microarray Analysis. All data management and analysis was conducted using the Genetrix suite of tools for microarray analysis (Epicenter Software, Pasadena, Calif.). Probe set modeling and data pre-processing were derived using the iterPlier algorithm (Affymetrix, Santa Clarita, Calif.). The mode of intensity values was used for background correction and sketch was used for normalization and probe modeling used a median polish routine. Outlier samples were identified by evaluating the median absolute deviation of the normalized expression values in each sample and $25^{th}$ percentile outlier samples. Two samples from the testing cohort were removed from further analysis because they were clearly outliers using both quality control metrics described above. Table 1 shows the composition of the subsets used in the analysis (for samples that passed microarray QC) and segregates specimens by the results of the original FNAB cytology diagnosis as well as the 'gold-standard' pathology review diagnosis (obtained from careful dissection and histopathological analysis of specimens after thyroidetomy procedures). A variance filter was applied to data pre-processed using the iterPlier algorithm, by removing probe set regions (PSRs) with a mean intensity of <10 intensity units of a normalized data range. PSRs are comprised of an average of four individual probes that interrogate the expression of RNA transcripts or portions thereof. PSR annotations and the sequences (RNAs) that they interrogate were downloaded from the Affymetrix website. An additional filter employed was to remove PSRs with known cross-hybridization properties (i.e., significant homology to more than one transcript from different genes or loci), leaving 1,134,588 PSRs for further analysis. Cross-hybridization properties of PSRs were downloaded from the Affymetrix website.

Example 1. Identification of PSRs Differentially Expressed in Benign and Malignant Thyroid in the Training Subset Supervised expression profiling was performed using t-tests and mean-fold difference criteria to determine differential expression of RNAs in the training cohort of 30 specimens between samples classified as malignant and benign thyroid nodule disease by review pathology. In the training cohort, 10 of the specimens were definitively diagnosed by FNAB cytology as benign disease (e.g., goiter), 8 of the specimens were definitively diagnosed by FNAB cytology as malignant disease (e.g., papillary carcinoma) and all 18 of these specimens were confirmed the same upon histological review pathology of surgical specimens after thyroidectomy. The remaining 12 samples evaluated in the training cohort were indeterminate by FNAB cytology, but 7 were confirmed malignant and 5 confirmed benign thyroid nodule disease upon histological review diagnosis of the surgical specimens. The final histological review diagnosis of the FFPE surgical specimen was the variable used to select for differentially expressed target sequences.

Using supervised selection criteria of at least 3-fold mean difference in expression (between malignant and benign groups) and t-test p value cut-off of $p<0.0001$, 242 RNAs were found at increased expression in malignant samples as compared to benign samples, while 342 found at increased expression in benign samples as compared to malignant samples (RNA forms of the sequences are depicted in SEQ TD NOs: 1-584).

A detailed literature review was conducted and identified 68 genes differentially expressed between malignant and benign thyroid tissue (see citations #1-15 supra). On the Affymetrix Human Exon 1.0 microarray these 68 genes are represented by 766 exonic target sequences. Analysis of the overlap between target sequences from the literature review and the 584 identified as having at least 3-fold difference in expression in the training subset indicated an overlap of only 67 PSRs (SEQ ID NOs: 44, 46, 48, 56, 63, 79, 81, 83, 86, 87, 89, 96, 98, 99, 103, 106, 109, 114, 115, 119, 121, 126, 127, 130, 138, 145, 146, 151, 157, 159-161, 165, 172, 174, 178, 181, 183, 188, 190, 196, 198, 202, 203, 205, 206, 219, 223, 230, 234, 244, 249, 255, 260, 274, 275, 300, 302, 314, 324, 326, 368, 369, 393, 403, 514 and 517). This relatively small overlap indicates that most of the differentially expressed target sequences characterized in the training subset analysis have not be previously characterized as being differentially expressed between benign and malignant thyroid nodule disease samples.

Previous reports have demonstrated genome-wide expression profiling using primarily fresh or frozen specimens, which are not routinely available in the clinic and are logistically difficult to transport to external laboratories for analysis (i.e., require flash freezing with liquid nitrogen and transport on dry ice). In contrast, the approach used in this Example allows for genome-wide expression profiling of more widely available FFPE thyroid nodule disease surgical specimens and FNAB cell blocks and demonstrates that this approach can successfully generate high-resolution whole-transcriptome expression data from the more fragmented RNA extracted from these routine clinical specimens. Moreover, this approach has identified target sequences that can be detected in such routine clinical specimens thereby providing for a diagnostic method that is broadly applicable and is not dependent on the availability of fresh or frozen specimens.

In addition to robust profiling from FFPE specimens, the use of Human Exon microarrays, which report relative expression of genes on the exon level, provided a higher resolution view of the transcriptome and allowed detection of differentially expressed RNA species that can not be detected with 3' biased gene-level microarrays (e.g., U133 Plus 2.0 GeneChips). FIG. 1 shows a pie chart of the types of RNA species comprised by the 584 RNAs selected in the present Example as differentially expressed in the training subset. These species can be seen to include not only exonic RNA species, but also intronic, promoter and antisense RNA species. In fact, a minority of the RNAs selected are from protein-encoding exons of genes that are represented in gene-level microarrays and the majority (70%) of the RNAs selected represent RNA sequences that are not profiled with gene-level microarray technology. This data demonstrates that gene-level analysis (e.g., using 3' biased microarrays such as U133 Plus 2.0) can miss important differences in transcription such as intron retention, alternative splicing or exon usage and non-coding (i.e., translated into protein) RNA expression or strand-specific expression observed in this type of whole-transcriptome analysis. In particular, non-coding RNA—the predominant RNA species (over 90% of the transcription in the genome)—represent functional RNA molecules that could convey key differences between pathological conditions through regulatory roles of protein-encoding gene expression. This is a potentially rich source of diagnostic information that cannot be captured by solely observing differences in protein-encoding gene expression or protein biomarker expression and may facilitate the diagnosis of specific pathological conditions of clinical importance, such as malignant vs. benign in thyroid nodule disease.

Example 2. Validation of Selected RNAs and Identification of Minimal Diagnostic Expression Signatures In order to identify a minimal expression signature capable of distinguishing malignant from benign thyroid nodule disease, the Nearest Shrunken Centroids (NSC) algorithm was employed as previously described (Davicioni et al., Molecular Classification of Rhabdomyosarcoma: Genotypic and Phenotypic Determinants of Diagnosis, American Journal of Pathology, 2009) on the 584 RNAs selected in the training subset (n=30) analysis. Using the NSC algorithm, a 10-RNA expression signature (Table 3) was identified in the testing subset (n=18) that independently discriminates the benign and malignant samples. A separate NSC algorithm analysis was implemented on the follicular lesion testing subset (n=10) and identified a 6-RNA minimal expression signature (Table 4) for discriminating benign and malignant disease (as definitively diagnosed by the surgical pathology review) from these follicular pattern lesions which in the clinic all fall into the ‘indeterminate’ diagnostic or ‘suspicious for cancer’ categories. Of note, out of these 16 RNAs, only one of these sequences (SEQ ID NO:5) is known to overlap with the protein-coding mRNA of a gene, it however is transcribed antisense to the gene.

Next, the expression levels of these 10- and 6-RNA signatures were summarized (for each of the 58 patients evaluated in the three subsets) into a ‘metagene’ by taking the expression level and multiplying it by a weighting factor for each PSR in the metagene signature and combining these values into a single variable. Weighting factors were derived from the signed log of the p value from the test statistic coefficients from a t-test for significance of differential expression in the training subset (Tables 3 and 4). Patient Outcome Predictor (POP') scores were then generated from the metagene values for each patient by scaling and normalizing the metagene scores within a range of 0 to 100. The interquartile range of POP scores generated from metagenes for benign and malignant specimens is shown separately for specimens definitively diagnosed by FNAB cytology and those that were indeterminate or suspicious for cancer (FIG. 3A and FIG. 3B).

Figure 3A:
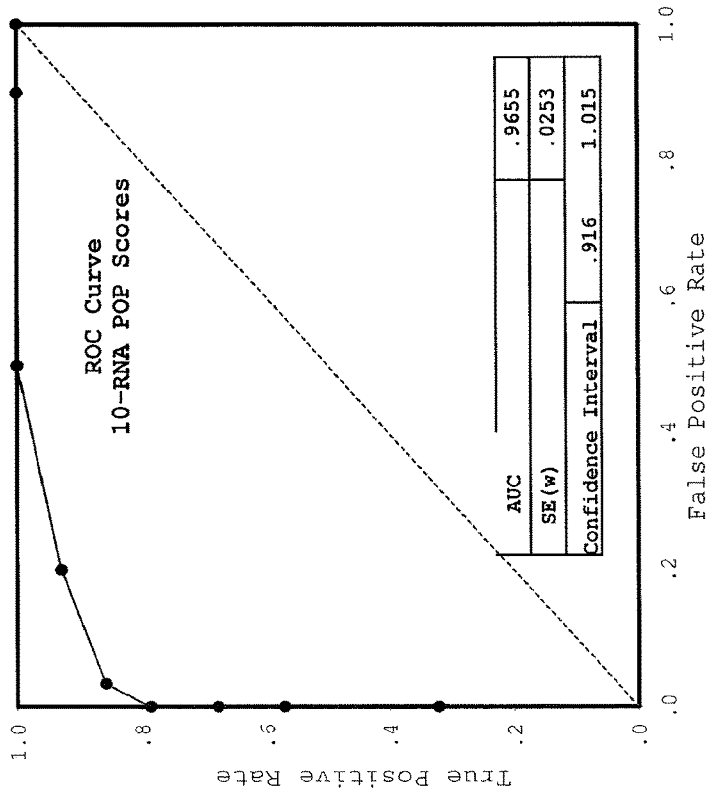
FIG. 3A depicts a receiver-operator curve (ROC) of the POP scores derived from the 10-RNA metagenes.
Figure 3B:
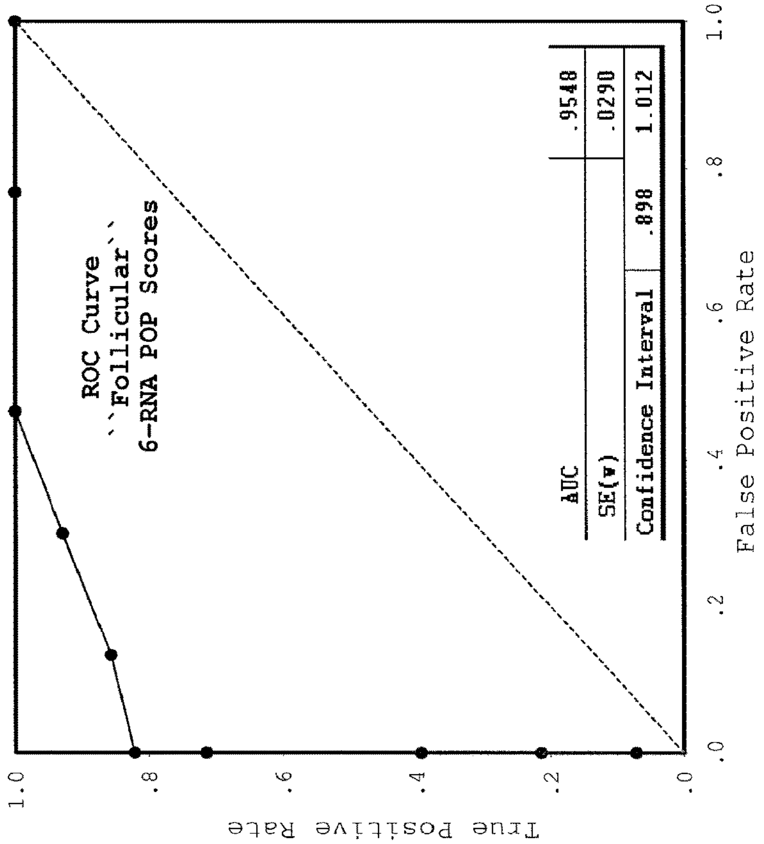
FIG. 3B depicts a receiver-operator curve (ROC) of the POP scores derived from the 6-RNA metagene. The area-under-the curves and their confidence intervals are indicated below the ROC curve and show that the POP scores are excellent discriminators of malignant and benign disease.

In FIG. 3A, it can be observed that POP scores generated from the 10-RNA metagene did not overlap at all between benign and malignant thyroid nodule disease specimens ($p<6e-18$). The performance of this metagene in terms of distinguishing indeterminate diagnoses was also highly significant, although diminished in comparison ($p<1.3e-5$). In contrast, the POP scores generated from the “follicular” 6-RNA metagene separated indeterminate diagnoses slightly better as the interquartile ranges for true malignant specimens was tighter ($p<6.9e-6$) (FIG. 3B).

Using an arbitrary POP score cut-off value of <50 to indicate a patient with benign thyroid nodule disease and a cut-off value of >50 points to indicate a patient with malignant thyroid nodule disease, 2×2 contingency (truth tables') reveal that both these expression signatures are highly accurate discriminators when compared to the ‘gold-standard’ histological review pathology diagnosis post-thryoidectomy. The sensitivity (82%) and specificity (100%) were equivalent for both the 10- and 6-RNA metagenes when evaluating POP scores for all specimens (Table 5). The specificity was maintained at 100% when evaluating only the FNAB indeterminate cytology specimens as a separate group but the sensitivity (64%) decreased and was less than that observed in the combined analysis of all specimens (Table 6). The high specificity shown by both the 10- and 6-RNA metagenes is significant in that it provides for a diagnostic assay with a very low false-positive rate. The overall accuracy in both groups, however, was significant: 91% in all specimens and 83% in indeterminate cytology specimens. Receiver-operator curves (ROC) for the 10- and 6-RNA metagene POP scores are depicted in FIG. 3A and FIG. 3B, respectively, and show that the area-under-the curve was above 95% in both cases. These ROC results are significant because they demonstrate in the absence of a specified cut-off value for POP scores that they are performing extremely well as a diagnostic test for malignant thyroid nodule disease.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

TABLE 1

The composition of specimens used in the training and testing subsets for the microarray analyses. The specimens are separated into the major diagnostic categories relevant to clinical practice. Thyroid nodule disease specimens that were indeterminate or suspicious for cancer on the original FNAB and the definitive diagnosis as determined by surgical pathology review after thyroidectomy.

| | Surgical Pathology Dx | |
|---|---|---|
| FNAB Cytology Diagnostic Category | Benign | Malignant |
| Training Subset | | |
| Benign | 10 | o |
| Indeterminate/Suspicious | 5 | 7 |
| Cancer | o | 8 |
| Testing Subset | | |
| Benign | 5 | o |
| Indeterminate/Suspicious | 5 | 2 |
| Cancer | o | 6 |
| Follicular Lesion Testing Subset | | |
| Benign | o | o |
| Indeterminate/Suspicious | 5 | 5 |
| Cancer | o | o |

TABLE 2

Examples of Suitable Genes for Inclusion in a Thyroid Classification Library

| Gene Symbol | Gene |
|---|---|
| Thyroid Malignant- Increased Expression | |
| ADORA1 | adenosine A1 receptor |
| CCL18 | chemokine (C-C motif) ligand 18 (pulmonary and activation-regulated) |
| CCND1 | cyclin D1 |
| CD44 | CD44 molecule (Indian blood group) |
| CDH3 | cadherin 3, type 1, P-cadherin (placental) |
| CITED1 | Cbp/p300-interacting transactivator, with Glu/Asp-rich carboxy-terminal domain, 1 |
| DPP4 | dipeptidyl-peptidase 4 (CD26, adenosine deaminase complexing protein 2) |
| DUSP6 | dual specificity phosphatase 6 |
| ENTPD1 | ectonucleoside triphosphate diphosphohydrolase 1 |
| EPSS | epidermal growth factor receptor pathway substrate 8 |
| ETVS | Ets variant gene 5 (ets-related molecule) |

TABLE 2-continued

| Examples of Suitable Genes for Inclusion in a Thyroid Classification Library | |
|---|---|
| Gene Symbol | Gene |
| MPZL2 | myelin protein zero-like 2 |
| FN1 | fibronectin 1 |
| GJB3 | gap junction protein, beta 3, 31 kDa |
| GABBR2 | gamma-aminobutyric acid (GABA) B receptor, 2 |
| HBB | hemoglobin, beta |
| HLA-DMA | major histocompatibility complex, class II, DM alpha |
| HLA-DQA1 | major histocompatibility complex, class II, DQ alpha 1 |
| HMGA2 | high mobility group AT-hook 2 |
| ICAM1 | intercellular adhesion molecule 1 (CD54), human rhinovirus receptor |
| IGSF1 | immunoglobulin superfamily, member 1 |
| IL13RA1 | interleukin 13 receptor, alpha 1 |
| ENDOD1 | endonuclease domain containing 1 |
| KRT19 | keratin 19 |
| LGALS3 | lectin, galactoside-binding, soluble, 3 |
| LRP4 | low density lipoprotein receptor-related protein 4 |
| MET | met proto-oncogene (hepatocyte growth factor receptor) |
| MKRN2 | makorin, ring finger protein, 2 |
| MRC2 | mannose receptor, C type 2 |
| MTMR4 | myotubularin related protein 4 |
| P4HA2 | procollagen-proline, 2-oxoglutarate 4-dioxygenase (proline 4-hydroxylase), alpha polypeptide II |
| PHLDA2 | pleckstrin homology-like domain, family A, member 2 |
| PROS1 | protein S (alpha) |
| PRSS23 | protease, serine, 23 |
| PSD3 | pleckstrin and Sec7 domain containing 3 |
| QPCT | glutaminyl-peptide cyclotransferase (glutaminyl cyclase) |
| RXRG | retinoid X receptor, gamma |
| SCG5 | secretogranin V (7B2 protein) |
| SDC4 | syndecan 4 |
| SERPINA1 | serpin peptidase inhibitor, Glade A (alpha-1 antiproteinase, antitrypsin), member 1 |
| SFTPB | surfactant, pulmonary-associated protein B |
| SPOCK1 | sparc/osteonectin, cwcv and kazal-like domains proteoglycan (testican) 1 |
| ST14 | suppression of tumorigenicity 14 (colon carcinoma) |
| SYN1 | synapsin I |
| TGFA | transforming growth factor, alpha |
| TIMP1 | TIMP metallopeptidase inhibitor 1 |
| TUSC3 | tumor suppressor candidate 3 |
| Thyroid Benign- Increased Expression | |
| BCL2 | BCL2-antagonist of cell death |
| CDH16 | cadherin 16, KSP-cadherin |
| COL9A3 | collagen, type IX, alpha 3 |
| CRABP1 | cellular retinoic acid binding protein 1 |
| CSNK1G2 | casein kinase 1, gamma 2 |
| DIO1 | deiodinase, iodothyronine, type I |
| FABP4 | fatty acid binding protein 4, adipocyte |
| FCGBP | Fc fragment of IgG binding protein |
| FCGRT | Fc fragment of IgG, receptor, transporter, alpha |
| HBA2 | hemoglobin, alpha 2 |
| ID4 | inhibitor of DNA binding 4, dominant negative helix-loop-helix protein |
| ITPR1 | inositol 1,4,5-triphosphate receptor, type 1 |
| KCNAB1 | potassium voltage-gated channel, shaker-related subfamily, beta member 1 |
| MPPED2 | metallophosphoesterase domain containing 2 |
| MT1G | metallothionein 1G |
| MT1X | metallothionein 1X |
| MTF1 | metal-regulatory transcription factor 1 |
| RAB23 | RAB23, member RAS oncogene family |
| RGS16 | regulator of G-protein signaling 16 |
| TFF3 | trefoil factor 3 (intestinal) |
| TPO | thyroid peroxidase |

TABLE 3

A subset of PSRs used to generate a 10-RNA metagene. These PSRs were identified based on differentially expression in a training subset of thyroid nodule disease specimens (Table 1), selected using an independent testing subset of thyroid nodule disease specimens with the Nearest Shrunken Centroids algorithm. Indicated are the Affymetrix PSR ID, mean-fold difference in expression (FD), positive and negative weighting factors, which indicate increased expression in malignant and benign samples, respectively. Also noted are the location of the PSRs in the genome and their location relative to the closest annotated gene as well as whether or not the RNA sequence targeted by the PSR overlaps with the protein-coding sequence of the gene. These PSRs were used to derive the 10-RNA metagenes by taking a linear combination of expression measurements multiplied by weighting factors and generate POP scores as depicted in FIG. 3A

| SEQ ID | Affymetrix ID | FD | Weights | CHR | Strand | Location | Proximal Gene | Probeset Overlaps CDS |
|---|---|---|---|---|---|---|---|---|
| 1 | 3536736 | 8.8 | 5.0 | 14 | + | In INTRON #4 | Lectin, galactoside-binding, soluble, 3 | FALSE |
| 2 | 3460518 | 19.0 | 7.4 | 12 | − | In INTRON #3 | High mobility group AT-hook 2 | FALSE |
| 3 | 2526817 | 11.1 | 6.5 | 2 | + | In INTRON #40 | Fibronectin 1 | FALSE |
| 4 | 3420374 | 10.4 | 6.0 | 12 | + | In INTRON #3 | High mobility group AT-hook 2 | FALSE |
| 5 | 3976358 | 10.3 | 6.9 | X | + | In INTRON #5 | Synapsin I | TRUE |
| 6 | 2828473 | 7.7 | 8.9 | 5 | + | In EXON #7 | PDZ and LIM domain 4 | FALSE |
| 7 | 3693001 | −12.5 | −6.3 | 16 | − | In EXON #3 | Metallothionein 1G | FALSE |
| 8 | 2508453 | −8.3 | −6.9 | 2 | + | In INTRON #1 | Low density lipoprotein-related protein 1B (deleted in tumors) | FALSE |
| 9 | 2537610 | −6.7 | −8.5 | 2 | − | In INTRON #15 | Thyroid peroxidase | FALSE |
| 10 | 2573597 | −6.3 | −7.4 | 2 | − | 4,295 3' | Transcription factor CP2-like 1 | FALSE |

TABLE 4

A subset of PSRs used to generate a 6-RNA metagene. These PSRs were identified based on differentially expression in a training subset of thyroid nodule disease specimens (Table 1), selected using an independent testing subset of thyroid nodule disease specimens with the Nearest Shrunken Centroids algorithm. Indicated are the Affymetrix PSR ID, mean-fold difference in expression (FD), positive and negative weighting factors, which indicate increased expression in malignant and benign samples, respectively. Also noted are the location of the PSRs in the genome and their location relative to the closest annotated gene as well as whether or not the RNA sequence targeted by the PSR overlaps with the protein-coding sequence of the gene. These PSRs were used to derive the 6-RNA metagenes by taking a linear combination of expression measurements multiplied by weighting factors and generate POP scores as depicted in FIG. 3B.

| SEQ ID | Affymetrix ID | FD | Weights | CHR | Strand | Location | Proximal Gene | Probeset Overlaps CDS |
|---|---|---|---|---|---|---|---|---|
| 1 | 3536736 | 8.8 | 5.0 | 14 | + | In INTRON #4 | Lectin, galactoside-binding, soluble, 3 | FALSE |
| 11 | 2830183 | 10.4 | 3.6 | 5 | + | In EXON #11 | Sparc/osteonectin, cwcv and kazal-like domains proteoglycan (testican) 1 | FALSE |
| 12 | 2491744 | 9.1 | 4.0 | 2 | + | In INTRON #10 | Surfactant, pulmonary-associated protein B | FALSE |
| 13 | 3329532 | 4.0 | 4.3 | 11 | + | In INTRON #2 | Low density lipoprotein receptor-related protein 4 | FALSE |
| 14 | 3104982 | −20.0 | −5.3 | 8 | + | In EXON #4 | Fatty acid binding protein 4, adipocyte | FALSE |
| 15 | 3913484 | −20.0 | −4.1 | 20 | − | In EXON #32 | Collagen, type IX, alpha 3 | FALSE |

TABLE 5

2 × 2 contigency table comparing the 'gold-standard' pathology review diagnosis of 58 thyroid nodule disease specimens with that of the POP scores using a cut-off ≥50 score for malignant disease and <50 score for benign disease classification. Note that both the 10-and 6-RNA metagene derived scores produced identical results using these cut-off criteria.

| | | Pathology Diagnosis | |
|---|---|---|---|
| | | Malignant | Benign |
| POP Scores | ≥50 | 23 | 0 |
| | <50 | 5 | 30 |

| | | 95% Cl |
|---|---|---|
| Sensitivity | 82 | (63-93) |
| Specificity | 100 | (88-100) |
| Positive Predictive Value | 100 | (85-100) |
| Negative Predictive Value | 86 | (69-95) |
| Accuracy | 91 | |
| Likelihood Ratio Positive Test | NaN | — |
| Likelihood Ratio Negative Test | 0.2 | (0.08-0.39) |

TABLE 6

2 × 2 contigency table comparing the 'gold-standard' pathology review diagnosis for 29 thyroid nodule disease specimens with that of the POP scores using a cut-off ≥50 score for malignant disease and <50 score for benign disease classification. This subset of specimens were all 'indeterminate' or 'suspicious for cancer' by FNAB cytology and could not be definitively diagnosed until review pathology was performed on the surgical specimens. Note that both the 10- and 6-RNA metagene derived scores produced identical results using these cut-off criteria.

| | | Pathology Diagnosis | |
|---|---|---|---|
| | | Malignant | Benign |
| POP Scores | ≥50 | 9 | 0 |
| | <50 | 5 | 15 |

| | | 95% Cl |
|---|---|---|
| Sensitivity | 64 | (35-87) |
| Specificity | 100 | (78-100) |
| Positive Predictive Value | 100 | (66-100) |
| Negative Predictive Value | 75 | (50-91) |
| Accuracy | 83 | |
| Likelihood Ratio Positive Test | NaN | — |
| Likelihood Ratio Negative Test | 0.36 | (0.18-0.72) |

TABLE 7

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 1 | 8.8 | 5.0 | 14 | + | intron | Lectin, galactoside-binding, soluble, 3 | NC |
| 2 | 19.0 | 7.4 | 12 | − | intron/ antisense | High mobility group AT-hook 2 | NC |
| 3 | 11.1 | 6.5 | 2 | + | intron/ antisense | Fibronectin 1 | NC |
| 4 | 10.4 | 6.0 | 12 | + | intron | High mobility group AT-hook 2 | NC |
| 5 | 10.3 | 6.9 | X | + | intron/ antisense | Synapsin I | CDS |
| 6 | 7.7 | 8.9 | 5 | + | exon | PDZ and LIM domain 4 | NC |
| 7 | −12.5 | −6.3 | 16 | − | exon | Metallothionein 1G | NC |
| 8 | −8.3 | −6.9 | 2 | + | intron/ antisense | Low density lipoprotein-related protein 1B (deleted in tumors) | NC |
| 9 | −6.7 | −8.5 | 2 | − | intron I antisense | Thyroid peroxidase | NC |
| 10 | −6.3 | −7.4 | 2 | − | extra-genic | Transcription factor CP2-like 1 | NC |
| 11 | 10.4 | 3.6 | 5 | + | exon | Sparc/osteonectin, cwcv and kazal-like domains proteoglycan (testican) 1 | NC |
| 12 | 9.1 | 4.0 | 2 | + | intron | Surfactant, pulmonary-associated protein B | NC |
| 13 | 4.0 | 4.3 | 11 | + | intron I antisense | Low density lipoprotein receptor-related protein 4 | NC |
| 14 | −20.0 | −5.3 | 8 | + | exon | Fatty acid binding protein 4, adipocyte | NC |
| 15 | −20.0 | −4.1 | 20 | − | exon | Collagen, type IX, alpha 3 | NC |
| 16 | 65.6 | 6.5 | 5 | + | exon | Solute carrier family 27 (fatty acid transporter), member 6 | CDS |
| 17 | 61.3 | 7.8 | 13 | + | extra-genic | Cysteinyl leukotriene receptor 2 | NC |
| 18 | 46.1 | 6.4 | 1 | + | exon | Chitinase 3-like 1 (cartilage glycoprotein-39) | NC |
| 19 | 34.0 | 7.2 | 19 | − | exon/ antisense | Apolipoprotein C-I | NC |
| 20 | 28.6 | 6.5 | 1 | + | exon | Tumor-associated calcium signal transducer 2 | NC |
| 21 | 27.7 | 6.7 | 1 | + | intron | ST6 (alpha-N-acetyl-neuraminyl-2,3-beta-galactosy1-1,3)-N-acetylgalactosaminide alpha-2,6-sialyltransferase 5 | NC |
| 22 | 27.6 | 5.1 | 2 | − | intron | Surfactant, pulmonary-associated protein B | NC |
| 23 | 26.3 | 4.7 | 5 | + | exon | Solute carrier family 27 (fatty acid transporter), member 6 | NC |
| 24 | 26.0 | 5.6 | 2 | − | intron | Fibronectin 1 | NC |
| 25 | 25.9 | 4.2 | 5 | + | exon | Chemokine (C—X—C motif) ligand 14 | NC |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 26 | 24.9 | 5.4 | 2 | − | intron | Fibronectin 1 | NC |
| 27 | 23.4 | 5.6 | 3 | − | extra-genic | Lipase, member H | NC |
| 28 | 22.6 | 7.2 | 2 | − | exon | Surfactant, pulmonary-associated protein B | NC |
| 29 | 20.9 | 4.4 | 2 | − | intron | Surfactant, pulmonary-associated protein B | NC |
| 30 | 20.7 | 7.0 | 3 | + | extra-genic | Ecotropic viral integration site 1 | NC |
| 31 | 20.6 | 6.5 | 1 | − | extra-genic | Retinoid X receptor, gamma | NC |
| 32 | 20.4 | 4.3 | 5 | − | exon | Chemokine (C—X—C motif) ligand 14 | CDS |
| 33 | 19.4 | 6.0 | 2 | − | intron | Fibronectin 1 | NC |
| 34 | 18.9 | 6.2 | 1 | − | exon | Tumor-associated calcium signal transducer 2 | NC |
| 35 | 18.8 | 5.0 | 2 | − | intron | Surfactant, pulmonary-associated protein B | NC |
| 36 | 18.5 | 5.4 | 2 | − | exon | Cytochrome P450, family 1, subfamily B, polypeptide 1 | NC |
| 37 | 18.3 | 8.9 | 12 | + | intron | High mobility group AT-hook 2 | NC |
| 38 | 18.2 | 6.1 | 2 | − | intron | Fibronectin 1 | NC |
| 39 | 18.0 | 4.7 | 10 | + | extra-genic | CUE domain containing 2 | NC |
| 40 | 17.8 | 4.7 | 1 | − | exon | Chitinase 3-like 1 (cartilage glycoprotein-39) | NC |
| 41 | 17.8 | 5.4 | 12 | − | intron/antisense | High mobility group AT-hook 2 | NC |
| 42 | 17.5 | 4.7 | 2 | − | exon | Fibronectin 1 | NC |
| 43 | 17.2 | 6.0 | 1 | + | intron | ST6 (alpha-N-acetyl-neuraminyl-2,3-beta-galactosy1-1,3)-N-acetylgalactosaminide alpha-2,6-sialyltransferase 5 | NC |
| 44 | 16.5 | 4.4 | 2 | − | exon | Fibronectin 1 | CDS |
| 45 | 16.2 | 4.9 | 4 | + | exon | Solute carrier family 34 (sodium phosphate), member 2 | CDS |
| 46 | 15.8 | 5.3 | 2 | − | exon | Fibronectin 1 | CDS |
| 47 | 15.7 | 5.3 | 2 | − | exon | Fibronectin 1 | NC |
| 48 | 15.6 | 6.4 | 2 | − | exon | Fibronectin 1 | CDS |
| 49 | 15.5 | 6.4 | 7 | − | exon | Putative binding protein 7a5 | NC |
| 50 | 14.4 | 4.0 | 2 | + | intron | Interleukin 1 receptor-like 1 | NC |
| 51 | 14.0 | 5.4 | 3 | − | exon | Lipase, member H | NC |
| 52 | 13.9 | 6.8 | 2 | + | exon | Cytochrome P450, family 1, subfamily B, polypeptide 1 | NC |
| 53 | 13.8 | 4.8 | 1 | − | extra-genic | Dehydrogenase/reductase (SDR family) member 3 | NC |
| 54 | 13.2 | 5.8 | 12 | + | intron | High mobility group AT-hook 2 | NC |
| 55 | 13.2 | 6.4 | 2 | + | exon/antisense | Fibronectin 1 | NC |
| 56 | 13.0 | 6.4 | 2 | − | exon | Fibronectin 1 | CDS |
| 57 | 12.6 | 5.0 | 7 | − | intron I antisense | Sidekick homolog 1, cell adhesion molecule (chicken) | NC |
| 58 | 12.6 | 5.4 | 14 | + | intron | Lectin, galactoside-binding, soluble, 3 | NC |
| 59 | 12.4 | 6.8 | 2 | + | exon | Cytochrome P450, family 1, subfamily B, polypeptide 1 | NC |
| 60 | 12.2 | 4.7 | 19 | + | exon | Cytochrome P450, family 2, subfamily S, polypeptide 1 | NC |
| 61 | 12.1 | 4.0 | 5 | − | exon | Chemokine (C—X—C motif) ligand 14 | NC |
| 62 | 12.1 | 4.5 | 8 | + | exon | Transmembrane 7 superfamily member 4 | NC |
| 63 | 12.0 | 4.9 | 1 | − | exon | Retinoid X receptor, gamma | CDS |
| 64 | 11.8 | 6.8 | 16 | − | exon | Cadherin 3, type 1, P-cadherin (placental) | NC |
| 65 | 11.7 | 5.5 | 1 | + | extra-genic | E74-like factor 3 (ets domain transcription factor, epithelial-specific) | NC |
| 66 | 11.6 | 4.8 | 19 | − | exon | [NM_000064] | CDS |
| 67 | 11.6 | 4.5 | 2 | + | intron/antisense | Fibronectin 1 | NC |
| 68 | 11.6 | 5.3 | 3 | + | extra-genic | Golgi integral membrane protein 4 | NC |
| 69 | 11.6 | 5.4 | 3 | + | extra-genic | Ecotropic viral integration site 1 | NC |
| 70 | 11.5 | 5.8 | 2 | − | intron | Fibronectin 1 | NC |
| 71 | 11.4 | 4.2 | 4 | − | exon/promoter | Chemokine (C—X—C motif) ligand 2 | NC |
| 72 | 11.2 | 5.1 | 12 | + | exon | Plexin Cl | CDS |
| 73 | 11.2 | 4.9 | 19 | + | exon | Apolipoprotein E | NC |
| 74 | 11.1 | 6.1 | 2 | − | intron | Fibronectin 1 | NC |
| 75 | 11.0 | 5.2 | 1 | − | exon | Chitinase 3-like 1 (cartilage glycoprotein-39) | NC |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 76 | 10.5 | 3.8 | 2 | − | intron | Ornithine decarboxylase 1 | NC |
| 77 | 10.4 | 4.1 | 9 | − | intron | Tenascin C (hexabrachion) | NC |
| 78 | 10.3 | 4.4 | 1 | + | exon | Stratifin | NC |
| 79 | 10.3 | 5.9 | 2 | − | exon | Fibronectin 1 | CDS |
| 80 | 10.3 | 5.6 | 2 | + | exon/ antisense | Fibronectin 1 | NC |
| 81 | 10.2 | 5.5 | 2 | − | exon | Fibronectin 1 | CDS |
| 82 | 10.1 | 4.9 | 3 | − | exon | Claudin 1 | CDS |
| 83 | 10.1 | 5.7 | 14 | − | exon | Serpin peptidase inhibitor, Glade A (alpha-1 antiproteinase, antitrypsin), member 1 | CDS |
| 84 | 10.0 | 4.0 | 2 | + | intron/ antisense | Fibronectin 1 | NC |
| 85 | 9.9 | 4.1 | 12 | + | intron | High mobility group AT-hook 2 | NC |
| 86 | 9.8 | 4.3 | 2 | − | exon | Fibronectin 1 | CDS |
| 87 | 9.7 | 5.6 | 2 | − | exon | Fibronectin 1 | CDS |
| 88 | 9.6 | 5.4 | 14 | + | intron | Lectin, galactoside-binding, soluble, 3 | NC |
| 89 | 9.6 | 5.9 | 2 | − | exon | Fibronectin 1 | CDS |
| 90 | 9.5 | 4.6 | 3 | + | extra-genic | Golgi integral membrane protein 4 | NC |
| 91 | 9.5 | 5.2 | 2 | − | intron | Fibronectin 1 | NC |
| 92 | 9.5 | 5.4 | 20 | − | exon | R-spondin family, member 4 | NC |
| 93 | 9.4 | 5.5 | 14 | + | exon I antisense | Serpin peptidase inhibitor, Glade A (alpha-1 antiproteinase, antitrypsin), member 1 | NC |
| 94 | 9.4 | 4.1 | 1 | + | exon | Regulator of G-protein signaling 1 | NC |
| 95 | 9.3 | 4.3 | 10 | + | intron | Protein tyrosine phosphatase, receptor type, E | NC |
| 96 | 9.2 | 4.6 | 2 | − | exon | Fibronectin 1 | CDS |
| 97 | 9.2 | 4.9 | 12 | − | exon | NEL-like 2 (chicken) | CDS |
| 98 | 9.1 | 5.6 | 2 | − | exon | Fibronectin 1 | CDS |
| 99 | 9.1 | 5.5 | 2 | − | exon | Fibronectin 1 | CDS |
| 100 | 9.1 | 4.3 | 3 | + | exon I promoter | Growth associated protein 43 | CDS |
| 101 | 9.1 | 4.6 | 3 | + | extra-genic | Ecotropic viral integration site 1 | NC |
| 102 | 9.0 | 4.1 | 2 | − | intron | Fibronectin 1 | NC |
| 103 | 9.0 | 4.5 | 2 | − | exon | Fibronectin 1 | CDS |
| 104 | 9.0 | 6.4 | 10 | + | intron | Protein tyrosine phosphatase, receptor type, E | NC |
| 105 | 9.0 | 3.8 | 12 | − | intron/ antisense | High mobility group AT-hook 2 | NC |
| 106 | 8.9 | 4.8 | 2 | − | exon | Fibronectin 1 | CDS |
| 107 | 8.8 | 5.2 | 1 | − | exon | Collagen, type VIII, alpha 2 | NC |
| 108 | 8.8 | 5.1 | 1 | − | exon | Calcium/calmodulin-dependent protein kinase II inhibitor 1 | NC |
| 109 | 8.8 | 4.5 | 2 | − | intron | Fibronectin 1 | CDS |
| 110 | 8.8 | 5.2 | 4 | + | exon | Solute carrier family 34 (sodium phosphate), member 2 | CDS |
| 111 | 8.8 | 4.7 | 12 | + | intron | High mobility group AT-hook 2 | NC |
| 112 | 8.7 | 4.0 | 12 | − | exon/ promoter | NEL-like 2 (chicken) | NC |
| 113 | 8.7 | 4.2 | 1 | − | extra-genic | Kin of IRRE like (*Drosophila*) | NC |
| 114 | 8.7 | 5.4 | 2 | − | exon | Fibronectin 1 | CDS |
| 115 | 8.6 | 5.8 | 2 | − | exon | Fibronectin 1 | CDS |
| 116 | 8.5 | 3.9 | 11 | − | intron | Ankyrin repeat and BTB (POZ) domain containing 2 | NC |
| 117 | 8.5 | 4.0 | 6 | + | intron/ antisense | Dystonin | NC |
| 118 | 8.4 | 4.1 | 4 | + | exon | Solute carrier family 34 (sodium phosphate), member 2 | NC |
| 119 | 8.3 | 5.0 | 14 | − | exon | Serpin peptidase inhibitor, Glade A (alpha-1 antiproteinase, antitrypsin), member 1 | CDS |
| 120 | 8.1 | 3.9 | 13 | + | exon | Sciellin | CDS |
| 121 | 8.1 | 4.3 | 2 | − | exon | Fibronectin 1 | CDS |
| 122 | 8.1 | 5.0 | 5 | + | intron | PDZ and LIM domain 4 | NC |
| 123 | 8.1 | 6.4 | 1 | − | exon | Calcium/calmodulin-dependent protein kinase II inhibitor 1 | NC |
| 124 | 8.1 | 5.1 | 21 | − | intron | T-cell lymphoma invasion and metastasis 1 | NC |
| 125 | 8.1 | 4.8 | 4 | + | exon | Solute carrier family 34 (sodium phosphate), member 2 | NC |
| 126 | 8.0 | 5.4 | 2 | − | exon | Fibronectin 1 | CDS |
| 127 | 8.0 | 4.8 | 2 | − | exon | Fibronectin 1 | CDS |
| 128 | 8.0 | 6.1 | 19 | + | exon | Kallikrein-related peptidase 7 | NC |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 129 | 7.9 | 5.3 | 2 | + | intron/ antisense | Fibronectin 1 | NC |
| 130 | 7.9 | 5.0 | 2 | − | exon | Fibronectin 1 | CDS |
| 131 | 7.9 | 4.1 | 2 | − | intron | Fibronectin 1 | NC |
| 132 | 7.9 | 4.3 | 3 | + | exon | Transmembrane 4 L six family member 4 | NC |
| 133 | 7.9 | 4.6 | 2 | − | intron | Fibronectin 1 | NC |
| 134 | 7.9 | 4.1 | 16 | + | exon | Tumor necrosis factor receptor superfamily, member 12A | CDS |
| 135 | 7.8 | 5.0 | 2 | − | exon | Transmembrane protein 166 | NC |
| 136 | 7.8 | 4.8 | 2 | − | exon | Fibronectin 1 | NC |
| 137 | 7.6 | 5.3 | 14 | + | exon/ antisense | Serpin peptidase inhibitor, Glade A (alpha-1 antiproteinase, antitrypsin), member 1 | NC |
| 138 | 7.6 | 5.5 | 2 | − | exon | Fibronectin 1 | CDS |
| 139 | 7.6 | 5.7 | 2 | − | intron | Fibronectin 1 | NC |
| 140 | 7.6 | 4.2 | 4 | + | exon | Solute carrier family 34 (sodium phosphate), member 2 | NC |
| 141 | 7.6 | 4.2 | 13 | + | exon | Cysteinyl leukotriene receptor 2 | NC |
| 142 | 7.5 | 6.4 | 12 | + | intron | Prickle homolog 1 (*Drosophila*) | NC |
| 143 | 7.5 | 3.7 | 15 | − | exon | Aldehyde dehydrogenase 1 family, member A3 | NC |
| 144 | 7.5 | 4.7 | 7 | + | extra-genic | Putative binding protein 7a5 | NC |
| 145 | 7.4 | 6.3 | 2 | − | exon | Fibronectin 1 | CDS |
| 146 | 7.4 | 5.1 | 2 | − | exon | Fibronectin 1 | CDS |
| 147 | 7.4 | 3.8 | 4 | + | exon | Solute carrier family 34 (sodium phosphate), member 2 | CDS |
| 148 | 7.4 | 6.3 | 2 | + | intron/ antisense | Fibronectin 1 | NC |
| 149 | 7.3 | 3.8 | 6 | − | exon | Triggering receptor expressed on myeloid cells 2 | NC |
| 150 | 7.3 | 5.1 | 2 | + | exon | Fibronectin 1 | NC |
| 151 | 7.3 | 4.5 | 2 | − | exon | Fibronectin 1 | CDS |
| 152 | 7.2 | 3.7 | 10 | + | extra-genic | Inositol polyphosphate multikinase | NC |
| 153 | 7.2 | 4.3 | 1 | + | extra-genic | Solute carrier family 6 (neurotransmitter transporter, glycine), member 9 | NC |
| 154 | 7.2 | 4.1 | 12 | − | exon | Oxidized low density lipoprotein (lectin-like) receptor 1 | NC |
| 155 | 7.2 | 5.1 | 11 | + | exon | Cystatin E/M | NC |
| 156 | 7.2 | 3.9 | 12 | − | exon | High mobility group AT-hook 2 | NC |
| 157 | 7.1 | 4.4 | 2 | − | exon | Fibronectin 1 | CDS |
| 158 | 7.1 | 4.3 | 16 | + | exon | Cadherin 3, type 1, P-cadherin (placental) | NC |
| 159 | 7.0 | 5.2 | 2 | − | exon | Fibronectin 1 | CDS |
| 160 | 7.0 | 5.1 | 2 | − | exon | Fibronectin 1 | CDS |
| 161 | 7.0 | 5.3 | 2 | − | exon | Fibronectin 1 | CDS |
| 162 | 7.0 | 4.1 | 11 | − | extra-genic | [NM_001004729] | NC |
| 163 | 6.9 | 3.9 | 4 | + | exon | Solute carrier family 34 (sodium phosphate), member 2 | NC |
| 164 | 6.9 | 4.3 | 10 | + | intron | Protein tyrosine phosphatase, receptor type, E | NC |
| 165 | 6.9 | 5.5 | 2 | − | exon | Fibronectin 1 | CDS |
| 166 | 6.8 | 4.0 | 3 | − | intron | Insulin-like growth factor 2 mRNA binding protein 2 | NC |
| 167 | 6.8 | 3.9 | 22 | − | exon | Leukemia inhibitory factor (cholinergic differentiation factor) | NC |
| 168 | 6.8 | 4.4 | X | + | extra-genic | Mastermind-like domain containing 1 | NC |
| 169 | 6.8 | 5.2 | 4 | + | exon | Secreted phosphoprotein 1 (osteopontin, bone sialoprotein I, early T-lymphocyte activation 1) | NC |
| 170 | 6.8 | 5.5 | 2 | − | intron | Fibronectin 1 | NC |
| 171 | 6.7 | 4.3 | 5 | + | intron | Integrin, alpha 2 (CD49B, alpha 2 subunit of VLA-2 receptor) | NC |
| 172 | 6.7 | 5.0 | 2 | − | exon | Fibronectin 1 | CDS |
| 173 | 6.7 | 3.8 | 4 | − | exon | Phosphodiesterase 5A, cGMP-specific | NC |
| 174 | 6.7 | 3.8 | 2 | − | exon | Fibronectin 1 | CDS |
| 175 | 6.7 | 7.0 | 17 | − | exon | Phospholipase C, delta 3 | NC |
| 176 | 6.6 | 3.7 | 2 | − | intron | LON peptidase N-terminal domain and ring finger 2 | NC |
| 177 | 6.5 | 5.0 | 7 | + | intron | Sidekick homolog 1, cell adhesion molecule (chicken) | NC |
| 178 | 6.5 | 5.6 | 2 | − | exon | Fibronectin 1 | CDS |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 179 | 6.4 | 4.2 | 1 | + | exon | Microfibrillar-associated protein 2 | NC |
| 180 | 6.3 | 6.8 | 1 | − | exon | Calcium/calmodulin-dependent protein kinase II inhibitor 1 | CDS |
| 181 | 6.3 | 5.2 | 2 | − | exon | Fibronectin 1 | CDS |
| 182 | 6.3 | 3.9 | 4 | + | exon | Solute carrier family 34 (sodium phosphate), member 2 | CDS |
| 183 | 6.2 | 5.7 | 2 | − | exon | Fibronectin 1 | CDS |
| 184 | 6.2 | 4.3 | 4 | + | exon | Solute carrier family 34 (sodium phosphate), member 2 | CDS |
| 185 | 6.2 | 3.7 | 17 | − | extra-genic | IKAROS family zinc finger 3 (Aiolos) | NC |
| 186 | 6.2 | 4.9 | 2 | − | intron | Fibronectin 1 | NC |
| 187 | 6.2 | 4.6 | 17 | − | intron | Family with sequence similarity 20, member A | NC |
| 188 | 6.2 | 5.4 | 14 | − | exon | Serpin peptidase inhibitor, Glade A (alpha-1 antiproteinase, antitrypsin), member 1 | CDS |
| 189 | 6.1 | 4.1 | 4 | + | exon | Complement factor I | NC |
| 190 | 6.1 | 5.5 | 2 | − | exon | Fibronectin 1 | CDS |
| 191 | 6.1 | 4.3 | 2 | + | intron/ antisense | Fibronectin 1 | NC |
| 192 | 6.1 | 5.7 | 10 | + | extra-genic | CUE domain containing 2 | NC |
| 193 | 6.1 | 3.7 | 12 | + | extra-genic | [NM_001013690] | NC |
| 194 | 6.1 | 5.6 | 2 | + | exon/ antisense | Fibronectin 1 | NC |
| 195 | 6.1 | 3.9 | 7 | − | intron | Putative binding protein 7a5 | NC |
| 196 | 6.1 | 4.8 | 2 | − | exon | Fibronectin 1 | CDS |
| 197 | 6.0 | 5.0 | 2 | − | exon | Fibronectin 1 | NC |
| 198 | 6.0 | 5.6 | 2 | − | exon | Fibronectin 1 | CDS |
| 199 | 6.0 | 3.7 | 5 | + | exon | Solute carrier family 27 (fatty acid transporter), member 6 | CDS |
| 200 | 6.0 | 3.9 | 11 | + | exon | Ets homologous factor | CDS |
| 201 | 6.0 | 5.5 | 7 | − | extra-genic | Putative binding protein 7a5 | NC |
| 202 | 6.0 | 5.0 | 2 | − | exon | Fibronectin 1 | CDS |
| 203 | 5.9 | 5.3 | 2 | − | exon | Fibronectin 1 | CDS |
| 204 | 5.9 | 4.1 | 12 | + | intron | High mobility group AT-hook 2 | NC |
| 205 | 5.8 | 4.1 | 2 | − | exon | Fibronectin 1 | CDS |
| 206 | 5.8 | 5.6 | 2 | − | exon | Fibronectin 1 | CDS |
| 207 | 5.8 | 4.0 | 12 | + | exon | Beta-1,4-N-acetyl-galactosaminyl transferase 3 | CDS |
| 208 | 5.7 | 4.9 | 4 | − | exon | Chemokine (C—X—C motif) ligand 2 | NC |
| 209 | 5.7 | 6.3 | 12 | − | intron | Prickle homolog 1 (*Drosophila*) | NC |
| 210 | 5.7 | 4.4 | 13 | − | extra-genic | Cysteinyl leukotriene receptor 2 | NC |
| 211 | 5.7 | 3.9 | 2 | + | exon/ antisense | Fibronectin 1 | NC |
| 212 | 5.7 | 4.5 | 19 | − | exon | Leucine-rich alpha-2-glycoprotein 1 | NC |
| 213 | 5.6 | 4.6 | 2 | − | intron | Fibronectin 1 | NC |
| 214 | 5.6 | 4.8 | 12 | + | exon | High mobility group AT-hook 2 | NC |
| 215 | 5.6 | 4.8 | 3 | + | extra-genic | Golgi integral membrane protein 4 | NC |
| 216 | 5.4 | 3.7 | 6 | − | exon | Runt-related transcription factor 2 | NC |
| 217 | 5.4 | 4.0 | 4 | + | exon | Solute carrier family 34 (sodium phosphate), member 2 | NC |
| 218 | 5.4 | 4.3 | 12 | − | exon | NEL-like 2 (chicken) | CDS |
| 219 | 5.4 | 4.7 | 2 | − | exon | Fibronectin 1 | CDS |
| 220 | 5.3 | 4.3 | 3 | + | exon | Claudin 1 | NC |
| 221 | 5.3 | 3.7 | 3 | − | exon | Claudin 1 | NC |
| 222 | 5.3 | 3.7 | 4 | + | exon | Solute carrier family 34 (sodium phosphate), member 2 | CDS |
| 223 | 5.3 | 4.7 | 2 | − | exon | Fibronectin 1 | CDS |
| 224 | 5.2 | 5.3 | 4 | + | intron | Hypothetical protein FLJ20184 | NC |
| 225 | 5.1 | 4.4 | 2 | − | intron | Fibronectin 1 | NC |
| 226 | 5.1 | 4.5 | 2 | − | extra-genic | Pellino homolog 1 (*Drosophila*) | NC |
| 227 | 5.1 | 5.7 | 2 | + | intron/ antisense | Fibronectin 1 | NC |
| 228 | 5.1 | 3.9 | 12 | − | intron/ antisense | High mobility group AT-hook 2 | NC |
| 229 | 5.1 | 4.6 | 10 | + | exon | Protein tyrosine phosphatase, receptor type, E | NC |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 230 | 5.1 | 4.2 | 2 | − | exon | Fibronectin 1 | CDS |
| 231 | 5.1 | 4.1 | 3 | + | exon | Claudin 1 | NC |
| 232 | 5.0 | 3.7 | 2 | + | exon | Dipeptidyl-peptidase 4 (CD26, adenosine deaminase complexing protein 2) | NC |
| 233 | 5.0 | 4.5 | 2 | − | exon | Cytochrome P450, family 1, subfamily B, polypeptide 1 | NC |
| 234 | 5.0 | 4.5 | 14 | + | exon | Lectin, galactoside-binding, soluble, 3 | CDS |
| 235 | 4.9 | 7.0 | 1 | + | extra-genic | Vang-like 1 (van gogh, *Drosophila*) | NC |
| 236 | 4.8 | 4.9 | 17 | + | exon | ATP-binding cassette, sub-family C (CFTR/MRP), member 3 | NC |
| 237 | 4.7 | 4.3 | 17 | − | extra-genic | Trinucleotide repeat containing 6C | NC |
| 238 | 4.6 | 4.0 | 2 | + | intron/antisense | Fibronectin 1 | NC |
| 239 | 4.5 | 3.9 | 3 | + | intron | Interleukin 1 receptor accessory protein | NC |
| 240 | 4.4 | 4.1 | 3 | − | intron | Protein S (alpha) | NC |
| 241 | 4.4 | 4.3 | 2 | + | exon/antisense | Fibronectin 1 | NC |
| 242 | 4.4 | 3.8 | 4 | + | exon | Solute carrier family 34 (sodium phosphate), member 2 | CDS |
| 243 | 4.3 | 5.0 | 11 | + | exon | Cystatin E/M | CDS |
| 244 | 4.3 | 4.9 | 14 | + | exon | Lectin, galactoside-binding, soluble, 3 | CDS |
| 245 | 3.9 | 3.9 | 8 | − | exon | Dual specificity phosphatase 4 | NC |
| 246 | 3.9 | 4.3 | 4 | + | exon | Solute carrier family 34 (sodium phosphate), member 2 | CDS |
| 247 | 3.8 | 4.2 | 2 | + | exon | Neuropilin 2 | NC |
| 248 | 3.4 | 4.1 | 2 | − | intron | Fibronectin 1 | CDS |
| 249 | −50.0 | −6.3 | 2 | + | exon | Thyroid peroxidase | CDS |
| 250 | −33.3 | −6.5 | 2 | + | intron | Thyroid peroxidase | NC |
| 251 | −33.3 | −6.8 | 2 | + | extra-genic | Thyroid peroxidase | NC |
| 252 | −33.3 | −6.4 | 11 | − | extra-genic | Recombination activating gene 2 | NC |
| 253 | −25.0 | −5.7 | 1 | − | extra-genic | KIAA1324 | NC |
| 254 | −25.0 | −6.5 | 2 | + | exon/promoter | Thyroid peroxidase | NC |
| 255 | −25.0 | −5.4 | 2 | + | exon | Thyroid peroxidase | CDS |
| 256 | −25.0 | −6.0 | 2 | − | intron | Low density lipoprotein-related protein 1B (deleted in tumors) | NC |
| 257 | −25.0 | −4.8 | 8 | − | exon | Fatty acid binding protein 4, adipocyte | NC |
| 258 | −25.0 | −5.4 | 11 | − | intron | Metallophosphoesterase domain containing 2 | NC |
| 259 | −25.0 | −5.2 | 11 | − | exon/promoter | Metallophosphoesterase domain containing 2 | NC |
| 260 | −20.0 | −8.8 | 2 | + | exon | Thyroid peroxidase | CDS |
| 261 | −20.0 | −7.5 | 2 | + | intron | Thyroid peroxidase | NC |
| 262 | −20.0 | −5.3 | 8 | + | exon | Polycystic kidney and hepatic disease 1 (autosomal recessive)-like 1 | CDS |
| 263 | −20.0 | −5.6 | 8 | − | intron/antisense | Polycystic kidney and hepatic disease 1 (autosomal recessive)-like 1 | NC |
| 264 | −20.0 | −5.3 | 12 | − | intron | Solute carrier family 5 (iodide transporter), member 8 | NC |
| 265 | −20.0 | −5.6 | 15 | + | extra-genic | Interferon stimulated exonuclease gene 20 kDa-like 1 | NC |
| 266 | −16.7 | −7.5 | 2 | − | exon/antisense | Thyroid peroxidase | NC |
| 267 | −16.7 | −5.3 | 2 | − | intron | Low density lipoprotein-related protein 1B (deleted in tumors) | NC |
| 268 | −16.7 | −4.3 | 8 | + | exon | Polycystic kidney and hepatic disease 1 (autosomal recessive)-like 1 | CDS |
| 269 | −16.7 | −6.1 | 8 | − | extra-genic | Zinc finger, matrin type 4 | NC |
| 270 | −16.7 | −5.4 | 8 | − | extra-genic | Polycystic kidney and hepatic disease 1 (autosomal recessive)-like 1 | NC |
| 271 | −16.7 | −6.6 | 11 | + | extra-genic | Chromosome 11 open reading frame 74 | NC |
| 272 | −16.7 | −5.2 | 11 | − | intron | Metallophosphoesterase domain containing 2 | NC |
| 273 | −16.7 | −5.7 | 21 | − | exon | Trefoil factor 3 (intestinal) | NC |
| 274 | −14.3 | −6.8 | 2 | + | exon | Thyroid peroxidase | CDS |
| 275 | −14.3 | −4.8 | 2 | + | exon | Thyroid peroxidase | CDS |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 276 | −14.3 | −6.1 | 2 | − | intron | Low density lipoprotein-related protein 1B (deleted in tumors) | NC |
| 277 | −14.3 | −5.4 | 2 | − | exon | Low density lipoprotein-related protein 2 | CDS |
| 278 | −14.3 | −6.9 | 6 | − | intron/ antisense | Opioid receptor, mu 1 | CDS |
| 279 | −14.3 | −6.0 | 6 | − | intron/ antisense | Opioid receptor, mu 1 | NC |
| 280 | −14.3 | −4.4 | 7 | − | exon | Sema domain, immunoglobulin domain (Ig), short basic domain, secreted, (semaphorin) 3D | CDS |
| 281 | −14.3 | −4.6 | 8 | + | exon | Polycystic kidney and hepatic disease 1 (autosomal recessive)-like 1 | CDS |
| 282 | −14.3 | −4.6 | 8 | + | exon | Polycystic kidney and hepatic disease 1 (autosomal recessive)-like 1 | CDS |
| 283 | −14.3 | −5.7 | 11 | − | exon | Metallophosphoesterase domain containing 2 | NC |
| 284 | −14.3 | −6.7 | 21 | − | exon | Trefoil factor 3 (intestinal) | NC |
| 285 | −12.5 | −6.2 | 2 | + | extra-genic | Thyroid peroxidase | NC |
| 286 | −12.5 | −8.5 | 2 | − | exon/ antisense | Thyroid peroxidase | NC |
| 287 | −12.5 | −3.7 | 2 | − | extra-genic | ST6 beta-galactosamide alpha-2,6-sialyltranferase 2 | NC |
| 288 | −12.5 | −4.9 | 2 | − | exon | Nebulin | CDS |
| 289 | −12.5 | −5.7 | 4 | + | intron | V-kit Hardy-Zuckerman 4 feline sarcoma viral oncogene homolog | NC |
| 290 | −12.5 | −6.6 | 4 | + | extra-genic | [NM_152620] | NC |
| 291 | −12.5 | −5.5 | 5 | + | intron/ antisense | Sparc/osteonectin, cwcv and kazal-like domains proteoglycan (testican) 1 | NC |
| 292 | −12.5 | −4.4 | 7 | − | extra-genic | Solute carrier family 26, member 4 | NC |
| 293 | −12.5 | −8.0 | 8 | + | intron | EF-hand domain family, member A2 | NC |
| 294 | −12.5 | −4.5 | 8 | + | exon | Matrilin 2 | CDS |
| 295 | −12.5 | −4.0 | 8 | + | exon | Polycystic kidney and hepatic disease 1 (autosomal recessive)-like 1 | CDS |
| 296 | −12.5 | −4.2 | 8 | + | exon | Polycystic kidney and hepatic disease 1 (autosomal recessive)-like 1 | CDS |
| 297 | −12.5 | −4.2 | 8 | + | exon | Polycystic kidney and hepatic disease 1 (autosomal recessive)-like 1 | CDS |
| 298 | −12.5 | −3.7 | 8 | + | exon | Polycystic kidney and hepatic disease 1 (autosomal recessive)-like 1 | CDS |
| 299 | −12.5 | −4.9 | 10 | + | extra-genic | BCL2-associated athanogene 3 | NC |
| 300 | −12.5 | −5.5 | 11 | − | exon | Metallophosphoesterase domain containing 2 | CDS |
| 301 | −12.5 | −4.1 | 16 | + | exon | Metallothionein 1H | NC |
| 302 | −12.5 | −4.0 | 20 | + | exon | Collagen, type IX, alpha 3 | CDS |
| 303 | −11.1 | −4.9 | 2 | + | exon | Thyroid peroxidase | NC |
| 304 | −11.1 | −4.9 | 2 | − | intron | Low density lipoprotein-related protein 1B (deleted in tumors) | NC |
| 305 | −11.1 | −4.6 | 4 | + | intron | Sorbin and SH3 domain containing 2 | NC |
| 306 | −11.1 | −5.5 | 5 | + | intron | Transmembrane protein 171 | NC |
| 307 | −11.1 | −5.0 | 7 | + | exon | Solute carrier family 26, member 4 | CDS |
| 308 | −11.1 | −4.7 | 7 | − | extra-genic | Solute carrier family 26, member 4 | NC |
| 309 | −11.1 | −4.1 | 8 | + | intron | Solute carrier family 26, member 7 | NC |
| 310 | −11.1 | −4.5 | 8 | + | exon | Polycystic kidney and hepatic disease 1 (autosomal recessive)-like 1 | CDS |
| 311 | −11.1 | −4.8 | 8 | + | exon | Polycystic kidney and hepatic disease 1 (autosomal recessive)-like 1 | CDS |
| 312 | −11.1 | −7.4 | 8 | − | extra-genic | [NM_054028] | NC |
| 313 | −11.1 | −5.4 | 8 | − | exon | Chromosome 8 open reading frame 13 | NC |
| 314 | −11.1 | −5.2 | 8 | − | exon | Fatty acid binding protein 4, adipocyte | CDS |
| 315 | −11.1 | −4.0 | 8 | − | intron/ antisense | Solute carrier family 26, member 7 | NC |
| 316 | −11.1 | −5.7 | 9 | − | extra-genic | Insulin-like growth factor binding protein-like 1 | NC |
| 317 | −11.1 | −6.5 | 11 | + | intron | Chromosome 11 open reading frame 74 | NC |
| 318 | −11.1 | −7.0 | 12 | + | intron | Mitochondrial ribosomal protein S35 | NC |
| 319 | −11.1 | −5.5 | 13 | + | intron/ antisense | [NM_130785] | NC |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 320 | −11.1 | −5.2 | 14 | + | exon | Tudor domain containing 9 | NC |
| 321 | −11.1 | −6.0 | 16 | + | exon | Metallothionein 1G | NC |
| 322 | −11.1 | −5.3 | 16 | − | exon | Cadherin 16, KSP-cadherin | NC |
| 323 | −11.1 | −6.2 | 18 | − | extra-genic | Maestro | NC |
| 324 | −11.1 | −4.0 | 20 | + | exon | Collagen, type IX, alpha 3 | CDS |
| 325 | −10.0 | −4.5 | 1 | + | extra-genic | Enoyl Coenzyme A hydratase domain containing 2 | NC |
| 326 | −10.0 | −5.5 | 2 | + | exon | Thyroid peroxidase | CDS |
| 327 | −10.0 | −5.0 | 2 | + | intron | Thyroid peroxidase | NC |
| 328 | −10.0 | −5.9 | 2 | + | intron | Thyroid peroxidase | NC |
| 329 | −10.0 | −4.7 | 2 | + | extra-genic | Solute carrier family 5 (choline transporter), member 7 | NC |
| 330 | −10.0 | −4.7 | 2 | − | exon | [NM_001002036] | CDS |
| 331 | −10.0 | −4.2 | 3 | − | intron/antisense | Zinc finger protein 167 | NC |
| 332 | −10.0 | −5.7 | 4 | − | intron | Sorbin and SH3 domain containing 2 | NC |
| 333 | −10.0 | −5.7 | 4 | − | intron | Sorbin and SH3 domain containing 2 | NC |
| 334 | −10.0 | −6.0 | 5 | − | intron | Protein phosphatase 2 (formerly 2A), regulatory subunit B, beta isoform | NC |
| 335 | −10.0 | −6.0 | 6 | + | intron | Opioid receptor, mu 1 | NC |
| 336 | −10.0 | −4.7 | 7 | + | exon | Solute carrier family 26, member 4 | CDS |
| 337 | −10.0 | −3.8 | 8 | + | intron | Solute carrier family 26, member 7 | NC |
| 338 | −10.0 | −4.3 | 8 | + | exon | Solute carrier family 26, member 7 | CDS |
| 339 | −10.0 | −4.5 | 8 | + | exon | Solute carrier family 26, member 7 | CDS |
| 340 | −10.0 | −5.6 | 8 | + | exon | Matrilin 2 | CDS |
| 341 | −10.0 | −5.3 | 8 | + | exon | Polycystic kidney and hepatic disease 1 (autosomal recessive)-like 1 | CDS |
| 342 | −10.0 | −4.4 | 8 | + | exon | Polycystic kidney and hepatic disease 1 (autosomal recessive)-like 1 | CDS |
| 343 | −10.0 | −5.2 | 8 | + | extra-genic | Estrogen receptor binding site associated, antigen, 9 | NC |
| 344 | −10.0 | −6.7 | 11 | + | exon | Chromosome 11 open reading frame 74 | CDS |
| 345 | −10.0 | −5.0 | 11 | − | intron | Metallophosphoesterase domain containing 2 | NC |
| 346 | −10.0 | −4.2 | 15 | + | exon | Cellular retinoic acid binding protein 1 | NC |
| 347 | −10.0 | −4.2 | 15 | − | intron | Integrin, alpha 11 | NC |
| 348 | −10.0 | −5.5 | 21 | + | extra-genic | U2 small nuclear RNA auxiliary factor 1 | NC |
| 349 | −9.1 | −6.3 | 1 | + | intron | Glutathione S-transferase M4 | NC |
| 350 | −9.1 | −5.9 | 2 | + | intron/antisense | Low density lipoprotein-related protein 1B (deleted in tumors) | NC |
| 351 | −9.1 | −4.0 | 2 | + | extra-genic | Insulin receptor substrate 1 | NC |
| 352 | −9.1 | −4.6 | 2 | − | intron/antisense | Thyroid peroxidase | NC |
| 353 | −9.1 | −6.2 | 2 | − | intron/antisense | Thyroid peroxidase | NC |
| 354 | −9.1 | −5.4 | 2 | − | exon | Low density lipoprotein-related protein 1B (deleted in tumors) | CDS |
| 355 | −9.1 | −4.3 | 4 | + | exon | Sorbin and SH3 domain containing 2 | NC |
| 356 | −9.1 | −3.8 | 8 | + | exon | Polycystic kidney and hepatic disease 1 (autosomal recessive)-like 1 | CDS |
| 357 | −9.1 | −4.0 | 8 | + | exon | Polycystic kidney and hepatic disease 1 (autosomal recessive)-like 1 | CDS |
| 358 | −9.1 | −4.6 | 8 | − | intron/antisense | Thyroglobulin | NC |
| 359 | −9.1 | −4.9 | 9 | − | exon | Aldehyde dehydrogenase 1 family, member A1 | CDS |
| 360 | −9.1 | −6.6 | 11 | + | extra-genic | Chromosome 11 open reading frame 74 | NC |
| 361 | −9.1 | −6.1 | 11 | − | intron | Metallophosphoesterase domain containing 2 | NC |
| 362 | −9.1 | −4.3 | 11 | − | intron | Metallophosphoesterase domain containing 2 | NC |
| 363 | −9.1 | −5.2 | 12 | + | extra-genic | Chromosome 12 open reading frame 39 | NC |
| 364 | −9.1 | −5.5 | 12 | − | exon | Solute carrier family 5 (iodide transporter), member 8 | CDS |
| 365 | −9.1 | −4.8 | 20 | + | exon | Chromosome 20 open reading frame 39 | NC |
| 366 | −8.3 | −4.1 | 1 | + | exon | KIAA1324 | CDS |
| 367 | −8.3 | −5.1 | 2 | + | intron/promoter | Thyroid peroxidase | NC |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 368 | −8.3 | −6.3 | 2 | + | exon | Thyroid peroxidase | CDS |
| 369 | −8.3 | −5.7 | 2 | + | exon | Thyroid peroxidase | CDS |
| 370 | −8.3 | −4.9 | 2 | + | intron/ antisense | Low density lipoprotein-related protein 1B (deleted in tumors) | NC |
| 371 | −8.3 | −5.9 | 2 | − | intron | Low density lipoprotein-related protein 1B (deleted in tumors) | NC |
| 372 | −8.3 | −5.3 | 2 | − | intron | Low density lipoprotein-related protein 2 | NC |
| 373 | −8.3 | −7.0 | 4 | + | exon/ antisense | Peroxisome proliferator-activated receptor gamma, coactivator 1 alpha | NC |
| 374 | −8.3 | −5.3 | 4 | − | exon | Peroxisome proliferator-activated receptor gamma, coactivator 1 alpha | NC |
| 375 | −8.3 | −4.8 | 4 | − | exon | Peroxisome proliferator-activated receptor gamma, coactivator 1 alpha | NC |
| 376 | −8.3 | −6.0 | 4 | − | intron | Sorbin and SH3 domain containing 2 | NC |
| 377 | −8.3 | −5.5 | 4 | − | exon | Sorbin and SH3 domain containing 2 | CDS |
| 378 | −8.3 | −4.3 | 4 | − | intron | Sorbin and SH3 domain containing 2 | NC |
| 379 | −8.3 | −4.9 | 7 | + | exon | Solute carrier family 26, member 4 | CDS |
| 380 | −8.3 | −5.2 | 7 | + | exon | Solute carrier family 26, member 4 | CDS |
| 381 | −8.3 | −5.3 | 7 | + | exon | Solute carrier family 26, member 4 | NC |
| 382 | −8.3 | −5.6 | 8 | + | extra-genic | Chromosome 8 open reading frame 79 | NC |
| 383 | −8.3 | −7.1 | 8 | + | exon | Zinc finger, matrin type 4 | NC |
| 384 | −8.3 | −3.8 | 8 | + | intron | Solute carrier family 26, member 7 | NC |
| 385 | −8.3 | −4.2 | 8 | + | exon | Polycystic kidney and hepatic disease 1 (autosomal recessive)-like 1 | CDS |
| 386 | −8.3 | −4.1 | 8 | + | exon | Polycystic kidney and hepatic disease 1 (autosomal recessive)-like 1 | CDS |
| 387 | −8.3 | −5.5 | 8 | + | exon | Polycystic kidney and hepatic disease 1 (autosomal recessive)-like 1 | CDS |
| 388 | −8.3 | −3.9 | 8 | + | exon | Polycystic kidney and hepatic disease 1 (autosomal recessive)-like 1 | CDS |
| 389 | −8.3 | −3.8 | 8 | + | extra-genic | Polycystic kidney and hepatic disease 1 (autosomal recessive)-like 1 | NC |
| 390 | −8.3 | −4.1 | 8 | + | intron | Thyroglobulin | NC |
| 391 | −8.3 | −4.6 | 9 | − | intron | Leucine rich repeat and Ig domain containing 2 | NC |
| 392 | −8.3 | −6.1 | 11 | + | extra-genic | Zinc finger, DHHC-type containing 13 | NC |
| 393 | −8.3 | −4.3 | 11 | − | exon | Metallophosphoesterase domain containing 2 | CDS |
| 394 | −8.3 | −6.6 | 12 | − | exon | Solute carrier family 5 (iodide transporter), member 8 | CDS |
| 395 | −8.3 | −4.7 | 13 | − | exon | Centromere protein J | CDS |
| 396 | −8.3 | −7.4 | 14 | + | extra-genic | Tumor necrosis factor, alpha-induced protein 2 | NC |
| 397 | −8.3 | −4.8 | 14 | + | exon | Tudor domain containing 9 | CDS |
| 398 | −8.3 | −3.8 | 14 | − | exon | Deiodinase, iodothyronine, type II | CDS |
| 399 | −8.3 | −6.3 | 16 | + | extra-genic | Chromodomain helicase DNA binding protein 9 | NC |
| 400 | −7.7 | −3.9 | 1 | + | exon | Bone morphogenetic protein 8a | NC |
| 401 | −7.7 | −5.3 | 1 | + | intron | 6-phosphofructo-2-kinase/fructose-2,6-biphosphatase 2 | NC |
| 402 | −7.7 | −5.0 | 1 | + | extra-genic | RAB4A, member RAS oncogene family | NC |
| 403 | −7.7 | −8.5 | 2 | + | exon | Thyroid peroxidase | CDS |
| 404 | −7.7 | −3.8 | 2 | + | extra-genic | ST6 beta-galactosamide alpha-2,6-sialyltranferase 2 | NC |
| 405 | −7.7 | −4.8 | 2 | − | intron | Thyroid peroxidase | NC |
| 406 | −7.7 | −4.0 | 2 | − | exon | Low density lipoprotein-related protein 1B (deleted in tumors) | CDS |
| 407 | −7.7 | −6.7 | 2 | − | exon | Low density lipoprotein-related protein 2 | CDS |
| 408 | −7.7 | −4.2 | 2 | − | exon | Low density lipoprotein-related protein 2 | CDS |
| 409 | −7.7 | −7.2 | 2 | − | exon | Low density lipoprotein-related protein 2 | CDS |
| 410 | −7.7 | −5.7 | 3 | + | intron | Inositol 1,4,5-triphosphate receptor, type 1 | NC |
| 411 | −7.7 | −4.8 | 3 | + | extra-genic | RING1 and YY1 binding protein | NC |
| 412 | −7.7 | −5.2 | 4 | + | exon | Solute carrier family 4, sodium bicarbonate cotransporter, member 4 | NC |
| 413 | −7.7 | −4.7 | 4 | − | exon | Sorbin and SH3 domain containing 2 | NC |
| 414 | −7.7 | −6.4 | 5 | + | exon | Orthopedia homeobox | NC |
| 415 | −7.7 | −5.4 | 5 | + | exon | G protein-coupled receptor 98 | CDS |
| 416 | −7.7 | −4.9 | 7 | + | exon | Solute carrier family 26, member 4 | CDS |
| 417 | −7.7 | −5.6 | 7 | + | exon | Solute carrier family 26, member 4 | CDS |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 418 | −7.7 | −4.3 | 8 | + | intron | Solute carrier family 26, member 7 | NC |
| 419 | −7.7 | −5.3 | 8 | + | exon | Polycystic kidney and hepatic disease 1 (autosomal recessive)-like 1 | CDS |
| 420 | −7.7 | −7.9 | 9 | + | intron | Ubiquitin-conjugating enzyme E2R 2 | NC |
| 421 | −7.7 | −5.5 | 10 | − | exon | Oxoglutarate dehydrogenase-like | NC |
| 422 | −7.7 | −7.0 | 11 | − | extra-genic | Metallophosphoesterase domain containing 2 | NC |
| 423 | −7.7 | −5.6 | 11 | − | intron | Metallophosphoesterase domain containing 2 | NC |
| 424 | −7.7 | −5.3 | 11 | − | exon | Neural cell adhesion molecule 1 | NC |
| 425 | −7.7 | −5.2 | 12 | − | exon | Ankyrin repeat and sterile alpha motif domain containing 1B | CDS |
| 426 | −7.7 | −5.6 | 15 | + | extra-genic | Interferon stimulated exonuclease gene 20 kDa-like 1 | NC |
| 427 | −7.7 | −4.6 | 17 | + | intron I antisense | Solute carrier family 39 (metal ion transporter), member 11 | NC |
| 428 | −7.7 | −5.3 | 22 | + | exon | Myo-inositol oxygenase | NC |
| 429 | −7.1 | −4.0 | 2 | + | extra-genic | Insulin receptor substrate 1 | NC |
| 430 | −7.1 | −6.2 | 2 | − | intron/ antisense | Thyroid peroxidase | NC |
| 431 | −7.1 | −8.3 | 2 | − | exon | Lymphocyte antigen 75 | NC |
| 432 | −7.1 | −5.4 | 2 | − | exon | Low density lipoprotein-related protein 2 | CDS |
| 433 | −7.1 | −5.2 | 2 | − | exon | Low density lipoprotein-related protein 2 | CDS |
| 434 | −7.1 | −5.8 | 3 | − | intron | Sodium channel, voltage-gated, type V, alpha subunit | NC |
| 435 | −7.1 | −6.1 | 4 | + | exon | Peroxisome proliferator-activated receptor gamma, coactivator 1 alpha | NC |
| 436 | −7.1 | −5.1 | 4 | + | extra-genic | Solute carrier family 4, sodium bicarbonate cotransporter, member 4 | CDS |
| 437 | −7.1 | −4.5 | 4 | + | intron I antisense | Sorbin and SH3 domain containing 2 | NC |
| 438 | −7.1 | −5.6 | 4 | − | exon | Peroxisome proliferator-activated receptor gamma, coactivator 1 alpha | NC |
| 439 | −7.1 | −4.5 | 4 | − | exon | Sorbin and SH3 domain containing 2 | CDS |
| 440 | −7.1 | −4.6 | 7 | − | intron | Engulfment and cell motility 1 | NC |
| 441 | −7.1 | −4.1 | 8 | + | exon | Polycystic kidney and hepatic disease 1 (autosomal recessive)-like 1 | CDS |
| 442 | −7.1 | −4.6 | 8 | + | exon | Polycystic kidney and hepatic disease 1 (autosomal recessive)-like 1 | CDS |
| 443 | −7.1 | −5.0 | 8 | − | exon | RecQ protein-like 4 | CDS |
| 444 | −7.1 | −4.5 | 9 | − | intron | Guanine nucleotide binding protein (G protein), alpha 14 | NC |
| 445 | −7.1 | −5.5 | 11 | + | intron/ antisense | Metallophosphoesterase domain containing 2 | NC |
| 446 | −7.1 | −4.5 | 11 | − | intron | Metallophosphoesterase domain containing 2 | NC |
| 447 | −7.1 | −5.2 | 11 | − | intron | Metallophosphoesterase domain containing 2 | NC |
| 448 | −7.1 | −4.2 | 12 | + | intron | Zinc finger protein 664 | NC |
| 449 | −7.1 | −5.4 | 12 | − | extra-genic | Arginine vasopressin receptor 1A | NC |
| 450 | −7.1 | −5.7 | 15 | − | exon | WD repeat domain 72 | CDS |
| 451 | −7.1 | −4.4 | 17 | + | exon | Hepatic leukemia factor | NC |
| 452 | −6.7 | −4.7 | 2 | − | intron | Insulin receptor substrate 1 | NC |
| 453 | −6.7 | −5.9 | 4 | + | exon | V-kit Hardy-Zuckerman 4 feline sarcoma viral oncogene homolog | NC |
| 454 | −6.7 | −6.7 | 4 | − | exon | Peroxisome proliferator-activated receptor gamma, coactivator 1 alpha | NC |
| 455 | −6.7 | −4.3 | 5 | + | exon | Leukemia inhibitory factor receptor alpha | NC |
| 456 | −6.7 | −4.1 | 5 | − | intron | Kelch-like 3 (*Drosophila*) | NC |
| 457 | −6.7 | −7.0 | 6 | − | intron | Lymphocyte antigen 6 complex, locus G5C | CDS |
| 458 | −6.7 | −4.5 | 8 | + | exon | Chromosome 8 open reading frame 79 | NC |
| 459 | −6.7 | −3.9 | 8 | + | intron | Solute carrier family 26, member 7 | NC |
| 460 | −6.7 | −5.0 | 8 | + | exon | Matrilin 2 | NC |
| 461 | −6.7 | −5.2 | 8 | + | exon | Polycystic kidney and hepatic disease 1 (autosomal recessive)-like 1 | CDS |
| 462 | −6.7 | −5.2 | 8 | − | exon/ antisense | Matrilin 2 | NC |
| 463 | −6.7 | −4.1 | 8 | − | intron/ antisense | Thyroglobulin | NC |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 464 | −6.7 | −4.1 | 8 | − | intron/ antisense | Thyroglobulin | NC |
| 465 | −6.7 | −5.9 | 8 | − | intron/ antisense | Thyroglobulin | NC |
| 466 | −6.7 | −7.8 | 10 | − | intron | Methionine adenosyltransferase I, alpha | NC |
| 467 | −6.7 | −6.9 | 11 | + | extra-genic | Chromosome 11 open reading frame 74 | NC |
| 468 | −6.7 | −5.6 | 11 | + | extra-genic | Transmembrane protein 123 | NC |
| 469 | −6.7 | −4.1 | 11 | + | exon | Neural cell adhesion molecule 1 | NC |
| 470 | −6.7 | −3.9 | 11 | + | intron | Neural cell adhesion molecule 1 | NC |
| 471 | −6.7 | −4.2 | 11 | − | exon | Neural cell adhesion molecule 1 | NC |
| 472 | −6.7 | −4.4 | 17 | + | extra-genic | Breast carcinoma amplified sequence 3 | NC |
| 473 | −6.7 | −7.1 | 20 | + | intron | Phospholipase C, beta 4 | NC |
| 474 | −6.3 | −4.3 | 2 | + | intron | Thyroid peroxidase | CDS |
| 475 | −6.3 | −5.2 | 2 | + | extra-genic | ATP synthase, H+ transporting, mitochondrial FO complex, subunit C3 (subunit 9) | NC |
| 476 | −6.3 | −6.1 | 2 | − | intron/ antisense | Thyroid peroxidase | NC |
| 477 | −6.3 | −4.2 | 2 | − | exon | Low density lipoprotein-related protein 1B (deleted in tumors) | CDS |
| 478 | −6.3 | −7.1 | 3 | + | extra-genic | Roundabout, axon guidance receptor, homolog 2 (*Drosophila*) | NC |
| 479 | −6.3 | −5.1 | 4 | + | exon | Solute carrier family 4, sodium bicarbonate cotransporter, member 4 | CDS |
| 480 | −6.3 | −5.4 | 4 | + | exon | Solute carrier family 4, sodium bicarbonate cotransporter, member 4 | NC |
| 481 | −6.3 | −5.3 | 4 | − | intron | Sorbin and SH3 domain containing 2 | NC |
| 482 | −6.3 | −4.6 | 5 | − | exon | Leukemia inhibitory factor receptor alpha | CDS |
| 483 | −6.3 | −6.0 | 5 | − | exon | Leukemia inhibitory factor receptor alpha | CDS |
| 484 | −6.3 | −6.0 | 7 | + | exon | Solute carrier family 26, member 4 | CDS |
| 485 | −6.3 | −5.3 | 7 | − | intron | Engulfment and cell motility 1 | NC |
| 486 | −6.3 | −5.3 | 8 | + | exon | Chondroitin beta 1,4 N-acetylgalactosaminyltransferase | NC |
| 487 | −6.3 | −4.4 | 8 | + | intron | Thyroglobulin | NC |
| 488 | −6.3 | −3.8 | 8 | + | intron | Thyroglobulin | NC |
| 489 | −6.3 | −7.1 | 8 | − | exon | Zinc finger, matrin type 4 | CDS |
| 490 | −6.3 | −5.1 | 11 | + | exon | Cdon homolog (mouse) | NC |
| 491 | −6.3 | −4.9 | 14 | − | extra-genic | General transcription factor IIA, 1. 19/37 kDa | NC |
| 492 | −6.3 | −5.1 | X | − | exon | Four and a half LIM domains 1 | NC |
| 493 | −5.9 | −4.5 | 1 | + | intron | Acyl-CoA thioesterase 11 | NC |
| 494 | −5.9 | −4.6 | 1 | + | exon | KIAA1324 | NC |
| 495 | −5.9 | −5.4 | 1 | − | exon | RAP1 GTPase activating protein | NC |
| 496 | −5.9 | −4.5 | 3 | + | intron | Inositol 1,4,5-triphosphate receptor, type 1 | NC |
| 497 | −5.9 | −4.5 | 4 | + | intron/ antisense | Peroxisome proliferator-activated receptor gamma, coactivator 1 alpha | NC |
| 498 | −5.9 | −6.1 | 4 | + | intron/ antisense | Sorbin and SH3 domain containing 2 | NC |
| 499 | −5.9 | −4.7 | 6 | − | exon/ antisense | Opioid receptor, mu 1 | CDS |
| 500 | −5.9 | −4.5 | 7 | + | extra-genic | CD36 molecule (thrombospondin receptor) | NC |
| 501 | −5.9 | −4.5 | 7 | − | intron | Engulfment and cell motility 1 | NC |
| 502 | −5.9 | −4.1 | 7 | − | extra-genic | Solute carrier family 26, member 4 | NC |
| 503 | −5.9 | −4.3 | 8 | + | exon I promoter | Solute carrier family 26, member 7 | NC |
| 504 | −5.9 | −4.0 | 8 | + | exon | Solute carrier family 26, member 7 | CDS |
| 505 | −5.9 | −4.1 | 8 | + | exon | Solute carrier family 26, member 7 | NC |
| 506 | −5.9 | −4.2 | 8 | + | exon | Polycystic kidney and hepatic disease 1 (autosomal recessive)-like 1 | CDS |
| 507 | −5.9 | −5.0 | 8 | + | intron | Thyroglobulin | NC |
| 508 | −5.9 | −4.5 | 8 | − | intron/ antisense | Thyroglobulin | CDS |
| 509 | −5.9 | −5.8 | 8 | − | intron/ antisense | Thyroglobulin | NC |
| 510 | −5.9 | −4.8 | 9 | − | exon | Ankyrin repeat domain 18A | CDS |
| 511 | −5.9 | −4.6 | 11 | + | exon | Neural cell adhesion molecule 1 | NC |
| 512 | −5.9 | −4.4 | 11 | − | intron | Metallophosphoesterase domain containing 2 | NC |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 513 | −5.9 | −4.0 | 15 | − | exon | WD repeat domain 72 | CDS |
| 514 | −5.9 | −6.7 | 16 | + | exon | Metallothionein 1F | CDS |
| 515 | −5.6 | −7.3 | 2 | + | intron | Thyroid peroxidase | NC |
| 516 | −5.6 | −4.2 | 2 | − | intron | Phospholipase A2 receptor 1, 180 kDa | NC |
| 517 | −5.6 | −4.0 | 3 | + | exon | Inositol 1,4,5-triphosphate receptor, type 1 | CDS |
| 518 | −5.6 | −3.8 | 3 | + | extra-genic | Polymerase (DNA directed), theta | CDS |
| 519 | −5.6 | −5.4 | 4 | + | exon | Superoxide dismutase 3, extracellular | NC |
| 520 | −5.6 | −6.0 | 4 | − | intron | Sorbin and SH3 domain containing 2 | NC |
| 521 | −5.6 | −4.1 | 5 | + | exon | G protein-coupled receptor 98 | CDS |
| 522 | −5.6 | −4.3 | 7 | + | intron/antisense | Engulfment and cell motility 1 | NC |
| 523 | −5.6 | −3.7 | 7 | + | intron/antisense | Engulfment and cell motility 1 | NC |
| 524 | −5.6 | −6.3 | 7 | + | exon | Solute carrier family 26, member 4 | CDS |
| 525 | −5.6 | −5.1 | 7 | + | exon | Solute carrier family 26, member 4 | NC |
| 526 | −5.6 | −4.3 | 7 | − | intron/antisense | Williams-Beuren syndrome chromosome region 17 | NC |
| 527 | −5.6 | −4.4 | 8 | + | exon | Thyroglobulin | CDS |
| 528 | −5.6 | −3.9 | 8 | + | intron | Thyroglobulin | NC |
| 529 | −5.6 | −4.3 | 8 | − | intron/antisense | Thyroglobulin | NC |
| 530 | −5.6 | −4.0 | 8 | − | intron/antisense | Thyroglobulin | NC |
| 531 | −5.6 | −4.5 | 8 | − | intron/antisense | Thyroglobulin | NC |
| 532 | −5.6 | −5.0 | 11 | + | intron/antisense | MACRO domain containing 1 | NC |
| 533 | −5.6 | −3.7 | 11 | + | exon | Neural cell adhesion molecule 1 | CDS |
| 534 | −5.6 | −4.9 | 11 | − | intron | Metallophosphoesterase domain containing 2 | NC |
| 535 | −5.6 | −5.5 | 11 | − | intron | Cdon homolog (mouse) | NC |
| 536 | −5.6 | −3.9 | 11 | − | exon | Cdon homolog (mouse) | CDS |
| 537 | −5.6 | −4.5 | 13 | − | exon | Centromere protein J | CDS |
| 538 | −5.6 | −4.5 | 21 | + | exon | SH3 domain binding glutamic acid-rich protein | NC |
| 539 | −5.3 | −4.0 | 2 | − | exon | Low density lipoprotein-related protein 1B (deleted in tumors) | CDS |
| 540 | −5.3 | −7.0 | 2 | − | exon | Low density lipoprotein-related protein 2 | CDS |
| 541 | −5.3 | −5.8 | 4 | + | exon | Sorbin and SH3 domain containing 2 | NC |
| 542 | −5.3 | −5.3 | 4 | − | intron | Sorbin and SH3 domain containing 2 | NC |
| 543 | −5.3 | −5.7 | 4 | − | exon | Sorbin and SH3 domain containing 2 | CDS |
| 544 | −5.3 | −4.6 | 7 | − | intron | Engulfment and cell motility 1 | NC |
| 545 | −5.3 | −4.3 | 7 | − | exon | Diacylglycerol kinase, iota | CDS |
| 546 | −5.3 | −3.9 | 8 | + | exon | Solute carrier family 26, member 7 | CDS |
| 547 | −5.3 | −6.1 | 10 | − | intron | Protocadherin 15 | NC |
| 548 | −5.3 | −8.2 | 11 | + | extra-genic | Sodium channel, voltage-gated, type III, beta | NC |
| 549 | −5.3 | −3.8 | 11 | + | exon | Cdon homolog (mouse) | NC |
| 550 | −5.3 | −4.2 | 11 | − | intron | Metallophosphoesterase domain containing 2 | NC |
| 551 | −5.3 | −7.1 | 14 | + | intron | Ras and Rab interactor 3 | NC |
| 552 | −5.3 | −6.1 | 16 | − | extra-genic | Metallothionein 4 | NC |
| 553 | −5.0 | −5.8 | 4 | − | intron | Sorbin and SH3 domain containing 2 | NC |
| 554 | −5.0 | −7.5 | 4 | − | exon | Sorbin and SH3 domain containing 2 | CDS |
| 555 | −5.0 | −5.6 | 5 | − | exon | Leukemia inhibitory factor receptor alpha | CDS |
| 556 | −5.0 | −4.6 | 6 | + | exon | Opioid receptor, mu 1 | CDS |
| 557 | −5.0 | −5.0 | 7 | + | exon | Solute carrier family 26, member 4 | CDS |
| 558 | −5.0 | −5.3 | 8 | + | intron | Zinc finger, matrin type 4 | NC |
| 559 | −5.0 | −3.7 | 8 | + | exon | Solute carrier family 26, member 7 | CDS |
| 560 | −5.0 | −5.4 | 8 | − | intron/antisense | Thyroglobulin | CDS |
| 561 | −5.0 | −6.8 | 9 | + | intron/antisense | Guanine nucleotide binding protein (G protein), alpha 14 | NC |
| 562 | −5.0 | −4.5 | 11 | + | exon | Neural cell adhesion molecule 1 | NC |
| 563 | −5.0 | −4.0 | 14 | − | exon/promoter | Deiodinase, iodothyronine, type II | CDS |
| 564 | −5.0 | −3.9 | 18 | + | intron | Katanin p60 subunit A-like 2 | NC |
| 565 | −4.8 | −6.2 | 2 | − | exon | Low density lipoprotein-related protein 2 | CDS |
| 566 | −4.8 | −4.5 | 4 | + | intron | Ankyrin 2, neuronal | NC |
| 567 | −4.8 | −3.7 | 4 | − | intron | Sorbin and SH3 domain containing 2 | NC |
| 568 | −4.8 | −4.1 | 8 | + | exon | Solute carrier family 26, member 7 | CDS |

TABLE 7-continued

Differentially expressed RNA transcripts identified from comparison tests described in Example 2. CDS-RNA overlaps with the coding sequence translations of mRNAs in RefSeq or GenBank databases, NC—'non-coding' RNA does not overlap with the CDS.

| SEQ ID | Fold Difference | Weights | CHR | Strand | Position | Proximal Gene | Overlaps CDS |
|---|---|---|---|---|---|---|---|
| 569 | −4.8 | −4.0 | 16 | + | intron | Splicing factor 3b, subunit 3, 130 kDa | NC |
| 570 | −4.5 | −5.2 | 7 | + | exon | Solute carrier family 26, member 4 | CDS |
| 571 | −4.5 | −5.1 | 8 | + | exon | Chromosome 8 open reading frame 13 | NC |
| 572 | −4.5 | −5.5 | 8 | − | intron/ antisense | Werner syndrome | NC |
| 573 | −4.5 | −4.2 | 11 | + | intron | Neural cell adhesion molecule 1 | NC |
| 574 | −4.3 | −5.2 | 2 | − | exon | Low density lipoprotein-related protein 2 | CDS |
| 575 | −4.3 | −3.9 | 3 | + | intron | Potassium voltage-gated channel, shaker-related subfamily, beta member 1 | NC |
| 576 | −4.3 | −4.1 | 4 | − | intron | Collagen, type XXV, alpha 1 | NC |
| 577 | −4.3 | −4.2 | 8 | + | exon | Solute carrier family 26, member 7 | CDS |
| 578 | −4.3 | −4.2 | 8 | + | exon | Matrilin 2 | CDS |
| 579 | −4.2 | −4.5 | 1 | + | exon | Deiodinase, iodothyronine, type I | NC |
| 580 | −4.2 | −5.4 | 4 | − | exon | Sorbin and SH3 domain containing 2 | CDS |
| 581 | −4.2 | −4.3 | 4 | − | intron | Sorbin and SH3 domain containing 2 | NC |
| 582 | −3.7 | −4.5 | 17 | + | exon | Glutamate receptor, ionotropic, N-methyl D-aspartate 2C | NC |
| 583 | −3.6 | −5.4 | 3 | + | intron | Inositol 1,4,5-triphosphate receptor, type 1 | NC |
| 584 | −3.6 | −3.8 | 17 | − | exon/ promoter | Hepatic leukemia factor | NC |

The embodiments of the invention in which an exclusive property or privilege is claimed are defined as follows:

1. A method, comprising:

(a) assaying by sequencing, array hybridization or nucleic acid amplification an expression level of each of a first group of transcripts and a second group of transcripts in a test sample from a thyroid of a subject, wherein said test sample is identified as indeterminate by cytological evaluation, wherein said first group of transcripts includes at least two transcripts having at least about 90% sequence homology to at least two sequences selected from SEQ ID No. 1-6, 11-13, 16-248, and said second group of transcripts includes at least two transcripts having at least about 90% sequence homology to at least two sequences selected from SEQ ID No. 7-10, 14, 15, 249-584, and wherein said assaying comprises use of probes selected for said at least two sequences; and (b) in a programmed computer, comparing said expression level of each of said first group of transcripts and said second group of transcripts with reference expression levels of transcripts corresponding to sequences as set forth in SEQ ID No. 1 to 584 to (1) classify said test sample as malignant for a thyroid condition if there is an increase in an expression level corresponding to said first group of transcripts or a decrease in an expression level corresponding to said second group of transcripts, or (2) classify said test sample as benign for said thyroid condition if there is an increase in said expression level corresponding to said second group of transcripts or a decrease in said expression level corresponding to said first group of transcripts.

2. The method of claim 1, further comprising (i) when said test sample is classified as malignant, treating said subject by surgical removal of at least a portion of a thyroid tissue, radioactive iodine treatment, or a combination thereof or (ii) when said test sample is classified as benign, monitoring said subject by repeating (a)-(b) on another test sample obtained from said subject at a later time.

3. The method of claim 1, further comprising performing a cytological analysis, an imaging analysis, a measurement of thyroid hormone levels, or any combination thereof to obtain a result, and combining said result with said expression level to determine a classification of said test sample as malignant or benign for said thyroid condition.

4. The method of claim 1, further comprising generating a report that designates said test sample as malignant or benign for said thyroid condition.

5. The method of claim 2, wherein said treating further comprises thyroid hormone suppression therapy, permanent thyroid hormone replacement therapy, or a combination thereof.

6. The method of claim 1, wherein an increased relative level of expression of one or more transcripts, a decreased relative level of expression of one or more transcripts, or a combination thereof is used to classify said test sample as malignant for said thyroid condition.

7. The method of claim 1, wherein an increased relative level of expression of one or more transcripts, a decreased relative level of expression of one or more transcripts, or a combination thereof is used to classify said test sample as benign for said thyroid condition.

8. The method of claim 1, wherein said at least two transcripts comprise at least two sequences having at least about 90% sequence homology to any one of SEQ ID NOs: 1, 2, 3, 4, 5, 6, 7, 8, 9, and 10.

9. The method of claim 1, wherein said at least two transcripts comprise at least two sequences having at least about 90% sequence homology to any one of SEQ ID NOs: 1, 11, 12, 13, 14, and 15.

10. The method of claim 1, wherein said assaying comprises determining said expression level by RT-PCR, Northern blotting, ligase chain reaction, or any combination thereof.

11. The method of claim 1, wherein said test sample is fresh-frozen or fixed.

12. The method of claim 1, wherein said expression level is measured by pattern recognition.

13. The method of claim 12, wherein said pattern recognition comprises a linear combination of expression levels of target sequences.

14. The method of claim 12, wherein said pattern recognition comprises a nonlinear combination of expression levels of target sequences.

15. The method of claim 1, wherein (b) comprises using said programmed computer to (1) classify said test sample as malignant for said thyroid condition if there is an increase in an expression level corresponding to said first group of transcripts and a decrease in an expression level corresponding to said second group of transcripts, or (2) classify said test sample as benign for said thyroid condition if there is an increase in said expression level corresponding to said second group of transcripts and a decrease in said expression level corresponding to said first group of transcripts.

16. The method of claim 1, wherein said assaying is by nucleic acid amplification using at least one probe that amplifies a transcript having at least about 90% sequence homology to a sequence as set forth in any one of SEQ ID No. 1 to 584.

17. The method of claim 1, wherein said first group of transcripts includes a sequence having at least about 90% sequence homology to a sequence as set forth in any one of SEQ ID No. 1-6 and 11-13.

18. The method of claim 1, wherein said second group of transcripts includes a sequence having at least about 90% sequence homology to a sequence as set forth in any one of SEQ ID No. 7-10 and 14.

* * * * *

SEQUENCE LISTING

```
<160> NUMBER OF SEQ ID NOS: 584

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence: Synthetic
      Affymetrix ID 3536736 oligonucleotide

<400> SEQUENCE: 1

cactttgaga aactcaggga tggggttagt caaagaggac ttgtgtttgc attaacctcc     60

agggag                                                                66


<210> SEQ ID NO 2
<211> LENGTH: 160
<212> TYPE: DNA
<213> ORGANISM: Artificial Sequence
<220> FEATURE:
<223> OTHER INFORMATION: Description of Artificial Sequence: Synthetic
      Affymetrix ID 3460518 polynucleotide

<400> SEQUENCE: 2

actcccgtgt gttgaaagaa ggccatgaaa cactgcaact cctccttgct ttgcaaaaga     60

gtaacatcca cgccattcac ctaggagtct ccaatgatat accctcctcc cattacactt    120

aagtggcaaa aagacccctg attactgcat ggtaacagtg                          160


<210> SEQ ID NO 3
<211> LENGTH: 105
<212> TYPE: DNA
<213> ORGANISM: Artificial Sequence
<220> FEATURE:
<223> OTHER INFORMATION: Description of Artificial Sequence: Synthetic
      Affymetrix ID 2526817 polynucleotide

<400> SEQUENCE: 3

cttcaaggac aaatcgtaaa ggtagtgttt tagacttctg cacacaaatg gaaattcagg     60
```

tagaatatct ttcttttcta gaatcatcta tcttactcaa aaagg 105

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
Affymetrix ID 3420374 oligonucleotide

<400> SEQUENCE: 4
tgcatggatc tattagtgga tgggcgccag aacgacacag tcaatgca 48

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
Affymetrix ID 3976358 oligonucleotide

<400> SEQUENCE: 5
agtccctgcg gtcccagata gcctga 26

<210> SEQ ID NO 6
<211> LENGTH: 82
<212> TYPE: DNA
<213> ORGANISM: Artificial Sequence
<220> FEATURE:
<223> OTHER INFORMATION: Description of Artificial Sequence: Synthetic
Affymetrix ID 2828473 oligonucleotide

<400> SEQUENCE: 6
tgctcccacg cctgcttctt aaggtccctg ctcggccggt gtaaatatgt ttcaccctgt 60
ccctctaata aagctcctct gc 82

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
Affymetrix ID 3693001 oligonucleotide

<400> SEQUENCE: 7
ccctgctccc aagtacaaat agagtgaccc gtaaaatcca ggat 44

<210> SEQ ID NO 8
<211> LENGTH: 87
<212> TYPE: DNA
<213> ORGANISM: Artificial Sequence
<220> FEATURE:
<223> OTHER INFORMATION: Description of Artificial Sequence: Synthetic
Affymetrix ID 2508453 oligonucleotide

<400> SEQUENCE: 8
tctctcttca tctcactact tccaacccta tgatcattgt ggcactagtc cattggtttt 60
cctggccctt cctcatatcc agctttc 87

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic -continued Affymetrix ID 2537610 oligonucleotide

<400> SEQUENCE: 9
ggaggttgca cagattgcgg gggatttggg gaga 34

<210> SEQ ID NO 10
<211> LENGTH: 47
<212> TYPE: DNA
<213> ORGANISM: Artificial Sequence
<220> FEATURE:
<223> OTHER INFORMATION: Description of Artificial Sequence: Synthetic
Affymetrix ID 2573597 oligonucleotide

<400> SEQUENCE: 10
atagtgcgga cgagaagtct gtatgtggga tctgtgcttg ggttaga 47

<210> SEQ ID NO 11
<211> LENGTH: 336
<212> TYPE: DNA
<213> ORGANISM: Artificial Sequence
<220> FEATURE:
<223> OTHER INFORMATION: Description of Artificial Sequence: Synthetic
Affymetrix ID 2830183 polynucleotide

<400> SEQUENCE: 11
ggaagtatcc agacaccaat ttttaataaa atgaattccc caaagggagt cttgactgaa 60
ttaaggctgt tgtttatagg aagccagata taatgatgtg aaaaaaacta atttttaata 120
ataatcaccg gcagtaacgg gggcaggggg aaaaagtaca gtgtggtgta ttttttgttt 180
ttttcttttt cacaacatct acaggacaca agagaagcac ttagacactg taaggctggg 240
aaccatgctg taataaccac cagtgtgggt aatcaaaaag ggtctttgac atttaagagg 300
gttggggctc cctgcactgt cagaattcca cgtaaa 336

<210> SEQ ID NO 12
<211> LENGTH: 572
<212> TYPE: DNA
<213> ORGANISM: Artificial Sequence
<220> FEATURE:
<223> OTHER INFORMATION: Description of Artificial Sequence: Synthetic
Affymetrix ID 2491744 polynucleotide

<400> SEQUENCE: 12
ggaatgggtc cctagcttgc acaaccccag ctgagctttc agcagataaa tcacagcaga 60
aatagaatca ccctaggact ttcaatcaaa agctggaagt ccaccttaca gaaagacaaa 120
aagaaacccc tttttatatc ttaacaaagc aatagctctc aagcagcaga gcatctcgag 180
gaagaaagct tgcccggtcg ccatcccatc atgccagagc gtgcagtgtc cacccttgac 240
tacgctgggg aattgctgat tttttgaaaa agcttaactt aacaatttct gatgtctatc 300
ttttagagtt ctgtatgttc ccattttttta ttcttctgaa ttttgaattg caagtagctg 360
taaaatccaa tctttgagtg catgggggtg ggtgtgaggc ggggctcagc ttcaacccccc 420 tgtcctgtaa agcagtggct ggtttttcct gagcccagcc ctgggaggtc gtggtaggtg 480
tggaggctgc agagctcctc cagatgctgc cctcgctgtg cctcacacca gagaggatgg 540
aagtgggctc tggtgtcaga ctgtggttga gc 572

<210> SEQ ID NO 13
<211> LENGTH: 272
<212> TYPE: DNA
<213> ORGANISM: Artificial Sequence
<220> FEATURE:

-continued

<223> OTHER INFORMATION: Description of Artificial Sequence: Synthetic
      Affymetrix ID 3329532 polynucleotide

<400> SEQUENCE: 13
tatagtcctt ccttactgac tcctaggccc atccccagct gatggagaag ctaagcagaa     60
actgcagcta agacagagat tcaaaaggta attgtggtga ggggttcaca gggtagggga    120
agaacaaccc aaagaactca caggagctaa gaaaacataa gaaaaacatg agcaagagaa    180
agaagcgcct ttttcccctc ctttcctctt gttaaatgat gattgacaca cccgggctca    240
atttccagtt cattacgtaa cactctgagc aa                                  272

<210> SEQ ID NO 14
<211> LENGTH: 85
<212> TYPE: DNA
<213> ORGANISM: Artificial Sequence
<220> FEATURE:
<223> OTHER INFORMATION: Description of Artificial Sequence: Synthetic
      Affymetrix ID 3104982 oligonucleotide

<400> SEQUENCE: 14
tcccacagaa tgttgtagag ttcaatgcga acttcagtcc aggtcaacgt cccttggctt     60
atgctctctc ataaactctc gtgga                                           85

<210> SEQ ID NO 15
<211> LENGTH: 233
<212> TYPE: DNA
<213> ORGANISM: Artificial Sequence
<220> FEATURE:
<223> OTHER INFORMATION: Description of Artificial Sequence: Synthetic
      Affymetrix ID 3913484 polynucleotide

<400> SEQUENCE: 15
ctgtagccag tcattaatct gaaggtttaa tatatcattt tattgggatg agatcatagt     60
ctttacacaa atgctatgta aacaagttac tgaatatttt tcacctcgtg gagttgtaca    120
caacctttta tatatacaca ccctaccttc tctcaaatgc tgggcttaca ggtttattag    180
ctagggcctt ttgaggtatg ctgtcaggcg acagcccgat gagggtgctc gct           233

<210> SEQ ID NO 16
<211> LENGTH: 94
<212> TYPE: DNA
<213> ORGANISM: Artificial Sequence
<220> FEATURE:
<223> OTHER INFORMATION: Description of Artificial Sequence: Synthetic
      Affymetrix ID 2827683 oligonucleotide

<400> SEQUENCE: 16
tttcagcaag ccagttttgg agtgactgca agaagtatga tgtgactgtg tttcagtata     60
ttggagaact ttgtcgctac ctttgcaaac aatc                                 94

<210> SEQ ID NO 17
<211> LENGTH: 153
<212> TYPE: DNA
<213> ORGANISM: Artificial Sequence
<220> FEATURE:
<223> OTHER INFORMATION: Description of Artificial Sequence: Synthetic
      Affymetrix ID 3489156 polynucleotide

<400> SEQUENCE: 17
tgatgaatag ctgtacaacc atattattta gcaataggag gtaaatacag gtagaagcag     60
aagaaagaat gggcaggggt tacctctatg gagaagctgg ggtgggagga tagggtgggg    120

-continued acttatttta cgaactgtgt aattgcctaa ctt 153

<210> SEQ ID NO 18
<211> LENGTH: 339
<212> TYPE: DNA
<213> ORGANISM: Artificial Sequence
<220> FEATURE:
<223> OTHER INFORMATION: Description of Artificial Sequence: Synthetic
Affymetrix ID 2375629 polynucleotide

<400> SEQUENCE: 18
taggataggg gacacgatta cgttcctaag tgaaggtttc aagctgggct ttgcaggggg 60
tataattagt atggtcactg tgtcttgtag gatgtttggc tccttggtga tagagcttgc 120
caaaatggtg tcctttgata aggagggctg gggggcaggg agttgaagaa attcccttgc 180
caggcttggg gatctgtaaa catttccatt aatcaacaag tgtgtactaa tcccgagtct 240
tacattgcga tgcctcacta tccccacagc cccatcccta cctctctgcc caccagggct 300
gagctcaaat ctgtgtgttg tggacctctg cataggccc 339

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
Affymetrix ID 3865081 oligonucleotide

<400> SEQUENCE: 19
aggtcctcat gagtcaatct tgagtttctc 30

<210> SEQ ID NO 20
<211> LENGTH: 739
<212> TYPE: DNA
<213> ORGANISM: Artificial Sequence
<220> FEATURE:
<223> OTHER INFORMATION: Description of Artificial Sequence: Synthetic
Affymetrix ID 2338243 polynucleotide

<400> SEQUENCE: 20
tctcctcggg taggccatga tacaagtgga actcatcaaa taatttaaac ccaaggcgat 60
aacaacgcta tttcccatct aaactcattt aagccttcac aatgtcgcaa tggattcagt 120
tacttgcaaa cgatcccggg ttgtcataca gatacttgtt ttttacacat aacgctatgc 180
catcccttcc ttcactgccc cagtcaggtt tcctgttgtt ggaccgaaag gggatacatt 240
ttagaaatgc ttccttcaag acagaagtga gaaagaaagg agaccctgag gccaggatct 300
attaaacctg gtgtgtgcgc aaaagggagg gggaaggcag gaatttgaaa ggataaacgt 360
ctcctttgcg ccgaggaatc aggaagcgtg actcacttgg gtctgggacg ataccgaaat 420
ccggtacccc accccatccc ctgccccgcc gggtacctac aagctcggtt cctttctcaa 480
ctcccccagt tccttgatct ccaccttctt gtacttcccc gactttctcc ggttggtgat 540
caccaggacg gccatgccgg cgacgagggc caccacgacc accacgatga cggcgatgag 600
gccggcggtg aggcgcttca tggagaactt cgggggaatc tcgtccaggt aatagatgag 660
cgtgcgctcc acctgcaggg gttctccgcg cacgcgcaag tccaggccgc cgcggccctg 720
gaatagagac tcgcccttg 739

<210> SEQ ID NO 21
<211> LENGTH: 51
<212> TYPE: DNA

<213> ORGANISM: Artificial Sequence
<220> FEATURE:
<223> OTHER INFORMATION: Description of Artificial Sequence: Synthetic
Affymetrix ID 2342929 oligonucleotide

<400> SEQUENCE: 21
atgccagatg gtaagaaggg tgaaagtcta ctacacatgt ctgcgaggtc g 51

<210> SEQ ID NO 22
<211> LENGTH: 101
<212> TYPE: DNA
<213> ORGANISM: Artificial Sequence
<220> FEATURE:
<223> OTHER INFORMATION: Description of Artificial Sequence: Synthetic
Affymetrix ID 2562441 polynucleotide

<400> SEQUENCE: 22
ttgattgaaa gtcctagggt gattctattt ctgctgtgat ttatctgctg aaagctcagc 60
tggggttgtg caagctaggg acccattcct gtgtaataca a 101

<210> SEQ ID NO 23
<211> LENGTH: 269
<212> TYPE: DNA
<213> ORGANISM: Artificial Sequence
<220> FEATURE:
<223> OTHER INFORMATION: Description of Artificial Sequence: Synthetic
Affymetrix ID 2827693 polynucleotide

<400> SEQUENCE: 23
tcatatgctt tcttaggaag agtgagaggg gggtatatga ttctttatga aatggggaaa 60
gggagctaac attaattatg catgtactat atttccttaa tatgagagat aattttttaa 120
ttgcataaga attttaattt cttttaattg atataaacag tagttgatta ttctttttat 180
ctatttggag attcagtgca taactaagta ttttccttaa tactaaagat tttaaataat 240
aaatagtggc tagcggtttg gacaatcac 269

<210> SEQ ID NO 24
<211> LENGTH: 393
<212> TYPE: DNA
<213> ORGANISM: Artificial Sequence
<220> FEATURE:
<223> OTHER INFORMATION: Description of Artificial Sequence: Synthetic
Affymetrix ID 2598368 polynucleotide

<400> SEQUENCE: 24
gccaccgcgc ttagcctgtt tttagttttc taaagcaagg tccctattga aaggcaggcc 60
ataaacagtg atgactaaga aaaatcctgg aagagcctga gaaggaaaaa gatgaaatat 120
aatgccagag aatgaagtta gtcaaaggaa cagtgtgaaa acaataaata aatagataaa 180
tgaaaatgtt atttgacaga gagatgaaac tagactaaac cattcagctg cctttccact 240
gtaacaaatg taatttcatc tttcagaagt gtaatacctt gcagcaccag agctgaatat 300
gaacatatta ccaaaaatag attaccaggc atagatagca ttccttttttt aagtttgaat 360 tgaccacttg cgactctcga cctgatgtat gta 393

<210> SEQ ID NO 25
<211> LENGTH: 182
<212> TYPE: DNA
<213> ORGANISM: Artificial Sequence
<220> FEATURE:
<223> OTHER INFORMATION: Description of Artificial Sequence: Synthetic
Affymetrix ID 2829806 polynucleotide -continued

<400> SEQUENCE: 25
gcgcatggtc atcttagctt tcgaaagagg actgcactgt ttaacattga agaattacat 60
ggggaatcac aaatatattg ctttagtact gcatgttctg ttgtggtgag ggaaagaaac 120
atgctttgaa ggttttccct tgtcaacaga atgtgtgtct gtagctgtgt attgcgcatg 180
ta 182

<210> SEQ ID NO 26
<211> LENGTH: 169
<212> TYPE: DNA
<213> ORGANISM: Artificial Sequence
<220> FEATURE:
<223> OTHER INFORMATION: Description of Artificial Sequence: Synthetic
Affymetrix ID 2598348 polynucleotide

<400> SEQUENCE: 26
gaatcgtgtc tttctcattg gctcaatgta gtctccgtag agtctagaat gcttcagcac 60
ctggcacact gcttaacaaa tggtgaatga aaaaaaaaaa aagaaaagtc attctttttc 120
ttctttcacc ctatgtccat aatctggcca tttgcagaac ttgatgtcc 169

<210> SEQ ID NO 27
<211> LENGTH: 223
<212> TYPE: DNA
<213> ORGANISM: Artificial Sequence
<220> FEATURE:
<223> OTHER INFORMATION: Description of Artificial Sequence: Synthetic
Affymetrix ID 2708858 polynucleotide

<400> SEQUENCE: 27
tctctttcct ggtaagcagg gagtcaaaac aatagcaaga aaatgccaga aatagaattt 60
ctactacttt gtaaactcta ggctcgtggg tctcctagct ctcagtacct ggctcactgt 120
aggatgggta gatgggtgaa tgaatggata aagaaaggaa gtttgttcac cggagaggag 180
atgaatttca gtaagtttca tgtaacagtg atcaggagaa ata 223

<210> SEQ ID NO 28
<211> LENGTH: 541
<212> TYPE: DNA
<213> ORGANISM: Artificial Sequence
<220> FEATURE:
<223> OTHER INFORMATION: Description of Artificial Sequence: Synthetic
Affymetrix ID 2562439 polynucleotide

<400> SEQUENCE: 28
ccgtccttta aagtgctgca gtatggccag acgtggtggc tcacacctgc aatcccagca 60
ccttaggagg ccgaggcagg aggatccttg aggtcaggag ttcgagacca gcctcgccaa 120
catggtgaaa ccccatttct actaaaaata caaaaaatta gccaagtgtg gtggcatatg 180
cctgtaatcc caactactca gaaggccgag gcaggagaat tacttgaacg caggagaatc 240
actgcagccc aggaggcaga ggttgcagtg agccgagatt gcaccactgc actccagcct 300
gggtgacaga gcaagactcc atctcagtaa ataaataaat aaataaaaag cgctgcagta 360
gctgtggcct caccctgaag tcagcgggcc caggcctacc tcactctctc ccttggcaga 420
gaagcagacg tccatagctc ctctccctca caagcgctcc cagcctgccc tccagctgct 480
gctctcccct cccagtctct actcactggg atgaggttag gtcatgagga caccaaaaac 540
c 541

<210> SEQ ID NO 29

<211> LENGTH: 32
<212> TYPE: DNA
<213> ORGANISM: Artificial Sequence
<220> FEATURE:
<223> OTHER INFORMATION: Description of Artificial Sequence: Synthetic
Affymetrix ID 2562440 oligonucleotide

<400> SEQUENCE: 29
ctgcaccaat gctaataaag tcctattctc tt 32

<210> SEQ ID NO 30
<211> LENGTH: 217
<212> TYPE: DNA
<213> ORGANISM: Artificial Sequence
<220> FEATURE:
<223> OTHER INFORMATION: Description of Artificial Sequence: Synthetic
Affymetrix ID 2651362 polynucleotide

<400> SEQUENCE: 30
ggcctacatt aaggcaggca acagcctgag agaccctggg acctggtggg tgtacgaaag 60
gatccaaaac ttggaagcca tagaaaagga gatagaggat catataagtt attatctaca 120
ttgggaaacc tgaaaaggac tctgttaact ttagaggtag ctctgtacta tccctggcaa 180
ttgggactag gatggcccta catggtggca tcataac 217

<210> SEQ ID NO 31
<211> LENGTH: 246
<212> TYPE: DNA
<213> ORGANISM: Artificial Sequence
<220> FEATURE:
<223> OTHER INFORMATION: Description of Artificial Sequence: Synthetic
Affymetrix ID 2442050 polynucleotide

<400> SEQUENCE: 31
gttgttgttc aacctcagtg agacacagag actgagatgg gtcccagaag gagtagggaa 60
gagggactga agagggtctg agtgagggat ggaggtggtt gttggcattt atttaggagc 120
attgcagagt tgccttttaa agatctcttt aaagacaata gaaaggagta gagaccgatc 180
cctttataac gtgggggttt agcattatct catttttgat atgcagaagg atatctcatt 240
attgtg 246

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
Affymetrix ID 2876632 oligonucleotide

<400> SEQUENCE: 32
accaagcgct tcatcaagtg gtacaacgcc tggaacgag 39

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
Affymetrix ID 2598312 oligonucleotide

<400> SEQUENCE: 33
tttcctaccc agttggtaga ttctgtaaag tagcttgctg t 41

<210> SEQ ID NO 34

<211> LENGTH: 305
<212> TYPE: DNA
<213> ORGANISM: Artificial Sequence
<220> FEATURE:
<223> OTHER INFORMATION: Description of Artificial Sequence: Synthetic
      Affymetrix ID 2414960 polynucleotide

<400> SEQUENCE: 34
gacaacccgg gatcgtttgc aagtaactga atccattgcg acattgtgaa ggcttaaatg     60
agtttagatg ggaaatagcg ttgttatcgc cttgggttta aattatttga tgagttccac    120
ttgtatcatg gcctacccga ggagaagagg agtttgttaa ctgggcctat gtagtagcct    180
catttaccat cgtttgtatt actgaccaca tatgcttgtc actgggaaag aagcctgttt    240
cagctgcctg aacgcagttt ggatgtcttt gaggacagac attgcccgga aactcagtct    300
attta                                                                305

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      Affymetrix ID 2562442 oligonucleotide

<400> SEQUENCE: 35
ctctgctgct tgagagctat tgctttgtta agat                                 34

<210> SEQ ID NO 36
<211> LENGTH: 425
<212> TYPE: DNA
<213> ORGANISM: Artificial Sequence
<220> FEATURE:
<223> OTHER INFORMATION: Description of Artificial Sequence: Synthetic
      Affymetrix ID 2548709 polynucleotide

<400> SEQUENCE: 36
gcaggcttgc ccagtacatt taaatttttt ggcacttgcc attccaaaat attatgcccc     60
accaaggctg agacagtgaa tttgggctgc tgtagcctat ttttttagat tgagaaatgt    120
gtagctgcaa aaataatcat gaaccaatct ggatgcctca ttatgtcaac caggtccaga    180
tgtgctataa tctgttttta cgtatgtagg cccagtcgtc atcagatgct tgcggcaaaa    240
ggaaagctgt gtttatatgg aagaaagtaa ggtgcttgga gtttacctgg cttatttaat    300
atgcttataa cctagttaaa gaaaggaaaa gaaaacaaaa aacgaatgaa aataactgaa    360
tttggaggct ggagtaatca gattactgct ttaatcagaa accctcattg tgtttctacc    420
ggaga                                                                425

<210> SEQ ID NO 37
<211> LENGTH: 71
<212> TYPE: DNA
<213> ORGANISM: Artificial Sequence
<220> FEATURE:
<223> OTHER INFORMATION: Description of Artificial Sequence: Synthetic
      Affymetrix ID 3420365 oligonucleotide

<400> SEQUENCE: 37
attctttgga gttgcgtcat taggagcttt acagtaagat atcttactag ccaatattag     60
cctgccacag g                                                          71

<210> SEQ ID NO 38
<211> LENGTH: 865

-continued

<212> TYPE: DNA
<213> ORGANISM: Artificial Sequence
<220> FEATURE:
<223> OTHER INFORMATION: Description of Artificial Sequence: Synthetic
      Affymetrix ID 2598349 polynucleotide

<400> SEQUENCE: 38
gtcttctata ctcagccagg ttatcaatca aatatgaggg caaaataata ttttcagaca 60
gattttaggc agtttatctt ccatatatcc ttttctttaa gggtatttgt agatacactc 120
cagaaaaaca agagtgaaat atgaaggaag ttgtggggtc cagcaaacag tgcttccaaa 180
tcagacccct gatagaggtg gaaaactttg caatgcaaca actgcgtagc tggcttagag 240
gacagccaat acagatggaa cagaaagatg aggatgggat tgagggatca gggattgagg 300
tctccaagaa taaaaaggga cttcatggaa aaagtaggct tgtggataat taatcacagg 360
ggcaaataat gcagttaaaa taacaacatg acaatcaggt ggaggaatgt ataataaacc 420
caaatgtggc tgggtagagt ggctcacacc tgtaatccca gcactttggg aggccaagcc 480
gggcagatta cctgaggtca ggagttcgag accagcttgg ccaacatggc gaaaccccgt 540
ctctactaaa aatacaaaaa ttagccaggc ttgggggcgc acgcctgtag tcccagctcc 600
tcaggagctg aggtaggaga atcacttgaa cccaggaggc aaaggttgca gggagttgag 660
ccaagatcgc gccattgcac cctagcctgg gcaacagagc gagattctgt ttcaaaaaac 720
ccccaagtgt attataaggc aataattcct atacgaagca aactaaaatg cagcaatatt 780
aaggtataaa aacaaagagg aataattcca ttgaaccttg attctggaaa ctttgatcca 840
cccagcagtc atgatgttag actca 865

<210> SEQ ID NO 39
<211> LENGTH: 91
<212> TYPE: DNA
<213> ORGANISM: Artificial Sequence
<220> FEATURE:
<223> OTHER INFORMATION: Description of Artificial Sequence: Synthetic
      Affymetrix ID 3261708 oligonucleotide

<400> SEQUENCE: 39
ctgggagcta agagtcctgg attcctgcct acagtttgag ctccggtgaa gcactccttc 60
ttgatggctc tggtttccca gcataatgta a 91

<210> SEQ ID NO 40
<211> LENGTH: 62
<212> TYPE: DNA
<213> ORGANISM: Artificial Sequence
<220> FEATURE:
<223> OTHER INFORMATION: Description of Artificial Sequence: Synthetic
      Affymetrix ID 2451596 oligonucleotide

<400> SEQUENCE: 40
gggatagtga ggcatcgcaa tgtaagactc gggattagta cacacttgtt gattaatgga 60
aa 62

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      Affymetrix ID 3460465 oligonucleotide

<400> SEQUENCE: 41

```
cagtatgttc attctgctct tgtgactaca gtctttttg                        39


<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      Affymetrix ID 2598269 oligonucleotide

<400> SEQUENCE: 42

tctctgccaa gatccatcta aactggagtg a                                31


<210> SEQ ID NO 43
<211> LENGTH: 97
<212> TYPE: DNA
<213> ORGANISM: Artificial Sequence
<220> FEATURE:
<223> OTHER INFORMATION: Description of Artificial Sequence: Synthetic
      Affymetrix ID 2342953 oligonucleotide

<400> SEQUENCE: 43

tgaatggtgc attatgtgct ccaagttcgg gtacaatcat tgaaccaaaa gagagggggc     60

aggggaatga gactgggctt tctcgtaata tttctga                          97


<210> SEQ ID NO 44
<211> LENGTH: 134
<212> TYPE: DNA
<213> ORGANISM: Artificial Sequence
<220> FEATURE:
<223> OTHER INFORMATION: Description of Artificial Sequence: Synthetic
      Affymetrix ID 2598330 polynucleotide

<400> SEQUENCE: 44

gaggcaccac gagaagtgac ttcagactca ggaagcatcg ttgtgtccgg cttgactcca     60

ggagtagaat acgtctacac catccaagtc ctgagagatg gacaggaaag agatgcgcca    120

attgtaaaca aagt                                                  134


<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      Affymetrix ID 2721991 oligonucleotide

<400> SEQUENCE: 45

gaatcggcgt gataaccatt gagagggctt atccactcac                       40


<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthetic
      Affymetrix ID 2598289 oligonucleotide

<400> SEQUENCE: 46

cttcatggac cagagatctt ggatgttcct tcca                             34


<210> SEQ ID NO 47
<211> LENGTH: 35
<212> TYPE: DNA
<213> ORGANISM: Artificial Sequence
<220> FEATURE:
```

<223> OTHER INFORMATION: Description of Artificial Sequence: Synthetic
      Affymetrix ID 2598267 oligonucleotide

<400> SEQUENCE: 47
gttctgcttc gaagtattca ataccgctca gtatt 35

<210> SEQ ID NO 48
<211> LENGTH: 65
<212> TYPE: DNA
<213> ORGANISM: Artificial Sequence
<220> FEATURE:
<223> OTHER INFORMATION: Description of Artificial Sequence: Synthetic
      Affymetrix ID 2598358 oligonucleotide

<400> SEQUENCE: 48
catctttggt gcagcacaac ttcgaattat gagcaggacc agaaatactc tttctgcaca 60
gacca 65

<210> SEQ ID NO 49
<211> LENGTH: 47
<212> TYPE: DNA
<213> ORGANISM: Artificial Sequence
<220> FEATURE:
<223> OTHER INFORMATION: Description of Artificial Sequence: Synthetic
      Affymetrix ID 3040564 oligonucleotide

<400> SEQUENCE: 49
ctgatgaaag cacagcctaa ctgataacca agatgggttt tatcctc 47

<210> SEQ ID NO 50
<211> LENGTH: 641
<212> TYPE: DNA
<213> ORGANISM: Artificial Sequence
<220> FEATURE:
<223> OTHER INFORMATION: Description of Artificial Sequence: Synthetic
      Affymetrix ID 2497097 polynucleotide

<400> SEQUENCE: 50
cttagcaggg gtcaggcaat tagcataagg aaccttgagg agtaagtgag gtgacatccc 60
tgaaagcacc tgccccaagc atttgctaat attgggaaca gggacacagc aattgcagtg 120
tttacatttg tttattgtac tttgtaattc atgatgcttt catgtatgca tctaatttca 180
tcttcatctc tatcccagag cttgggatgg agacctgcag ggtgttcatt ctgggcaatg 240
gtagccagat ccggtaaaac atgtttatct tcaaagtagc ttatggagag atgaagagag 300
ttctgtagaa agatgtggaa gagggcagtt ggaaagaaac tctaatttct agtagagggc 360
aatcctttta ctagaaatcc tttgtaatgt ggggttggtg aaggcagaat cattggcctt 420
gttagtttcc catgcagatg agaatatagt gggagctgag cttcaaaccc agctgggtga 480
atgaaggtaa tggaagcagg gaggaggcaa gagaggacat agaaagagga aggtgctaga 540
gatgagggag ggaggtcctg gtggggtgca tactaagtgt tcagtaaggt ttttttttta 600
cattaaatgg gataaaatgc cagtcgcaga agttaatttt a 641

<210> SEQ ID NO 51
<211> LENGTH: 170
<212> TYPE: DNA
<213> ORGANISM: Artificial Sequence
<220> FEATURE:
<223> OTHER INFORMATION: Description of Artificial Sequence: Synthetic
      Affymetrix ID 2708860 polynucleotide

<400> SEQUENCE: 51

-continued

```
ctgctgggac tagatagtgg atgaagaaag aaggacgagg aagccgtggg gcagcctctt      60

cacatgggga caggggatgg agcatgaggc aagggaagga aaagcagagc ttatttttca     120

cctaaggtgg agaaggatca ctttacaggc aacgctcatt ttaagcaacc                170


<210> SEQ ID NO 52
<211> LENGTH: 268
<212> TYPE: DNA
<213> ORGANISM: Artificial Sequence
<220> FEATURE:
<223> OTHER INFORMATION: Description of Artificial Sequence: Synthetic
      Affymetrix ID 2477711 polynucleotide

<400> SEQUENCE: 52

tctctctccg gtagaaacac aatgagggtt tctgattaaa gcagtaatct gattactcca      60

gcctccaaat tcagttattt tcattcgttt tttgttttct tttcctttct ttaactaggt     120

tataagcata ttaaataagc caggtaaact ccaagcacct tactttcttc catataaaca     180

cagctttcct tttgccgcaa gcatctgatg acgactgggc ctacatacgt aaaaacagat     240

tatagcacat ctggacctgg ttgacata                                        268


<210> SEQ ID NO 53
<211> LENGTH: 261
<212> TYPE: DNA
<213> ORGANISM: Artificial Sequence
<220> FEATURE:
<223> OTHER INFORMATION: Description of Artificial Sequence: Synthetic
      Affymetrix ID 2397080 polynucleotide

<400> SEQUENCE: 53

tggggctgct ttttagtgac tcacctccca gacttcctgc aacagacaac tctaaatagc      60

tcggtcccac cctccagcag gggagacatt ccggtcggga agggcaggag gttagaaggt     120

gggtgccccg ccagggcagt ccagggagac ccaaggacag gagacgctgg ctgcacagca     180

caggggcgca cgaataggac gttttgttta caggcttttg ttattaagga aattggtgtc     240

agtcaaggta attctagctc a                                               261


<210> SEQ ID NO 54
<211> LENGTH: 221
<212> TYPE: DNA
<213> ORGANISM: Artificial Sequence
<220> FEATURE:
<223> OTHER INFORMATION: Description of Artificial Sequence: Synthetic
      Affymetrix ID 3420394 polynucleotide

<400> SEQUENCE: 54

agcagcacgc tgttcattcc aggaaaggaa aaaaaaagtg cttttctgcg tgaccatgtt      60

gatcactgtt accatgcagt aatcaggggt ctttttgcca cttaagtgta atgggaggag     120

ggtatatcat tggagactcc taggtgaatg gcgtggatgt tactcttttg caaagcaagg     180

aggagttgca gtgtttcatg gccttctttc aacacacggg a                         221


<210> SEQ ID NO 55
<211> LENGTH: 260
<212> TYPE: DNA
<213> ORGANISM: Artificial Sequence
<220> FEATURE:
<223> OTHER INFORMATION: Description of Artificial Sequence: Synthetic
      Affymetrix ID 2526824 polynucleotide

<400> SEQUENCE: 55

tgtctccacg gccagtgaca gcatacacag tgatggtata atcaactcca ggtttaaggc      60
```

cgctgatggt agctgtagac ttgctcccag gcacagtgaa ctcctggaca gggctatttc 120
ctcctgtatg aaaaagggtt agttcagagt gtgaggggtt tagagctact tgggtattac 180
tgattaattg aattaccaca tttatagcag catgtaaatc acatcttctt gcttattccc 240
ttttaaagag cgctatcttg 260

<210> SEQ ID NO 56
<211> LENGTH: 65
<212> TYPE: DNA
<213> ORGANISM: Artificial Sequence
<220> FEATURE:
<223> OTHER INFORMATION: Description of Artificial Sequence: Synthetic
Affymetrix ID 2598340 oligonucleotide

<400> SEQUENCE: 56
tgatgcccct cctgacacga ctgtggacca agttgatgac acctcaattg ttgttcgctg 60
gagca 65

<210> SEQ ID NO 57
<211> LENGTH: 34
<212> TYPE: DNA
<213> ORGANISM: Artificial Sequence
<220> FEATURE:
<223> OTHER INFORMATION: Description of Artificial Sequence: Synthetic
Affymetrix ID 3036168 oligonucleotide

<400> SEQUENCE: 57
aacaaaaacg cagctattcg cattcttccc tggc 34

<210> SEQ ID NO 58
<211> LENGTH: 192
<212> TYPE: DNA
<213> ORGANISM: Artificial Sequence
<220> FEATURE:
<223> OTHER INFORMATION: Description of Artificial Sequence: Synthetic
Affymetrix ID 3536718 polynucleotide

<400> SEQUENCE: 58
tcagcactta gtccagattc tggggagaag tttgatgatg gtccttgaat atttagcact 60
tagaagtgct aggaggatgc ctcactaagt tacgtaagaa gcagaagagg acgagtaccg 120
cctgatggat tgaccccgaa aactagctgt gtccaagtag aataggtgtc tcgctctgtt 180
aagcggtctt ta 192

<210> SEQ ID NO 59
<211> LENGTH: 136
<212> TYPE: DNA
<213> ORGANISM: Artificial Sequence
<220> FEATURE:
<223> OTHER INFORMATION: Description of Artificial Sequence: Synthetic
Affymetrix ID 2477709 polynucleotide

<400> SEQUENCE: 59
tggtgtccca gtataagtaa tgagatacaa ttttttttta atttggtata tcaaacagta 60
aaggctacat ataaatgttg tttccccaga atgtactttg tctacaacta tgcactgtag 120
ctattatgca cacact 136

<210> SEQ ID NO 60
<211> LENGTH: 72
<212> TYPE: DNA
<213> ORGANISM: Artificial Sequence
<220> FEATURE:

<223> OTHER INFORMATION: Description of Artificial Sequence: Synthetic
      Affymetrix ID 3834035 oligonucleotide

<400> SEQUENCE: 60
gccagtttcc aattcaccct gtcagggagt gagccggatc tgacgttcct tgtgacttaa 60
gggtccggct tg 72

<210> SEQ ID NO 61
<211> LENGTH: 429
<212> TYPE: DNA
<213> ORGANISM: Artificial Sequence
<220> FEATURE:
<223> OTHER INFORMATION: Description of Artificial Sequence: Synthetic
      Affymetrix ID 2876625 polynucleotide

<400> SEQUENCE: 61
tcctgtgatg gcgagacaaa tgatccttaa agaaggtgtg gggtctttcc caacctgagg 60
atttctgaaa ggttcacagg ttcaatattt aatgcttcag aagcatgtga ggttcccaac 120
actgtcagca aaaaccttag gagaaaactt aaaaatatat gaatacatgc gcaatacaca 180
gctacagaca cacattctgt tgacaaggga aaaccttcaa agcatgtttc tttccctcac 240
cacaacagaa catgcagtac taaagcaata tatttgtgat tccccatgta attcttcaat 300
gttaaacagt gcagtcctct ttcgaaagct aagatgacca tgcgcccttt cctctgtaca 360
tataccctta agaacgcccc ctccacacac tgccccccag tatatgccgc attgtactgc 420
tgtgttata 429

<210> SEQ ID NO 62
<211> LENGTH: 368
<212> TYPE: DNA
<213> ORGANISM: Artificial Sequence
<220> FEATURE:
<223> OTHER INFORMATION: Description of Artificial Sequence: Synthetic
      Affymetrix ID 3110627 polynucleotide

<400> SEQUENCE: 62
ggcagtcact attcatgccg gataatagag aactatgtga cgcagtcctc tcaggagtct 60
gagtttacag agccaacttg cagcacctgg ttatgcctcc tttcatctca aagccaaaga 120
gctgccaggt aaatggttat gtggtctatg ttccaaacaa accacatgat cttgcctgtg 180
tcacaatgta acaagactct agctgggtcc cctggtgatg agtttcagca tagaataatg 240
ttcaaggaaa agaaaacgaa aacagtttaa atctctacca cagcctcaca agcaaatgct 300
aaggggaaca tacatgtaaa aagccagcaa actatcttca aactcttccg tccttaatgt 360
cttccatg 368

<210> SEQ ID NO 63
<211> LENGTH: 73
<212> TYPE: DNA
<213> ORGANISM: Artificial Sequence
<220> FEATURE:
<223> OTHER INFORMATION: Description of Artificial Sequence: Synthetic
      Affymetrix ID 2442021 oligonucleotide

<400> SEQUENCE: 63
aggcagaatg tgctaccagt ggtcatgaag acatgcctgt ggagaggatt ctagaagctg 60
aacttgctgt tga 73

<210> SEQ ID NO 64
<211> LENGTH: 92

<212> TYPE: DNA
<213> ORGANISM: Artificial Sequence
<220> FEATURE:
<223> OTHER INFORMATION: Description of Artificial Sequence: Synthetic
Affymetrix ID 3696401 oligonucleotide

<400> SEQUENCE: 64
gggcaaccta ggcacactca gtataaaaac gcagagatcc atccgaatgg gaggcattgg 60
ggtctggaaa ccagaaatgc aggacggcca gt 92

<210> SEQ ID NO 65
<211> LENGTH: 37
<212> TYPE: DNA
<213> ORGANISM: Artificial Sequence
<220> FEATURE:
<223> OTHER INFORMATION: Description of Artificial Sequence: Synthetic
Affymetrix ID 2375037 oligonucleotide

<400> SEQUENCE: 65
tggaaatacc aatcagattg ttggctgaag tgatgtg 37

<210> SEQ ID NO 66
<211> LENGTH: 99
<212> TYPE: DNA
<213> ORGANISM: Artificial Sequence
<220> FEATURE:
<223> OTHER INFORMATION: Description of Artificial Sequence: Synthetic
Affymetrix ID 3848041 oligonucleotide

<400> SEQUENCE: 66
ctacatcatc gggaaggaca cttgggtgga gcactggccc gaggaggacg aatgccaaga 60
cgaagagaac cagaaacaat gccaggacct cggcgcctt 99

<210> SEQ ID NO 67
<211> LENGTH: 317
<212> TYPE: DNA
<213> ORGANISM: Artificial Sequence
<220> FEATURE:
<223> OTHER INFORMATION: Description of Artificial Sequence: Synthetic
Affymetrix ID 2526822 polynucleotide

<400> SEQUENCE: 67
ggcctcaatc agtgctcccg gcttagcctc ccaaagcact aggattacat gtgtgagcca 60
ctgcacccgg cctccttttt ctattctaca taaagtatct ttgtatggat aaccatttca 120
cgcagtattc catccaaaaa agagagaata atgtttttat tgtctcttta tttggaccct 180
atggcagata tggctgctaa atttgacgtt ctctctgtaa tgcggcgtaa gaagaaaact 240
ggctcccaac agaagcagaa aagagaagcg aaaagcaata atacagactg tcacctctag 300
ggtttatgct gtcacta 317

<210> SEQ ID NO 68
<211> LENGTH: 437
<212> TYPE: DNA
<213> ORGANISM: Artificial Sequence
<220> FEATURE:
<223> OTHER INFORMATION: Description of Artificial Sequence: Synthetic
Affymetrix ID 2651264 polynucleotide

<400> SEQUENCE: 68
aaggtgcttg caatatccac agagagattt tgatggtaac agatctggta agggctgctt 60
gagaggtaca caggcatttt tataagagaa aagaacaggc agaaatgagt ttggactatg 120
ggagaacata taaagctttc ctgtagagaa ggcagttggt ttgggcctta aaggagatat 180
gaggtttttg accaatgatg atgggaggag gaaagggaac cctgggcacg gaaaagcgta 240
catggtagta catataagct ggaatacata atgtgtgttt ggtgctttct caaagtcaac 300
aaaggcttct gaagaggaaa gaacaccatt agaactttag gagataaact tttgggagga 360
gataacacaa aaagaccagt taggagctac tgaattagct tagagaagag gtaataactg 420
cttgttctag gtaagcc 437

<210> SEQ ID NO 69
<211> LENGTH: 669
<212> TYPE: DNA
<213> ORGANISM: Artificial Sequence
<220> FEATURE:
<223> OTHER INFORMATION: Description of Artificial Sequence: Synthetic
Affymetrix ID 2651422 polynucleotide

<400> SEQUENCE: 69
agctcaatgg atgagttcaa cagcagaatg aagtggacag aggaacaaac caatgaactt 60
gaaggaatga tggaaattac ccaacctgaa caacaaagag agaaaaaaat agcaaccaac 120
aaacacacac acacagcctc agagacctgt agtactataa gaaaatatct accattatgt 180
catctgagtc ccagaagagg aaaaagaggg tggaaatgaa aaaatattta aaggaataat 240
ggctgaaaat tttctgaatg tgacaataaa cataaaccta catattgaag aagctgtgtt 300
aatgccaaac aagataaact caaagaaatt tacaaaagtc atatcaacat caaacttctg 360
aaaattatat actgatttaa ctaatatata aatatatgtt aaataatgta ttcaatcaat 420
tgatatatta aatataatct atattttaat tcaattaata aatattgaat aaactatatt 480
cattttaata tgaataatta atacatattt tatatatcaa atacattaat atatatttca 540
ttttcagaag cttgatattg atatttcttt tgtagatagg tgttgagaga gaaacaacaa 600
caccttagct atagaagaaa tactaataga atgatagaat gacagcagcg ttctcatcaa 660
aagtcatgg 669

<210> SEQ ID NO 70
<211> LENGTH: 87
<212> TYPE: DNA
<213> ORGANISM: Artificial Sequence
<220> FEATURE:
<223> OTHER INFORMATION: Description of Artificial Sequence: Synthetic
Affymetrix ID 2598350 oligonucleotide

<400> SEQUENCE: 70
atcttatcaa ttctgatggt ttcttttttt cccagctttt gagccaacaa ctctgattaa 60
ctattcctat agcatttact atatttg 87

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
Affymetrix ID 2773437 oligonucleotide

<400> SEQUENCE: 71
gagcagagag gtttcgatat ttattga 27

<210> SEQ ID NO 72
<211> LENGTH: 135
<212> TYPE: DNA
<213> ORGANISM: Artificial Sequence
<220> FEATURE:
<223> OTHER INFORMATION: Description of Artificial Sequence: Synthetic
Affymetrix ID 3426549 polynucleotide

<400> SEQUENCE: 72
tctacattaa gtccattgag ccacagaaag tatcgacatt agggaaaagc aacgtgatag 60
taacgggagc aaactttacc cgggcatcga acatcacaat gatcctgaaa ggaaccagta 120
cctgtgataa ggatg 135

<210> SEQ ID NO 73
<211> LENGTH: 83
<212> TYPE: DNA
<213> ORGANISM: Artificial Sequence
<220> FEATURE:
<223> OTHER INFORMATION: Description of Artificial Sequence: Synthetic
Affymetrix ID 3835890 oligonucleotide

<400> SEQUENCE: 73
cgcgcagcct gcagcgggag accctgtccc cgccccagcc gtcctcctgg ggtggaccct 60
agtttaataa agattcacca agt 83

<210> SEQ ID NO 74
<211> LENGTH: 215
<212> TYPE: DNA
<213> ORGANISM: Artificial Sequence
<220> FEATURE:
<223> OTHER INFORMATION: Description of Artificial Sequence: Synthetic
Affymetrix ID 2598305 polynucleotide

<400> SEQUENCE: 74
gtctgaatgc ccacgacatg tcttttgcaa ttacacatag ggaaagtgaa cttgttggtt 60
agtttatgtc ttgagctgag ccctttacga acatcttttt tccttctcag tgccaagcga 120
ggaatttaca gagaaagaag ttgtgaaacc accatagtta gttgctgtgc tttgaatttc 180
ttttgctcaa atggcctcag cgaaatctta tttgc 215

<210> SEQ ID NO 75
<211> LENGTH: 127
<212> TYPE: DNA
<213> ORGANISM: Artificial Sequence
<220> FEATURE:
<223> OTHER INFORMATION: Description of Artificial Sequence: Synthetic
Affymetrix ID 2451595 polynucleotide

<400> SEQUENCE: 75
caaaggacac cattttggca agctctatca ccaaggagcc aaacatccta caagacacag 60
tgaccatact aattataccc cctgcaaagc ccagcttgaa accttcactt aggaacgtaa 120
tcgtgtc 127

<210> SEQ ID NO 76
<211> LENGTH: 191
<212> TYPE: DNA
<213> ORGANISM: Artificial Sequence
<220> FEATURE:
<223> OTHER INFORMATION: Description of Artificial Sequence: Synthetic
Affymetrix ID 2540190 polynucleotide

<400> SEQUENCE: 76
tgctcggcca tgacttagag gtgtttattt aaggactgtg aatgactcgg tgatttcgga 60
aaagcttggc ttagatgaac ggacatacac aggggagaca gccctaaggt ttgcagaaaa 120
ggctgattgt gctgtttgcg aagtcgaaat aattggtgaa agtgtagaag gcagaacctc 180
tcaggaatgt c 191

<210> SEQ ID NO 77
<211> LENGTH: 858
<212> TYPE: DNA
<213> ORGANISM: Artificial Sequence
<220> FEATURE:
<223> OTHER INFORMATION: Description of Artificial Sequence: Synthetic
Affymetrix ID 3222204 polynucleotide

<400> SEQUENCE: 77
ctaccggatc gccatgactt taacatcttt gttcacattc cctacttaat ccataaatgt 60
agtctactgt ttcaccttct ccccacactc cctcttgtca tatgtactta atgaacactc 120
cccactccca ccccagaaat gagaaggtcg aaatatttct gctttgtatt caaaatcctt 180
tagaccttgt cttgtccata gctcttgtgt gcttacctca tatcatcgtc ccttgtgatc 240
aacctggctg gtccccagct acatttcagc cttctcaaaa gaaatatacc aatgagtata 300
tttccaaaac gtatttaaaa cttttgccat ctcaaaatct caaccatgat cttaacaaac 360
ttacccagtg ggctcgtcat tggaaaacca aatgtgaact tattttatcg gtaatcacta 420
atatcagaga gactctgcaa cacggactaa atccataatt ttctcaagac taatgattcc 480
tacagaaatt aacaacggaa tagtcaaaca tctgtgtttc ccaaagtctt tctagagatt 540
actagctcca cagaatgttc aaaggtccta ctcggtgagg aaattccacg ttcaaataag 600
tttggaaaga ctgagttaaa caaagttaaa gaggatcttt aactgcacgg cttttcagaa 660
caccctaacg tgcatcatct ccaagaagta cttatccagg cagtattttc caaacttatt 720
tgacaaagga tactttttaa ggaagaggat caaacaggaa tagttcactg tgagcacact 780
ttgggaaact cagctctaaa tctacattga cattgagttt tgtctagtta aggcaatgca 840
agatgaaacc ctgggtcc 858

<210> SEQ ID NO 78
<211> LENGTH: 49
<212> TYPE: DNA
<213> ORGANISM: Artificial Sequence
<220> FEATURE:
<223> OTHER INFORMATION: Description of Artificial Sequence: Synthetic
Affymetrix ID 2326780 oligonucleotide

<400> SEQUENCE: 78
tgcgcgcgcg ccagtgcaag accgagattg agggaaagca tgtctgctg 49

<210> SEQ ID NO 79
<211> LENGTH: 84
<212> TYPE: DNA
<213> ORGANISM: Artificial Sequence
<220> FEATURE:
<223> OTHER INFORMATION: Description of Artificial Sequence: Synthetic
Affymetrix ID 2598354 oligonucleotide

<400> SEQUENCE: 79
tgacatcact tacaatgtga acgacacatt ccacaagcgt catgaagagg ggcacatgct 60
gaactgtaca tgcttcggtc aggg 84

<210> SEQ ID NO 80
<211> LENGTH: 279
<212> TYPE: DNA
<213> ORGANISM: Artificial Sequence
<220> FEATURE:
<223> OTHER INFORMATION: Description of Artificial Sequence: Synthetic Affymetrix ID 2526827 polynucleotide

<400> SEQUENCE: 80
gcccgggctt ctttaccata ttctaaggaa gatgtttctc cacattttct cacttccctc 60
tccatgtacc atgacaatga tctatttttt tttttttttt tttttttttt gagagctgat 120
gacagacaac agcaagctac tttacagaat ctaccaactg ggtaggaaag tcttctgagt 180
ttctttgcag acaagaaaag ttacctgttg attgttggcc aatcaataag ggactttcct 240
ctctgccatt aagagcaacg atgctgacca catactctg 279

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
Affymetrix ID 2598328 oligonucleotide

<400> SEQUENCE: 81
gcaaaccctg acactggagt gctcac 26

<210> SEQ ID NO 82
<211> LENGTH: 64
<212> TYPE: DNA
<213> ORGANISM: Artificial Sequence
<220> FEATURE:
<223> OTHER INFORMATION: Description of Artificial Sequence: Synthetic
Affymetrix ID 2710609 oligonucleotide

<400> SEQUENCE: 82
gttgccacag catggtatgg caatagaatc gttcaagaat tctatgaccc tatgacccca 60
gtca 64

<210> SEQ ID NO 83
<211> LENGTH: 60
<212> TYPE: DNA
<213> ORGANISM: Artificial Sequence
<220> FEATURE:
<223> OTHER INFORMATION: Description of Artificial Sequence: Synthetic
Affymetrix ID 3577632 oligonucleotide

<400> SEQUENCE: 83
gggtcaactg ggcatcacta aggtcttcag caatggggct gacctctccg gggtcacaga 60

<210> SEQ ID NO 84
<211> LENGTH: 504
<212> TYPE: DNA
<213> ORGANISM: Artificial Sequence
<220> FEATURE:
<223> OTHER INFORMATION: Description of Artificial Sequence: Synthetic
Affymetrix ID 2526835 polynucleotide

<400> SEQUENCE: 84
tcagcttacg tgtggtaaag actccagtgg ctttggggct ctcttggttg ccctttatgg 60
ccacgaggga tacggtgtac tcagatgcag gctgcagatt cctcagtggg tacttggaga 120
cagagggacc cacattgtac tgcctgggct gtcctcttcg ggtaaggccc acggtcagtc 180
ggtatcctgt tatctgggcc cgaggtggag tccatctcac caggacagta gaatcagttt 240
cattgacaaa ctggaggtta gtgggagcat ccagttctag gaaaaaagat gaaacatgcc 300
aagaaatatt tagatcagta atgatcataa ctcaagtcct gaaacttgat tgaatgtcta 360
agttttctct cctcaaggtt gtaactatgt gaaagtcaaa accctggaaa aactgagcca 420
gtaagagatt gagtgctaca caaaactttg ccaaaactct gccagtcatg agaaattgtg 480
gaaccatttt gcttgactgt gatc 504

<210> SEQ ID NO 85
<211> LENGTH: 191
<212> TYPE: DNA
<213> ORGANISM: Artificial Sequence
<220> FEATURE:
<223> OTHER INFORMATION: Description of Artificial Sequence: Synthetic
Affymetrix ID 3420370 polynucleotide

<400> SEQUENCE: 85
tgactacaat tttcaaagca ccttgagatg taaaaaaatg tttctgtagg agggaagggg 60
tacggttctg ataaatctct cagcaggatg aaaaagaaaa gggaggtcta gacagtcttg 120
tttcatctaa tagaattttc ccacagaaga tgggcaaaca tcagataaga acatttatca 180
gacctcacac a 191

<210> SEQ ID NO 86
<211> LENGTH: 188
<212> TYPE: DNA
<213> ORGANISM: Artificial Sequence
<220> FEATURE:
<223> OTHER INFORMATION: Description of Artificial Sequence: Synthetic
Affymetrix ID 2598334 polynucleotide

<400> SEQUENCE: 86
gaaactgatt ctactgtcct ggtgagatgg actccacctc gggcccagat aacaggatac 60
cgactgaccg tgggccttac ccgaagagga cagcccaggc agtacaatgt gggtccctct 120
gtctccaagt acccactgag gaatctgcag cctgcatctg agtacaccgt atccctcgtg 180
gccataaa 188

<210> SEQ ID NO 87
<211> LENGTH: 84
<212> TYPE: DNA
<213> ORGANISM: Artificial Sequence
<220> FEATURE:
<223> OTHER INFORMATION: Description of Artificial Sequence: Synthetic
Affymetrix ID 2598374 oligonucleotide

<400> SEQUENCE: 87
atcaacagtg ggagcggacc tacctaggca atgcgttggt ttgtacttgt tatggaggaa 60
gccgaggttt taactgcgag agta 84

<210> SEQ ID NO 88
<211> LENGTH: 230
<212> TYPE: DNA
<213> ORGANISM: Artificial Sequence
<220> FEATURE:
<223> OTHER INFORMATION: Description of Artificial Sequence: Synthetic
Affymetrix ID 3536724 polynucleotide

<400> SEQUENCE: 88
ggtcattgtc tttcctgtct cagtagtaat caatcactgc ttatcttcaa aaacccagag 60
taggggatgg ggcagttagt ggggacagag ggcagatggg taagattcag agcacaggct 120
agtgtgacgg aagtttaaac ttgtgagtta aatagggttt ggcaatctag ctggatagca 180
tccctgcccc ttgaagagat gtttttgtgg cgccacacta ctgacttagg 230

<210> SEQ ID NO 89

-continued

<211> LENGTH: 125
<212> TYPE: DNA
<213> ORGANISM: Artificial Sequence
<220> FEATURE:
<223> OTHER INFORMATION: Description of Artificial Sequence: Synthetic
      Affymetrix ID 2598372 polynucleotide

<400> SEQUENCE: 89
ccatgaaggg ggtcagtcct acaagattgg tgacacctgg aggagaccac atgagactgg     60
tggttacatg ttagagtgtg tgtgtcttgg taatggaaaa ggagaatgga cctgcaagcc    120
catag                                                                125

<210> SEQ ID NO 90
<211> LENGTH: 148
<212> TYPE: DNA
<213> ORGANISM: Artificial Sequence
<220> FEATURE:
<223> OTHER INFORMATION: Description of Artificial Sequence: Synthetic
      Affymetrix ID 2651270 polynucleotide

<400> SEQUENCE: 90
aatatttata taccaggctg tgtgctaggt acttcagaga ccaaaacaaa taaggtatcc     60
ttaatgtagt gggaaataga gagcaggaaa ccagtgatta tgatatagcc cacaaatagt    120
atgatggaga gagttcatct atgtcgta                                       148

<210> SEQ ID NO 91
<211> LENGTH: 240
<212> TYPE: DNA
<213> ORGANISM: Artificial Sequence
<220> FEATURE:
<223> OTHER INFORMATION: Description of Artificial Sequence: Synthetic
      Affymetrix ID 2598327 polynucleotide

<400> SEQUENCE: 91
tagttcttat ctttgccggg gcacagagct aaggctatca tctctaaatc tgattaatgt     60
atgcaaacac acagaatgaa actagctcag aatatctctt ttaatctccc tctgaagtag    120
agtgattttg gtaaagtttt cattatctgc ggaaacattg tttaagccaa agctatacaa    180
tttccagctg agttgctctg aatttgaaac tttaagttga caatcttcgt gcttgttagc    240

<210> SEQ ID NO 92
<211> LENGTH: 741
<212> TYPE: DNA
<213> ORGANISM: Artificial Sequence
<220> FEATURE:
<223> OTHER INFORMATION: Description of Artificial Sequence: Synthetic
      Affymetrix ID 3894443 polynucleotide

<400> SEQUENCE: 92
gggaagatcc gtgcactcgt ccacacccac caccacactc gctgacaccc acccccacac     60
gctgacaccc acccccacac ttgcccacac ccatcaccgc actcgcccac acccaccacc    120
acactgcccc acacccacca ccacactccc ccacacccac caccacactc gcccacaccc    180
accaccagtg acttgagcat ctgtgcttcg ctgtgacgcc cctcgcccta ggcaggaacg    240
acgctgggag gagtctccag gtcagaccca gcttggaagc aagtctgtcc tcactgccta    300
tccttctgcc atcataacac cccctccctg ctctgctccc cggaatcctc agaaacggga    360
tttgtatttg ccgtgactgg ttggcctgaa cacgtagggc tccgtgactg ggacaggaat    420
gggcaggaga agcaagagtc ggagctccaa ggggcccagg ggtggcctgg ggaaggaaga    480
tggtcagcag gctgggggag aggctctagg tgatgaaata ttacattccc gaccccaaga    540
gagcacccac cctcagacct gccctccacc tggcagctgg ggagccctgg cctgaacccc 600
cccctcccag caggcccacc ctctctctga cttccctgct ctcacctccc cgagaacagc 660
tagagccccc tcctccgcct ggccaggcca ccagcttctc ttctgcaaac gtttgtgcct 720
ctgaaatgct ccgttgttat t 741

<210> SEQ ID NO 93
<211> LENGTH: 221
<212> TYPE: DNA
<213> ORGANISM: Artificial Sequence
<220> FEATURE:
<223> OTHER INFORMATION: Description of Artificial Sequence: Synthetic
Affymetrix ID 3549675 polynucleotide

<400> SEQUENCE: 93
ccaggaactt ggtgatgata tcgtgggtga gttcattttc caggtgctgt agtttcccct 60
catcaggcag gaagaagatg gcggtggcat tgcccaggta tttcatcagc agcacccagc 120
tggacagctt cttacagtgc tggatgttaa acatgcctaa acgcttcatc ataggcacct 180
tcacggtggt cacctggtcc acgtggaagt cctcttcctc g 221

<210> SEQ ID NO 94
<211> LENGTH: 154
<212> TYPE: DNA
<213> ORGANISM: Artificial Sequence
<220> FEATURE:
<223> OTHER INFORMATION: Description of Artificial Sequence: Synthetic
Affymetrix ID 2372800 polynucleotide

<400> SEQUENCE: 94
ccattgctac tattgcttgt cggtgttatt ttattttatt gtttttgact ttggaagaga 60
tgaactgtgt atttaactta agctattgct cttaaaacca gggagtcaga atatatttgt 120
aagttaaatc attggtgcta ataataaatg tgga 154

<210> SEQ ID NO 95
<211> LENGTH: 314
<212> TYPE: DNA
<213> ORGANISM: Artificial Sequence
<220> FEATURE:
<223> OTHER INFORMATION: Description of Artificial Sequence: Synthetic
Affymetrix ID 3270276 polynucleotide

<400> SEQUENCE: 95
accgactcag caggttggat ttataggcaa catgaccatg tgggtgagag gatgagagtg 60
agaaccaagg ccccgcagtt ttcggccagg gtgactggat gcatccggac cagacacagg 120
cttacgagat gatggtgcgc ccagggtgtg agctgagttt gagggtgcca gagggggaag 180
ccgctccaac atgtggaatc caagcagctg attccagcag ggagggtctg tccaaaggga 240
agcgaagaga gtttttcagc atgaaactga tggtgccaat gtttgtgctt cactgcgcta 300
aactgtcatc tttc 314

<210> SEQ ID NO 96
<211> LENGTH: 76
<212> TYPE: DNA
<213> ORGANISM: Artificial Sequence
<220> FEATURE:
<223> OTHER INFORMATION: Description of Artificial Sequence: Synthetic
Affymetrix ID 2598290 oligonucleotide

<400> SEQUENCE: 96
ccgggaaccg aatatacaat ttatgtcatt gccctgaaga ataatcagaa gagcgagccc 60
ctgattggaa ggaaaa 76

<210> SEQ ID NO 97
<211> LENGTH: 89
<212> TYPE: DNA
<213> ORGANISM: Artificial Sequence
<220> FEATURE:
<223> OTHER INFORMATION: Description of Artificial Sequence: Synthetic
Affymetrix ID 3451841 oligonucleotide

<400> SEQUENCE: 97
gcacagctgt gccaatgata ccatttgctt caatttggat ggcggatatg attgtcgatg 60
tcctcatgga aagaattgca caggggact 89

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
Affymetrix ID 2598277 oligonucleotide

<400> SEQUENCE: 98
gatggtgcca tgacaatggt gtgaacta 28

<210> SEQ ID NO 99
<211> LENGTH: 88
<212> TYPE: DNA
<213> ORGANISM: Artificial Sequence
<220> FEATURE:
<223> OTHER INFORMATION: Description of Artificial Sequence: Synthetic
Affymetrix ID 2598296 oligonucleotide

<400> SEQUENCE: 99
ttacaaccag gcactgacta caagatctac ctgtacacct tgaatgacaa tgctcggagc 60
tcccctgtgg tcatcgacgc ctccactg 88

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
Affymetrix ID 2637146 oligonucleotide

<400> SEQUENCE: 100
atgctgtgct gtatgagaag aaccaaacag 30

<210> SEQ ID NO 101
<211> LENGTH: 838
<212> TYPE: DNA
<213> ORGANISM: Artificial Sequence
<220> FEATURE:
<223> OTHER INFORMATION: Description of Artificial Sequence: Synthetic
Affymetrix ID 2651371 polynucleotide

<400> SEQUENCE: 101
gtcatggtgc agctgatata aagccattaa gttgagtagc ggttgatttg gtctgtagaa 60
gatttgtctt cctatctgta tttttgaaaa gttaatattc aaattagctg tcatttttag 120
tacatacctg ctaaaggggg gccaagaatt gttctgtttt ctacttgatc accttccagt 180
gtctcaatta gatcattaaa aacaaagtta atcatgtcat tactttataa acctcattga 240
gctactgata ctgttcataa tgaagttcgt agcactaaag acccatcatc aacctgtctc 300
tagccagctt ttgaccatgc ttacgtatac cctacatatt ttagtcattc ccccaacatc 360
atgtacattt aaaacatggt gccattgttc attgctcttt cctgtaatac atgttttctt 420
cttccatttt tattccctca agcatttatt cctcaagcat ttttattttc cagtatatgt 480
aaacaaaata ctagagccct tctttccata gcagcaccaa tcatattgta ttataattag 540
ttgcctgcta ttaagactgc ttatcattaa tttttgtaca ccccactttt caatatacaa 600
ggggtactca ataaagattt gctagattca attaaagaac atttttgaca acttaaaatt 660
ccatcgaaat aatttactga gtaaaaaaaa aaaaaacttg caaaacacag cgtttatgat 720
actgaaaaat acccagtaac caatactcgt taaactggat tgaattactc agccttttaa 780
tatagcaaga ggaaatcaag aaagctgtag caccacagct ttattggtct gtactcca 838

<210> SEQ ID NO 102
<211> LENGTH: 75
<212> TYPE: DNA
<213> ORGANISM: Artificial Sequence
<220> FEATURE:
<223> OTHER INFORMATION: Description of Artificial Sequence: Synthetic
Affymetrix ID 2598365 oligonucleotide

<400> SEQUENCE: 102
tttccgcaaa tccatctttc ctttgacatg ccatttgagg ataatttgca gtgtttcagc 60
taataaccta agata 75

<210> SEQ ID NO 103
<211> LENGTH: 126
<212> TYPE: DNA
<213> ORGANISM: Artificial Sequence
<220> FEATURE:
<223> OTHER INFORMATION: Description of Artificial Sequence: Synthetic
Affymetrix ID 2598325 polynucleotide

<400> SEQUENCE: 103
cctacaaacg gccagcaggg aaattctttg gaagaagtgg tccatgctga tcagagctcc 60
tgcacttttg ataacctgag tcccggcctg gagtacaatg tcagtgttta cactgtcaag 120
gatgac 126

<210> SEQ ID NO 104
<211> LENGTH: 293
<212> TYPE: DNA
<213> ORGANISM: Artificial Sequence
<220> FEATURE:
<223> OTHER INFORMATION: Description of Artificial Sequence: Synthetic
Affymetrix ID 3270275 polynucleotide

<400> SEQUENCE: 104
cttagctagc caacaacatt ctttcaaagg atattttttg gttttcatca aatgtaaata 60
gtgtttaaga gtctgtaata tcatttagaa ggaacaaatg gaagtattaa acctttattg 120
actacctaca gtatatagag gatctataac ttatgatggt tttattatag tttctcaacc 180
ttacaatggg tttattgggc attgggtaca ttttaaactt atgatatatt ctatttacaa 240
ggggttcatc aggatatgac ctcactgtaa gcccaggagc atccgtacgt aca 293

<210> SEQ ID NO 105
<211> LENGTH: 49
<212> TYPE: DNA
<213> ORGANISM: Artificial Sequence
<220> FEATURE:

<223> OTHER INFORMATION: Description of Artificial Sequence: Synthetic
Affymetrix ID 3460458 oligonucleotide

<400> SEQUENCE: 105
tcaaacaaga acaatgaatt cctcaagccc aagcaagaat gtgacaagg 49

<210> SEQ ID NO 106
<211> LENGTH: 110
<212> TYPE: DNA
<213> ORGANISM: Artificial Sequence
<220> FEATURE:
<223> OTHER INFORMATION: Description of Artificial Sequence: Synthetic
Affymetrix ID 2598357 polynucleotide

<400> SEQUENCE: 106
ccttcctata caacaaccac aattacactg attgcacttc tgagggcaga agagacaaca 60
tgaagtggtg tgggaccaca cagaactatg atgccgacca gaagtttggg 110

<210> SEQ ID NO 107
<211> LENGTH: 152
<212> TYPE: DNA
<213> ORGANISM: Artificial Sequence
<220> FEATURE:
<223> OTHER INFORMATION: Description of Artificial Sequence: Synthetic
Affymetrix ID 2406581 polynucleotide

<400> SEQUENCE: 107
gtcatttcac ttctaacttg gtataggaag cttagctctc tacataccta tcatgtgccc 60
tgtatcacag aagattcagg aaaaatgcac ttgggaatca aagaaaatgg aacttctttt 120
tgaaaagaca agcaaccatg ttaactgtat tg 152

<210> SEQ ID NO 108
<211> LENGTH: 700
<212> TYPE: DNA
<213> ORGANISM: Artificial Sequence
<220> FEATURE:
<223> OTHER INFORMATION: Description of Artificial Sequence: Synthetic
Affymetrix ID 2400178 polynucleotide

<400> SEQUENCE: 108
tgttggcatt cttcgctgat ttggctgttc ccaatgttta cattatttaa tcttgcaaaa 60
atggttctgt gcacttggat gtgaaatgct gtccagtttt attttttta tgttgttatc 120 cttggatgta caaaaaattc agaaaatgat ctctgtagat attctgtttt attttggtca 180
tctttagaag ttatcaggaa tgtgtttaaa acaagaagag aactttcta aggaatgata 240 catagaaaag attttatttt aaaatgagtt gtaaagcttg tgtttctttg ttgctgcaag 300
ctatctgccc aagttaatgc aaatggacac attttttatg tcagaaaaac acacacacac 360
acacacacac acacacacac acacgaaaaa caaagaaaaa aatgcttgag ctttttctaa 420 cttcccttg cagtctgttg tgtgagcagc ctgtttattt ctctaatatt atgtcagttt 480
attctcttta atggactgta aaaaaatgta atcacaagag tgccaaatat cttgaaatgc 540
caaaaggcat tttagtttct tttctctgtg ctctgagtcc acgtacagga atgcttggag 600
tgtcttttct gttatttata gggattctct taaggcacac cagctgcctg ttttgcatgg 660
tatttgcaaa aatgcctctt gcgtgaggaa atcttttacc 700

<210> SEQ ID NO 109
<211> LENGTH: 148
<212> TYPE: DNA
<213> ORGANISM: Artificial Sequence
<220> FEATURE:
<223> OTHER INFORMATION: Description of Artificial Sequence: Synthetic
Affymetrix ID 2598321 polynucleotide

<400> SEQUENCE: 109
ttgggtaccg catcacagta gttgcggcag gagaaggtat ccctattttt gaagattttg 60
tggactcctc agtaggatac tacacagtca cagggctgga gccgggcatt gactatgata 120
tcagcgttat cactctcatt aatggcgg 148

<210> SEQ ID NO 110
<211> LENGTH: 60
<212> TYPE: DNA
<213> ORGANISM: Artificial Sequence
<220> FEATURE:
<223> OTHER INFORMATION: Description of Artificial Sequence: Synthetic
Affymetrix ID 2721993 oligonucleotide

<400> SEQUENCE: 110
ttcttcaaca tctccggcat cttgctgtgg tacccgatcc cgttcactcg cctgcccatc 60

<210> SEQ ID NO 111
<211> LENGTH: 306
<212> TYPE: DNA
<213> ORGANISM: Artificial Sequence
<220> FEATURE:
<223> OTHER INFORMATION: Description of Artificial Sequence: Synthetic
Affymetrix ID 3420343 polynucleotide

<400> SEQUENCE: 111
gaggagtttt acattgcagc ttagaagcct ttcttccaat agcagagatt tggtgtcatg 60
tggtgttcat cagtttgaaa agaagtattt ctgctgtttg cctcaagatg tacatacaga 120
gatgtgctga ttctcagaac ttctatagaa ttccattagc cagtcctgcc aattgaaatt 180
tggcatttaa ttatttgcat ttttctattc ttgcctagga aaggagctcg tcacatacct 240
agtttagtga tggaaagtat ttggagaaag ttttagagag tggggctcag gctcaagaat 300
acaatg 306

<210> SEQ ID NO 112
<211> LENGTH: 31
<212> TYPE: DNA
<213> ORGANISM: Artificial Sequence
<220> FEATURE:
<223> OTHER INFORMATION: Description of Artificial Sequence: Synthetic
Affymetrix ID 3451913 oligonucleotide

<400> SEQUENCE: 112
agggagacga tggactgagc tgatccgcac c 31

<210> SEQ ID NO 113
<211> LENGTH: 83
<212> TYPE: DNA
<213> ORGANISM: Artificial Sequence
<220> FEATURE:
<223> OTHER INFORMATION: Description of Artificial Sequence: Synthetic
Affymetrix ID 2439191 oligonucleotide

<400> SEQUENCE: 113
tctgactaaa gatgtcggtg gtggtgatgg agaggggata ttggagagga tgttgttacc 60
tcagaccagg ttaaccagta aag 83

<210> SEQ ID NO 114
<211> LENGTH: 26

<212> TYPE: DNA
<213> ORGANISM: Artificial Sequence
<220> FEATURE:
<223> OTHER INFORMATION: Description of Artificial Sequence: Synthetic
      Affymetrix ID 2598270 oligonucleotide

<400> SEQUENCE: 114
ctgacagaga agattcccga gagtaa 26

<210> SEQ ID NO 115
<211> LENGTH: 143
<212> TYPE: DNA
<213> ORGANISM: Artificial Sequence
<220> FEATURE:
<223> OTHER INFORMATION: Description of Artificial Sequence: Synthetic
      Affymetrix ID 2598367 polynucleotide

<400> SEQUENCE: 115
atgcaacgat caggacacaa ggacatccta tagaattgga gacacctgga gcaagaagga 60
taatcgagga aacctgctcc agtgcatctg cacaggcaac ggccgaggag agtggaagtg 120
tgagaggcac acctctgtgc aga 143

<210> SEQ ID NO 116
<211> LENGTH: 183
<212> TYPE: DNA
<213> ORGANISM: Artificial Sequence
<220> FEATURE:
<223> OTHER INFORMATION: Description of Artificial Sequence: Synthetic
      Affymetrix ID 3369077 polynucleotide

<400> SEQUENCE: 116
tcatggattt gggattcaac ataccacccc cagcctcatt attatcccca ttgtgttcaa 60
gctctctctt cctcgtggct tattcattcg gtcttgatca tctctggcca tcatgttcta 120
agtgatgtgg atacgatggt gggacaaggt ggctctctga ctgtggaaca tgcatccttt 180
cac 183

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic
      Affymetrix ID 2911184 oligonucleotide

<400> SEQUENCE: 117
catggcctct aagtagtgga aatgtga 27

<210> SEQ ID NO 118
<211> LENGTH: 129
<212> TYPE: DNA
<213> ORGANISM: Artificial Sequence
<220> FEATURE:
<223> OTHER INFORMATION: Description of Artificial Sequence: Synthetic
      Affymetrix ID 2722004 polynucleotide

<400> SEQUENCE: 118
gtggctaaag tctaacgctc ctctcttggt cagataacaa aagccctccc tgttggatct 60
tttgaaataa aacgtgcaag ttatccaggc tcgtagcctg catgctgcca ccttgaatcc 120
cagggagta 129

<210> SEQ ID NO 119
<211> LENGTH: 47

<212> TYPE: DNA
<213> ORGANISM: Artificial Sequence
<220> FEATURE:
<223> OTHER INFORMATION: Description of Artificial Sequence: Synthetic
Affymetrix ID 3577630 oligonucleotide

<400> SEQUENCE: 119
ccgtgcataa ggctgtgctg accatcgacg agaaagggac tgaagct 47

<210> SEQ ID NO 120
<211> LENGTH: 59
<212> TYPE: DNA
<213> ORGANISM: Artificial Sequence
<220> FEATURE:
<223> OTHER INFORMATION: Description of Artificial Sequence: Synthetic
Affymetrix ID 3494642 oligonucleotide

<400> SEQUENCE: 120
taaatgagag agatgtgcca aaagctacaa ttagtcggta cagttctgat gacactttg 59

<210> SEQ ID NO 121
<211> LENGTH: 70
<212> TYPE: DNA
<213> ORGANISM: Artificial Sequence
<220> FEATURE:
<223> OTHER INFORMATION: Description of Artificial Sequence: Synthetic
Affymetrix ID 2598308 oligonucleotide

<400> SEQUENCE: 121
tgggagcaag tctacagcta ccatcagcgg ccttaaacct ggagttgatt ataccatcac 60
tgtgtatgct 70

<210> SEQ ID NO 122
<211> LENGTH: 115
<212> TYPE: DNA
<213> ORGANISM: Artificial Sequence
<220> FEATURE:
<223> OTHER INFORMATION: Description of Artificial Sequence: Synthetic
Affymetrix ID 2828456 polynucleotide

<400> SEQUENCE: 122
gaaggggtat tgaagccaag acctgaaggg ctaggaatgg taaggcaggc aaaggggtat 60
agggagagga agtgtggccc agaggtgagg tcttgcacca caagttcaga gaaaa 115

<210> SEQ ID NO 123
<211> LENGTH: 41
<212> TYPE: DNA
<213> ORGANISM: Artificial Sequence
<220> FEATURE:
<223> OTHER INFORMATION: Description of Artificial Sequence: Synthetic
Affymetrix ID 2400180 oligonucleotide

<400> SEQUENCE: 123
ggagagaata agaacggcgg taacagttat tggcaaaaag c 41

<210> SEQ ID NO 124
<211> LENGTH: 114
<212> TYPE: DNA
<213> ORGANISM: Artificial Sequence
<220> FEATURE:
<223> OTHER INFORMATION: Description of Artificial Sequence: Synthetic
Affymetrix ID 3928670 polynucleotide

<400> SEQUENCE: 124
cataaggtca tgacgtgtct atgtcaaaag ttcttatata tttcttttat aagctgaaag 60

-continued aaggtctatt tttatgtttt taggtctatg aatggaacgt tgtaaatgct tgtc 114

<210> SEQ ID NO 125
<211> LENGTH: 334
<212> TYPE: DNA
<213> ORGANISM: Artificial Sequence
<220> FEATURE:
<223> OTHER INFORMATION: Description of Artificial Sequence: Synthetic
Affymetrix ID 2722006 polynucleotide

<400> SEQUENCE: 125
tccaccatcc cagcaagtca ggatatcaga cagtcctccc ctgaccctcc cccttgtaga 60
tatcaattcc caaacagagc caaatactct atatctatag tcacagccct gtacagcatt 120
tttcataagt tatatagtaa atggtctgca tgatttgtgc ttctagtgct ctcatttgga 180
aatgaggcag gcttcttcta tgaaatgtaa agaaagaaac cactttgtat attttgtaat 240
accacctctg tggccatgcc tgccccgccc actctgtata tatgtaagtt aaacccgggc 300
aggggctgtg gccgtctttg tactctggtg attt 334

<210> SEQ ID NO 126
<211> LENGTH: 90
<212> TYPE: DNA
<213> ORGANISM: Artificial Sequence
<220> FEATURE:
<223> OTHER INFORMATION: Description of Artificial Sequence: Synthetic
Affymetrix ID 2598342 oligonucleotide

<400> SEQUENCE: 126
tccaagcaca gccacttctg tgaacatccc tgacctgctt cctggccgaa aatacattgt 60
aaatgtctat cagatatctg aggatgggga 90

<210> SEQ ID NO 127
<211> LENGTH: 145
<212> TYPE: DNA
<213> ORGANISM: Artificial Sequence
<220> FEATURE:
<223> OTHER INFORMATION: Description of Artificial Sequence: Synthetic
Affymetrix ID 2598356 polynucleotide

<400> SEQUENCE: 127
ggaaatctgc acaaccaatg aaggggtcat gtaccgcatt ggagatcagt gggataagca 60
gcatgacatg ggtcacatga tgaggtgcac gtgtgttggg aatggtcgtg gggaatggac 120
atgcattgcc tactcgcagc ttcga 145

<210> SEQ ID NO 128
<211> LENGTH: 241
<212> TYPE: DNA
<213> ORGANISM: Artificial Sequence
<220> FEATURE:
<223> OTHER INFORMATION: Description of Artificial Sequence: Synthetic
Affymetrix ID 3839600 polynucleotide

<400> SEQUENCE: 128
tctcggtgta cgttgaccaa gtgtcttccg taaagactgt acgaacgtcc agttccagtg 60
tttgagagtg ctggtctcac tgactcttct ccagcactga gggttttgtg tttctttatt 120
tgttttggtt ttaggtcttt accaatttga ttggtttatc aacagggcat gaggttggtt 180
taaatatatc tttgaggaaa ggtaaagtca aatttgactt cataggtcat cggcgtcctc 240
a 241

<210> SEQ ID NO 129
<211> LENGTH: 146
<212> TYPE: DNA
<213> ORGANISM: Artificial Sequence
<220> FEATURE:
<223> OTHER INFORMATION: Description of Artificial Sequence: Synthetic
      Affymetrix ID 2526815 polynucleotide

<400> SEQUENCE: 129
tagcacagtc ttctatcaga tgagggaagg ggctaaaatt aaacaactgg ccttaggaat     60
aaaatctgtc acttggcata gacaggactt agcactctct gttggtgtgg agtagagaac    120
tctcctgttg gaagattggg gattca                                         146

<210> SEQ ID NO 130
<211> LENGTH: 48
<212> TYPE: DNA
<213> ORGANISM: Artificial Sequence
<220> FEATURE:
<223> OTHER INFORMATION: Description of Artificial Sequence: Synthetic
      Affymetrix ID 2598363 oligonucleotide

<400> SEQUENCE: 130
tctggcccct tcaccgatgt tcgtgcagct gtttaccaac cgcagcct                  48

<210> SEQ ID NO 131
<211> LENGTH: 479
<212> TYPE: DNA
<213> ORGANISM: Artificial Sequence
<220> FEATURE:
<223> OTHER INFORMATION: Description of Artificial Sequence: Synthetic
      Affymetrix ID 2598309 polynucleotide

<400> SEQUENCE: 131
tctgttgtgg ataacctgaa agcccaacag tgaacaaaga attaaagaaa ctttggcaag     60
tccattcaac ggagcccttg ttttttccaa gaaaatacgt aagatataga tgatataatt    120
tgttctaaaa cccaaataaa aagttgttta tatactacaa ctagaggggg aacggcagag    180
ctgaggaaat aaaaggattg taaattcaca aacatattat cagtggtgga aataagtgat    240
ttttattttt tcttctcttt acttttctgt attttccaaa ttttatttaa aaggaatgta    300
ttctgttaaa agttttaaaa aggacacaat gcatgcaatc ctgggttgag ggcttacctt    360
ctcccacttc taatgctact ctactactca gtgacatttt aaagctgaaa tgttaaaaca    420
gcgctaactg taattttctc tcaatgttta tacacttacc aaggtttgct acatgcata     479

<210> SEQ ID NO 132
<211> LENGTH: 302
<212> TYPE: DNA
<213> ORGANISM: Artificial Sequence
<220> FEATURE:
<223> OTHER INFORMATION: Description of Artificial Sequence: Synthetic
      Affymetrix ID 2647356 polynucleotide

<400> SEQUENCE: 132
taccaacagg ttcaaagcat acttttcatg atttttttat tacaaatgta aaatgtataa     60
agtcacatgt actgccatac tacttctttg tatataaaga tgtttatatc tttggaagtt    120
ttacataaat caaaggaaga aagcacattt aaaatgagaa actaagacca atttctgttt    180
ttaagaggaa aaagaatgat tgatgtatcc taagtattgt tatttgttgt cttttttttgc    240 tgccttgctt gagttgcttg tgactgatct tttgaggctg tcatcatggc tagggttctt    300
tt                                                                   302

<210> SEQ ID NO 133
<211> LENGTH: 559
<212> TYPE: DNA
<213> ORGANISM: Artificial Sequence
<220> FEATURE:
<223> OTHER INFORMATION: Description of Artificial Sequence: Synthetic
      Affymetrix ID 2598320 polynucleotide

<400> SEQUENCE: 133
acatagatgg tgttgcatgc tgccaccagt tactccggtt aaatatggat gtttcatggg     60
ggaagtcagc aattggccaa agattcagat agggtggatt ggggggataa ggaatcaaat    120
gcatctgcta aactgattgg agaaaaacac atgcaagtat tcttcagtac actctcattt    180
aaaccacaag tagatataaa gctagagaaa tacagatgtc tgctctgtta aatataaaat    240
agcaaatgtt cattcaattt gaagacctag aatttttcgt cttaaatacc aaacacgaat    300
accaaattgc gtaagtacca attaattata agaaatatat caccaaaatg taccatcatg    360
atcttccttc taccctttga taaactctac catgctcctt ctttgtagct aaaaacccat    420
caaaatttag ggtagagtgg atgggcattg ttttgaggta ggagaaaagt aaacttggga    480
gcattctagg ttttgttgct gtcactaggt aaagaaacac ctctttaacc acagtctggg    540
gacaagcatg caacatttt                                                 559

<210> SEQ ID NO 134
<211> LENGTH: 53
<212> TYPE: DNA
<213> ORGANISM: Artificial Sequence
<220> FEATURE:
<223> OTHER INFORMATION: Description of Artificial Sequence: Synthetic
      Affymetrix ID 3645563 oligonucleotide

<400> SEQUENCE: 134
ccatagagga gaccggcgga gagggctgcc cagctgtggc gctgatccag tga            53

<210> SEQ ID NO 135
<211> LENGTH: 120
<212> TYPE: DNA
<213> ORGANISM: Artificial Sequence
<220> FEATURE:
<223> OTHER INFORMATION: Description of Artificial Sequence: Synthetic
      Affymetrix ID 2560630 polynucleotide

<400> SEQUENCE: 135
ttattatgac tctagataat tgtgatttta aacactttgt tttttttttt ttttttaatt     60
ggatttcaaa gaaaagaatg gaaatgagag gtaaggatta aagccaaagt taggatggga    120

<210> SEQ ID NO 136
<211> LENGTH: 27
<212> TYPE: DNA
<213> ORGANISM: Artificial Sequence
<220> FEATURE:
<223> OTHER INFORMATION: Description of Artificial Sequence: Synthetic
      Affymetrix ID 2598268 oligonucleotide

<400> SEQUENCE: 136
tgttagcaga cccagcttag agttctt                                         27

<210> SEQ ID NO 137
<211> LENGTH: 179
<212> TYPE: DNA
<213> ORGANISM: Artificial Sequence
<220> FEATURE:
<223> OTHER INFORMATION: Description of Artificial Sequence: Synthetic Affymetrix ID 3549673 polynucleotide

<400> SEQUENCE: 137
ggtgggattc accacttttc ccatgaagag gggagacttg gtattttgtt caatcattaa 60
gaagacaaag ggtttgttga acttgacctc ggggggata gacatgggta tggcctctaa 120
aaacatggcc ccagcagctt cagtcccttt ctcgtcgatg gtcagcacag ccttatgca 179

<210> SEQ ID NO 138
<211> LENGTH: 222
<212> TYPE: DNA
<213> ORGANISM: Artificial Sequence
<220> FEATURE:
<223> OTHER INFORMATION: Description of Artificial Sequence: Synthetic
Affymetrix ID 2598313 polynucleotide

<400> SEQUENCE: 138
ccaactggca ttgacttttc tgatattact gccaactctt ttactgtgca ctggattgct 60
cctcgagcca ccatcactgg ctacaggatc cgccatcatc ccgagcactt cagtgggaga 120
cctcgagaag atcgggtgcc ccactctcgg aattccatca ccctcaccaa cctcactcca 180
ggcacagagt atgtggtcag catcgttgct cttaatggca ga 222

<210> SEQ ID NO 139
<211> LENGTH: 389
<212> TYPE: DNA
<213> ORGANISM: Artificial Sequence
<220> FEATURE:
<223> OTHER INFORMATION: Description of Artificial Sequence: Synthetic
Affymetrix ID 2598278 polynucleotide

<400> SEQUENCE: 139
ggagcgggga tgtcaagttc atttatgtga ctctttggct caacttacat aatctttgtt 60
ttgatatcac agttgtctaa ttattttact ttgtagctta aggcaggctg aattgttgat 120
aaaatggaaa aagtagtata ttgttatata agcttctgag gtgtgttttg ttgtataagc 180
cctggaggtt aaaaagtcat cccttatgta tagtagttaa aggcataaaa ctgtgacttt 240
tagatattcc acagaaccag acttatttga tgtggataat aaccaatgat ttagcatttt 300
gtttgctttt gttttatttt atccgggttc attttttact cttcccatgt acatgaaaca 360
ggtggtggcg tgtagagatc agctgatcc 389

<210> SEQ ID NO 140
<211> LENGTH: 42
<212> TYPE: DNA
<213> ORGANISM: Artificial Sequence
<220> FEATURE:
<223> OTHER INFORMATION: Description of Artificial Sequence: Synthetic
Affymetrix ID 2722001 oligonucleotide

<400> SEQUENCE: 140
ctgggtcagg ggacatagtg tcattgtttg gaaactgcag ac 42

<210> SEQ ID NO 141
<211> LENGTH: 670
<212> TYPE: DNA
<213> ORGANISM: Artificial Sequence
<220> FEATURE:
<223> OTHER INFORMATION: Description of Artificial Sequence: Synthetic
Affymetrix ID 3489154 polynucleotide

<400> SEQUENCE: 141
cctactagag tcctgtgggc tgaaatatca gactgggaaa aaatgcaaag cacattggat 60
cctacttttc ttcagatatt gaaccagatc tctggcccat caggctttct aaattcttca 120
aaagagccac aacttcccca gcttctccag ctcccctgtc ctcttcaatc ccttgagata 180
tagccaacta acgacgctac tggaagcccc agagcagaaa agaagcacat cctaagattc 240
agggaaagac taactgtgaa aaggaaggct gtcctataac aaagcagcat caagtcccaa 300
gtaaggacag tgagagaaaa gggggagaag gattggagca aaagagaact ggcaataagt 360
aggggaagga agaatttcat tttgcattgg gagagaggtt ctaacacact gaaggcaacc 420
ctatttctac tgtttctctc ttgccagggt attaggaagg acaggaaaag taggaggagg 480
atctggggca ttgccctagg aaatgaaaga attgtgtata gaatggaagg gggatcatca 540
aggacatgta tctcaaattt tctttgagat gcaggttagt tgaccttgct gcagttctcc 600
ttcccattaa ttcattggga tggaagccaa aaataaaaga ggtgcctctg aggattaggg 660
ttgagcactc 670

<210> SEQ ID NO 142
<211> LENGTH: 117
<212> TYPE: DNA
<213> ORGANISM: Artificial Sequence
<220> FEATURE:
<223> OTHER INFORMATION: Description of Artificial Sequence: Synthetic
Affymetrix ID 3412131 polynucleotide

<400> SEQUENCE: 142
cagacataat gttggggacg gtcaaacaag gctgccggct cccaaggggc tagagtccac 60
tcctgataat agaaggcggc tgaacactga cacttcactg aggataatgg agacagc 117

<210> SEQ ID NO 143
<211> LENGTH: 461
<212> TYPE: DNA
<213> ORGANISM: Artificial Sequence
<220> FEATURE:
<223> OTHER INFORMATION: Description of Artificial Sequence: Synthetic
Affymetrix ID 3641988 polynucleotide

<400> SEQUENCE: 143
tcggaattcc caggcctata gatttttaaa ccacaccaca ggggtaaacc ttaaaagaag 60
tgaaacctaa cactatatat atttccattt ctaaatacag tatattacag aagtttaaat 120
ataccacctc tgtgtactta caactataaa aagatacaat aactctacca attataaata 180
atgtagcatt tcatattaaa gacattatcg tacaatggaa gaataggaac cctctaacgt 240
atcactatca aggttagtgt ctatatctac ttgagataaa atactgaaaa ttcagtgtat 300
gaagccaaat cctgatttaa caagttattg gtagtataag tgataagtgt tagctgatga 360
agggaaggca aatgtggtaa tttatatctc tgacaagggt gataggccca ttttatacat 420
ggttttcgtt atacacacac tggttctgtt acgggccctc a 461

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
Affymetrix ID 2991805 oligonucleotide

<400> SEQUENCE: 144
aaattctagc agccttaatg gccctaa 27

<210> SEQ ID NO 145
<211> LENGTH: 131
<212> TYPE: DNA
<213> ORGANISM: Artificial Sequence
<220> FEATURE:
<223> OTHER INFORMATION: Description of Artificial Sequence: Synthetic
      Affymetrix ID 2598307 polynucleotide

<400> SEQUENCE: 145
ttgacaaacc atcccagatg caagtgaccg atgttcagga caacagcatt agtgtcaagt     60
ggctgccttc aagttcccct gttactggtt acagagtaac caccactccc aaaaatggac    120
caggaccaac a                                                         131

<210> SEQ ID NO 146
<211> LENGTH: 63
<212> TYPE: DNA
<213> ORGANISM: Artificial Sequence
<220> FEATURE:
<223> OTHER INFORMATION: Description of Artificial Sequence: Synthetic
      Affymetrix ID 2598306 oligonucleotide

<400> SEQUENCE: 146
gcccacagtg gagtatgtgg ttagtgtcta tgctcagaat ccaagcggag agagtcagcc     60
tct                                                                   63

<210> SEQ ID NO 147
<211> LENGTH: 72
<212> TYPE: DNA
<213> ORGANISM: Artificial Sequence
<220> FEATURE:
<223> OTHER INFORMATION: Description of Artificial Sequence: Synthetic
      Affymetrix ID 2721983 oligonucleotide

<400> SEQUENCE: 147
agttatcagc caaattgcaa tgaacgatga aaaagcgaaa aacaagagtc ttgtcaagat     60
ttggtgcaaa ac                                                         72

<210> SEQ ID NO 148
<211> LENGTH: 163
<212> TYPE: DNA
<213> ORGANISM: Artificial Sequence
<220> FEATURE:
<223> OTHER INFORMATION: Description of Artificial Sequence: Synthetic
      Affymetrix ID 2526831 polynucleotide

<400> SEQUENCE: 148
gagctacagt tccattcagt gaattctact tacaagtgaa catgttcatg caaattggtt     60
ctcagcatgt ttcttttccc atgcacagca gagaaccttt aaaatgttgc atgcttgtcc    120
ccagactgtg gttaaagagg tgtttcttta cctagtgaca gca                      163

<210> SEQ ID NO 149
<211> LENGTH: 76
<212> TYPE: DNA
<213> ORGANISM: Artificial Sequence
<220> FEATURE:
<223> OTHER INFORMATION: Description of Artificial Sequence: Synthetic
      Affymetrix ID 2953502 oligonucleotide

<400> SEQUENCE: 149
gggaggtggt aagaacacct gacaacttct gaatattgga cattttaaac acttacaaat     60
aaatccaaga ctgtca                                                     76

-continued

<210> SEQ ID NO 150
<211> LENGTH: 353
<212> TYPE: DNA
<213> ORGANISM: Artificial Sequence
<220> FEATURE:
<223> OTHER INFORMATION: Description of Artificial Sequence: Synthetic
Affymetrix ID 2526809 polynucleotide

<400> SEQUENCE: 150
ttcctacagt attgcgggcc agacacttaa gtgaaagcag aagtgtttgg gtgactttcc 60
tacttaaaat tttggtcata tcatttcaaa acatttgcat cttggttggc tgcatatgct 120
ttcctattga tcccaaacca aatcttagaa tcacttcatt taaaatactg agcggtattg 180
aatacttcga agcagaacag gcaatgtgca gccctcattt atgagaaaac cctcaggaaa 240
ctcccagggt gatgcttgga gaagctgtga gttgagctga agctggagaa cttcctccag 300
agcaaagggc ttaagaaaga aagaagaact ctaagctggg tctgctaaca tca 353

<210> SEQ ID NO 151
<211> LENGTH: 96
<212> TYPE: DNA
<213> ORGANISM: Artificial Sequence
<220> FEATURE:
<223> OTHER INFORMATION: Description of Artificial Sequence: Synthetic
Affymetrix ID 2598310 oligonucleotide

<400> SEQUENCE: 151
ggacctggaa gttgttgctg cgaccccac cagcctactg atcagctggg atgctcctgc 60
tgtcacagtg agatattaca ggatcactta cggaga 96

<210> SEQ ID NO 152
<211> LENGTH: 54
<212> TYPE: DNA
<213> ORGANISM: Artificial Sequence
<220> FEATURE:
<223> OTHER INFORMATION: Description of Artificial Sequence: Synthetic
Affymetrix ID 3247647 oligonucleotide

<400> SEQUENCE: 152
ttatctgtat gcacatttca tccggttctc agatatcgtc acttgttcac caca 54

<210> SEQ ID NO 153
<211> LENGTH: 53
<212> TYPE: DNA
<213> ORGANISM: Artificial Sequence
<220> FEATURE:
<223> OTHER INFORMATION: Description of Artificial Sequence: Synthetic
Affymetrix ID 2333767 oligonucleotide

<400> SEQUENCE: 153
ctgagcctta ggcattacct gtcatcttca ctcttggaga cctcaatcct cag 53

<210> SEQ ID NO 154
<211> LENGTH: 249
<212> TYPE: DNA
<213> ORGANISM: Artificial Sequence
<220> FEATURE:
<223> OTHER INFORMATION: Description of Artificial Sequence: Synthetic
Affymetrix ID 3444044 polynucleotide

<400> SEQUENCE: 154
cacaccttgt ggagaacatg catactacaa ttaagagagt gaacatatcc atcatccctc 60
aaagtgtcac aatgctcctc ctgatgactc ctccccagaa aaccaccaat cggctttcat 120
tttgcatttt gtagttttat gtgaatggaa tcatatagta tgtctttttt ttttgtctgg 180
cttctttcac tttgcataat tattttgaga ttcatatgtc tccatcttga tgctcgtatg 240
aattcattc 249

<210> SEQ ID NO 155
<211> LENGTH: 39
<212> TYPE: DNA
<213> ORGANISM: Artificial Sequence
<220> FEATURE:
<223> OTHER INFORMATION: Description of Artificial Sequence: Synthetic
Affymetrix ID 3335899 oligonucleotide

<400> SEQUENCE: 155
ggcacttcag gtccgtgggc cgtatctgtc acaataaat 39

<210> SEQ ID NO 156
<211> LENGTH: 133
<212> TYPE: DNA
<213> ORGANISM: Artificial Sequence
<220> FEATURE:
<223> OTHER INFORMATION: Description of Artificial Sequence: Synthetic
Affymetrix ID 3460538 polynucleotide

<400> SEQUENCE: 156
cgttgtaaca ttcagaggta gtattgagta gtggggatat attgcatctc tggctaaaag 60
tgcagtttga atgaagagat ggtgaactca agccgaagaa aagcaccttg gtcaaccatc 120
ttatgtcaaa acg 133

<210> SEQ ID NO 157
<211> LENGTH: 168
<212> TYPE: DNA
<213> ORGANISM: Artificial Sequence
<220> FEATURE:
<223> OTHER INFORMATION: Description of Artificial Sequence: Synthetic
Affymetrix ID 2598318 polynucleotide

<400> SEQUENCE: 157
ctgacctgcg attcaccaac attggtccag acaccatgcg tgtcacctgg gctccacccc 60
catccattga tttaaccaac ttcctggtgc gttactcacc tgtgaaaaat gaggaagatg 120
ttgcagagtt gtcaatttct ccttcagaca atgcagtggt cttaacaa 168

<210> SEQ ID NO 158
<211> LENGTH: 385
<212> TYPE: DNA
<213> ORGANISM: Artificial Sequence
<220> FEATURE:
<223> OTHER INFORMATION: Description of Artificial Sequence: Synthetic
Affymetrix ID 3666402 polynucleotide

<400> SEQUENCE: 158
tctgacgtta gagtggtggc ttccttagcc tttcaggatg gaggaatgtg ggcagtttga 60
cttcagcact gaaaacctct ccacctgggc cagggttgcc tcagaggcca agtttccaga 120
agcctcttac ctgccgtaaa atgctcaacc ctgtgtcctg ggcctgggcc tgctgtgact 180
gacctacagt ggactttctc tctggaatgg aaccttctta ggcctcctgg tgcaacttaa 240 ttttttttt taatgctatc ttcaaaacgt tagagaaagt tcttcaaaag tgcagcccag 300
agctgctggg cccactggcc gtcctgcatt tctggtttcc agaccccaat gcctcccatt 360
cggatggatc tctgcgtttt tatac 385

<210> SEQ ID NO 159

<211> LENGTH: 110
<212> TYPE: DNA
<213> ORGANISM: Artificial Sequence
<220> FEATURE:
<223> OTHER INFORMATION: Description of Artificial Sequence: Synthetic
Affymetrix ID 2598371 polynucleotide

<400> SEQUENCE: 159
gacttcctat gtggtcggag aaacgtggga gaagccctac caaggctgga tgatggtaga 60
ttgtacttgc ctgggagaag gcagcggacg catcacttgc acttctagaa 110

<210> SEQ ID NO 160
<211> LENGTH: 67
<212> TYPE: DNA
<213> ORGANISM: Artificial Sequence
<220> FEATURE:
<223> OTHER INFORMATION: Description of Artificial Sequence: Synthetic
Affymetrix ID 2598286 oligonucleotide

<400> SEQUENCE: 160
caagaagctc tctctcagac aaccatctca tgggccccat tccaggacac ttctgagtac 60
atcattt 67

<210> SEQ ID NO 161
<211> LENGTH: 181
<212> TYPE: DNA
<213> ORGANISM: Artificial Sequence
<220> FEATURE:
<223> OTHER INFORMATION: Description of Artificial Sequence: Synthetic
Affymetrix ID 2598302 polynucleotide

<400> SEQUENCE: 161
ctattcctgc accaactgac ctgaagttca ctcaggtcac acccacaagc ctgagcgccc 60
agtggacacc acccaatgtt cagctcactg gatatcgagt gcgggtgacc cccaaggaga 120
agaccggacc aatgaaagaa atcaaccttg ctcctgacag ctcatccgtg gttgtatcag 180
g 181

<210> SEQ ID NO 162
<211> LENGTH: 48
<212> TYPE: DNA
<213> ORGANISM: Artificial Sequence
<220> FEATURE:
<223> OTHER INFORMATION: Description of Artificial Sequence: Synthetic
Affymetrix ID 3374652 oligonucleotide

<400> SEQUENCE: 162
aggaaactgg tattggagtc ccaggaaaca gcagtcgggg aaaatata 48

<210> SEQ ID NO 163
<211> LENGTH: 309
<212> TYPE: DNA
<213> ORGANISM: Artificial Sequence
<220> FEATURE:
<223> OTHER INFORMATION: Description of Artificial Sequence: Synthetic
Affymetrix ID 2722005 polynucleotide

<400> SEQUENCE: 163
atgggctttg attagctgtc ctctctccat gcctgcaaag ctccagattt ttggggaaag 60
ctgtacccaa ctggactgcc cagtgaactg ggatcattaa gtacagtcga gcacacgtgt 120
gtgcatgggt caaaggggtg tgttccttct catcctagat gccttctctg tgccttccac 180
agcctcctgc ctgattacac cactgccccc gccccaccct cagccatccc aattcttcct 240
ggccagtgcg ctccagcctt atctaggaaa ggaggagtgg gtgtagccgt gcagcaagat 300
tggggcctc 309

<210> SEQ ID NO 164
<211> LENGTH: 177
<212> TYPE: DNA
<213> ORGANISM: Artificial Sequence
<220> FEATURE:
<223> OTHER INFORMATION: Description of Artificial Sequence: Synthetic
Affymetrix ID 3270278 polynucleotide

<400> SEQUENCE: 164
ttcctctaca ggaatggggt ttggcagtga tccaaagact cactgttatg acatgttctc 60
agggaagtag gtcatatgtc cccagggtat tcagagaggc ctgtgagtgt gagatgtttg 120
ggctgagcag ggctttcttc ctctcaaggc tccaaagggc gggccaacag gtcattt 177

<210> SEQ ID NO 165
<211> LENGTH: 38
<212> TYPE: DNA
<213> ORGANISM: Artificial Sequence
<220> FEATURE:
<223> OTHER INFORMATION: Description of Artificial Sequence: Synthetic
Affymetrix ID 2598280 oligonucleotide

<400> SEQUENCE: 165
aaactgttgt gccagtgctt aggctttgga agtggtca 38

<210> SEQ ID NO 166
<211> LENGTH: 34
<212> TYPE: DNA
<213> ORGANISM: Artificial Sequence
<220> FEATURE:
<223> OTHER INFORMATION: Description of Artificial Sequence: Synthetic
Affymetrix ID 2708981 oligonucleotide

<400> SEQUENCE: 166
tgaaggctca ttctggcaca cttgtgaact gcag 34

<210> SEQ ID NO 167
<211> LENGTH: 2051
<212> TYPE: DNA
<213> ORGANISM: Artificial Sequence
<220> FEATURE:
<223> OTHER INFORMATION: Description of Artificial Sequence: Synthetic
Affymetrix ID 3957167 polynucleotide

<400> SEQUENCE: 167
tgtgcgtctg acctggcatg atttctattt attatgatat cctatttata ttaacttatt 60
ggtgctttca gtggccaagt taattcccct ttccctggtc cctactcaac aaaatatgat 120
gatggctccc gacacaagcg ccagggccag ggcttagcag ggcctggtct ggaagtcgac 180
aatgttacaa gtggaataag ccttacgggt gaagctcaga gaagggtcgg atctgagaga 240
atggggaggc ctgagtggga gtggggggcc ttgctccacc cccccccatc ccctactgtg 300
acttgcttta gggtgtcagg gtccaggctg caggggctgg gccaatttgt ggagaggccg 360
ggtgcctttc tgtcttgatt ccagggggct ggttcacact gttcttgggc gccccagcat 420
tgtgttgtga ggcgcactgt tcctggcaga tattgtgccc cctggagcag tgggcaagac 480
agtccttgtg gcccaccctg tccttgtttc tgtgtcccca tgctgcctct gaaatagcgc 540
cctggaacaa ccctgcccct gcacccagca tgctccgaca cagcagggaa gctcctcctg 600
tggcccggac acccatagac ggtgcggggg gcctggctgg gccagacccc aggaaggtgg 660
ggtagactgg ggggatcagc tgcccattgc tcccaagagg aggagaggga ggctgcagat 720
gcctgggact cagaccagga agctgtgggc cctcctgctc cacccccatc ccactcccac 780
ccatgtctgg gctcccaggc agggaacccg atctcttcct ttgtgctggg gccaggcgag 840
tggagaaacg ccctccagtc tgagagcagg ggagggaagg aggcagcaga gttggggcag 900
ctgctcagag cagtgttctg gcttcttctc aaaccctgag cgggctgccg gcctccaagt 960
tcctccgaca agatgatggt actaattatg gtacttttca ctcactttgc acctttccct 1020
gtcgctctct aagcacttta cctggatggc gcgtgggcag tgtgcaggca ggtcctgagg 1080
cctggggttg gggtggaggg tgcggcccgg agttgtccat ctgtccatcc caacagcaag 1140
acgaggatgt ggctgttgag atgtgggcca cactcaccct tgtccaggat gcagggactg 1200
ccttctcctt cctgcttcat ccggcttagc ttggggctgg ctgcattccc ccaggatggg 1260
cttcgagaaa gacaaacttg tctggaaacc agagttgctg attccacccg gggggcccgg 1320
ctgactcgcc catcacctca tctccctgtg gacttgggag ctctgtgcca ggcccacctt 1380
gcggccctgg ctctgagtcg ctctcccacc cagcctggac ttggccccat gggacccatc 1440
ctcagtgctc cctccagatc ccgtccggca gcttggcgtc caccctgcac agcatcactg 1500
aatcacagag cctttgcgtg aaacagctct gccaggccgg gagctgggtt tctcttccct 1560
ttttatctgc tggtgtggac cacacctggg cctggccgga ggaagagaga gtttaccaag 1620
agagatgtct ccgggccctt atttattatt taaacatttt tttaaaaagc actgctagtt 1680
tacttgtctc tcctccccat cgtccccatc gtcctccttg tccctgactt ggggcacttc 1740
caccctgacc cagccagtcc agctctgcct tgccggctct ccagagtaga catagtgtgt 1800
ggggttggag ctctggcacc cggggaggta gcatttccct gcagatggta cagatgttcc 1860
tgccttagag tcatctctag ttccccacct caatcccggc atccagcctt cagtcccgcc 1920
cacgtgctag ctccgtgggc ccaccgtgcg gccttagagg tttccctcct tcctttccac 1980
tgaaaagcac atggccttgg gtgacaaatt cctctttgat gaatgtaccc tgtggggatg 2040
tttcatactg a 2051

<210> SEQ ID NO 168
<211> LENGTH: 128
<212> TYPE: DNA
<213> ORGANISM: Artificial Sequence
<220> FEATURE:
<223> OTHER INFORMATION: Description of Artificial Sequence: Synthetic
Affymetrix ID 3994738 polynucleotide

<400> SEQUENCE: 168
caccctagca tgtcgtttgc cctggccatc gatgaccagg cagttctctc acaatcactt 60
cctccatcac agacttcaag gccaactgag gagttctatc ctttgtacat taaagatcat 120
tctcctat 128

<210> SEQ ID NO 169
<211> LENGTH: 56
<212> TYPE: DNA
<213> ORGANISM: Artificial Sequence
<220> FEATURE:
<223> OTHER INFORMATION: Description of Artificial Sequence: Synthetic
Affymetrix ID 2735072 oligonucleotide

<400> SEQUENCE: 169
tttggtggtg tcaattgctt atttgttttc ccacggttgt ccagcaatta ataaaa 56

-continued

<210> SEQ ID NO 170
<211> LENGTH: 86
<212> TYPE: DNA
<213> ORGANISM: Artificial Sequence
<220> FEATURE:
<223> OTHER INFORMATION: Description of Artificial Sequence: Synthetic
Affymetrix ID 2598282 oligonucleotide

<400> SEQUENCE: 170
tttaaactcc ttattcccag cagcagtatt ctacattcta accaggttct cccagctttg 60
agacgtctca gacttaccag ttctcc 86

<210> SEQ ID NO 171
<211> LENGTH: 85
<212> TYPE: DNA
<213> ORGANISM: Artificial Sequence
<220> FEATURE:
<223> OTHER INFORMATION: Description of Artificial Sequence: Synthetic
Affymetrix ID 2809255 oligonucleotide

<400> SEQUENCE: 171
tggaattaga accagtcaga gctagagaag caaggtcctc aaggctgaga atatgttctc 60
atgcatccag acatcaaagt tacaa 85

<210> SEQ ID NO 172
<211> LENGTH: 32
<212> TYPE: DNA
<213> ORGANISM: Artificial Sequence
<220> FEATURE:
<223> OTHER INFORMATION: Description of Artificial Sequence: Synthetic
Affymetrix ID 2598329 oligonucleotide

<400> SEQUENCE: 172
cattgtctcc accaacaaac ttgcatctgg ag 32

<210> SEQ ID NO 173
<211> LENGTH: 32
<212> TYPE: DNA
<213> ORGANISM: Artificial Sequence
<220> FEATURE:
<223> OTHER INFORMATION: Description of Artificial Sequence: Synthetic
Affymetrix ID 2783628 oligonucleotide

<400> SEQUENCE: 173
gtaggaatgc agcaacatcc tttggaaaag tc 32

<210> SEQ ID NO 174
<211> LENGTH: 79
<212> TYPE: DNA
<213> ORGANISM: Artificial Sequence
<220> FEATURE:
<223> OTHER INFORMATION: Description of Artificial Sequence: Synthetic
Affymetrix ID 2598276 oligonucleotide

<400> SEQUENCE: 174
tgatgggaag acataccacg taggagaaca gtggcagaag gaatatctcg gtgccatttg 60
ctcctgcaca tgctttgga 79

<210> SEQ ID NO 175
<211> LENGTH: 78
<212> TYPE: DNA
<213> ORGANISM: Artificial Sequence
<220> FEATURE:
<223> OTHER INFORMATION: Description of Artificial Sequence: Synthetic
Affymetrix ID 3759590 oligonucleotide

<400> SEQUENCE: 175
ctggcctggc cgtaggtttg taactgtttc atagaagagc cctggagaag acagtagaat 60
gagcctatct agtttaaa 78

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic Affymetrix ID 2567212 oligonucleotide

<400> SEQUENCE: 176
ttgttagctt tggagataat caatgtg 27

<210> SEQ ID NO 177
<211> LENGTH: 399
<212> TYPE: DNA
<213> ORGANISM: Artificial Sequence
<220> FEATURE:
<223> OTHER INFORMATION: Description of Artificial Sequence: Synthetic Affymetrix ID 2987929 polynucleotide

<400> SEQUENCE: 177
agtcccataa tggtaccgcc tgctgtttag tgcatattta gtagatggca ttattatctc 60
tcaacatttc tcccctcttg cgtggttaag aagataaatt ccagcatgtt ctgaaccgat 120
attcctgtag ggaaggagag gatttccctg aactctccac cccgctgccc tggtgagagc 180
ttgctgccat cccaggggtg gatccacttt gaagttttaa tgtgatgtga agccagcaga 240
tgttaaggac ataggtggga ctgttgaagc atcctgcatg aatttttcat ggccagctcc 300
cactgctcag gtgcacacca gaaaaagaag ggtttgggcc tgcctgagag tagatgtgtc 360
ttccgaggtc agacccggga aagctttatg aacctgtca 399

<210> SEQ ID NO 178
<211> LENGTH: 32
<212> TYPE: DNA
<213> ORGANISM: Artificial Sequence
<220> FEATURE:
<223> OTHER INFORMATION: Description of Artificial Sequence: Synthetic Affymetrix ID 2598271 oligonucleotide

<400> SEQUENCE: 178
tgttaattgc ccaattgagt gcttcatgcc tt 32

<210> SEQ ID NO 179
<211> LENGTH: 258
<212> TYPE: DNA
<213> ORGANISM: Artificial Sequence
<220> FEATURE:
<223> OTHER INFORMATION: Description of Artificial Sequence: Synthetic Affymetrix ID 2322740 polynucleotide

<400> SEQUENCE: 179
ctgtaggaaa tccaagcaga ccagctgggg tggggggatg tagcctacct cgggggactg 60
tctgtcctca aaacgggctg agaaggcccg tcaggggccc aggtcccaca gagaggcctg 120
ggatactccc ccaacccgag gggcagactg ggcagtgggg agccccccatt gtgccccaga 180 ggtggccaca ggctgaagga ggggcctgag gcaccgcagc ctgcaacccc cagggctgca 240
gtccactaac tttttaca 258

<210> SEQ ID NO 180
<211> LENGTH: 69
<212> TYPE: DNA
<213> ORGANISM: Artificial Sequence
<220> FEATURE:
<223> OTHER INFORMATION: Description of Artificial Sequence: Synthetic
Affymetrix ID 2400179 oligonucleotide

<400> SEQUENCE: 180
gaaatttatt actagcttgc tacccacgat gaaatcaaca acctgtatct ggtatcaggc 60
cgggagaca 69

<210> SEQ ID NO 181
<211> LENGTH: 54
<212> TYPE: DNA
<213> ORGANISM: Artificial Sequence
<220> FEATURE:
<223> OTHER INFORMATION: Description of Artificial Sequence: Synthetic
Affymetrix ID 2598352 oligonucleotide

<400> SEQUENCE: 181
gctcaagtgg tcctgtcgaa gtatttatca ctgagactcc gagtcagccc aact 54

<210> SEQ ID NO 182
<211> LENGTH: 70
<212> TYPE: DNA
<213> ORGANISM: Artificial Sequence
<220> FEATURE:
<223> OTHER INFORMATION: Description of Artificial Sequence: Synthetic
Affymetrix ID 2721985 oligonucleotide

<400> SEQUENCE: 182
gttccctcga ctgctaactg cacctcccct tccctctgtt ggacggatgg catccaaaac 60
tggaccatga 70

<210> SEQ ID NO 183
<211> LENGTH: 105
<212> TYPE: DNA
<213> ORGANISM: Artificial Sequence
<220> FEATURE:
<223> OTHER INFORMATION: Description of Artificial Sequence: Synthetic
Affymetrix ID 2598299 polynucleotide

<400> SEQUENCE: 183
caagaagggc tcgtgtgaca gatgctactg agaccaccat caccattagc tggagaacca 60
agactgagac gatcactggc ttccaagttg atgccgttcc agcca 105

<210> SEQ ID NO 184
<211> LENGTH: 165
<212> TYPE: DNA
<213> ORGANISM: Artificial Sequence
<220> FEATURE:
<223> OTHER INFORMATION: Description of Artificial Sequence: Synthetic
Affymetrix ID 2721982 polynucleotide

<400> SEQUENCE: 184
ttcttcaact ggctgtccgt gttggtgctc ttgcccgtgg aggtggccac ccattacctc 60
gagatcataa cccagcttat agtggagagc ttccacttca agaatggaga agatgcccca 120
gatcttctga aagtcatcac taagcccttc acaaagctca ttgtc 165

<210> SEQ ID NO 185
<211> LENGTH: 152
<212> TYPE: DNA

```
<213> ORGANISM: Artificial Sequence
<220> FEATURE:
<223> OTHER INFORMATION: Description of Artificial Sequence: Synthetic
      Affymetrix ID 3755859 polynucleotide

<400> SEQUENCE: 185

gggacaactt catggagcct atttacaaat taagagtcag cttaatttgt aacatttcta     60

ccagagccaa gaatcccaaa ttcctggtag attagtgttt tatttctaag ggcttatgc    120

attcggctcc aactcaactc gtctatgtgc tg                                 152


<210> SEQ ID NO 186
<211> LENGTH: 1027
<212> TYPE: DNA
<213> ORGANISM: Artificial Sequence
<220> FEATURE:
<223> OTHER INFORMATION: Description of Artificial Sequence: Synthetic
      Affymetrix ID 2598303 polynucleotide

<400> SEQUENCE: 186

caaactcggg catttcatag cagcatgatt ctgagcacac gtgggtaaga cctttcttct     60

ctggttagat atcatatgct ggtgtataat tagcttaaat gattgtgatt tagacaccta    120

ggaaataatc aatagggcaa ttgctttcca taatacttta tcttcttgtg ctttatttct    180

gaagcagagt agaatgctaa agatgtatcc tagtgacagc ataaacccta gaggtgacag    240

tctgtattat tgcttttcgc ttctcttttc tgcttctgtt gggagccagt tttcttctta    300

cgccgcatta cagagagaac gtcaaattta gcagccatat ctgccatagg gtccaaataa    360

agagacaata aaaacattat tctctctttt ttggatggaa tactgcgtga aatggttatc    420

catacaaaga tactttatgt agaatagaaa aaggaggccg ggtgcagtgg ctcacacatg    480

taatcctagt gctttgggag gctaagccgg gagcactgat tgaggccagg agttcatgat    540

cagcctgggc aatgaagtga gaccccgtct ctacaaaaaa atatgaaaaa attagcgagg    600

tgtggtgaca catgcctgta gtcccagcta ctcaagaggc tgaggtagag gatcacttga    660

gcctacgagt tcaaggctgc agtgagctat gataactcca ctgcactgcc gcctggatga    720

cacagagaga ccgtttctaa attaattaat taacaatttt aagaaagaaa aagggccatt    780

gcttattttt ccatacaaaa gtaaaataaa tcataatggc caataagcca atgtaacttt    840

ttttttaaag ggaaagcaaa acttgtaaaa cctaaaatct cttagagttt tggcatttac    900

ccaaatgttt tcagtgattc tgagaattgg tggatataaa acacatttct cagcaaacac    960

tttcttcatt ttgcatccct tactgtacgt actttcttgt actgaatctt tgcttgacca   1020

gggaacc                                                            1027


<210> SEQ ID NO 187
<211> LENGTH: 420
<212> TYPE: DNA
<213> ORGANISM: Artificial Sequence
<220> FEATURE:
<223> OTHER INFORMATION: Description of Artificial Sequence: Synthetic
      Affymetrix ID 3768560 polynucleotide

<400> SEQUENCE: 187

tcacatctgg ttggttgtag gactggaaaa gattcaagga ggaagttcca tgggagtttg     60

gctgggagga atttctggag atgaaagtgt agaagaaggc attccaaggt gatggaacag    120

catgaggtgg gaggaaagta caggaacact aaacatagaa cttaggtagg agggcaatgg    180

gtggggagga agatttaaag aagtaaaaca cttggggaaa tgctaaagta ggaatttgga    240
```

tgagagtcca cggacaacaa ggacctattg aaggatttca taggagggaa ataagtgctt 300
gcagctgtgc cctggacagt gaatttggca gtgatggagg cctggagtgg agaagggaag 360
aagactgagg tcgtgaatat cagtaaagag actattccag gatccagata agagggttaa 420

<210> SEQ ID NO 188
<211> LENGTH: 258
<212> TYPE: DNA
<213> ORGANISM: Artificial Sequence
<220> FEATURE:
<223> OTHER INFORMATION: Description of Artificial Sequence: Synthetic
Affymetrix ID 3577642 polynucleotide

<400> SEQUENCE: 188
tgagttcgcc ttcagcctat accgccagct ggcacaccag tccaacagca ccaatatctt 60
cttctcccca gtgagcatcg ctacagcctt tgcaatgctc tccctgggga ccaaggctga 120
cactcacgat gaaatcctgg agggcctgaa tttcaacctc acggagattc cggaggctca 180
gatccatgaa ggcttccagg aactcctccg taccctcaac cagccagaca gccagctcca 240
gctgaccacc ggcaatgg 258

<210> SEQ ID NO 189
<211> LENGTH: 33
<212> TYPE: DNA
<213> ORGANISM: Artificial Sequence
<220> FEATURE:
<223> OTHER INFORMATION: Description of Artificial Sequence: Synthetic
Affymetrix ID 2739228 oligonucleotide

<400> SEQUENCE: 189
acaaaattcc aatatggcat aaactctgtg gag 33

<210> SEQ ID NO 190
<211> LENGTH: 150
<212> TYPE: DNA
<213> ORGANISM: Artificial Sequence
<220> FEATURE:
<223> OTHER INFORMATION: Description of Artificial Sequence: Synthetic
Affymetrix ID 2598338 polynucleotide

<400> SEQUENCE: 190
gacagacgtg aaggtcacca tcatgtggac accgcctgag agtgcagtga ccggctaccg 60
tgtggatgtg atccccgtca acctgcctgg cgagcacggg cagaggctgc ccatcagcag 120
gaacaccttt gcagaagtca ccgggctgtc 150

<210> SEQ ID NO 191
<211> LENGTH: 523
<212> TYPE: DNA
<213> ORGANISM: Artificial Sequence
<220> FEATURE:
<223> OTHER INFORMATION: Description of Artificial Sequence: Synthetic
Affymetrix ID 2526825 polynucleotide

<400> SEQUENCE: 191
aggtaagccc tcaacccagg attgcatgca ttgtgtcctt tttaaaactt ttaacagaat 60
acattccttt taaataaaat ttggaaaata cagaaaagta aagagaagaa aaaataaaaa 120
tcacttattt ccaccactga taatatgttt gtgaatttac aatcctttta tttcctcagc 180
tctgccgttc cccctctagt tgtagtatat aaacaacttt ttatttgggt tttagaacaa 240
attatatcat ctatatctta cgtattttct tggaaaaaac aagggctccg ttgaatggac 300
ttgccaaagt ttctttaatt ctttgttcac tgttgggctt tcaggttatc cacaacagaa 360
tctgatttaa tcagagtgta aaatagcatt ttactgctgt acctgtctct ccgtaagtga 420
tcctgtaata tctcactgtg acagcaggag catcccagct gatcagtagg ctggtggggg 480
tcgcagcaac aacttccagg tccctcggaa catcagaaac tag 523

<210> SEQ ID NO 192
<211> LENGTH: 169
<212> TYPE: DNA
<213> ORGANISM: Artificial Sequence
<220> FEATURE:
<223> OTHER INFORMATION: Description of Artificial Sequence: Synthetic
Affymetrix ID 3261704 polynucleotide

<400> SEQUENCE: 192
atggtttggg ctcccaactt cccagccagg tgcttctgca ggcccacatc ttgcccactg 60
gccaaacctt taaataactt tgactcgggc tactcttatg ctcaaagacg tcaggggctc 120
tcccaaatct ctttaccctg ccagaaagtc ttctatagta cggcctcca 169

<210> SEQ ID NO 193
<211> LENGTH: 51
<212> TYPE: DNA
<213> ORGANISM: Artificial Sequence
<220> FEATURE:
<223> OTHER INFORMATION: Description of Artificial Sequence: Synthetic
Affymetrix ID 3415065 oligonucleotide

<400> SEQUENCE: 193
gagccattcc tttggcaact cttgctgtca gccatcttcc aaagagcttt g 51

<210> SEQ ID NO 194
<211> LENGTH: 77
<212> TYPE: DNA
<213> ORGANISM: Artificial Sequence
<220> FEATURE:
<223> OTHER INFORMATION: Description of Artificial Sequence: Synthetic
Affymetrix ID 2526813 oligonucleotide

<400> SEQUENCE: 194
tttccgttcc caagacatgt gcagctcatc atctggccat tttctccctg acggtcccac 60
ttctctccaa tcttgta 77

<210> SEQ ID NO 195
<211> LENGTH: 252
<212> TYPE: DNA
<213> ORGANISM: Artificial Sequence
<220> FEATURE:
<223> OTHER INFORMATION: Description of Artificial Sequence: Synthetic
Affymetrix ID 3040586 polynucleotide

<400> SEQUENCE: 195
agcaagtgag gagtcaccgc agatcagaga accgctggcc acaaacctta cctaaattcc 60
agatcttgct gtttctgctc tacctttcta gcatatccac aaaattatta aaatagcaaa 120
tgttttcttt aaacatggct tcttaaaggt gtgtgtgggg gcgggggaat aaagatggca 180
gagccggggt tggagaacag tgatgtcagc tgtttgcttt ctggctccta agggttttac 240
tttgccattc at 252

<210> SEQ ID NO 196
<211> LENGTH: 65
<212> TYPE: DNA
<213> ORGANISM: Artificial Sequence
<220> FEATURE:

```
<223> OTHER INFORMATION: Description of Artificial Sequence: Synthetic
      Affymetrix ID 2598301 oligonucleotide

<400> SEQUENCE: 196

gtgagtgtct atgctcttaa ggacactttg acaagcagac cagctcaggg agttgtcacc     60

actct                                                                 65


<210> SEQ ID NO 197
<211> LENGTH: 125
<212> TYPE: DNA
<213> ORGANISM: Artificial Sequence
<220> FEATURE:
<223> OTHER INFORMATION: Description of Artificial Sequence: Synthetic
      Affymetrix ID 2598263 polynucleotide

<400> SEQUENCE: 197

taaaattgct agtttaccgt tcagaagtat aatagaaata atctttagtt gctcttttct     60

aaccattgta attcttccct tcttccctcc acctttcctt cattgaataa acctctgttc    120

aaaga                                                                125


<210> SEQ ID NO 198
<211> LENGTH: 139
<212> TYPE: DNA
<213> ORGANISM: Artificial Sequence
<220> FEATURE:
<223> OTHER INFORMATION: Description of Artificial Sequence: Synthetic
      Affymetrix ID 2598346 polynucleotide

<400> SEQUENCE: 198

tggaaggaag ctaccatacc aggccactta aactcctaca ccatcaaagg cctgaagcct     60

ggtgtggtat acgagggcca gctcatcagc atccagcagt acggccacca agaagtgact    120

cgctttgact tcaccacca                                                 139


<210> SEQ ID NO 199
<211> LENGTH: 86
<212> TYPE: DNA
<213> ORGANISM: Artificial Sequence
<220> FEATURE:
<223> OTHER INFORMATION: Description of Artificial Sequence: Synthetic
      Affymetrix ID 2827686 oligonucleotide

<400> SEQUENCE: 199

aaaaggatca taaggtgcgt ttggcaattg gaaatggcat acggagtgat gtatggagag     60

aatttttaga cagatttgga aatata                                          86


<210> SEQ ID NO 200
<211> LENGTH: 43
<212> TYPE: DNA
<213> ORGANISM: Artificial Sequence
<220> FEATURE:
<223> OTHER INFORMATION: Description of Artificial Sequence: Synthetic
      Affymetrix ID 3326488 oligonucleotide

<400> SEQUENCE: 200

tggacagcaa aactttctgc cgggctcaga tctccatgac aac                       43


<210> SEQ ID NO 201
<211> LENGTH: 472
<212> TYPE: DNA
<213> ORGANISM: Artificial Sequence
<220> FEATURE:
<223> OTHER INFORMATION: Description of Artificial Sequence: Synthetic
      Affymetrix ID 3040561 polynucleotide
```

<400> SEQUENCE: 201
ggaccctggg tcagtataaa tgctaatggc tgacaaagtt cacaaagaga tgtattttgc 60
ttactcctct gttcaatcct ctggttgcct gccagtgttt atgtgtgtat ttggacagac 120
attcatttat tgtcattcag tcaataggta gagtatatgt gtctattttt tggcaggcat 180
atagatgctt gaggctaatg ggaaaaaacc agcatgaact ctgactttag tagtgctaag 240
taatagataa ttttaaaaaa tgacaccgtt aaatagaaaa tggcatgcat actaacagtt 300
gcaatggaga ggctgtgatg ctacgagata taaacgtaga gatgccatca tgtgaaactg 360
gaagtggggg tgggtcaggg aaatttgttc ttggaaagaa ataatgaacc tcaaggaaga 420
gtaggcattg tcctggtgtg gtggggtgta agcggtgatc ccacaaagca ct 472

<210> SEQ ID NO 202
<211> LENGTH: 106
<212> TYPE: DNA
<213> ORGANISM: Artificial Sequence
<220> FEATURE:
<223> OTHER INFORMATION: Description of Artificial Sequence: Synthetic
Affymetrix ID 2598339 polynucleotide

<400> SEQUENCE: 202
tattcgccat cagtagaagg tagcagcaca gaactcaacc ttcctgaaac tgcaaactcc 60
gtcaccctca gtgacttgca acctggtgtt cagtataaca tcacta 106

<210> SEQ ID NO 203
<211> LENGTH: 30
<212> TYPE: DNA
<213> ORGANISM: Artificial Sequence
<220> FEATURE:
<223> OTHER INFORMATION: Description of Artificial Sequence: Synthetic
Affymetrix ID 2598324 oligonucleotide

<400> SEQUENCE: 203
gtgtccctat ctctgatacc atcatcccag 30

<210> SEQ ID NO 204
<211> LENGTH: 85
<212> TYPE: DNA
<213> ORGANISM: Artificial Sequence
<220> FEATURE:
<223> OTHER INFORMATION: Description of Artificial Sequence: Synthetic
Affymetrix ID 3420360 oligonucleotide

<400> SEQUENCE: 204
gatttatggg ccatacatca ccttcctggt tggctttgtt gacaccttgt cacattcttg 60
cttgggcttg aggaattcat tgttc 85

<210> SEQ ID NO 205
<211> LENGTH: 110
<212> TYPE: DNA
<213> ORGANISM: Artificial Sequence
<220> FEATURE:
<223> OTHER INFORMATION: Description of Artificial Sequence: Synthetic
Affymetrix ID 2598284 polynucleotide

<400> SEQUENCE: 205
cactctgaca ggcctcacca gaggtgccac ctacaacgtc atagtggagg cactgaaaga 60
ccagcagagg cataaggttc gggaagaggt tgttaccgtg ggcaactctg 110

<210> SEQ ID NO 206

<211> LENGTH: 82
<212> TYPE: DNA
<213> ORGANISM: Artificial Sequence
<220> FEATURE:
<223> OTHER INFORMATION: Description of Artificial Sequence: Synthetic
Affymetrix ID 2598281 oligonucleotide

<400> SEQUENCE: 206
tcaacgaagg cttgaaccaa cctacggatg actcgtgctt tgacccctac acagtttccc 60
attatgccgt tggagatgag tg 82

<210> SEQ ID NO 207
<211> LENGTH: 34
<212> TYPE: DNA
<213> ORGANISM: Artificial Sequence
<220> FEATURE:
<223> OTHER INFORMATION: Description of Artificial Sequence: Synthetic
Affymetrix ID 3400270 oligonucleotide

<400> SEQUENCE: 207
tgaggtgttc gagtacgtac ctgtgtttga cccg 34

<210> SEQ ID NO 208
<211> LENGTH: 234
<212> TYPE: DNA
<213> ORGANISM: Artificial Sequence
<220> FEATURE:
<223> OTHER INFORMATION: Description of Artificial Sequence: Synthetic
Affymetrix ID 2773438 polynucleotide

<400> SEQUENCE: 208
tgattgaatc tacttgcaca ctctcccatt atatttattg tttattttag gtcaaaccca 60
agttagttca atcctgattc atatttaatt tgaagataga aggtttgcag atattctcta 120
gtcatttgtt aatatttctt cgtgatgaca tatcacatgt cagccactgt gatagaggct 180
gaggaatcca agaaaatggc cagtgagatc aatgtgacgg cagggaaatg tatg 234

<210> SEQ ID NO 209
<211> LENGTH: 49
<212> TYPE: DNA
<213> ORGANISM: Artificial Sequence
<220> FEATURE:
<223> OTHER INFORMATION: Description of Artificial Sequence: Synthetic
Affymetrix ID 3451420 oligonucleotide

<400> SEQUENCE: 209
tgggctcagg ggctattcag gcatcagatg acccaaagaa agtggcagc 49

<210> SEQ ID NO 210
<211> LENGTH: 35
<212> TYPE: DNA
<213> ORGANISM: Artificial Sequence
<220> FEATURE:
<223> OTHER INFORMATION: Description of Artificial Sequence: Synthetic
Affymetrix ID 3513631 oligonucleotide

<400> SEQUENCE: 210
cagaggactc tggtgtcgtt ttttggtcat tatct 35

<210> SEQ ID NO 211
<211> LENGTH: 102
<212> TYPE: DNA
<213> ORGANISM: Artificial Sequence
<220> FEATURE:
<223> OTHER INFORMATION: Description of Artificial Sequence: Synthetic
Affymetrix ID 2526816 polynucleotide

<400> SEQUENCE: 211
ttcccgaacc ttatgcctct gctggtcttt cagtgcctcc actatgacgt tgtaggtggc 60
acctctggtg aggcctgtca gagtggcact ggtagaagtt cc 102

<210> SEQ ID NO 212
<211> LENGTH: 67
<212> TYPE: DNA
<213> ORGANISM: Artificial Sequence
<220> FEATURE:
<223> OTHER INFORMATION: Description of Artificial Sequence: Synthetic
Affymetrix ID 3846851 oligonucleotide

<400> SEQUENCE: 212
cttccccaag tcagggggct ctctgagtgc agggtctgat gctgagtccc acttagcttg 60
gggtcag 67

<210> SEQ ID NO 213
<211> LENGTH: 112
<212> TYPE: DNA
<213> ORGANISM: Artificial Sequence
<220> FEATURE:
<223> OTHER INFORMATION: Description of Artificial Sequence: Synthetic
Affymetrix ID 2598326 polynucleotide

<400> SEQUENCE: 213
gcccacacat atggatgacc actagcaagt gtaatgatct caatatttat ttctcattca 60
gttgggtttc cttgtatttg ccacattagt gtttaccctg ttcctaatgg ca 112

<210> SEQ ID NO 214
<211> LENGTH: 1904
<212> TYPE: DNA
<213> ORGANISM: Artificial Sequence
<220> FEATURE:
<223> OTHER INFORMATION: Description of Artificial Sequence: Synthetic
Affymetrix ID 3420390 polynucleotide

<400> SEQUENCE: 214
ggcgccaacg ttcgatttct acctcagcag cagttggatc ttttgaaggg agaagacact 60
gcagtgacca cttattctgt attgccatgg tctttccact ttcatctggg gtggggtggg 120
gtggggtggg ggagggggg gtggggtggg gagaaatcac ataaccttaa aaaggactat 180
attaatcacc ttctttgtaa tcccttcaca gtcccaggtt tagtgaaaaa ctgctgtaaa 240
cacaggggac acagcttaac aatgcaactt ttaattactg ttttcttttt tcttaaccta 300
ctaatagttt gttgatctga taagcaagag tgggcgggtg agaaaaaccg aattgggttt 360
agtcaatcac tgcactgcat gcaaacaaga aacgtgtcac acttgtgacg tcgggcattc 420
atataggaag aacgcggtgt gtaacactgt gtacacctca aataccaccc caacccactc 480
cctgtagtga atcctctgtt tagaacacca aagataagga ctagatacta ctttctcttt 540
ttcgtataat cttgtagaca cttacttgat gatttttaac tttttatttc taaatgagac 600
gaaatgctga tgtatccttt cattcagcta acaaactaga aaaggttatg ttcatttttc 660
aaaaagggaa gtaagcaaac aaatattgcc aactcttcta tttatggata tcacacatat 720
cagcaggagt aataaattta ctcacagcac ttgttttcag gacaacactt cattttcagg 780
aaatctactt cctacagagc caaaatgcca tttagcaata aataacactt gtcagcctca 840
gagcatttaa ggaaactaga caagtaaaat tatcctcttt gtaatttaat gaaaaggtac 900
aacagaataa tgcatgatga actcacctaa ttatgaggtg ggaggagcga aatctaaatt 960
tcttttgcta tagttataca tcaatttaaa aagcaaaaaa aaaaaagggg ggggcaatct 1020
ctctctgtgt ctttctctct ctctcttcct ctccctctct cttttcattg tgtatcagtt 1080
tccatgaaag acctgaatac cacttacctc aaattaagca tatgtgttac ttcaagtaat 1140
acgttttgac ataagatggt tgaccaaggt gcttttcttc ggcttgagtt caccatctct 1200
tcattcaaac tgcactttta gccagagatg caatatatcc ccactactca atactacctc 1260
tgaatgttac aacgaattta cagtctagta cttattacat gctgctatac acaagcaatg 1320
caagaaaaaa acttactggg taggtgattc taatcatctg cagttctttt tgtacactta 1380
attacagtta aagaagcaat ctccttactg tgtttcagca tgactatgta tttttctatg 1440
tttttttaat taaaaatttt taaaatactt gtttcagctt ctctgctaga tttctacatt 1500
aacttgaaaa ttttttaacc aagtcgctcc taggttctta aggataattt tcctcaatca 1560
cactacacat cacacaagat ttgactgtaa tatttaaata ttaccctcca agtctgtacc 1620
tcaaatgaat tctttaagga gatggactaa ttgacttgca aagacctacc tccagacttc 1680
aaaaggaatg aacttgttac ttgcagcatt catttgtttt ttcaatgttt gaaatagttc 1740
aaactgcagc taaccctagt caaaactatt tttgtaaaag acatttgata gaaaggaaca 1800
cgtttttaca tacttttgca aaataagtaa ataataaata aaataaaagc caaccttcaa 1860
agaaacttga agctttgtag gtgagatgca acaagccctg cttt 1904

<210> SEQ ID NO 215
<211> LENGTH: 61
<212> TYPE: DNA
<213> ORGANISM: Artificial Sequence
<220> FEATURE:
<223> OTHER INFORMATION: Description of Artificial Sequence: Synthetic Affymetrix ID 2651259 oligonucleotide

<400> SEQUENCE: 215
actggggaga ataatctgta tgaggctaca gtaaaagata agtttagggc tgttgagtcc 60
a 61

<210> SEQ ID NO 216
<211> LENGTH: 206
<212> TYPE: DNA
<213> ORGANISM: Artificial Sequence
<220> FEATURE:
<223> OTHER INFORMATION: Description of Artificial Sequence: Synthetic Affymetrix ID 2955423 polynucleotide

<400> SEQUENCE: 216
gagcactttt agagaccgaa gtcaacatat caatacacta agaaatgttt caagggtcca 60
aatgtcatta aataattata aatatatctt taaagttata tgaccattca cgttagcaag 120
ttacctcaga ttttacacat attcataatt taaaaaaaaa gaaaacaaca catagccaaa 180
cgcaatcact atctatacca ttatgg 206

<210> SEQ ID NO 217
<211> LENGTH: 155
<212> TYPE: DNA
<213> ORGANISM: Artificial Sequence
<220> FEATURE:
<223> OTHER INFORMATION: Description of Artificial Sequence: Synthetic Affymetrix ID 2722000 polynucleotide

<400> SEQUENCE: 217
gatgtctaat cctgcgccta gctgggttgg tcagtagaac ctattttcag actcaaaaac 60
catcttcaga aagaaaaggc ccagggaagg aatgtatgag aggctctccc agatgaggaa 120
gtgtactctc tatgactatc aagctcaggc ctctc 155

<210> SEQ ID NO 218
<211> LENGTH: 54
<212> TYPE: DNA
<213> ORGANISM: Artificial Sequence
<220> FEATURE:
<223> OTHER INFORMATION: Description of Artificial Sequence: Synthetic
Affymetrix ID 3451912 oligonucleotide

<400> SEQUENCE: 218
atggagtctc gggtcttact gagaacattc tgtttgatct tcggtctcgg agca 54

<210> SEQ ID NO 219
<211> LENGTH: 138
<212> TYPE: DNA
<213> ORGANISM: Artificial Sequence
<220> FEATURE:
<223> OTHER INFORMATION: Description of Artificial Sequence: Synthetic
Affymetrix ID 2598344 polynucleotide

<400> SEQUENCE: 219
acaggagaga cgactccctt ttctcctctt gtggccactt ctgaatctgt gaccgaaatc 60
acagccagta gctttgtggt ctcctgggtc tcagcttccg acaccgtgtc gggattccgg 120
gtggaatatg agctgagt 138

<210> SEQ ID NO 220
<211> LENGTH: 26
<212> TYPE: DNA
<213> ORGANISM: Artificial Sequence
<220> FEATURE:
<223> OTHER INFORMATION: Description of Artificial Sequence: Synthetic
Affymetrix ID 2657792 oligonucleotide

<400> SEQUENCE: 220
caaaatgtct attggtctgt ttccag 26

<210> SEQ ID NO 221
<211> LENGTH: 1238
<212> TYPE: DNA
<213> ORGANISM: Artificial Sequence
<220> FEATURE:
<223> OTHER INFORMATION: Description of Artificial Sequence: Synthetic
Affymetrix ID 2710605 polynucleotide

<400> SEQUENCE: 221
agctttgggt gcctttgcca caagacctag cctaatttac caaggatgaa ttctttcaat 60
tcttcatgcg tgcccttttc atatacttat tttattttt accataatct tatagcactt 120
gcatcgttat taagccctta tttgttttgt gtttcattgg tctctatctc ctgaatctaa 180
cacatttcat agcctacatt ttagtttcta aagccaagaa gaatttatta caaatcagaa 240
ctttggaggc aaatctttct gcatgaccaa agtgataaat tcctgttgac cttcccacac 300
aatccctgta ctctgaccca tagcactctt gtttgctttg aaaatatttg tccaattgag 360
tagctgcatg ctgttccccc aggtgttgta acacaacttt attgattgaa tttttaagct 420
acttattcat agttttatat ccccctaaac tacctttttg ttccccattc cttaattgta 480
ttgttttccc aagtgtaatt atcatgcgtt ttatatcttc ctaataaggt gtggtctgtt 540
tgtctgaaca aagtgctaga ctttctggag tgataatctg gtgacaaata ttctctctgt 600

-continued

```
agctgtaagc aagtcactta atctttctac ctcttttttc tatctgccaa attgagataa    660

tgatacttaa ccagttagaa gaggtagtgt gaatattaat tagtttatat tactctcatt    720

ctttgaacat gaactatgcc tatgtagtgt ctttatttgc tcagctggct gagacactga    780

agaagtcact gaacaaaacc tacacacgta ccttcatgtg attcactgcc ttcctctctc    840

taccagtcta tttccactga acaaaaccta cacacatacc ttcatgtggt tcagtgcctt    900

cctctctcta ccagtctatt tccactgaac aaaacctacg cacatacctt catgtggctc    960

agtgccttcc tctctctacc agtctatttc cattctttca gctgtgtctg acatgtttgt   1020

gctctgttcc attttaacaa ctgctcttac ttttccagtc tgtacagaat gctatttcac   1080

ttgagcaaga tgatgtaatg gaaagggtgt tggcattggt gtctggagac ctggatttga   1140

gtcttggtgc tatcaatcac cgtctgtgtt tgagcaaggc atttggctgc tgtaagctta   1200

ttgcttcatc tgtaagcggt ggtttgtaat tcctgatc                           1238
```

<210> SEQ ID NO 222
<211> LENGTH: 88
<212> TYPE: DNA
<213> ORGANISM: Artificial Sequence
<220> FEATURE:
<223> OTHER INFORMATION: Description of Artificial Sequence: Synthetic
      Affymetrix ID 2721976 oligonucleotide

<400> SEQUENCE: 222

```
cctactccac ggctacactg atagatgagc ccactgaggt ggatgacccc tggaacctac     60

ccactcttca ggactcgggg atcaagtg                                        88
```

<210> SEQ ID NO 223
<211> LENGTH: 164
<212> TYPE: DNA
<213> ORGANISM: Artificial Sequence
<220> FEATURE:
<223> OTHER INFORMATION: Description of Artificial Sequence: Synthetic
      Affymetrix ID 2598288 polynucleotide

<400> SEQUENCE: 223

```
cacccaccct gggtatgaca ctggaaatgg tattcagctt cctggcactt ctggtcagca     60

acccagtgtt gggcaacaaa tgatctttga ggaacatggt tttaggcgga ccacaccgcc    120

cacaacggcc acccccataa ggcataggcc aagaccatac ccgc                     164
```

<210> SEQ ID NO 224
<211> LENGTH: 71
<212> TYPE: DNA
<213> ORGANISM: Artificial Sequence
<220> FEATURE:
<223> OTHER INFORMATION: Description of Artificial Sequence: Synthetic
      Affymetrix ID 2738247 oligonucleotide

<400> SEQUENCE: 224

```
gatgttgata ttgggcagca ttttaagtct tttcttcggt acttgttatg tggtcctcca     60

gaacttgcct c                                                          71
```

<210> SEQ ID NO 225
<211> LENGTH: 480
<212> TYPE: DNA
<213> ORGANISM: Artificial Sequence
<220> FEATURE:
<223> OTHER INFORMATION: Description of Artificial Sequence: Synthetic
      Affymetrix ID 2598332 polynucleotide

<400> SEQUENCE: 225

```
ctacattcta ttactttggg cattgaatag taactataaa tgcagaataa aaatatctat     60

ggattgaatg ggaaccaact aattgaacat gaagccaagg aaatgatttc tttatgagtg    120

ttggctgcag aagattaaag tacttttgca gacggaatcg ctcttttctt aaattactct    180

tgaaattcct cagaggagaa aaatactaac aataattttt ggtcatgtct atccttttgc    240

tcaacatttt aaaggaagtg gtcttaaatc tcccacatat ctacatcaca ataacaacct    300

ctattcacaa accgattcct attaaataca tttccattta cattacagag aattatgaga    360

ctccttattt ctagctgaac atcatttgtt attttcaact cgacattttg aattatagaa    420

gcacctaaca taagtacttt ttcagcatat attctaacca tggactagtt tgcaattttc    480


<210> SEQ ID NO 226
<211> LENGTH: 337
<212> TYPE: DNA
<213> ORGANISM: Artificial Sequence
<220> FEATURE:
<223> OTHER INFORMATION: Description of Artificial Sequence: Synthetic
      Affymetrix ID 2556336 polynucleotide

<400> SEQUENCE: 226

agtcctgtct agtggtcagt cctaacagtg tggttaaagg ggagctaaat ttcaactttc     60

aggggtcagc tgagacaacc acctagattt tccaagttag ttccaatttc aagtacaata    120

atcctttgac aacatagaaa agaattatag ttagcaaaat tgcaattgtc acagtcaagg    180

tcttgttggt aatagagggt tggggaaaaa gttaaaacag cattaaatga atatattttt    240

aacataacaa aagttcccag aagacatcca cttcaaattc aagccatatt catcaatgtt    300

aaaaacctta ctcttctccc tgatagtgtg aggaaaa                             337


<210> SEQ ID NO 227
<211> LENGTH: 437
<212> TYPE: DNA
<213> ORGANISM: Artificial Sequence
<220> FEATURE:
<223> OTHER INFORMATION: Description of Artificial Sequence: Synthetic
      Affymetrix ID 2526829 polynucleotide

<400> SEQUENCE: 227

acgcccagga ctatttgaac tgatgaaata tccaaatgtc cagtcctata gcctacttac     60

acctaagtga acactacagc gaagtgttca gtgaacagac cttgagaagg tctgtaatta    120

gatgataagg aagggtcacc ttgccccatg gcctctcgaa gccctccatt ccacctgtga    180

gtgtgactca gctggatttc gagtgggatg aagttgctgc aacagctgga tatttctcgc    240

atccacctga gagtatgtct ctggagggca catgataatc cttgctgtgg tgctgtggat    300

tgccatttat gcctcacaac aaccctggaa ggtagtttgc tccttttaaa agcaatttct    360

tgtcatacaa cgtactgcat atctttaaag tgatgggttt ttacatatgt gtgacttggg    420

agaccatcac cgcattc                                                   437


<210> SEQ ID NO 228
<211> LENGTH: 222
<212> TYPE: DNA
<213> ORGANISM: Artificial Sequence
<220> FEATURE:
<223> OTHER INFORMATION: Description of Artificial Sequence: Synthetic
      Affymetrix ID 3460456 polynucleotide

<400> SEQUENCE: 228

ttctgagatg gagcaccaaa ctggaaaagg gagagatgag cccattgggg caaatcttta     60
```

aactcttcta ctatttttaa gcgtacttgt gaaaatgttt acctgtatgt atacatacag 120
aaaaacaaat gagtttgaac tatgattatc cattacttta ttttttttaaa aaagatatct 180 tgccaagtct taaggtggtt ctgcgggtaa atcagggtag ca 222

<210> SEQ ID NO 229
<211> LENGTH: 821
<212> TYPE: DNA
<213> ORGANISM: Artificial Sequence
<220> FEATURE:
<223> OTHER INFORMATION: Description of Artificial Sequence: Synthetic
Affymetrix ID 3270357 polynucleotide

<400> SEQUENCE: 229
ggccacctgc tatacagttg ttaaatctta aatatgcttt ttaaaaattg gaataatgta 60
ttaaggtcaa ataatatccc ataaaatata tatttctgct aatattagta aatatcttaa 120
tttttcatta gattcatatc atttaatttc acatattcaa cacctttaaa tgttgtaatc 180
ttaatatgcg aagtgtgcct ctgcaagata ctaacacaaa gctcatgtta agaaaacagt 240
tgaggactca gaagtcagtt cgaaaatgca ctttcctaac agtgaattca caaccctgaa 300
cagcagcatt tttggaaggc aaactgttcg tgatggtaca atgtaaatgg ggacttctgt 360
aaagttctca gtttcggtcc atgtggttta tctttacatt ttaaagatca aagaagtctt 420
tacaacctga atccaggtct aaaacacact agagtagctg gtgactataa ataatatttt 480
aaaatgctgt gtctacacca tcaagactgt gtctacacta tcttggctga acgagaagag 540
atgtaaatgc tgggtggtcc cgttgaccca cggcgttggg tacaacaaaa ccagccatcg 600
gagttacacc ccaaagcacc atttgctgtc cagctgcctg tcgtttggcc cagaccaccc 660
tcagaaaaaa accagctgcc tctcccattc tcccctcccg ttctgccaca gcggcctggg 720
ctggtccagt gctatgcctg gaggctcaac acaaaacttc ccatccaaac attcagatga 780
actgagcgtc ttacacacgc agtacagagg agcacacatt a 821

<210> SEQ ID NO 230
<211> LENGTH: 76
<212> TYPE: DNA
<213> ORGANISM: Artificial Sequence
<220> FEATURE:
<223> OTHER INFORMATION: Description of Artificial Sequence: Synthetic
Affymetrix ID 2598273 oligonucleotide

<400> SEQUENCE: 230
gctgtgacaa ctgccgcaga cctgggggtg aacccagtcc cgaaggcact actggccagt 60
cctacaacca gtattc 76

<210> SEQ ID NO 231
<211> LENGTH: 157
<212> TYPE: DNA
<213> ORGANISM: Artificial Sequence
<220> FEATURE:
<223> OTHER INFORMATION: Description of Artificial Sequence: Synthetic
Affymetrix ID 2657795 polynucleotide

<400> SEQUENCE: 231
ataaagttgt gttacaacac ctgggggaac agcatgcagc tactcaattg gacaaatatt 60
ttcaaagcaa acaagagtgc tatgggtcag agtacaggga ttgtgtggga aggtcaacag 120
gaatttatca ctttggtcat gcagaaagat ttgcctc 157

-continued

<210> SEQ ID NO 232
<211> LENGTH: 236
<212> TYPE: DNA
<213> ORGANISM: Artificial Sequence
<220> FEATURE:
<223> OTHER INFORMATION: Description of Artificial Sequence: Synthetic
Affymetrix ID 2512878 polynucleotide

<400> SEQUENCE: 232
catcatcttg acagtgcagt tttgagataa tgaaaacaaa aatgagtttt aataagcttt 60
aaatggcatg gtattttgag gtgctaaggt aaagagaaac attgttttat gaagtggctc 120
atgtgggtat atatatgttg gtgtgctgtg ctgctagcta ttccatggtc ttcatcagta 180
taccactaga gagagaaaga aaagaagtta gaattaggaa gtcagtactc ttctta 236

<210> SEQ ID NO 233
<211> LENGTH: 1211
<212> TYPE: DNA
<213> ORGANISM: Artificial Sequence
<220> FEATURE:
<223> OTHER INFORMATION: Description of Artificial Sequence: Synthetic
Affymetrix ID 2548712 polynucleotide

<400> SEQUENCE: 233
ggtgtgctcc atacccagcg gttcttcatg agtagtgggc tatgcaggag cttctgggag 60 attttttga gtcaaagact taaagggccc aatgaattat tatatacata ctgcatcttg 120
gttatttctg aaggtagcat tctttggagt taaaatgcac atatagacac atacacccaa 180
acacttacac caaactactg aatgaagcag tattttggta accaggccat ttttggtggg 240
aatccaagat tggtctccca tatgcagaaa tagacaaaaa gtatattaaa caaagtttca 300
gagtatattg ttgaagagac agagacaagt aatttcagtg taaagtgtgt gattgaaggt 360
gataagggaa aagataaaga ccagaaattc ccttttcacc ttttcaggaa aataacttag 420
actctagtat ttatgggtgg atttatcctt ttgccttctg gtatacttcc ttacttttaa 480
ggataaatca taaagtcagt tgctcaaaaa gaaatcaata gttgaattag tgagtatagt 540
ggggttccat gagttatcat gaattttaaa gtatgcatta ttaaattgta aaactccaag 600
gtgatgttgt acctcttttg cttgccaaag tacagaattt gaattatcag caaagaaaaa 660
aaaaaaagcc agccaagctt taaattatgt gaccataatg tactgatttc agtaagtctc 720
ataggttaaa aaaaaaagtc accaaatagt gtgaaatata ttacttaact gtccgtaagc 780
agtatattag tattatcttg ttcaggaaaa ggttgaataa tatatgcctt gtataatatt 840
gaaaattgaa aagtacaact aacgcaacca agtgtgctaa aaatgagctt gattaaatca 900
accacctatt tttgacatgg aaatgaagca gggtttcttt tcttcactca aattttggcg 960
aatctcaaaa ttagatccta agatgtgttc ttatttttat aacatcttta ttgaaattct 1020
atttataata cagaatcttg ttttgaaaat aacctaatta atatattaaa attccaaatt 1080
catggcatgc ttaaatttta actaaatttt aaagccattc tgattattga gttccagttg 1140
aagttagtgg aaatctgaac attctcctgt ggaaggcaga gaaatctaag ctgtgtctgc 1200
ccaatgaata a 1211

<210> SEQ ID NO 234
<211> LENGTH: 67
<212> TYPE: DNA
<213> ORGANISM: Artificial Sequence
<220> FEATURE:
<223> OTHER INFORMATION: Description of Artificial Sequence: Synthetic
Affymetrix ID 3536745 oligonucleotide

<400> SEQUENCE: 234
accttacatg tgtaaaggtt tcatgttcac tgtgagtgaa aatttttaca ttcatcaata 60
tccctct 67

<210> SEQ ID NO 235
<211> LENGTH: 60
<212> TYPE: DNA
<213> ORGANISM: Artificial Sequence
<220> FEATURE:
<223> OTHER INFORMATION: Description of Artificial Sequence: Synthetic
Affymetrix ID 2353193 oligonucleotide

<400> SEQUENCE: 235
agttaataaa gtgtggtagt gcctatgaat gcagcaaact ggtgcagaca aggacagcag 60

<210> SEQ ID NO 236
<211> LENGTH: 206
<212> TYPE: DNA
<213> ORGANISM: Artificial Sequence
<220> FEATURE:
<223> OTHER INFORMATION: Description of Artificial Sequence: Synthetic
Affymetrix ID 3726763 polynucleotide

<400> SEQUENCE: 236
tgacaccaaa tatgtccgca gaatggactt gatagcaaac actgggggca ccttaagatt 60
ttgcacctgt aaagtgcctt acagggtaac tgtgctgaat gctttagatg aggaaatgat 120
ccccaagtgg tgaatgacac gcctaaggtc acagctagtt tgagccagtt agactagtcc 180
ccggtctccc gattcccaac tgagtg 206

<210> SEQ ID NO 237
<211> LENGTH: 197
<212> TYPE: DNA
<213> ORGANISM: Artificial Sequence
<220> FEATURE:
<223> OTHER INFORMATION: Description of Artificial Sequence: Synthetic
Affymetrix ID 3772092 polynucleotide

<400> SEQUENCE: 237
tggctgtgcc tctcgatgat gattaagatt tcaatattta cagcaaaacc acaaagcaaa 60
tgatagaata aagcaaaaca atggaaaatc tgagttcact cgtgagagag gtacgtatgt 120
gagctctgag gaaattacag agggaacgca tgcagcggga cagctctccc aatcgcagcg 180
tgcaaagtag acatcca 197

<210> SEQ ID NO 238
<211> LENGTH: 603
<212> TYPE: DNA
<213> ORGANISM: Artificial Sequence
<220> FEATURE:
<223> OTHER INFORMATION: Description of Artificial Sequence: Synthetic
Affymetrix ID 2526820 polynucleotide

<400> SEQUENCE: 238
gcctctgctc aaattagacc taatggaact gaaatgtgca gtctttctct ttctctcttt 60 ctttttttaaa tttgagaagc aagttgtagg aagtagaatc cagactaatc atatcagtgt 120
cataagtatg agaattacag aggtttggct caacagtttt tcatggtttg aaatggtaaa 180
aatagataaa acacacatgt tcatttttga aattttccta tatcaggaat acacattttc 240
ttgaaattaa ctgaaactgg atgcaaaagt aagacattat ttagctctaa gttgtagaaa 300

-continued ccaaataaag ataaatgtga gaggtttctc tccctccttt aaaaaaggaa acattttaaa 360
attcaacaga aggtataaaa gaagagcaat gatagctctt cttttacatt ttaacatctt 420
gtttgaattt ttaaaaggtg aataacaagg ctttatattg agtggctgta gtaaagaaaa 480
aaaataaaac caaactctgc agtgcatgtt aaattatttc tcctattaaa gaatacaata 540
tatacactat gctgttagat aaaaaaaatc acaagaaatg catcaaaaca tggagaacct 600
ttt 603

<210> SEQ ID NO 239
<211> LENGTH: 148
<212> TYPE: DNA
<213> ORGANISM: Artificial Sequence
<220> FEATURE:
<223> OTHER INFORMATION: Description of Artificial Sequence: Synthetic
Affymetrix ID 2657898 polynucleotide

<400> SEQUENCE: 239
agttggaagt tgcagctgtg ttacagatta ttctaagcct tctatccttg ctctcttagg 60
tcagtcgagc aaccttacat ttttcatcta gtatcagaaa acaaacaaaa ttctcatata 120
tttcttttgg attgtacaga gatgctgc 148

<210> SEQ ID NO 240
<211> LENGTH: 65
<212> TYPE: DNA
<213> ORGANISM: Artificial Sequence
<220> FEATURE:
<223> OTHER INFORMATION: Description of Artificial Sequence: Synthetic
Affymetrix ID 2685329 oligonucleotide

<400> SEQUENCE: 240
gaaatgattt tatatacaac cgtgcatgca tttctgtatt ggtcggctta tctggatgca 60
atttt 65

<210> SEQ ID NO 241
<211> LENGTH: 437
<212> TYPE: DNA
<213> ORGANISM: Artificial Sequence
<220> FEATURE:
<223> OTHER INFORMATION: Description of Artificial Sequence: Synthetic
Affymetrix ID 2526814 polynucleotide

<400> SEQUENCE: 241
gtaggggtca aagcacgagt catccgtagg ttggttcaag ccttcgttga ctatgaagaa 60
aaggaagaaa aagcaaaaag agacatctta ttaatcgatt tggaccataa gaagaaaatc 120
gaatgactgt atacaatgac ttaatctaaa acaagaattc caggaggatt aagaggcatt 180
catctgttct atcaaggcat taactgctct aaaaaaccat ggttagatgt gacacctgtc 240
acaggcaccc gacaggaagc ccatctttta tttttccctt gcttctaaga taattgccat 300
ttctgttgaa actacttcat agaacatgga acagatcttg aggcaattga agctagtgga 360
gaactttagt gggatgcaaa gactaatgat gcctctccat tggtacctga gtgaccttgg 420
gccagctatt taatacc 437

<210> SEQ ID NO 242
<211> LENGTH: 104
<212> TYPE: DNA
<213> ORGANISM: Artificial Sequence
<220> FEATURE:
<223> OTHER INFORMATION: Description of Artificial Sequence: Synthetic
Affymetrix ID 2721988 polynucleotide

<400> SEQUENCE: 242
gtgaatttcc acctcccgga tcttgctgtg ggcaccatct tgctcatact ctccctgctg 60
gtcctctgtg gttgcctgat catgattgtc aagatcctgg gctc 104

<210> SEQ ID NO 243
<211> LENGTH: 82
<212> TYPE: DNA
<213> ORGANISM: Artificial Sequence
<220> FEATURE:
<223> OTHER INFORMATION: Description of Artificial Sequence: Synthetic
Affymetrix ID 3335898 oligonucleotide

<400> SEQUENCE: 243
aagctgcgct gtgactttga ggtccttgtg gttccctggc agaactcctc tcagctccta 60
aagcacaact gtgtgcagat gt 82

<210> SEQ ID NO 244
<211> LENGTH: 110
<212> TYPE: DNA
<213> ORGANISM: Artificial Sequence
<220> FEATURE:
<223> OTHER INFORMATION: Description of Artificial Sequence: Synthetic
Affymetrix ID 3536744 polynucleotide

<400> SEQUENCE: 244
tgcagtgaat gatgctcact tgttgcagta caatcatcgg gttaaaaaac tcaatgaaat 60
cagcaaactg ggaatttctg gtgacataga cctcaccagt gcttcatata 110

<210> SEQ ID NO 245
<211> LENGTH: 238
<212> TYPE: DNA
<213> ORGANISM: Artificial Sequence
<220> FEATURE:
<223> OTHER INFORMATION: Description of Artificial Sequence: Synthetic
Affymetrix ID 3129733 polynucleotide

<400> SEQUENCE: 245
atgtcaaaca gctgagcacc gtagcatgca gatgtcaagg cagttaggaa gtaaatggtg 60
tcttgtagat atgtgcaagg tagcatgatg agcaacttga gtttgttgcc actgagaagc 120
aggcgggttg ggtgggagga ggaagaaagg gaagaattag gtttgaattg ctttttaaaa 180
aaaaaagaaa agaaaaagac agcatctcac tatgttgcca aggctcatct tgagaagc 238

<210> SEQ ID NO 246
<211> LENGTH: 70
<212> TYPE: DNA
<213> ORGANISM: Artificial Sequence
<220> FEATURE:
<223> OTHER INFORMATION: Description of Artificial Sequence: Synthetic
Affymetrix ID 2721989 oligonucleotide

<400> SEQUENCE: 246
tgcatggttg actggctacc tggccatcct cgtcggggca ggcatgacct tcatcgtaca 60
gagcagctct 70

<210> SEQ ID NO 247
<211> LENGTH: 33
<212> TYPE: DNA
<213> ORGANISM: Artificial Sequence
<220> FEATURE:
<223> OTHER INFORMATION: Description of Artificial Sequence: Synthetic
Affymetrix ID 2524447 oligonucleotide

<400> SEQUENCE: 247
ggtttgcagt tagaggtatt cgaccattca ctg 33

<210> SEQ ID NO 248
<211> LENGTH: 79
<212> TYPE: DNA
<213> ORGANISM: Artificial Sequence
<220> FEATURE:
<223> OTHER INFORMATION: Description of Artificial Sequence: Synthetic
Affymetrix ID 2598287 oligonucleotide

<400> SEQUENCE: 248
aggaaatcca aattggtcac atccccaggg aagatgtaga ctatcacctg tacccacacg 60
gtccgggact caatccaaa 79

<210> SEQ ID NO 249
<211> LENGTH: 114
<212> TYPE: DNA
<213> ORGANISM: Artificial Sequence
<220> FEATURE:
<223> OTHER INFORMATION: Description of Artificial Sequence: Synthetic
Affymetrix ID 2466570 polynucleotide

<400> SEQUENCE: 249
tgctgagcat cattgcaaac atgtctggat gtctccctta catgctgccc ccaaaatgcc 60
caaacacttg cctggcgaac aaatacaggc ccatcacagg agcttgcaac aaca 114

<210> SEQ ID NO 250
<211> LENGTH: 26
<212> TYPE: DNA
<213> ORGANISM: Artificial Sequence
<220> FEATURE:
<223> OTHER INFORMATION: Description of Artificial Sequence: Synthetic
Affymetrix ID 2466601 oligonucleotide

<400> SEQUENCE: 250
atgcattctg gcacatggaa gaaaca 26

<210> SEQ ID NO 251
<211> LENGTH: 215
<212> TYPE: DNA
<213> ORGANISM: Artificial Sequence
<220> FEATURE:
<223> OTHER INFORMATION: Description of Artificial Sequence: Synthetic
Affymetrix ID 2466637 polynucleotide

<400> SEQUENCE: 251
tcacagggac tttataccaa ggttctccac gttgcacaaa gatcactaca ccttccaaaa 60
ccctgctcag gacgtcttag tcatgcattc acaatgggaa ctggaagtaa aaagcattga 120
gactgttcca ctgacaattg ttttacttct tttttatctt cattagcagg catcaggcaa 180
ctttaaccaa ccttctaggc agttgtcagt gatca 215

<210> SEQ ID NO 252
<211> LENGTH: 337
<212> TYPE: DNA
<213> ORGANISM: Artificial Sequence
<220> FEATURE:
<223> OTHER INFORMATION: Description of Artificial Sequence: Synthetic
Affymetrix ID 3369932 polynucleotide

<400> SEQUENCE: 252
tagttaacat gtggagattg ctgccagtga atattataaa atcagtgatc ttgccaaggt 60

```
ctaattagac actcgctagg atgaaactag ttaaaatgac tgttaatttt aagggttcaa    120

gacatcagtt gataactaga tgaccttaga aacaaatgtc tttcctcctg aaatattttc    180

cggaaaaaaa aattttctgg aaaaacctta tcttaagagc ttcagccaca gttacagtga    240

agactcttac tcctcactga aagtctacag tgtgtaaggt acaactaaca aatttacggg    300

aaacatgaat tatgcaagag atgaaacgct ggagtac                             337


<210> SEQ ID NO 253
<211> LENGTH: 605
<212> TYPE: DNA
<213> ORGANISM: Artificial Sequence
<220> FEATURE:
<223> OTHER INFORMATION: Description of Artificial Sequence: Synthetic
      Affymetrix ID 2426915 polynucleotide

<400> SEQUENCE: 253

cccagcttgg tgaacacctt gtttattttt aaatttttta gagacagggt ctcactgtgt     60

tgcccaggct ggtcttgaac tcctgagctc aagccaccat tctgccttgg gattacaggt    120

gtgagccacc atgctgggcc cagtgaaaat cttgttaaac tctcctagcc ttccttcctt    180

gaagactggt ttgattctgg tgctggcgta tgggcctggg attcagttcc tttttggcc    240

agcctagacg tttattctgt gcctgagcag atgcgttaag cttagaagca gacatcacgg    300

ccacctcagg cccatgccat tgtgggctgt atcccctaaa gtgcccccatt aaaatcttgg    360

cctccttgtg ctcttttcaa ataagagacc cctgttccat aatatggccc aaacttctag    420

gacgggggca ctcaaggatg gggaattttc ctcactgaca gggtttgcta tgtctgtggg    480

taaacccaac agaggataag gctggaacat ctgggtttgg ggcttacctg gttcttttca    540

gtgtcataga gtgatagtgg aaggtttaaa aaaaagatag ggaggatgta tccaccaggg    600

ctttg                                                                605


<210> SEQ ID NO 254
<211> LENGTH: 62
<212> TYPE: DNA
<213> ORGANISM: Artificial Sequence
<220> FEATURE:
<223> OTHER INFORMATION: Description of Artificial Sequence: Synthetic
      Affymetrix ID 2466562 oligonucleotide

<400> SEQUENCE: 254

gtccctggaa ggcaattaag gcgcccattt cagaagagtt acagccgtga aaattactca     60

gc                                                                    62


<210> SEQ ID NO 255
<211> LENGTH: 106
<212> TYPE: DNA
<213> ORGANISM: Artificial Sequence
<220> FEATURE:
<223> OTHER INFORMATION: Description of Artificial Sequence: Synthetic
      Affymetrix ID 2466569 polynucleotide

<400> SEQUENCE: 255

cctgagccaa caagcggagt gattgcccga gcagcagaga taatggaaac atcaatacaa     60

gcgatgaaaa gaaaagtcaa cctgaaaact caacaatcac agcatc                  106


<210> SEQ ID NO 256
<211> LENGTH: 430
<212> TYPE: DNA
<213> ORGANISM: Artificial Sequence
```

<220> FEATURE:
<223> OTHER INFORMATION: Description of Artificial Sequence: Synthetic
Affymetrix ID 2579138 polynucleotide

<400> SEQUENCE: 256
acagtggttc cagagtcaaa ctacctgggt ttaaactata tgtgtttatg cctcagtttt 60
cccagtaaat gaggttaata atgtgttttc tcatagtttt tataagaatt aagtgaggtg 120
gtgtttgtaa ggagtttaga ttagtacgtg gtacatggta aactccccaa ggagcagatg 180
ttttgtctca aaaaaagtat taacctttta ctatataacc agtaacctat aagatacagc 240
tttgagaaaa gaggatataa gggactcaat tttatgtcct ttgagtttga atcagatgat 300
taccaaagga aaatgtccaa taagccacta aaactaggga tttggagctc atatgaacag 360
cctgaaatag agatatagtc aattatacca gataatggtt gatgacatgg gaagatatgg 420
gcggatcctt 430

<210> SEQ ID NO 257
<211> LENGTH: 142
<212> TYPE: DNA
<213> ORGANISM: Artificial Sequence
<220> FEATURE:
<223> OTHER INFORMATION: Description of Artificial Sequence: Synthetic
Affymetrix ID 3142383 polynucleotide

<400> SEQUENCE: 257
acctggactg aagttcgcat tgaactctac aacattctgt gggatatatt gttcaaaaag 60
atattgttgt tttccatgat ttagcaagca actaattttc tcccaagctg attttattca 120
atatggttac gttggttaaa ta 142

<210> SEQ ID NO 258
<211> LENGTH: 228
<212> TYPE: DNA
<213> ORGANISM: Artificial Sequence
<220> FEATURE:
<223> OTHER INFORMATION: Description of Artificial Sequence: Synthetic
Affymetrix ID 3367706 polynucleotide

<400> SEQUENCE: 258
ttttgcctgc acattctgag agagccattt ggcaaacaac aataataaat ttacatttgg 60
atggtgtatt tcactcagag aactttcata tgtattatct catttggggc tcacaacaat 120
tctttaacca gggtatgtat tactaataat aattaacaat agccagcatt tacagtgttt 180
atatgtcaac tgctgttcat tattgcctcc ttttgacaga gaccaaca 228

<210> SEQ ID NO 259
<211> LENGTH: 33
<212> TYPE: DNA
<213> ORGANISM: Artificial Sequence
<220> FEATURE:
<223> OTHER INFORMATION: Description of Artificial Sequence: Synthetic
Affymetrix ID 3367743 oligonucleotide

<400> SEQUENCE: 259
aaatgcacag cggtattgat gagtagatcc ttg 33

<210> SEQ ID NO 260
<211> LENGTH: 125
<212> TYPE: DNA
<213> ORGANISM: Artificial Sequence
<220> FEATURE:
<223> OTHER INFORMATION: Description of Artificial Sequence: Synthetic
Affymetrix ID 2466585 polynucleotide

<400> SEQUENCE: 260
cgctattctg acctcctgat ggcatgggga caatacatcg accacgacat cgcgttcaca 60
ccacagagca ccagcaaagc tgccttcggg ggaggggctg actgccagat gacttgtgag 120
aacca 125

<210> SEQ ID NO 261
<211> LENGTH: 58
<212> TYPE: DNA
<213> ORGANISM: Artificial Sequence
<220> FEATURE:
<223> OTHER INFORMATION: Description of Artificial Sequence: Synthetic
Affymetrix ID 2466621 oligonucleotide

<400> SEQUENCE: 261
atctcaacct ggcttcgaat gttcaagtct gacacatcgc aaaggctaca cccaaaca 58

<210> SEQ ID NO 262
<211> LENGTH: 99
<212> TYPE: DNA
<213> ORGANISM: Artificial Sequence
<220> FEATURE:
<223> OTHER INFORMATION: Description of Artificial Sequence: Synthetic
Affymetrix ID 3111603 oligonucleotide

<400> SEQUENCE: 262
gttactacca atggatttca agccacagca agggatgctt ttagttataa ttgtttacag 60
acaccaatta taactgattt tagtccaaaa gtacgaaca 99

<210> SEQ ID NO 263
<211> LENGTH: 526
<212> TYPE: DNA
<213> ORGANISM: Artificial Sequence
<220> FEATURE:
<223> OTHER INFORMATION: Description of Artificial Sequence: Synthetic
Affymetrix ID 3148840 polynucleotide

<400> SEQUENCE: 263
gtgagctctt tacgggtatt tattcattct ctccatgagt gtttatgcag tgtttactgt 60
gtgtcaggtt tctgcttgtt tgcgtgtttg ctgtttaatc ttcaggattc aagtggtgaa 120
gaaccctatc cccctgtaga tagaggccac ccgtctaaga caaagaagcc aatgattatc 180
gtactaaggc tcaagggagg catctaactc acataaaagc atcaagaaag atgactcagg 240
ggaagtgaca aatgagttaa gtctttaaag ataaatagca gctgttggaa tggaaaagag 300
gtgtcaaagg cactgtgcaa atggtaaaaa gaaagtaggg gcttcagaga gagtccaaaa 360
tgtgtgcaaa aaagcagagg tgtgagagag catggtgctg ggaatgcaaa ctgtaaggtt 420
aggtgcagca tggaaatgca tgtgagggtg gtgatgagaa atgaagtagg aaaggagtag 480
gaggtaaatt acatgtacca tcctcatggc tgctagtact acgttc 526

<210> SEQ ID NO 264
<211> LENGTH: 33
<212> TYPE: DNA
<213> ORGANISM: Artificial Sequence
<220> FEATURE:
<223> OTHER INFORMATION: Description of Artificial Sequence: Synthetic
Affymetrix ID 3467957 oligonucleotide

<400> SEQUENCE: 264
acctcagtga ctgggatcca gtaatagaaa aca 33

<210> SEQ ID NO 265
<211> LENGTH: 99
<212> TYPE: DNA
<213> ORGANISM: Artificial Sequence
<220> FEATURE:
<223> OTHER INFORMATION: Description of Artificial Sequence: Synthetic
Affymetrix ID 3607269 oligonucleotide

<400> SEQUENCE: 265
tgagtacaga ccacttcagt cagtcttttt ttggttcttg gcaggagggg atactgggaa 60
tggatagatg cctgatcatc acggtgctat caagagcca 99

<210> SEQ ID NO 266
<211> LENGTH: 89
<212> TYPE: DNA
<213> ORGANISM: Artificial Sequence
<220> FEATURE:
<223> OTHER INFORMATION: Description of Artificial Sequence: Synthetic
Affymetrix ID 2537568 oligonucleotide

<400> SEQUENCE: 266
tccaactttc acgagaagat taagaaaatc cacaaacaat acctgttgtt gcaagctcct 60
gtgatgggcc tgtatttgtt cgccaggca 89

<210> SEQ ID NO 267
<211> LENGTH: 359
<212> TYPE: DNA
<213> ORGANISM: Artificial Sequence
<220> FEATURE:
<223> OTHER INFORMATION: Description of Artificial Sequence: Synthetic
Affymetrix ID 2579178 polynucleotide

<400> SEQUENCE: 267
tcatcttagg gctggacttg gatccccagg gtttgcattt ggtgaatcat gccactaaat 60
gcctattact tcttaaaaat cagaattctc tccccaatga taatacttgg tataatattt 120
ggtggtcttt tctaatagtt accttccaaa tgagaaaaaa aagccaaagt aatttttttt 180
aagtttgatt catcttgcct gtgtttgtta gggtggagtt gagtccaaat gtgagaaaat 240
gtatcacata ttggcatatg ggaagtaatt caggcattct tgatgtagta gagaaatttt 300
agtactaata atctcattta ttttcttcaa tatttcttga aaagtgctta ttgactgtg 359

<210> SEQ ID NO 268
<211> LENGTH: 100
<212> TYPE: DNA
<213> ORGANISM: Artificial Sequence
<220> FEATURE:
<223> OTHER INFORMATION: Description of Artificial Sequence: Synthetic
Affymetrix ID 3111646 polynucleotide

<400> SEQUENCE: 268
gttgggatac tgagtaggaa catcaaaata gttggtgaag attaccccgg ttggtctgag 60
gactcttttg gagcacgcgt actggttggc tcattcactg 100

<210> SEQ ID NO 269
<211> LENGTH: 142
<212> TYPE: DNA
<213> ORGANISM: Artificial Sequence
<220> FEATURE:
<223> OTHER INFORMATION: Description of Artificial Sequence: Synthetic
Affymetrix ID 3132617 polynucleotide

<400> SEQUENCE: 269

```
tgaccagaat aaggagggtc caatcaacat attattgtgg agatagcctt tttttttttt     60

ttctggcttc tacctaattt atttataata aagacaagct aggctacctc ataggattct    120

ggtgtggatt cgctaattaa ta                                              142


<210> SEQ ID NO 270
<211> LENGTH: 80
<212> TYPE: DNA
<213> ORGANISM: Artificial Sequence
<220> FEATURE:
<223> OTHER INFORMATION: Description of Artificial Sequence: Synthetic
      Affymetrix ID 3148853 oligonucleotide

<400> SEQUENCE: 270

ctgaggggag tataaaagtg ctctgttacc tggtgctgta caatgaagta tcaatgctct     60

ctggacatgg caaatgttcc                                                  80


<210> SEQ ID NO 271
<211> LENGTH: 316
<212> TYPE: DNA
<213> ORGANISM: Artificial Sequence
<220> FEATURE:
<223> OTHER INFORMATION: Description of Artificial Sequence: Synthetic
      Affymetrix ID 3327190 polynucleotide

<400> SEQUENCE: 271

cgccatgtca ttgttgcatc ttgtggctgg ttggaggaga tgggagtggg aaatgggaac     60

aggaatcagc atctatggaa agatccattt tgatgaaagc attgcactaa gtgatgtggg    120

gtgctgtatc aaaggtcaga aacatgatcc cactttcttg agagtaaaga acaattgcag    180

atgaaaacac attgtagcat attagagaaa aattgccaat atgagtaggt ctgggtccta    240

gctgtccaga gatagtgcta tcaatgtgag tgttgttgag agattaggct tctggaattg    300

attgggaaag gcttta                                                     316


<210> SEQ ID NO 272
<211> LENGTH: 76
<212> TYPE: DNA
<213> ORGANISM: Artificial Sequence
<220> FEATURE:
<223> OTHER INFORMATION: Description of Artificial Sequence: Synthetic
      Affymetrix ID 3367709 oligonucleotide

<400> SEQUENCE: 272

gttctgcatt gctgataccg ctagtggttt taaaaataga aatcaaaata agaaccctga     60

tattaaggat tcacag                                                      76


<210> SEQ ID NO 273
<211> LENGTH: 96
<212> TYPE: DNA
<213> ORGANISM: Artificial Sequence
<220> FEATURE:
<223> OTHER INFORMATION: Description of Artificial Sequence: Synthetic
      Affymetrix ID 3933539 oligonucleotide

<400> SEQUENCE: 273

atgcgaggct cggagcaccc ttgcccggct gtgattgctg ccaggcactg ttcatctcag     60

cttttctgtc cctttgctcc cggcaagcgc ttctgc                                96


<210> SEQ ID NO 274
<211> LENGTH: 99
<212> TYPE: DNA
<213> ORGANISM: Artificial Sequence
```

<220> FEATURE:
<223> OTHER INFORMATION: Description of Artificial Sequence: Synthetic
Affymetrix ID 2466620 oligonucleotide

<400> SEQUENCE: 274
ctccgggagg ctccctcggg tgacttggat ctccatgtcg ctggctgctc tgctgatcgg 60
aggcttcgca ggtctcacct cgacggtgat ttgcaggtg 99

<210> SEQ ID NO 275
<211> LENGTH: 84
<212> TYPE: DNA
<213> ORGANISM: Artificial Sequence
<220> FEATURE:
<223> OTHER INFORMATION: Description of Artificial Sequence: Synthetic
Affymetrix ID 2466628 oligonucleotide

<400> SEQUENCE: 275
ttcatgttcc caaaatcacc gtacgactct tttccaaaca caggcaaatc cgaaatcagc 60
aggacgactg ttttcccaac acgg 84

<210> SEQ ID NO 276
<211> LENGTH: 237
<212> TYPE: DNA
<213> ORGANISM: Artificial Sequence
<220> FEATURE:
<223> OTHER INFORMATION: Description of Artificial Sequence: Synthetic
Affymetrix ID 2579064 polynucleotide

<400> SEQUENCE: 276
gagatcttca cacatgttaa agaagcttga aaacaatgaa gaaaaaccca ggggagaccg 60
ttagagagag ggaaagacag agatgagagt ggtagggaaa aacagtgagg gatcagagca 120
gcaccctgag agcgcacctg gacatcagcc attacacgtg aggggaggga acttttctga 180
gtttccctaa aaggcttaaa gtaaggggtt gttgggtgga ccacacatga catatta 237

<210> SEQ ID NO 277
<211> LENGTH: 115
<212> TYPE: DNA
<213> ORGANISM: Artificial Sequence
<220> FEATURE:
<223> OTHER INFORMATION: Description of Artificial Sequence: Synthetic
Affymetrix ID 2586155 polynucleotide

<400> SEQUENCE: 277
gattgccaga tatggggaat ttgtgaccag aagtgtgaaa gccgacctgg ccgtcacctg 60
tgccactgtg aagaagggta tatcttggag cgtggacagt attgcaaagc taatg 115

<210> SEQ ID NO 278
<211> LENGTH: 80
<212> TYPE: DNA
<213> ORGANISM: Artificial Sequence
<220> FEATURE:
<223> OTHER INFORMATION: Description of Artificial Sequence: Synthetic
Affymetrix ID 2980450 oligonucleotide

<400> SEQUENCE: 278
tggctgcgtt ttgatcgtct acaacaaggt tacagtgccc tctggtggca gtcatcaaaa 60
tcgcttctag acttgttttt 80

<210> SEQ ID NO 279
<211> LENGTH: 39
<212> TYPE: DNA
<213> ORGANISM: Artificial Sequence
<220> FEATURE:
<223> OTHER INFORMATION: Description of Artificial Sequence: Synthetic
Affymetrix ID 2980481 oligonucleotide

<400> SEQUENCE: 279
gagacttttg cagtttcggc tgattcagat agtcattgg 39

<210> SEQ ID NO 280
<211> LENGTH: 256
<212> TYPE: DNA
<213> ORGANISM: Artificial Sequence
<220> FEATURE:
<223> OTHER INFORMATION: Description of Artificial Sequence: Synthetic
Affymetrix ID 3059669 polynucleotide

<400> SEQUENCE: 280
gggctactga ttcgaagttt gcagaagaag gattctggga tgtattactg caaagcccag 60
gagcacactt tcatccacac catagtgaag ctgactttga atgtcattga gaatgaacag 120
atggaaaata cccagagggc agagcatgag gaggggaagg tcaaggatct attggctgag 180
tcacggttga gatacaaaga ctacatccaa atccttagca gcccaaactt cagcctcgac 240
cagtactgcg aacaga 256

<210> SEQ ID NO 281
<211> LENGTH: 120
<212> TYPE: DNA
<213> ORGANISM: Artificial Sequence
<220> FEATURE:
<223> OTHER INFORMATION: Description of Artificial Sequence: Synthetic
Affymetrix ID 3111567 polynucleotide

<400> SEQUENCE: 281
ctatggagtt gataacgctg agttgggaaa cagtgtgcaa ttaatttctt ctttccagtc 60
aattacttgt gatgtagaaa aagatgcaag tcattcaact caaattacat gctatactag 120

<210> SEQ ID NO 282
<211> LENGTH: 75
<212> TYPE: DNA
<213> ORGANISM: Artificial Sequence
<220> FEATURE:
<223> OTHER INFORMATION: Description of Artificial Sequence: Synthetic
Affymetrix ID 3111641 oligonucleotide

<400> SEQUENCE: 282
gataaataca atgtaggagc tgcagaatct tcttacagag aagttgtttt gaatgctacc 60
tacatatcac tgcag 75

<210> SEQ ID NO 283
<211> LENGTH: 811
<212> TYPE: DNA
<213> ORGANISM: Artificial Sequence
<220> FEATURE:
<223> OTHER INFORMATION: Description of Artificial Sequence: Synthetic
Affymetrix ID 3367675 polynucleotide

<400> SEQUENCE: 283
gttagtgttc gccaaaggac agccaagctt tcttttaaaa agtgataaaa gtcttatttt 60
aatatgcttt aagctgaaag aaaaaaaaat aagaaacagg cagtgtttta aaaaccaaca 120
cagatttgca caactgttta agagtattgt ttgaaatatt ttaattttca atgttttgtt 180
gttgttgttt tcttggtaat gcttcttttt tgcagatgtg gtcccaattt atagcaatct 240
tctcaacaga agtaggcatg gaaaagactt cttttcatac tctcactata aagaaagctg 300

```
cattgagaag aaaatggctg tcatttaaag gatggtttaa ctagtgagat tcctattgtg    360

gttatacaag gtctcattgt ttgtttgttt cttttaaatt atttcagctt taaaaataca    420

gaaatggaat ctgtcaagag caggtatttc atacggttaa aaaaatgaac atgcagactc    480

cttttcaata tgggtttata tatataagta ttttttgtgt attatgacta cgttaggagt    540

ttattattgt caaggacagt acaactgcaa agggatgctg tatagcaaca catcagaagt    600

cggaaggaac tgacacattc tctcagagct caaggtctta aagagcttga gttaaatcta    660

ggtacagtta caggcatgta tagacttaaa tggatgcaat ggaagctaac taaaataagg    720

cttagttgtc ctttctattt aaataccccca agttgtcttc ttacttcctc tcccctctcc    780

cattttgcac tgtgtgtcga tgcaatcttc g                                   811
```

<210> SEQ ID NO 284
<211> LENGTH: 48
<212> TYPE: DNA
<213> ORGANISM: Artificial Sequence
<220> FEATURE:
<223> OTHER INFORMATION: Description of Artificial Sequence: Synthetic
      Affymetrix ID 3933538 oligonucleotide

<400> SEQUENCE: 284

```
agttcatatc tggagcctga tgtcttaacg aataaaggtc ccatgctc                  48
```

<210> SEQ ID NO 285
<211> LENGTH: 662
<212> TYPE: DNA
<213> ORGANISM: Artificial Sequence
<220> FEATURE:
<223> OTHER INFORMATION: Description of Artificial Sequence: Synthetic
      Affymetrix ID 2466631 polynucleotide

<400> SEQUENCE: 285

```
ctcctgggaa gagcactcct ggcttcctgc agggccggtg ggaggaggaa agtgattctg     60

agggagaggc tggagcctta aggaccaaca aggcaaagtg acttgtctca tcctccagag    120

attcaccaac acatgagcct cagaccccag gcttctgcct ccagcagccg ccctgccgca    180

cactgctctt actcctcctt ataccctcac tcacggggaa cacagcccag tgatcccgga    240

ggaaactcac tccctccctg actcaacaag gcagtctcgg gggcaccgtt agccacgcga    300

ccctgtaaag ctgccgtcct catttcacat gtgaagcagc tgaattccag agtgctgggt    360

cccagcccag gcagccctca gcctcacgca aggcaatagt taggagtcct tcggcattga    420

aagcaaactc agacacatct gacctggagt tctacctgca ctaagagaag agagtggtaa    480

ctaattcatg gataaaacag accatcgagg cagcactgaa tgatctcacc cacgaatgac    540

aacagtggca caggagggct atgaacattt tgcttcagga tgttttattt cgctctactg    600

ttatgtagag aaagcatggt ttgcttttta taacttttgt gacccaaaaa taccagactg    660

tt                                                                   662
```

<210> SEQ ID NO 286
<211> LENGTH: 647
<212> TYPE: DNA
<213> ORGANISM: Artificial Sequence
<220> FEATURE:
<223> OTHER INFORMATION: Description of Artificial Sequence: Synthetic
      Affymetrix ID 2537615 polynucleotide

<400> SEQUENCE: 286

```
agcctgtgag tatcccggcc ttccatccca gcactctcct gcaaaaatgc agaacaaaca     60
```

```
ttaataacgt ctgaattctg actgctccag taacagcaca cacttgatac aagacagaag    120

ggcctggaca ggagctcttt tcacaaagga ccgctggcga gatgagccat ccttcttgct    180

tgtcatgctg gagggaagtt tctggcttcc ggacaaatgc ttgtttgcag gaggccacag    240

aggatccacg tggcaaaggt tcctactcac agagtgggat ctgcaatccg caggcagggt    300

ccttcaggaa gaagccgtgc tgagcacaca ggtccctgcg accacagatg aacagaacgc    360

ctggccttgc ccctggtgtc agtcagacta attaggggcc caggggactt gctggcactg    420

cccttgctgt ggctggaaaa gctatttaaa ttcacaaaga gcctcacttc caggccaggt    480

ccttttggtt ccatgcgtgg gagccaggtg caaagacgaa tgtgctctca gcagaacgac    540

cctgggctct gcttatctcc gaggacagga tctaatctca cactgaattt cagaagggag    600

accgatcatg ttggcaatgc ccccctcctg tatgcaagta agtgact                647


<210> SEQ ID NO 287
<211> LENGTH: 219
<212> TYPE: DNA
<213> ORGANISM: Artificial Sequence
<220> FEATURE:
<223> OTHER INFORMATION: Description of Artificial Sequence: Synthetic
      Affymetrix ID 2569317 polynucleotide

<400> SEQUENCE: 287

tgctgacaag gggtaaaatg aattcttggt ctttgttcga atggaaaaaa gtctctacat     60

tattaggcgc cataatattt tattcaaatc ttcttagaaa tttttggata ttgcatctgg    120

gggtaagtgt gcctctttga tgtcattcag aagtgtgtgt atcttggtta ctgtgtacaa    180

aatgcactgg tccagttttt tcaaagtgcc ttgacgcta                          219


<210> SEQ ID NO 288
<211> LENGTH: 73
<212> TYPE: DNA
<213> ORGANISM: Artificial Sequence
<220> FEATURE:
<223> OTHER INFORMATION: Description of Artificial Sequence: Synthetic
      Affymetrix ID 2581079 oligonucleotide

<400> SEQUENCE: 288

tgaaagacaa gtacactccg gttccagata cgccaatcct catcagagcc aagagggctt     60

actggaatgc cag                                                        73


<210> SEQ ID NO 289
<211> LENGTH: 26
<212> TYPE: DNA
<213> ORGANISM: Artificial Sequence
<220> FEATURE:
<223> OTHER INFORMATION: Description of Artificial Sequence: Synthetic
      Affymetrix ID 2727647 oligonucleotide

<400> SEQUENCE: 289

ttctttgcag tggcttaatg tttgaa                                          26


<210> SEQ ID NO 290
<211> LENGTH: 42
<212> TYPE: DNA
<213> ORGANISM: Artificial Sequence
<220> FEATURE:
<223> OTHER INFORMATION: Description of Artificial Sequence: Synthetic
      Affymetrix ID 2750491 oligonucleotide

<400> SEQUENCE: 290
```

gtggcccctg tcaggacaga gcatgtgctg ggctatccag ct 42

<210> SEQ ID NO 291
<211> LENGTH: 31
<212> TYPE: DNA
<213> ORGANISM: Artificial Sequence
<220> FEATURE:
<223> OTHER INFORMATION: Description of Artificial Sequence: Synthetic
      Affymetrix ID 2830194 oligonucleotide

<400> SEQUENCE: 291
atgaactccc tcgtggcggc cgaaggcctg g 31

<210> SEQ ID NO 292
<211> LENGTH: 2123
<212> TYPE: DNA
<213> ORGANISM: Artificial Sequence
<220> FEATURE:
<223> OTHER INFORMATION: Description of Artificial Sequence: Synthetic
      Affymetrix ID 3067233 polynucleotide

<400> SEQUENCE: 292
ggagctggag ctatcctacc tcatcagtgt tttgtcttct gttgggatga actttgttaa 60
aactaatgca tggttaagat gaaaggcaga aggaagggtt tgataaacca gaacattctc 120
gcctgattgt tagtgttctg aagtaaatac agaagaggct ccaaaataca gacctctgta 180
catcaacctt ccgtaatcca cctgccttgc atatgcagac catgacaatt ctacgagctc 240
ctggaaacag aactcagaac tcctccccag agaaccctga tgcaaattct ctgaaatggt 300
agtcagcatg tgcgttttcc tgagaagtga atgagtcaac agctttcaac agatcttcaa 360
aggcttactt cacccaatga agttaagaac cactaaagaa gaaacctaaa aggaaaatcc 420
aggtcatgaa ctttgcaatt tttattcaca tacagagaag aggggaggaa tctcttgtgt 480
atgttttact tatgtatacc actggttctt aataaagggc ttttttgcc tccagaggtc 540 aatgcctgga gacatttttg gttgtcacac ctagggagat gctattggga tctagtgagt 600
agagaccaga gatgctgcta aacatcctac aatgaagttt gctatcactc caaggttttg 660
catgcgactt aaactgtaca tttattaatc aattgctaca tgtactaaaa tatgtatctc 720
tctccatata tgtatatatg cgtgtatttt ttcattattg ttggatgtat agctcaactc 780
cactacaaca gaggaaagta tttgttttaa agtagaatct gaatatactc actctgtata 840
ccctcatcca taccttcaag atctggtgaa aacactatct cttgcaagaa cattctttga 900
tgctgttcag aattaatcca gacccttttc tgtattctct taatacctta tctgatcctc 960
tcttaagtta cttctcacta tctaccttag taacacaatt ttatttacat acaagttctc 1020
tctccctcac tagacaaaaa cttcttgagg gcaagcactg tgtctccttt caaccattat 1080
tatcttctct catgtttttt gaacagattt atctatagcc caaacatacc ttttcaaaaa 1140
actaaaaatt actttacata tttgatctaa ggctttgttt ttctccatta agagcatgct 1200
gtggatatct ttgcaagtga gtgcataagg atttttctta accttggaga tggctgtcta 1260
ggatttcaga atatcaactc atatttgtag ctccatggca actcacctac acaactcaca 1320
actctttatt gaaggcattc tgtaccaata taaatatagt ccatatccca ttctaatatg 1380
gatttctgct ccttgttgct tgctattttg aacactttta gtctggtcca gtcaggccta 1440
taaaccactt tgcatcagaa cttggcaatg gtttgctggt tcagaggatt aaggagtggg 1500
gtaaggctgg cagaaggaca gaagagaaaa gacttgagta acaacaggag gcaaaagagt 1560
aacttagctt ggctaataga attcttattt gaaatgcatc tctctatata agagtttggt 1620

```
tcaataatca caatataata agtcctgcat gtatctggat gaagataatt gctttttttct   1680

gttcaatgct tttccatagc agaaatagct ggggcagaac aaaatggtat ctctgttaca   1740

ggattctata agggtataga actgcttttc tcataggtaa aaggcagacc gtttgaattt   1800

ggctttttaa aaacagaaga gtaggaggaa ataacagctt gctctctcca ccctatttaa   1860

ttgtgatatt aaacacctta gattactcac ttgggcttta taaggcaacc ttctcctgtt   1920

tcacacagag gtgggtggtt cttatttatc agacttttaa aatattcagg acttctttcc   1980

aaagaaatag atgcatcact taaaaataaa tatcagacaa tattattgat actttacagt   2040

acttatttag cagttaatac ttttttaaaa ggcattttct tatttatcat ttaggcattt   2100

gcagtgtaag acaaactccc ttg                                            2123
```

<210> SEQ ID NO 293
<211> LENGTH: 44
<212> TYPE: DNA
<213> ORGANISM: Artificial Sequence
<220> FEATURE:
<223> OTHER INFORMATION: Description of Artificial Sequence: Synthetic Affymetrix ID 3087444 oligonucleotide

<400> SEQUENCE: 293

```
tctcaccttg ctgctttgta cattcttgag acttggtacc ctgt                        44
```

<210> SEQ ID NO 294
<211> LENGTH: 87
<212> TYPE: DNA
<213> ORGANISM: Artificial Sequence
<220> FEATURE:
<223> OTHER INFORMATION: Description of Artificial Sequence: Synthetic Affymetrix ID 3108602 oligonucleotide

<400> SEQUENCE: 294

```
gggaccacgg ttgtgaacat tcgtgtgtaa gcagtgaaga ttcgtttgtg tgccagtgct     60

ttgaaggtta tatactccgt gaagatg                                          87
```

<210> SEQ ID NO 295
<211> LENGTH: 88
<212> TYPE: DNA
<213> ORGANISM: Artificial Sequence
<220> FEATURE:
<223> OTHER INFORMATION: Description of Artificial Sequence: Synthetic Affymetrix ID 3111577 oligonucleotide

<400> SEQUENCE: 295

```
tcacaaggaa gcattcgagg tggcaccacg ctgacaataa gtgggcgttt ctttgatcag     60

acagatttcc ccgtcagagt tctagttg                                         88
```

<210> SEQ ID NO 296
<211> LENGTH: 36
<212> TYPE: DNA
<213> ORGANISM: Artificial Sequence
<220> FEATURE:
<223> OTHER INFORMATION: Description of Artificial Sequence: Synthetic Affymetrix ID 3111621 oligonucleotide

<400> SEQUENCE: 296

```
gaagctgaca ttgaactcca ggcagaaaat attcta                                36
```

<210> SEQ ID NO 297
<211> LENGTH: 89
<212> TYPE: DNA

<213> ORGANISM: Artificial Sequence
<220> FEATURE:
<223> OTHER INFORMATION: Description of Artificial Sequence: Synthetic
Affymetrix ID 3111651 oligonucleotide

<400> SEQUENCE: 297
aagaatatgg gggaatgcca accgagtccg agggaatttg attgcacttt cggtttggcc 60
aggaacctat cagaacagaa aagatttaa 89

<210> SEQ ID NO 298
<211> LENGTH: 105
<212> TYPE: DNA
<213> ORGANISM: Artificial Sequence
<220> FEATURE:
<223> OTHER INFORMATION: Description of Artificial Sequence: Synthetic
Affymetrix ID 3111674 polynucleotide

<400> SEQUENCE: 298
ggaattactg cactaacttt gagggccata ctcaaggact ccaataataa ccaagtcaat 60
ggccttagtg gaaatacaac aattccgttt agcagctgtt gggcc 105

<210> SEQ ID NO 299
<211> LENGTH: 35
<212> TYPE: DNA
<213> ORGANISM: Artificial Sequence
<220> FEATURE:
<223> OTHER INFORMATION: Description of Artificial Sequence: Synthetic
Affymetrix ID 3267337 oligonucleotide

<400> SEQUENCE: 299
atgcctgctg catccgttcg gaccgaccca gccaa 35

<210> SEQ ID NO 300
<211> LENGTH: 32
<212> TYPE: DNA
<213> ORGANISM: Artificial Sequence
<220> FEATURE:
<223> OTHER INFORMATION: Description of Artificial Sequence: Synthetic
Affymetrix ID 3367712 oligonucleotide

<400> SEQUENCE: 300
gtgaagggat tcaggatata cggtgcacct tg 32

<210> SEQ ID NO 301
<211> LENGTH: 28
<212> TYPE: DNA
<213> ORGANISM: Artificial Sequence
<220> FEATURE:
<223> OTHER INFORMATION: Description of Artificial Sequence: Synthetic
Affymetrix ID 3662219 oligonucleotide

<400> SEQUENCE: 301
ctacaactcc gactcatttg ctacattc 28

<210> SEQ ID NO 302
<211> LENGTH: 33
<212> TYPE: DNA
<213> ORGANISM: Artificial Sequence
<220> FEATURE:
<223> OTHER INFORMATION: Description of Artificial Sequence: Synthetic
Affymetrix ID 3893026 oligonucleotide

<400> SEQUENCE: 302
gtcggggaga aatcaggctc tcgaagctca taa 33

<210> SEQ ID NO 303
<211> LENGTH: 44
<212> TYPE: DNA
<213> ORGANISM: Artificial Sequence
<220> FEATURE:
<223> OTHER INFORMATION: Description of Artificial Sequence: Synthetic
Affymetrix ID 2466629 oligonucleotide

<400> SEQUENCE: 303
atctagtacc atgtcgtagt tactctcagg catggatgaa taaa 44

<210> SEQ ID NO 304
<211> LENGTH: 132
<212> TYPE: DNA
<213> ORGANISM: Artificial Sequence
<220> FEATURE:
<223> OTHER INFORMATION: Description of Artificial Sequence: Synthetic
Affymetrix ID 2579057 polynucleotide

<400> SEQUENCE: 304
gcacagagaa atggtggagg cgatggagga cagagacagc atatcaaggt tttgtttgaa 60
ccagacaaaa gccagagttt gatcagcaaa tcacagaagg gaacaaatcc tacttgtgtc 120
atgtggaaat ga 132

<210> SEQ ID NO 305
<211> LENGTH: 59
<212> TYPE: DNA
<213> ORGANISM: Artificial Sequence
<220> FEATURE:
<223> OTHER INFORMATION: Description of Artificial Sequence: Synthetic
Affymetrix ID 2754804 oligonucleotide

<400> SEQUENCE: 305
ttgcagaatt aacccacaaa acagtatcct atgggccaac cggtgatgag actgagttt 59

<210> SEQ ID NO 306
<211> LENGTH: 406
<212> TYPE: DNA
<213> ORGANISM: Artificial Sequence
<220> FEATURE:
<223> OTHER INFORMATION: Description of Artificial Sequence: Synthetic
Affymetrix ID 2815230 polynucleotide

<400> SEQUENCE: 306
agagcccact ccattagcca atatgccttc ctgccgtcct tcaggtttgt ggcttaatgt 60
tttaattttc catatgcaaa agtttgtcta ccttatgtta gctgtcccag aagacagaat 120
agcagagaac agtaagtgtg tgtgtgtgtg tgtgtgtgtc tatgttctct ttggatggtg 180
tctgtaaatt tgttttcaat gtcttttcaa tgacaaaggg aatgacagca ggagtgagac 240
tgtcttaatg ttacactcag ctctaggaaa aggaagaggt aagaaatcaa aacaaatcta 300
tgaaaagtag agtgagggag aaattactcc tcagattctt gcaaatactc ttaagtgcat 360
gtaatcaaac atttgaaaag aacctagtac taaaggggtg tcactg 406

<210> SEQ ID NO 307
<211> LENGTH: 75
<212> TYPE: DNA
<213> ORGANISM: Artificial Sequence
<220> FEATURE:
<223> OTHER INFORMATION: Description of Artificial Sequence: Synthetic
Affymetrix ID 3018631 oligonucleotide

<400> SEQUENCE: 307
gaagaacctc aaggagtgaa gattcttaga ttttccagtc ctattttcta tggcaatgtc 60
gatggtttta aaaaa 75

<210> SEQ ID NO 308
<211> LENGTH: 592
<212> TYPE: DNA
<213> ORGANISM: Artificial Sequence
<220> FEATURE:
<223> OTHER INFORMATION: Description of Artificial Sequence: Synthetic
Affymetrix ID 3067232 polynucleotide

<400> SEQUENCE: 308
cctgacagag tatctatgct tttgagtgac tacgtgtgct acaagaatga tttaattgaa 60
tccttcgttt atttaactta agagcagtca atcttgctac attatttttg tctgagagcg 120
aatattgtgg tataaatttt ttcttttttt tttttttttt acaatttaaa atgttctcaa 180
atcagaagaa ttgcaaaaga atgcaaacat gttggctggg cgctgtggct cacagtgtaa 240
tcccaacact ttgagaagct gaggcgggag gatcacttga gccaggccta atcctgagct 300
tttatttcat tatgcgtgtt aattttctca agatagcaaa tgctaaattt ttgtcatact 360
tatacaaaaa gagaactgaa ctgaactttc tttctatatt tctgatctct tcttctctga 420
gcaacttatt gggcttattc tcagtaatca tacagttttg cactcaattg ttttcttggt 480
tttttgttgt tatttttatc ttgcactcaa ttgttttcta tttgtttact gtatgctact 540
ttattttctt ctccagttat aagatatgct ccctagggac ataaatagta ta 592

<210> SEQ ID NO 309
<211> LENGTH: 490
<212> TYPE: DNA
<213> ORGANISM: Artificial Sequence
<220> FEATURE:
<223> OTHER INFORMATION: Description of Artificial Sequence: Synthetic
Affymetrix ID 3106615 polynucleotide

<400> SEQUENCE: 309
ggctctaggg gcaatccatt ttcttgactt ttctagtttc tagaggcttc ctgcattctt 60
tggctcatgg acctttcaac catgcgatat gtaaacatgc agtatcgcat cttcaaattc 120
tctttgactc tgatcttttg cctccatttt ccatgtttaa aggacacttg tgattacatt 180
gggcacacct ggataatcca ggctgctctt cttattttaa gatcagctgc ttggcaactt 240
taatttcatc tgcaatgtta attctctctt accatatagc ataacatact cacaggttct 300
ggggattagg atgggaacat atttgagagg tcataattct gcctactaca ttgatacaca 360
tattttctgt taacataaca ttttatttat gtagatttgg ctttttaaat caattaattt 420
tgttatgagg gaaggaacaa cacttatcaa tcacttacaa catttctgcc taaagtgtgg 480
ctcatgaacc 490

<210> SEQ ID NO 310
<211> LENGTH: 139
<212> TYPE: DNA
<213> ORGANISM: Artificial Sequence
<220> FEATURE:
<223> OTHER INFORMATION: Description of Artificial Sequence: Synthetic
Affymetrix ID 3111580 polynucleotide

<400> SEQUENCE: 310
ccagttgggt agattcagct tcctatattt ggctcatgga acaagacaca tttgttgcac 60
gctttagtgg atttttggtg gctccagatt ctgatgttta tagattctac atcaagggtg 120
atgaccgtta tgctattta 139

<210> SEQ ID NO 311
<211> LENGTH: 84
<212> TYPE: DNA
<213> ORGANISM: Artificial Sequence
<220> FEATURE:
<223> OTHER INFORMATION: Description of Artificial Sequence: Synthetic
Affymetrix ID 3111669 oligonucleotide

<400> SEQUENCE: 311
tcttttccac acttcaacgt ttggatgtct atgtgaacaa cttattggtc tgtccaaaaa 60
ctacaatatg gaatgcccag caga 84

<210> SEQ ID NO 312
<211> LENGTH: 31
<212> TYPE: DNA
<213> ORGANISM: Artificial Sequence
<220> FEATURE:
<223> OTHER INFORMATION: Description of Artificial Sequence: Synthetic
Affymetrix ID 3124381 oligonucleotide

<400> SEQUENCE: 312
ggagcagtca cggagctgta accctgcctc t 31

<210> SEQ ID NO 313
<211> LENGTH: 1571
<212> TYPE: DNA
<213> ORGANISM: Artificial Sequence
<220> FEATURE:
<223> OTHER INFORMATION: Description of Artificial Sequence: Synthetic
Affymetrix ID 3124395 polynucleotide

<400> SEQUENCE: 313
gccagacccg tagaatcctg agataaggag tgtttctgac ctttggtgtc atctagtcga 60
gtcctctcat tagtaaagga gcaaagtgaa acctggggga ggagaaggac ttccctcagg 120
ttgcacagct gtttaggcta tagaatattg atgtgtgaaa ccattattga taatgcctag 180
tagatcacat gtcaatgaac ttgaacccca aagatggtcg tgatgctttg ccaaacccgc 240
acactgccaa cccctctact ctccacctca gcccccaccc acatctccca gagtattgca 300
attcagaaca tttgggtcaa ggtggagcaa ggcactgaca gtggccccac agggcatgtg 360
tcactaatca ctgtcccatg gtctacgcac ggcatctggc tgctctgtct actgtgactt 420
cttcctgtgt aatctcagtg gggcccgtgt ccacccacac atcgtgaccc acatagggga 480
gaggttgctt ttcttttgtg ggctgagagt aggacaatgc aaatgaatga tctctagtag 540
acagaaaaga acttggtctc ttttttaaaa tttcaaagag ccagaagttc tatgcctcct 600
tcaaagtagg cagaacaacg cagccaagat ctactgtctg ccatgctctg tgcaatgaag 660
tctgcaggcc tgaggaccat gtactgctgt ccttcctcag agctctgcac aaacactgcc 720
aagtcctgaa gacgcattcc tttcctgcca acctctttcc agataagccc ttgaggtctc 780
gggctgacct acacacacac acacacacac acacacacac acccccacac acacacacac 840
gacagagaac atgccataaa catccttgaa cccatgcagg aaagcccatc ccatattctg 900
aaaaaatgcc aaattaggtt tttctttctt tttggaaatc agtcattaca gtaaccgaaa 960
ccattgggtt cagcgaaaat ggaaagattt agctgaatgt agtcagtcca attaagttgg 1020
atgcaactga gtgatttagt tgcttgggta acccagtgct tgcttgcttt cttcattctc 1080
tgggtggaaa ctaagatcaa gacacatgtt tggggataag ttaaatgtct gagctatttt 1140
gctcggttta tcctaagaga actttattat gggatgagga ggtgacccaa gatgagaagt 1200
ggagggggac agcgatgttt tctaaacatc gtccagtgtt gactggcttc cttactttgc 1260
acagtgaaca caactaacca cattaattca gctttgtgaa gtccctgctc tctgtgggtc 1320
tatgagtcag cagcaacatt ggcctaacct ccgtcccagc ctcctggctc accacatgtg 1380
tacagtgctg tttgcagttg tactcattat ccatccatct ctctgccatc cccaagcatc 1440
gctgggtgta aaacgcaaac tctccaccga cactgccatg cgtggtcatg tcttgatgcc 1500
ttcaggggct cagtagctat caaagaggcc tggagggcct gggcaggctt gacgatgcct 1560
gaccgagttc a 1571

<210> SEQ ID NO 314
<211> LENGTH: 50
<212> TYPE: DNA
<213> ORGANISM: Artificial Sequence
<220> FEATURE:
<223> OTHER INFORMATION: Description of Artificial Sequence: Synthetic Affymetrix ID 3142384 oligonucleotide

<400> SEQUENCE: 314
gaatgcgtca tgaaaggcgt cacttccacg agagtttatg agagagcata 50

<210> SEQ ID NO 315
<211> LENGTH: 317
<212> TYPE: DNA
<213> ORGANISM: Artificial Sequence
<220> FEATURE:
<223> OTHER INFORMATION: Description of Artificial Sequence: Synthetic Affymetrix ID 3144282 polynucleotide

<400> SEQUENCE: 315
gctgacaaac tggtgcaatc aaattaagtc agtgatgaga gaaaagcaat ttcacacaaa 60
gaaacaggac accatcaact tttatcacaa tcacagtgat ggcttttttg tttaatagtg 120
aaagtgacat ttcaattaaa atttctttag cctgttgttg tttagcctga ctcccctcct 180
tattttgtag gaggttgttt gagcaataac tgaatatgtg gcttaggatt tttctgtgct 240
gataatttcc actgaagcat ttaccttgtt ctttggattt ctttgttagt aaaggctcaa 300
gttgtggagt agttata 317

<210> SEQ ID NO 316
<211> LENGTH: 1013
<212> TYPE: DNA
<213> ORGANISM: Artificial Sequence
<220> FEATURE:
<223> OTHER INFORMATION: Description of Artificial Sequence: Synthetic Affymetrix ID 3205788 polynucleotide

<400> SEQUENCE: 316
cggtgctgct actcagggtc atctcaaaac tatgtaaagg cagatgttgc caatccacag 60
gcttcaggga ctcttatcaa gactcatccc aacttttaag gcacactttc acaccgctca 120
cattgtgcat tacattttgg agtccttgtt ggaagtgaac tttccgcctg taagcctgcc 180
attccatgtc taatatattg ggatggcatc accttctgta ctatgcagca gaaggagact 240
ggcctgggat tctggaaaca tgagatccat ttgcatatta atccccggct cgctgtgtga 300
ccctgagcaa gtctccttca ctttctgtgc ctcagtgtcc ttatttgagt aaaaagggaa 360
taaaactaga tgagtggttt tcaaacttta aaacactgga agctctcttt gaaaacaaaa 420
gatgagaatt gaaatggatg gcactggaag ctgttcttgt ctactggggt ttggagctgc 480
caggggacct gctcacatcc actcctcact cagcccctcc cgcccctccc ttctccacgc 540
actgtgactg acttccatgt gtgaaggcct gcagttaatt ctcctgtgtc ttgaatggtt 600
gggagatgag ttggtcagac ccttagtgaa atgatgtggg aaggaacagg aatgctgtgg 660
ctctgaagaa ggtagtagaa catcccacac ctgctaataa gcacattttg caaactcagt 720
tgactcacct cagatttgcc tagtgaaaac tgaagggctg gatgtagacc cagagagcag 780
ggtggacaga gcccatgctg gaagtactga gcatcaggac tgtatggggc tggctttagc 840
atcatcattc tgtgcaaaga caaataatta atgtcacact gtctgaaatt ttcaccaaaa 900
ccaaaaaggc gcattaacat gattgttcca acctcatggt ttttcaagtg tgagcgccca 960
gagacctctt cagaggctaa gagagcatgc gctgccacag ctgttagcat ttg 1013

<210> SEQ ID NO 317
<211> LENGTH: 593
<212> TYPE: DNA
<213> ORGANISM: Artificial Sequence
<220> FEATURE:
<223> OTHER INFORMATION: Description of Artificial Sequence: Synthetic
Affymetrix ID 3327171 polynucleotide

<400> SEQUENCE: 317
gtgatgtcct gtgcaccaaa tgttaaagga aacaaaacat agcacagatt tcttgacttt 60
taagagttaa ttcttaatat gcttcaaaag cagtataaac aatggctgag tgtggactct 120
gaatgcttac tggctggatt caaatcctgg ctctgccact aactacatga ctttgggcaa 180
gttatgtaac ctctgtgtgc ctcagtttcc tcatctgaaa actgagataa taattttacc 240
aacctcatat attgatgtca gttatgatta atagttgaat atacgtaaag tacttagaac 300
agggatttgc atatagtaga cgatagttat gattatttta aaatttacca aaaataaggt 360
ctagtgcata cgcacctgcc agtaatggca gttgataagg ttggagagga tgagaagggg 420
ctttaggata tgggaatcag gtcagtgggt atagacagat aaacatttga actaaaagaa 480
ttggataaac atatatgatg agggtgctgg tagtagttaa tttattaaca gaagatagtt 540
aatattttat tcttcttgtc accctttgtc taactgggga taatcttggt ata 593

<210> SEQ ID NO 318
<211> LENGTH: 260
<212> TYPE: DNA
<213> ORGANISM: Artificial Sequence
<220> FEATURE:
<223> OTHER INFORMATION: Description of Artificial Sequence: Synthetic
Affymetrix ID 3409349 polynucleotide

<400> SEQUENCE: 318
tgtccacctt tatctcggcg gtttgctccg gctgtgtggc tcccgcgacc cccatgcctg 60
cggcttccca gaaggctctc ccctgccttc agggtcagca gcttaaccct ttatctgggc 120
atgtgcaagc cgagctgtgt cctggctccc tcctgtccag acggacagct ttggctgtct 180
ctctttctct gggcaccagt gcctgcacaa gagccatgtt gagccaggct gcgccccaag 240
agcgcctgta caacggtagc 260

<210> SEQ ID NO 319
<211> LENGTH: 125
<212> TYPE: DNA
<213> ORGANISM: Artificial Sequence
<220> FEATURE:
<223> OTHER INFORMATION: Description of Artificial Sequence: Synthetic
Affymetrix ID 3479997 polynucleotide

<400> SEQUENCE: 319
tttcaggatg catagttcag gattctatac attgcattat agaaggagaa agaaagggta 60
aggagaccac tgcagaaatc tacgctgagc aaaggagatt ctggacaatt agtggcagtg 120
agaac 125

<210> SEQ ID NO 320
<211> LENGTH: 94
<212> TYPE: DNA
<213> ORGANISM: Artificial Sequence
<220> FEATURE:
<223> OTHER INFORMATION: Description of Artificial Sequence: Synthetic
Affymetrix ID 3554058 oligonucleotide

<400> SEQUENCE: 320
atctaatttt tataagacta agttgagtta tacttcttgg ttcacatttt ggaaatcaga 60
gattacagat tacatggcca tagcttatct gtgt 94

<210> SEQ ID NO 321
<211> LENGTH: 41
<212> TYPE: DNA
<213> ORGANISM: Artificial Sequence
<220> FEATURE:
<223> OTHER INFORMATION: Description of Artificial Sequence: Synthetic
Affymetrix ID 3662230 oligonucleotide

<400> SEQUENCE: 321
gattttacgg gtcactctat ttgtacttgg gagcagggct g 41

<210> SEQ ID NO 322
<211> LENGTH: 92
<212> TYPE: DNA
<213> ORGANISM: Artificial Sequence
<220> FEATURE:
<223> OTHER INFORMATION: Description of Artificial Sequence: Synthetic
Affymetrix ID 3695316 oligonucleotide

<400> SEQUENCE: 322
accatcacca ggcatgtctg cagagcctgg acaccaactt tatggactgc ccatgggagt 60
gctccaaatg tcagggtgtt tgcccaataa ta 92

<210> SEQ ID NO 323
<211> LENGTH: 345
<212> TYPE: DNA
<213> ORGANISM: Artificial Sequence
<220> FEATURE:
<223> OTHER INFORMATION: Description of Artificial Sequence: Synthetic
Affymetrix ID 3807971 polynucleotide

<400> SEQUENCE: 323
ttatctgtac tccaatgcct aggtcaaagt cctgatcccc ccaatcaggg gagagctcaa 60
gtctctgaat tcccagaaca ttctagcaat attataccac ttatatctta tctgaaaagt 120
ttttttttgt atatggcttt atgttttttt ttttatcctg ttagattgaa actacagaag 180
gcagggctgt atcttgtaca tcattgtatc tccccggtga ctgcaaaagt actctgtaaa 240
tgaatgttga ttagggggaa aaatgtcaga aagtcatctg aagctgtcat tccttactgg 300
gaggagccca ttttgacaaa tgagggtcac caatttcatt cctta 345

<210> SEQ ID NO 324
<211> LENGTH: 27
<212> TYPE: DNA
<213> ORGANISM: Artificial Sequence
<220> FEATURE:

<223> OTHER INFORMATION: Description of Artificial Sequence: Synthetic
Affymetrix ID 3893028 oligonucleotide

<400> SEQUENCE: 324
ttaatgactg gctacagagt aacaaaa 27

<210> SEQ ID NO 325
<211> LENGTH: 335
<212> TYPE: DNA
<213> ORGANISM: Artificial Sequence
<220> FEATURE:
<223> OTHER INFORMATION: Description of Artificial Sequence: Synthetic
Affymetrix ID 2336566 polynucleotide

<400> SEQUENCE: 325
ttgggtgtct atctttggca tgtttcctgt tatgtgagca tgacatgctg tgtatgtgag 60
tgagcttgta gggcgtggtg ggacttaggc atttgcagac agtgtttaga tgaaagatta 120
catgtaatga taaatctgaa tccctccatt ttatttgggt ggaaccatga ccaaaaatgg 180
taggaagacg aaaggccaga aagagacttt gccagagagt tcacggagtt ttcttacccc 240
gcatgctgac taaagaaaac atgggctttt ctgaaaccag cttcaactac agtataaact 300
atatcagaag cttacttgat aagccttgcg gagct 335

<210> SEQ ID NO 326
<211> LENGTH: 86
<212> TYPE: DNA
<213> ORGANISM: Artificial Sequence
<220> FEATURE:
<223> OTHER INFORMATION: Description of Artificial Sequence: Synthetic
Affymetrix ID 2466564 oligonucleotide

<400> SEQUENCE: 326
cgctcgctgt gctgtctgtc acgctggtta tggcctgcac agaagccttc ttccccttca 60
tctcgagagg gaaagaactc ctttgg 86

<210> SEQ ID NO 327
<211> LENGTH: 348
<212> TYPE: DNA
<213> ORGANISM: Artificial Sequence
<220> FEATURE:
<223> OTHER INFORMATION: Description of Artificial Sequence: Synthetic
Affymetrix ID 2466574 polynucleotide

<400> SEQUENCE: 327
tgacgtctac atccacctgc aaagcctgcc cctgggtcct gcagtagagc ctgaaccttt 60
ctttggtttg atgcttcctg attcataaat catgatcact caaaaaaaac tctttaaaaa 120
atgtattgtg cctaagttta cattttaaca acctcaagac cagggcctca gccggcagca 180
gtgagttcct gctcggccct tctgaaaggc cctgctgctg tcttgggcgc ctctgcccca 240
gctgctgggc gggctccact gacgctcctg ggagaatctc tgctgaccac acaatgacat 300
tggcactggg agctgtgatc tggggacact tagatctgag ctggtttc 348

<210> SEQ ID NO 328
<211> LENGTH: 133
<212> TYPE: DNA
<213> ORGANISM: Artificial Sequence
<220> FEATURE:
<223> OTHER INFORMATION: Description of Artificial Sequence: Synthetic
Affymetrix ID 2466583 polynucleotide

<400> SEQUENCE: 328
gtgctgcgtg caatcccttc agatcctccc agcctccctt tgatgtagca atcactgttt 60
ctgccctatg gcttaggagc caaggctcag ggagattgaa atctcttagt gagtggaacc 120
ctgcagattt aaa 133

<210> SEQ ID NO 329
<211> LENGTH: 435
<212> TYPE: DNA
<213> ORGANISM: Artificial Sequence
<220> FEATURE:
<223> OTHER INFORMATION: Description of Artificial Sequence: Synthetic
Affymetrix ID 2498676 polynucleotide

<400> SEQUENCE: 329
aggttcactt ttttgcagga ctgtaaggag gggttcattc atgatttttc tttattgctg 60
agagacaaaa aacctagata cctagataca tatatcttac ccataagata ctataagatc 120
ttcgtgaaca gaaatgactt atccccataa aagctaagtc tattctgtcc ctattcaata 180
gccaatatta aagatgataa tcaaatctat actacttaca gctaaaatta caaataggta 240
aatctaaacg tgtcattgta gtagagccgc ctctccaata ccatgaactt tatttggctt 300
agttgggtat agaaaataga aatatacagt ggcaatgcag atatatatgg ctctttcctg 360
atggtgtttt gaggacagta ctatttgtcc ctgagatctt tcttctgcct ggctgatctg 420
gtagcctgta tatta 435

<210> SEQ ID NO 330
<211> LENGTH: 107
<212> TYPE: DNA
<213> ORGANISM: Artificial Sequence
<220> FEATURE:
<223> OTHER INFORMATION: Description of Artificial Sequence: Synthetic
Affymetrix ID 2565105 polynucleotide

<400> SEQUENCE: 330
gccggggcat tgtccttcat gagctcatgc atgtgctggg cttctggcac gagcacacgc 60
gggccgaccg ggaccgctat atccgtgtca actggaacga gatcctg 107

<210> SEQ ID NO 331
<211> LENGTH: 39
<212> TYPE: DNA
<213> ORGANISM: Artificial Sequence
<220> FEATURE:
<223> OTHER INFORMATION: Description of Artificial Sequence: Synthetic
Affymetrix ID 2671521 oligonucleotide

<400> SEQUENCE: 331
acaactcagt gcaccggtct ccgaaatggc agcgacagt 39

<210> SEQ ID NO 332
<211> LENGTH: 105
<212> TYPE: DNA
<213> ORGANISM: Artificial Sequence
<220> FEATURE:
<223> OTHER INFORMATION: Description of Artificial Sequence: Synthetic
Affymetrix ID 2797068 polynucleotide

<400> SEQUENCE: 332
ttgagaatat ttgcagacgt tgcacacttc ctcccagctg cccccatttt gctccattca 60
tgtcattctg tttgtgtagc tggtgctgtc aacactcaat ttcta 105

<210> SEQ ID NO 333
<211> LENGTH: 120

<212> TYPE: DNA
<213> ORGANISM: Artificial Sequence
<220> FEATURE:
<223> OTHER INFORMATION: Description of Artificial Sequence: Synthetic
Affymetrix ID 2797084 polynucleotide

<400> SEQUENCE: 333
aaggaaattt gcgatccaga gcagagaggt ttctggggaa gcgaggacaa gggcctgact 60
ttgcatgcta cgaagagggc agcaagacga atatgttaca gataaaaaag ggcagtttgc 120

<210> SEQ ID NO 334
<211> LENGTH: 139
<212> TYPE: DNA
<213> ORGANISM: Artificial Sequence
<220> FEATURE:
<223> OTHER INFORMATION: Description of Artificial Sequence: Synthetic
Affymetrix ID 2880196 polynucleotide

<400> SEQUENCE: 334
gaagagataa caggctccag gcatgttttg gaggcaatag gctagatttt aggggagaag 60
taaactaagg aattaagata gttttcaggt tttagctttg aacaattggg tggttggtgg 120
acaccgttac taacactgg 139

<210> SEQ ID NO 335
<211> LENGTH: 175
<212> TYPE: DNA
<213> ORGANISM: Artificial Sequence
<220> FEATURE:
<223> OTHER INFORMATION: Description of Artificial Sequence: Synthetic
Affymetrix ID 2932285 polynucleotide

<400> SEQUENCE: 335
gctgacacag gatgagagca cagtaaaact taagctaaga tttccacatt aatatcttgc 60
ccccaaacac catgcagtgc taaaagtcac attcccatca tgcaagcaca ttaaaatata 120
tggcgattaa aactcctggt ttctatttta cggcatttgc tctttccacg aggca 175

<210> SEQ ID NO 336
<211> LENGTH: 111
<212> TYPE: DNA
<213> ORGANISM: Artificial Sequence
<220> FEATURE:
<223> OTHER INFORMATION: Description of Artificial Sequence: Synthetic
Affymetrix ID 3018636 polynucleotide

<400> SEQUENCE: 336
tgcgggttct ttgacgacaa cattagaaag gacacattct ttttgacggt ccatgatgct 60
atactctatc tacagaacca agtgaaatct caagagggtc aaggttccat t 111

<210> SEQ ID NO 337
<211> LENGTH: 135
<212> TYPE: DNA
<213> ORGANISM: Artificial Sequence
<220> FEATURE:
<223> OTHER INFORMATION: Description of Artificial Sequence: Synthetic
Affymetrix ID 3106608 polynucleotide

<400> SEQUENCE: 337
gcactcctaa atgctacata caaggaggga ggctatggtg tcagcacaga tgtatccctg 60
gatagacgat ggccttgcca gcctgacact tcaaaacaaa ataggaactt catgggaacc 120
tgcagaatag aagct 135

<210> SEQ ID NO 338
<211> LENGTH: 62
<212> TYPE: DNA
<213> ORGANISM: Artificial Sequence
<220> FEATURE:
<223> OTHER INFORMATION: Description of Artificial Sequence: Synthetic
      Affymetrix ID 3106630 oligonucleotide

<400> SEQUENCE: 338
gtggcttgtc taatatcttg cattttcgtc cttatagtca tctatgcaat aggacctttg     60
ct                                                                    62

<210> SEQ ID NO 339
<211> LENGTH: 44
<212> TYPE: DNA
<213> ORGANISM: Artificial Sequence
<220> FEATURE:
<223> OTHER INFORMATION: Description of Artificial Sequence: Synthetic
      Affymetrix ID 3106643 oligonucleotide

<400> SEQUENCE: 339 tttttgaat cggtatctgc tgcaataagt catatccatt caaa                       44

<210> SEQ ID NO 340
<211> LENGTH: 61
<212> TYPE: DNA
<213> ORGANISM: Artificial Sequence
<220> FEATURE:
<223> OTHER INFORMATION: Description of Artificial Sequence: Synthetic
      Affymetrix ID 3108616 oligonucleotide

<400> SEQUENCE: 340
aaaacacgat caatgcaaat gtgaaaacct tataatgttc cagaaccttg caaacgaaga     60
a                                                                     61

<210> SEQ ID NO 341
<211> LENGTH: 52
<212> TYPE: DNA
<213> ORGANISM: Artificial Sequence
<220> FEATURE:
<223> OTHER INFORMATION: Description of Artificial Sequence: Synthetic
      Affymetrix ID 3111579 oligonucleotide

<400> SEQUENCE: 341
tgaagcttga ggtgtggaat aatagccgtc caatacgttt ggaagagata ct             52

<210> SEQ ID NO 342
<211> LENGTH: 72
<212> TYPE: DNA
<213> ORGANISM: Artificial Sequence
<220> FEATURE:
<223> OTHER INFORMATION: Description of Artificial Sequence: Synthetic
      Affymetrix ID 3111585 oligonucleotide

<400> SEQUENCE: 342
cccaacttgg agacattcac actgaattgg gatgggatcg cttctaagcc actcactcta     60
tggtcatcag aa                                                         72

<210> SEQ ID NO 343
<211> LENGTH: 219
<212> TYPE: DNA
<213> ORGANISM: Artificial Sequence
<220> FEATURE:
<223> OTHER INFORMATION: Description of Artificial Sequence: Synthetic
      Affymetrix ID 3111692 polynucleotide

<400> SEQUENCE: 343
agttctgaca gctgctcttt catcctatgc ctttaaaaca aagggaacaa agaagggaac 60
aaagaaggta gaagcggggg tatggagggt tgacttctgg ctgtccctcc ctgtttccct 120
ttgttaatat attgctagta gacatgtcta cttctggttg ctgatgacat aaaattcacc 180
tctatttctt ggaagcacta ttccatgttg tgagctaaa 219

<210> SEQ ID NO 344
<211> LENGTH: 160
<212> TYPE: DNA
<213> ORGANISM: Artificial Sequence
<220> FEATURE:
<223> OTHER INFORMATION: Description of Artificial Sequence: Synthetic
      Affymetrix ID 3327188 polynucleotide

<400> SEQUENCE: 344
ttggagatga agttcaactt ttttcacttg atgaagaatt tgattatgac aatgtgatgc 60
taacctccaa gtttagtcct gcagagatag agaacatcaa agagctatgc aagcagcaga 120
agagaaagga caccagccca gacttagaga aatcctgtga 160

<210> SEQ ID NO 345
<211> LENGTH: 513
<212> TYPE: DNA
<213> ORGANISM: Artificial Sequence
<220> FEATURE:
<223> OTHER INFORMATION: Description of Artificial Sequence: Synthetic
      Affymetrix ID 3367697 polynucleotide

<400> SEQUENCE: 345
agtgcttgtt aacccagtgc ctcagccctt cttagacatg aatcagaacc tttggtggta 60
gagcaggaaa ttggcacttt agcacccagg gtgattttta tgcctactaa agtgtgagaa 120
caactgactt tgaagctgta ggtgtttggg ttggtggcgt atttatccct agaattgctc 180
cgtgtaattt gatgatgagg acatctttct gtttctttcc tccaaaatgg aaggcaaact 240
aaattaaaat ccagttaatt caggttctga gttgattggg acatggataa ttgtgatctt 300
tttgctgatt tctaaaatat tttcccttca ttatctgttg gatttcaagt gcattctgct 360
ctgtgttata gaatgagggt tgatgtgaaa cttagggaga ctccaattat atacatggtt 420
caattactgg ttccataatt tagggtgtcc tcttttccca ttgactttca ctttcttcgt 480
acttaaatgg caaggttgta ctctctgatc tca 513

<210> SEQ ID NO 346
<211> LENGTH: 184
<212> TYPE: DNA
<213> ORGANISM: Artificial Sequence
<220> FEATURE:
<223> OTHER INFORMATION: Description of Artificial Sequence: Synthetic
      Affymetrix ID 3603305 polynucleotide

<400> SEQUENCE: 346
ccctgaggaa tatgtcatag ttctgagctg ccagtggacc gcccttttcc cctaccaata 60
ttaggtgatc ccgttttccc catgacaatg ttgtagtgtc ccccaccccc accccccagg 120
ccttggtgcc tcttgtatcc ctagtgctcc atagtttggc atttgcacgg tttcgaagtc 180
atta 184

<210> SEQ ID NO 347
<211> LENGTH: 118
<212> TYPE: DNA

<213> ORGANISM: Artificial Sequence
<220> FEATURE:
<223> OTHER INFORMATION: Description of Artificial Sequence: Synthetic
Affymetrix ID 3630807 polynucleotide

<400> SEQUENCE: 347
actgccaccg tgatgccatc agatgggaga aaacacagaa ctcgggatga aacgtcacac 60
ggtctgggct aaagatcttg ctctttaatt tcccagcagg taaccttgtg gcagtcac 118

<210> SEQ ID NO 348
<211> LENGTH: 29
<212> TYPE: DNA
<213> ORGANISM: Artificial Sequence
<220> FEATURE:
<223> OTHER INFORMATION: Description of Artificial Sequence: Synthetic
Affymetrix ID 3923071 oligonucleotide

<400> SEQUENCE: 348
aaattatcca agcataaggg catgtgcct 29

<210> SEQ ID NO 349
<211> LENGTH: 119
<212> TYPE: DNA
<213> ORGANISM: Artificial Sequence
<220> FEATURE:
<223> OTHER INFORMATION: Description of Artificial Sequence: Synthetic
Affymetrix ID 2350941 polynucleotide

<400> SEQUENCE: 349
ttgttccgtt acctcctttc agatgctttc ccagtcctgg agctacataa agaataactt 60
gcatttattg agtgctggct tcatgccagg aaccttgccc agcacattat acctatcgt 119

<210> SEQ ID NO 350
<211> LENGTH: 106
<212> TYPE: DNA
<213> ORGANISM: Artificial Sequence
<220> FEATURE:
<223> OTHER INFORMATION: Description of Artificial Sequence: Synthetic
Affymetrix ID 2508448 polynucleotide

<400> SEQUENCE: 350
aggactggaa taagactgga aagacggaaa gcgggatggg aagggtgtaa tgtggaggct 60
cttaaaggaa gtaatgttaa actcttaaaa ctgtataagc aaaact 106

<210> SEQ ID NO 351
<211> LENGTH: 26
<212> TYPE: DNA
<213> ORGANISM: Artificial Sequence
<220> FEATURE:
<223> OTHER INFORMATION: Description of Artificial Sequence: Synthetic
Affymetrix ID 2530202 oligonucleotide

<400> SEQUENCE: 351
agagagctgt tactggccat ggtgtc 26

<210> SEQ ID NO 352
<211> LENGTH: 165
<212> TYPE: DNA
<213> ORGANISM: Artificial Sequence
<220> FEATURE:
<223> OTHER INFORMATION: Description of Artificial Sequence: Synthetic
Affymetrix ID 2537572 polynucleotide

<400> SEQUENCE: 352
ctgcagtttt gttctattgg tcaaaatata ttctgacaaa aatgtatttg aagtgcatga 60
taaggtaaag gtgtgttgaa tattttgatt tcacacttag ttccgagtgt actgtgttaa 120
gcaaggtgcc cctaagttga aggggtgtag gcacaattaa cagtc 165

<210> SEQ ID NO 353
<211> LENGTH: 131
<212> TYPE: DNA
<213> ORGANISM: Artificial Sequence
<220> FEATURE:
<223> OTHER INFORMATION: Description of Artificial Sequence: Synthetic
Affymetrix ID 2537609 polynucleotide

<400> SEQUENCE: 353
gttggattta tggaggttgc acagaaagga gatctgggga ggttgcacac agagtggggg 60
ggatttgggg aggtttcaca aagctagggg catttgagga gaatgcacac agtggggcga 120
tttggggacg t 131

<210> SEQ ID NO 354
<211> LENGTH: 96
<212> TYPE: DNA
<213> ORGANISM: Artificial Sequence
<220> FEATURE:
<223> OTHER INFORMATION: Description of Artificial Sequence: Synthetic
Affymetrix ID 2578830 oligonucleotide

<400> SEQUENCE: 354
ggtgtcactg ttggcccagt tattcaggag aaagatgtga agtcaaccac tgtagcaact 60
actgccagaa tggaggaact tgcgtaccat cagttc 96

<210> SEQ ID NO 355
<211> LENGTH: 265
<212> TYPE: DNA
<213> ORGANISM: Artificial Sequence
<220> FEATURE:
<223> OTHER INFORMATION: Description of Artificial Sequence: Synthetic
Affymetrix ID 2754755 polynucleotide

<400> SEQUENCE: 355
agctgcatgc agttgactta atttcaaacc tgaagccttt aaaatatgaa gctggttatg 60
aacttgacag aaatcaaggt aggctactca acgatgtttc tttaccttct tcctaatgaa 120
attcccttgt catcagtcag tagatatgta catttcattt ggcttctacg atcttttaac 180
ttcatagatt tttgcataaa tgctatctga cagaatcaca ctatctaggg gtgcttgtga 240
tctgtgagat aaggagaggc tagtc 265

<210> SEQ ID NO 356
<211> LENGTH: 857
<212> TYPE: DNA
<213> ORGANISM: Artificial Sequence
<220> FEATURE:
<223> OTHER INFORMATION: Description of Artificial Sequence: Synthetic
Affymetrix ID 3111629 polynucleotide

<400> SEQUENCE: 356
tccggttggg gcgatatcca atacattggc acctgcttgg agacttacag tttaaatctt 60
atgtaagagg ctgtgcaatt caccaggcct ataacagagc tgttactatt cataacacac 120
accatcttct ggttgagagg aatattatat atgatattaa gggaggagca ttttttatag 180
aagatggtat tgaacatggc aatatcctcc agtataactt ggcagtattt gtacagcaaa 240
gtaccagtct tctgaatgat gatgtgaccc cggctgcatt ttgggtcacc aacccgaaca 300

```
ataccatacg acacaatgct gttgctggtg gcactcactt tggcttttgg taccggatga    360

acaaccaccc tgatgggcca tcctatgaca gaaacatttg tcaaaaaaga gttccccttg    420

gcgaattttt taacaatact gtccattctc aaggttggtt tggaatgtgg atctttgagg    480

aatatttccc catgcaaacg ggatcttgta catctacagt gcctgcacct gcaatattta    540

actcacttac tacttggaat tgtcaaaaag gagctgaatg ggtcaatgga ggtgcccttc    600

agttccataa ctttgtgatg gtgaataact atgaggctgg aattgagact aagaggatcc    660

tggctcctta tgttggaggg tggggtgaaa ccaatggagc ggtgattaaa aatgccaaaa    720

tagtcggcca tcttgatgaa ctgggaatgg ggtctgcatt ttgcacagca aaaggcctgg    780

ttctcccatt tagtgaaggc ttgactgtct cttctgtgca ctttatgaac tttgaccgtc    840

ccaactgtgt agctttg                                                   857
```

<210> SEQ ID NO 357
<211> LENGTH: 125
<212> TYPE: DNA
<213> ORGANISM: Artificial Sequence
<220> FEATURE:
<223> OTHER INFORMATION: Description of Artificial Sequence: Synthetic
Affymetrix ID 3111642 polynucleotide

<400> SEQUENCE: 357

```
tagattaatc ggtggctggg aagataaccc ttttaaagga gacttaaaga ttgttcttag     60

aggaaatcat actacacaag actgggctct tccagaagga ccaaatcaag ggcaaaggt    120

cttag                                                                125
```

<210> SEQ ID NO 358
<211> LENGTH: 203
<212> TYPE: DNA
<213> ORGANISM: Artificial Sequence
<220> FEATURE:
<223> OTHER INFORMATION: Description of Artificial Sequence: Synthetic
Affymetrix ID 3154260 polynucleotide

<400> SEQUENCE: 358

```
tctatggcag gcatatatgc ggccccgcca ggggctctgg gctcttgtcc tcacaggtag     60

agactgtggg ttccaaatac agtgaggaac agtggaggag catgggcctt gagaccagac    120

acacataggc ctgaatgcta gccagctagg agaccttgat catgttcttg tacctctcct    180

ttgccagcta ggagaccttg atc                                            203
```

<210> SEQ ID NO 359
<211> LENGTH: 89
<212> TYPE: DNA
<213> ORGANISM: Artificial Sequence
<220> FEATURE:
<223> OTHER INFORMATION: Description of Artificial Sequence: Synthetic
Affymetrix ID 3209748 oligonucleotide

<400> SEQUENCE: 359

```
ttggcaagtt gatcaaagaa gctgccggga aaagcaatct gaagagggtg accctggagc     60

ttggaggaaa gagcccttgc attgtgtta                                       89
```

<210> SEQ ID NO 360
<211> LENGTH: 140
<212> TYPE: DNA
<213> ORGANISM: Artificial Sequence
<220> FEATURE:
<223> OTHER INFORMATION: Description of Artificial Sequence: Synthetic
Affymetrix ID 3327193 polynucleotide

<400> SEQUENCE: 360
cttgatttca tgttgcccta gagtcaagtg tctgccacat ttatttttac ttattcaaca 60
aactttcata aagctccatt tgtgtgttca agctttatgc taggcagtgg ggaggataca 120
ggcaagttag acatggtcca 140

<210> SEQ ID NO 361
<211> LENGTH: 204
<212> TYPE: DNA
<213> ORGANISM: Artificial Sequence
<220> FEATURE:
<223> OTHER INFORMATION: Description of Artificial Sequence: Synthetic
Affymetrix ID 3367689 polynucleotide

<400> SEQUENCE: 361
ctgcatctct tgagaccttg ttagaagtgc aagttctttg gctccatcct atagccacag 60
aaccttggag tggcttcaag tgactgatgt ctaaagtttg agaaacattg cattacagga 120
tgctactttt ccagacttgg ttcttacatt ccataaatat ttatcaagta ctcaataagt 180
ggcagggact attggagata cagc 204

<210> SEQ ID NO 362
<211> LENGTH: 182
<212> TYPE: DNA
<213> ORGANISM: Artificial Sequence
<220> FEATURE:
<223> OTHER INFORMATION: Description of Artificial Sequence: Synthetic
Affymetrix ID 3367693 polynucleotide

<400> SEQUENCE: 362
ggccgaatta attggtgtga ttccattctc aatttaagaa atcaaggtta aatgacttgc 60
ccacaattgc attgagctgg aactagggca taggtctgct gtctccagat ctccagctga 120
cttcccaccg cagcctgtca gtcagtgaaa ttaatctgca gtcattcgca gacacctgaa 180
aa 182

<210> SEQ ID NO 363
<211> LENGTH: 1001
<212> TYPE: DNA
<213> ORGANISM: Artificial Sequence
<220> FEATURE:
<223> OTHER INFORMATION: Description of Artificial Sequence: Synthetic
Affymetrix ID 3407861 polynucleotide

<400> SEQUENCE: 363
agccagtacc tgtcttgatc ttagttgtgt ttttttttca ttttgttacc cacttgcatt 60
ttgttttcac tcagcagaaa ttctccttct ctgttttcct tttatcccat ccccaagaat 120
gtggaaggaa ggtgagaaac atggcaggat gggaaatagg agagtatgac tctctatagc 180
tcatccagga gtaatcaatt aagaagataa attggatgac tgtggagaag ctctgtgata 240
ggaacacttc agtgtggttg ctgagaggag acagtcattg aggtagaagg tttgccaaag 300
atccagagct cagagctccc tttgtgctct ttgggaatta ccttgcattc agtttagaaa 360
catggatcta aaagttactg ggaaataagc agatggagac acactctgtt gtttacgtat 420
tggaagaagg gaacaagcca gttttgttag aggtaactca ttttccatga ccaaacagac 480
tcaacagatt caagtactct gcttactcta attgactaga ctctaggttt tatttgacat 540
catagcatta cataaatcac tctgataaca taagtgcaca gtaatatgcc tgatctcttc 600
ctttttaaaa gccaacttga gttcagtacc atctgaatac acacacatgc acatataccc 660
acacacgcat acacacatac tcctgtggca aacataataa tgtatttatt tagaattata 720
atatgaccat catgttaatt attttttacc taatcagagt tgttattgac aaatgtcata 780
agtggaaagt attaattctt attgtcatca gtatttagcc attatttagt agctcaagaa 840
tatctttatg tgaatgtctc tgtaacttgg aattgcaatt tcactgtgtt aagtaatcag 900
aactctgctt ataagattta tctgtatctt gtttcataat ttaataatga aactaaattc 960
aagttaatgt aatgttgatc tccgtcgaaa aataacttgt g 1001

<210> SEQ ID NO 364
<211> LENGTH: 83
<212> TYPE: DNA
<213> ORGANISM: Artificial Sequence
<220> FEATURE:
<223> OTHER INFORMATION: Description of Artificial Sequence: Synthetic
Affymetrix ID 3467971 oligonucleotide

<400> SEQUENCE: 364
atggtggctg gatttgcatc cgtgattata caggctgtgg tgatgcaagg tggaatcagc 60
actattttaa atgatgccta tga 83

<210> SEQ ID NO 365
<211> LENGTH: 726
<212> TYPE: DNA
<213> ORGANISM: Artificial Sequence
<220> FEATURE:
<223> OTHER INFORMATION: Description of Artificial Sequence: Synthetic
Affymetrix ID 3880528 polynucleotide

<400> SEQUENCE: 365
gacgggcact gctaatcctt ccaaaggaaa gctccaaaga tcccagcccg caaggctgtc 60
tctggatgga ttctggtgga tgaatggcaa cgcggctctc tgcagcctgc cagtgcccag 120
agtgccaccg cattagcaat atacaaacag tccaaaaaag tgtttatttt ttatggaata 180
cggtgcaata ggcagaggac aagggacaca tcactcttct gtctgtggcc ctgctggagt 240
cctttgtgcc ccccggagtc cacacgcctt ccctgcaaga cgagaatggg gctgggaaga 300
aagaggcaac accacggctg gcaggagccc cgctgcactg ctctgcagac ccattggcct 360
gaccctgaga agcagagcca gcaaagcccg ggacctgccc ctctttcttt cccttcacac 420
caccccagcc tcaggatgtc aagccacctc cggaacgtgt ctacactcca cagctacccc 480
gcagcaatac gcactcttgg gacctcgctg atctaggatg gggaggcagg ccaccgcccc 540
tcccaagact cctcaagaaa gagccccgcg gttgctccgg aaactcgagg cactgcagct 600
atgggcactg cctcagccta aagacacagg ggcgcctccc aatcaccgcg ctggcggatg 660
ctcaccccgt cataagcaga aactagtgat cctggaaatg agatgggcct tactctgtcg 720
actaaa 726

<210> SEQ ID NO 366
<211> LENGTH: 155
<212> TYPE: DNA
<213> ORGANISM: Artificial Sequence
<220> FEATURE:
<223> OTHER INFORMATION: Description of Artificial Sequence: Synthetic
Affymetrix ID 2350526 polynucleotide

<400> SEQUENCE: 366
tgacgttgcc aagatctact ccatcaatgt caccaatgtt atgaatggtg tggcctccta 60
ctgccgtccc tgtgccctag aagcctctga tgtgggctcc tcctgcacct cttgtcctgc 120
tggttactat attgaccgag attcaggaac ctgcc 155

<210> SEQ ID NO 367
<211> LENGTH: 48
<212> TYPE: DNA
<213> ORGANISM: Artificial Sequence
<220> FEATURE:
<223> OTHER INFORMATION: Description of Artificial Sequence: Synthetic
Affymetrix ID 2466563 oligonucleotide

<400> SEQUENCE: 367
ttggaacttg taaagtggcc caagagtggc tgtaatttgg gccattat 48

<210> SEQ ID NO 368
<211> LENGTH: 77
<212> TYPE: DNA
<213> ORGANISM: Artificial Sequence
<220> FEATURE:
<223> OTHER INFORMATION: Description of Artificial Sequence: Synthetic
Affymetrix ID 2466566 oligonucleotide

<400> SEQUENCE: 368
gaaagcctga ggagtctcgt gtctctagcg tcttggagga aagcaagcgc ctggtggaca 60
ccgccatgta cgccacg 77

<210> SEQ ID NO 369
<211> LENGTH: 150
<212> TYPE: DNA
<213> ORGANISM: Artificial Sequence
<220> FEATURE:
<223> OTHER INFORMATION: Description of Artificial Sequence: Synthetic
Affymetrix ID 2466608 polynucleotide

<400> SEQUENCE: 369
agccacgtct tcacggatgc acagaggcgt gagctggaga agcactccct gtctcgggtc 60
atctgtgaca acactggcct caccagggtg cccatggatg ccttccaagt cggcaaattc 120
cccgaagact ttgagtcttg tgacagcatc 150

<210> SEQ ID NO 370
<211> LENGTH: 27
<212> TYPE: DNA
<213> ORGANISM: Artificial Sequence
<220> FEATURE:
<223> OTHER INFORMATION: Description of Artificial Sequence: Synthetic
Affymetrix ID 2508401 oligonucleotide

<400> SEQUENCE: 370
tgcttgggca atcagactta ctcttca 27

<210> SEQ ID NO 371
<211> LENGTH: 36
<212> TYPE: DNA
<213> ORGANISM: Artificial Sequence
<220> FEATURE:
<223> OTHER INFORMATION: Description of Artificial Sequence: Synthetic
Affymetrix ID 2579066 oligonucleotide

<400> SEQUENCE: 371
gtaagtgaga gttgagtgca atttgtaata agaata 36

<210> SEQ ID NO 372
<211> LENGTH: 135
<212> TYPE: DNA
<213> ORGANISM: Artificial Sequence
<220> FEATURE:
<223> OTHER INFORMATION: Description of Artificial Sequence: Synthetic
Affymetrix ID 2586195 polynucleotide

<400> SEQUENCE: 372
agggattcat cagtgagggc atttcacacc ctcatgtggc atttcacttg gtagtgtcca 60
gatcggattg ggttttttt cctctggtta gtcacggtcc ttggaaagaa agatatgctg 120
gctcatgttg ttatg 135

<210> SEQ ID NO 373
<211> LENGTH: 393
<212> TYPE: DNA
<213> ORGANISM: Artificial Sequence
<220> FEATURE:
<223> OTHER INFORMATION: Description of Artificial Sequence: Synthetic
Affymetrix ID 2721311 polynucleotide

<400> SEQUENCE: 373
ctgcctggag accttgatct tgacctggaa tatggtgatc gggaacacga cctgtgtcga 60
gaaaaggacc ttgaacgaga gcgcatcctt tggggtcttt gagaaaataa ggatttgggt 120
ggtgacacag aatctctaca tggagagtta aaagaagaac aagaaggaga cacattgaac 180
aatgaatagg attgcgtgcc atcccaaggg tagctcagtt tatcactttc atcttcgctg 240
tcatcaaaca ggccatccat ggctagtcct gaatttataa acataggtag tttggagaat 300
tgttcattac tgaaatcact gtccctcagt tcaccggtct tgtctgcttc gtcgtcaaaa 360
acagcttgac tgggatgacc gaagtgcttg ttc 393

<210> SEQ ID NO 374
<211> LENGTH: 493
<212> TYPE: DNA
<213> ORGANISM: Artificial Sequence
<220> FEATURE:
<223> OTHER INFORMATION: Description of Artificial Sequence: Synthetic
Affymetrix ID 2763557 polynucleotide

<400> SEQUENCE: 374
tggtaaccga actggtgctt tagtaatgtg gattttttc tttttaaaa gagatgtagc 60 agaataattc ttccagtgca acaaaatcaa ttttttgcta aacgactccg agaacaacag 120
ttgggctgtc aacattcaaa gcagcagaga gggaactttg cactattggg gtatgatgtt 180
tgggtcagtt gataaaagga aaccttttca tgcctttaga tgtgagcttc cagtaggtaa 240
tgattatgtg tcctttcttg atggctgtaa tgagaacttc aatcactgta gtctaagacc 300
tgatctatag atgacctaga atagccatgt actataatgt gatgattcta aatttgtacc 360
tatgtgacag acattttcaa taatgtgaac tgctgatttg atggagctac tttaagattt 420
gtaggtgaaa gtgtaatact gttggttgaa ctatgctgaa gagggaaagt gagcgattag 480
ttgagccctt gcc 493

<210> SEQ ID NO 375
<211> LENGTH: 82
<212> TYPE: DNA
<213> ORGANISM: Artificial Sequence
<220> FEATURE:
<223> OTHER INFORMATION: Description of Artificial Sequence: Synthetic
Affymetrix ID 2763566 oligonucleotide

<400> SEQUENCE: 375
atgacagagg gatggcgaat acctcatggg acagcgcgtc cttccctaaa gactattgca 60
agtcatactt aggaatttct cc 82

<210> SEQ ID NO 376
<211> LENGTH: 105
<212> TYPE: DNA
<213> ORGANISM: Artificial Sequence
<220> FEATURE:
<223> OTHER INFORMATION: Description of Artificial Sequence: Synthetic
Affymetrix ID 2797066 polynucleotide

<400> SEQUENCE: 376 acttttggt gatcagctgt gtgtgagggt gtcccacgaa agccgtgatc tgcacagacg 60
ccgatgctct caggctcttc agtgtcgctc ttctgcaaac gagta 105

<210> SEQ ID NO 377
<211> LENGTH: 43
<212> TYPE: DNA
<213> ORGANISM: Artificial Sequence
<220> FEATURE:
<223> OTHER INFORMATION: Description of Artificial Sequence: Synthetic
Affymetrix ID 2797085 oligonucleotide

<400> SEQUENCE: 377
tcgaccggcc caaggactgg tacaagacga tgtttaagca aat 43

<210> SEQ ID NO 378
<211> LENGTH: 259
<212> TYPE: DNA
<213> ORGANISM: Artificial Sequence
<220> FEATURE:
<223> OTHER INFORMATION: Description of Artificial Sequence: Synthetic
Affymetrix ID 2797159 polynucleotide

<400> SEQUENCE: 378
tttcaaggag ccaacgtgga gtctacgatg gaaatttgcc ccataggaat atgaaagtgc 60
tgtggcatag agtattttat agaagttaaa tgtctaacct taatggattg ctaacgttgg 120
cttagattat tgctaatgac tacaggattt tacagaatgt gataagcttt gaaataatga 180
ctatattagt aacataagac catgagagca actaacagaa ttataactaa ggaaccctgt 240
tacaggcaat agaataacg 259

<210> SEQ ID NO 379
<211> LENGTH: 108
<212> TYPE: DNA
<213> ORGANISM: Artificial Sequence
<220> FEATURE:
<223> OTHER INFORMATION: Description of Artificial Sequence: Synthetic
Affymetrix ID 3018615 polynucleotide

<400> SEQUENCE: 379
gcctttggtg tgctaaagac tcttgtgccc atcttggagt ggctccccaa ataccgagtc 60
aaggaatggc tgcttagtga cgtcatttcg ggagttagta ctgggcta 108

<210> SEQ ID NO 380
<211> LENGTH: 103
<212> TYPE: DNA
<213> ORGANISM: Artificial Sequence
<220> FEATURE:
<223> OTHER INFORMATION: Description of Artificial Sequence: Synthetic
Affymetrix ID 3018616 polynucleotide

<400> SEQUENCE: 380
tatgccctac tagctgcagt tcctgtcgga tatggtctct actctgcttt tttccctatc 60

```
ctgacatact ttatctttgg aacatcaaga catatctcag ttg                    103


<210> SEQ ID NO 381
<211> LENGTH: 1859
<212> TYPE: DNA
<213> ORGANISM: Artificial Sequence
<220> FEATURE:
<223> OTHER INFORMATION: Description of Artificial Sequence: Synthetic
      Affymetrix ID 3018642 polynucleotide

<400> SEQUENCE: 381

taataatgtt cacgtgggcc ctggcatatc tctgttcagt tagagtgagt gctgacccaa     60

cagcctctgt ggtcaagcga gtcacgaatg attaatcata aagaaaaatc agtttttgac    120

tgacctggat atccatgagc tgcactgatc accatgtaag gtcacattta gtaaatgctg    180

aaataaaatg attaatgcat ttatcaataa aagcctttga aaatactttg gataataaat    240

tggagtttta aaaatgcaaa tttgcttagt atctaataat gaagtgttat tacatatagc    300

cggaattgag gatctctttg atcctggaaa tggtttacct aaaagctaca gaaccaggcc    360

aatatatttt gaaatattga tgcagacaaa tgaaataata aagagatttt catggtttat    420

aaaaatcttt tttgatatga taataatcat gatcacaact gagatcaaaa aaatatatga    480

cagattattt tgtttaaaaa tgcagtttta attatcttag tctatagaaa tgatcattgc    540

atggaggcat gtataggtat gatctgtgta aaatctgaca taaaaacagt gctattctga    600

gtgaaaattt ttttgatgtg cttacataac catggtgatt aaaatgagtt tatatttttt    660

ctcaaaaatt ttagcagtgt gtaaagtaag taatctttaa ctgaactctg accacttaaa    720

aaaaaatcta aaaattgaac tacctatagt agtctgtgtt taaagtgaat ttttaaagac    780

aaagcattct aaatgaactc aatataaaaa cattcatttg gaatgtacat actgaaaaat    840

acaggttttt ttgaccaaaa gtttttatat cttttctttt tatttatttt tttcctaagt    900

gccaacaatt ttctagatat tatatacaac acaggctttg atcttgggga cttttcccat    960

atatttcaca ctggagtgaa tgaagttgta cttcatttct agagaaaagt tatacccagg   1020

tccccaattg agaatgtctt gcttgattga aaacgacatc atcccttggt atactccagg   1080

gattggtttc aggacccctg catttaccaa aatttgtgca cactcaagtc ctgcagtcac   1140

ccctgcctaa agatagaatg gcttctctgt ttttcttctg aaatacaacc agaaacaatg   1200

tgtctatttc tgaaagaata ggattaatga tcatacaaat gggttaatcc tgaattctgg   1260

ttgtaaatct ggttacagca taactaggat tataatgctg cctcattttc acagcactac   1320

ttgcttatat tgacaacaaa tcatctcgct aaagagtgaa tgtaggccag gcgcggtggc   1380

tcatgcctgt aatcccagca ctttgggagg ccgaggcggg tggatcacga ggtcaggaga   1440

tcgagaccat cctggctaac atggtaaaac cccgtctcta ctaaaaatag aaaaaaagaa   1500

attagcctag cgtggtggct ggcgggcgcc tgtagtccca gctatttggg aggctaaggc   1560

aggagaatgg cgtgaacccg ggaggcggag cttgcagtga gccgaggtcg tgccactgca   1620

ctccagcctg ggcgacagag caagactccg tctcaaaaaa aaaaaaaaaa aaaaaaaaag   1680

agtgaatgta atagtcttgc agaaaatgaa tgaatacctt tgttcaataa aggaaatatg   1740

cactgctcac ttttttgaag gaaatgccaa agttacgttt tacaacaagg ctagagtttg   1800

taaattctgg gttcatttgt gatgacataa gtcagcaaac tgcgggaata ctgtctctt    1859


<210> SEQ ID NO 382
<211> LENGTH: 430
<212> TYPE: DNA
```

```
<213> ORGANISM: Artificial Sequence
<220> FEATURE:
<223> OTHER INFORMATION: Description of Artificial Sequence: Synthetic
      Affymetrix ID 3086831 polynucleotide

<400> SEQUENCE: 382

aacgctggca atacattaag gctcactaat gtggacctaa gtgagtatct gagaggcttt     60

gaatatgtat gtgcaaactg tcctattttc tttatatgct ctcttaaata tgtatgtctg    120

taaatatata tataacacac atatatatat attcctagac atctagtgtt tgctgtcatt    180

agtgaccaag aaaaagtagt tcttttgtgc acgcgtgaat acatcaaatt agcaattacc    240

atagaaatgt atttcattga ataaatagct tttgtttgtt tgtttgtttg tttcagggaa    300

atttagaaca attattagat gttatagtgc ctcttctcgt gttgatacgt gtatttgggt    360

caaaagtgca aaaacttttt tctacaatgt acagttattt tgacttttcc caggggaagc    420

tagcaatagt                                                           430


<210> SEQ ID NO 383
<211> LENGTH: 33
<212> TYPE: DNA
<213> ORGANISM: Artificial Sequence
<220> FEATURE:
<223> OTHER INFORMATION: Description of Artificial Sequence: Synthetic
      Affymetrix ID 3095405 oligonucleotide

<400> SEQUENCE: 383

cttattttac acatccgaag aaacaccatc aca                                  33


<210> SEQ ID NO 384
<211> LENGTH: 152
<212> TYPE: DNA
<213> ORGANISM: Artificial Sequence
<220> FEATURE:
<223> OTHER INFORMATION: Description of Artificial Sequence: Synthetic
      Affymetrix ID 3106639 polynucleotide

<400> SEQUENCE: 384

ggcccgtatg ggagacttaa cttgctctgg atcatgcagc tagttagggg tagtagaggc     60

aggacttaag tccctgttga aagtaggcta tatacatgaa aggggatact taaaattgag    120

attcaagagg attggtctaa atgcagcctg ca                                  152


<210> SEQ ID NO 385
<211> LENGTH: 38
<212> TYPE: DNA
<213> ORGANISM: Artificial Sequence
<220> FEATURE:
<223> OTHER INFORMATION: Description of Artificial Sequence: Synthetic
      Affymetrix ID 3111565 oligonucleotide

<400> SEQUENCE: 385

gcagtataaa tggagcaaca aggctgacta taagaggg                             38


<210> SEQ ID NO 386
<211> LENGTH: 113
<212> TYPE: DNA
<213> ORGANISM: Artificial Sequence
<220> FEATURE:
<223> OTHER INFORMATION: Description of Artificial Sequence: Synthetic
      Affymetrix ID 3111602 polynucleotide

<400> SEQUENCE: 386

ctctactgac tttatctgga tttggcttta atgaaaattc aaaggtatta gttggaaatg     60
```

-continued

```
aaacctgcaa tgtgattgaa ggggatttga ataggataac ctgcaggaca cca           113


<210> SEQ ID NO 387
<211> LENGTH: 146
<212> TYPE: DNA
<213> ORGANISM: Artificial Sequence
<220> FEATURE:
<223> OTHER INFORMATION: Description of Artificial Sequence: Synthetic
      Affymetrix ID 3111618 polynucleotide

<400> SEQUENCE: 387

tgagtgtggt taatgggaaa gatttgtcac agtccatgac tccgtttacg tacgcagtgt     60

cactgactcc actcatcact gcagtatctc ctaagagagg cagtacagca gggggcacca    120

gactgacagt cgtgggatca ggattc                                         146


<210> SEQ ID NO 388
<211> LENGTH: 50
<212> TYPE: DNA
<213> ORGANISM: Artificial Sequence
<220> FEATURE:
<223> OTHER INFORMATION: Description of Artificial Sequence: Synthetic
      Affymetrix ID 3111657 oligonucleotide

<400> SEQUENCE: 388

ggatttgttg gcctaccttt gcttcagctc ataacatggc accccgaaag                50


<210> SEQ ID NO 389
<211> LENGTH: 335
<212> TYPE: DNA
<213> ORGANISM: Artificial Sequence
<220> FEATURE:
<223> OTHER INFORMATION: Description of Artificial Sequence: Synthetic
      Affymetrix ID 3111682 polynucleotide

<400> SEQUENCE: 389

ggttccctta actggtggat gcttattcac tgtttactgg atgaatgaag tataaagtgt     60

gggaagtcaa caacagaaca gaacttattt tcaagaagat aaattagaga atgcaaaaaa    120

gctacagact aaggtagcta agttaaccga actctctaac agtattgaaa atagcaattc    180

tttactcaga aaattctaaa gggaatactt aatttgacag aactcctaat aaagacattg    240

tagccagatc cagagccttc cagcaagtga cactcagcaa acatttggga cagctgagag    300

aattcaacaa agcccatacc gttgtctctt gtata                               335


<210> SEQ ID NO 390
<211> LENGTH: 37
<212> TYPE: DNA
<213> ORGANISM: Artificial Sequence
<220> FEATURE:
<223> OTHER INFORMATION: Description of Artificial Sequence: Synthetic
      Affymetrix ID 3116838 oligonucleotide

<400> SEQUENCE: 390

gccgtcacac ctttcgaaga attagattcc agtagac                              37


<210> SEQ ID NO 391
<211> LENGTH: 363
<212> TYPE: DNA
<213> ORGANISM: Artificial Sequence
<220> FEATURE:
<223> OTHER INFORMATION: Description of Artificial Sequence: Synthetic
      Affymetrix ID 3202583 polynucleotide

<400> SEQUENCE: 391
```

cctcattggc tgctgtaaaa cttgctggtg gtgaggtagg agattgtttt tgttgttagt 60
cctctgctca tgattactgg gccaatacca ctgcaatgac tgtcagaaca attcttgtga 120
aagttgtttt tataagcctt gtagtttgtt gaagttgagg ttcaagggca gaagtaggga 180
gaaaaagaat aaagggaatt aaaaaaggaa gaaaggcaat attaaaggca attttgtttg 240
tttaacacaa tctattcaaa taaaatatct aatgatttgt aaattgagtt aacaaagtaa 300
tttcagggaa acatggaaga gagtctttag ggaggtatct ttcaggaggc gatattcaag 360
ttg 363

<210> SEQ ID NO 392
<211> LENGTH: 45
<212> TYPE: DNA
<213> ORGANISM: Artificial Sequence
<220> FEATURE:
<223> OTHER INFORMATION: Description of Artificial Sequence: Synthetic
Affymetrix ID 3322962 oligonucleotide

<400> SEQUENCE: 392
tggtggtgat gcttatagtg gagagcctct accttgctgc agctc 45

<210> SEQ ID NO 393
<211> LENGTH: 76
<212> TYPE: DNA
<213> ORGANISM: Artificial Sequence
<220> FEATURE:
<223> OTHER INFORMATION: Description of Artificial Sequence: Synthetic
Affymetrix ID 3367676 oligonucleotide

<400> SEQUENCE: 393
gttatggcat catgaccgac ggttacacaa cgtacatcaa tgcctcgacg tgtacagtca 60
gctttcaacc gaccaa 76

<210> SEQ ID NO 394
<211> LENGTH: 62
<212> TYPE: DNA
<213> ORGANISM: Artificial Sequence
<220> FEATURE:
<223> OTHER INFORMATION: Description of Artificial Sequence: Synthetic
Affymetrix ID 3467963 oligonucleotide

<400> SEQUENCE: 394
tgtggtgtat ggagccctgt gtattggaat ggctgcgctg gcgtcactta tgggagcttt 60
gt 62

<210> SEQ ID NO 395
<211> LENGTH: 29
<212> TYPE: DNA
<213> ORGANISM: Artificial Sequence
<220> FEATURE:
<223> OTHER INFORMATION: Description of Artificial Sequence: Synthetic
Affymetrix ID 3505974 oligonucleotide

<400> SEQUENCE: 395
tattttctga ggcacagtat caagaagca 29

<210> SEQ ID NO 396
<211> LENGTH: 30
<212> TYPE: DNA
<213> ORGANISM: Artificial Sequence
<220> FEATURE:
<223> OTHER INFORMATION: Description of Artificial Sequence: Synthetic
Affymetrix ID 3553610 oligonucleotide

<400> SEQUENCE: 396
caatgcccag cacacgaggc tgtcggaaag 30

<210> SEQ ID NO 397
<211> LENGTH: 104
<212> TYPE: DNA
<213> ORGANISM: Artificial Sequence
<220> FEATURE:
<223> OTHER INFORMATION: Description of Artificial Sequence: Synthetic Affymetrix ID 3554056 polynucleotide

<400> SEQUENCE: 397
ctgcatccta aaggcctttt ctttcttctt ttctctttgg gtgatagtca gagagtggtg 60
tttttgttca ggtgggaagg attggaaact ctagtctttt ctag 104

<210> SEQ ID NO 398
<211> LENGTH: 214
<212> TYPE: DNA
<213> ORGANISM: Artificial Sequence
<220> FEATURE:
<223> OTHER INFORMATION: Description of Artificial Sequence: Synthetic Affymetrix ID 3573884 polynucleotide

<400> SEQUENCE: 398
ccaggaagat cgatgtgcag cagcccagca gcttctggag cgtttctcct tgccgcccca 60
gtgccgagtt gtggctgacc gcatggacaa taacgccaac atagcttacg ggtagccttt 120
tgaacgtgtg tgcattgtgc agagacagaa aattgcttat ctgggaggaa agggccccttt 180 ctcctacaac cttcaagaag tccggcattg gctg 214

<210> SEQ ID NO 399
<211> LENGTH: 26
<212> TYPE: DNA
<213> ORGANISM: Artificial Sequence
<220> FEATURE:
<223> OTHER INFORMATION: Description of Artificial Sequence: Synthetic Affymetrix ID 3660627 oligonucleotide

<400> SEQUENCE: 399
ttacatggta cccagcacat gctttc 26

<210> SEQ ID NO 400
<211> LENGTH: 279
<212> TYPE: DNA
<213> ORGANISM: Artificial Sequence
<220> FEATURE:
<223> OTHER INFORMATION: Description of Artificial Sequence: Synthetic Affymetrix ID 2331563 polynucleotide

<400> SEQUENCE: 400
ctgaaaagtc ttgagcaaac agttgccgct ctccaccccc tgctttttaa aaaaaatttt 60
ttctcacgta agaaaatgtt atctgtgtgc tggggaaaat tttgaaaata acaaaaacca 120
gaatacaaac acccataatc aatcacagag ataaccactg ttcataattc cttccagtct 180
tcttacttgg cacatataca tttgtctttc tttatatatg acatatggat attttacaaa 240
gttaggatcc tactctatgc actgcttggt gatcggatc 279

<210> SEQ ID NO 401
<211> LENGTH: 660
<212> TYPE: DNA
<213> ORGANISM: Artificial Sequence
<220> FEATURE:
<223> OTHER INFORMATION: Description of Artificial Sequence: Synthetic Affymetrix ID 2377124 polynucleotide

<400> SEQUENCE: 401
ggctctagct cttgcagggc tcttagagag cagtcatgtc ttttctccca tgactctcag 60
gttctttgcc aatcacagca acttttcctg ccaaagccag tatcctctgg ggctgtttag 120
aagggcagtt agattcagga gtcaccactg atgtttgagt tgctcaaggc aagaggcaga 180
gaagagttca ctaaaactgc ttatttttga ataatttcag cacactgtcc ttaagaagaa 240
agaaacatca aaacaaaata gtttttacat gaccattttt ttcccaaatg tggaaaagct 300
tgatgatgaa tttaatctct ctcattggag tattcttttg ttcataaaga gaaactatct 360
catcttgatg tccagagaag tccttggaac cctgtgggat ctagctcgta actgtttgta 420
tttctctatt cacttctgtc atttcatttt ctttgtaggg ttaaacagaa aatgtttagg 480
gaagaaattc ttagcccctt gatgaccatg atggcttatt ctctttccca attttgcatg 540
caaaatgtac gaatatatgt atgtttttct gagaggcaag tttagggttc tcatgggatt 600
ttaaaaagag ataggtgact ccccacctta aagttatctg ctggtctttt agaggtaacc 660

<210> SEQ ID NO 402
<211> LENGTH: 108
<212> TYPE: DNA
<213> ORGANISM: Artificial Sequence
<220> FEATURE:
<223> OTHER INFORMATION: Description of Artificial Sequence: Synthetic
Affymetrix ID 2384545 polynucleotide

<400> SEQUENCE: 402
tgctgctgtt taaaatcacc aatgcaaaca ttgccatttt tggtaatcct gctgttttca 60
tttatgagaa aacctgcaga aagtactctg cctacaccaa agtgaagt 108

<210> SEQ ID NO 403
<211> LENGTH: 88
<212> TYPE: DNA
<213> ORGANISM: Artificial Sequence
<220> FEATURE:
<223> OTHER INFORMATION: Description of Artificial Sequence: Synthetic
Affymetrix ID 2466609 oligonucleotide

<400> SEQUENCE: 403
cgacaagtgt ggcttcccag agagcgtgga gaatggggac tttgtgcact gtgaggagtc 60
tgggaggcgc gtgctggtgt attcctgc 88

<210> SEQ ID NO 404
<211> LENGTH: 99
<212> TYPE: DNA
<213> ORGANISM: Artificial Sequence
<220> FEATURE:
<223> OTHER INFORMATION: Description of Artificial Sequence: Synthetic
Affymetrix ID 2498631 oligonucleotide

<400> SEQUENCE: 404
ttttggatca agatgttcta acaatatcgt gatgggcgtc aacacctgga ttaatgatca 60
caagggaaag attcccctgt ggctacacgg attcaaatt 99

<210> SEQ ID NO 405
<211> LENGTH: 200
<212> TYPE: DNA
<213> ORGANISM: Artificial Sequence
<220> FEATURE:
<223> OTHER INFORMATION: Description of Artificial Sequence: Synthetic
Affymetrix ID 2537607 polynucleotide

<400> SEQUENCE: 405
atttgaggag gttgctcgca gtagggggat ttgaggaggt tgcacacagt ggggggattt 60
ttggggggtg cacacagtgg gggactagag gaggttgcac acagtgggag ggatttgggg 120
aggctggaca cagtgggggg atttgaggag gttgcacata gtgggggaga ttttgcgagg 180
ttgcacatag ggagattttg 200

<210> SEQ ID NO 406
<211> LENGTH: 96
<212> TYPE: DNA
<213> ORGANISM: Artificial Sequence
<220> FEATURE:
<223> OTHER INFORMATION: Description of Artificial Sequence: Synthetic
Affymetrix ID 2578963 oligonucleotide

<400> SEQUENCE: 406
caatcggcag atttttgtga cttcaaagat gctgtggcca aacggtttaa ctctggactt 60
tcacaccaac acattatact ggtgtgatgc ctatta 96

<210> SEQ ID NO 407
<211> LENGTH: 65
<212> TYPE: DNA
<213> ORGANISM: Artificial Sequence
<220> FEATURE:
<223> OTHER INFORMATION: Description of Artificial Sequence: Synthetic
Affymetrix ID 2586050 oligonucleotide

<400> SEQUENCE: 407
tgtgctgttg acaatcctct tgatcgtcgt aattggagct ctggcaattg caggattctt 60
ccact 65

<210> SEQ ID NO 408
<211> LENGTH: 129
<212> TYPE: DNA
<213> ORGANISM: Artificial Sequence
<220> FEATURE:
<223> OTHER INFORMATION: Description of Artificial Sequence: Synthetic
Affymetrix ID 2586057 polynucleotide

<400> SEQUENCE: 408
gaacctaaaa tcgagtctgc ctggatgaat ggagaggacc gcaacatcct ggttttcgag 60
gaccttggtt ggccaactgg cctttctatc gattatttga acaatgaccg aatctactgg 120
agtgacttc 129

<210> SEQ ID NO 409
<211> LENGTH: 60
<212> TYPE: DNA
<213> ORGANISM: Artificial Sequence
<220> FEATURE:
<223> OTHER INFORMATION: Description of Artificial Sequence: Synthetic
Affymetrix ID 2586118 oligonucleotide

<400> SEQUENCE: 409
atgccgccga atcctcaaat ggctgtagca acaacatgaa tgcctgtcag cagatttgcc 60

<210> SEQ ID NO 410
<211> LENGTH: 133
<212> TYPE: DNA
<213> ORGANISM: Artificial Sequence
<220> FEATURE:
<223> OTHER INFORMATION: Description of Artificial Sequence: Synthetic
Affymetrix ID 2608604 polynucleotide

<400> SEQUENCE: 410
ttgtgctatg aaatagcagg tcttgttcat tttttgtaac tatttttttg gtacccatta 60
accatcccca cctgtcccct gtcttggaga attgatgcct gagataaatg ggtagccaga 120
tgcacctgta ctc 133

<210> SEQ ID NO 411
<211> LENGTH: 33
<212> TYPE: DNA
<213> ORGANISM: Artificial Sequence
<220> FEATURE:
<223> OTHER INFORMATION: Description of Artificial Sequence: Synthetic
Affymetrix ID 2629459 oligonucleotide

<400> SEQUENCE: 411
gtccgactag gccttatcca gcacatgcta ttc 33

<210> SEQ ID NO 412
<211> LENGTH: 381
<212> TYPE: DNA
<213> ORGANISM: Artificial Sequence
<220> FEATURE:
<223> OTHER INFORMATION: Description of Artificial Sequence: Synthetic
Affymetrix ID 2730820 polynucleotide

<400> SEQUENCE: 412
tcgtctcagt ttttggtcac aggccaaata atacagcgct ctctctgctt ctctcttgca 60
tagacacaat caagacaata gtgcaccgtt ccttaaaaac agcatctgag gaatccccct 120
tttgttctta aactttcaga tgtgtccttt gataaccaaa ttctgtcact caagacacag 180
acacgcacag accctgtcct ttgcctctat taagcagagg atggaagtat taaggatttt 240
gtaacacctt ttatgaaaat gttgaaggaa cttaaaactt tagctttgga gctgtgctta 300
ctggcttgtc tttgtctggt agaacaaacc ttgacctcca gacagagtcc cttctcactt 360
atagagctct ccaggactgg a 381

<210> SEQ ID NO 413
<211> LENGTH: 34
<212> TYPE: DNA
<213> ORGANISM: Artificial Sequence
<220> FEATURE:
<223> OTHER INFORMATION: Description of Artificial Sequence: Synthetic
Affymetrix ID 2797114 oligonucleotide

<400> SEQUENCE: 413
caggagacac tgaacggaga tgctacatat tcct 34

<210> SEQ ID NO 414
<211> LENGTH: 27
<212> TYPE: DNA
<213> ORGANISM: Artificial Sequence
<220> FEATURE:
<223> OTHER INFORMATION: Description of Artificial Sequence: Synthetic
Affymetrix ID 2816853 oligonucleotide

<400> SEQUENCE: 414
ggtttggatt tgaccagcac atgcaga 27

<210> SEQ ID NO 415
<211> LENGTH: 159
<212> TYPE: DNA
<213> ORGANISM: Artificial Sequence
<220> FEATURE:

<223> OTHER INFORMATION: Description of Artificial Sequence: Synthetic
      Affymetrix ID 2819800 polynucleotide

<400> SEQUENCE: 415
gtgatgatgt ctatggccta ataacatttt ttcctatgga aaaccagaag attgaaagca     60
gcccaggtga acgatactta tccttgagtt ttacaagact aggagggact aaaggagatg    120
tgaggttgct ttattctgta ctttacattc ctgctggag                           159

<210> SEQ ID NO 416
<211> LENGTH: 53
<212> TYPE: DNA
<213> ORGANISM: Artificial Sequence
<220> FEATURE:
<223> OTHER INFORMATION: Description of Artificial Sequence: Synthetic
      Affymetrix ID 3018628 oligonucleotide

<400> SEQUENCE: 416
cctgaaaggg atgtttatgc agctgtgtga cattcctcgt ctgtggagac aga            53

<210> SEQ ID NO 417
<211> LENGTH: 81
<212> TYPE: DNA
<213> ORGANISM: Artificial Sequence
<220> FEATURE:
<223> OTHER INFORMATION: Description of Artificial Sequence: Synthetic
      Affymetrix ID 3018629 oligonucleotide

<400> SEQUENCE: 417
tctgggtgtt tacgtgtata gtgtccatca ttctggggct ggatctcggt ttactagctg     60
gccttatatt tggactgttg a                                               81

<210> SEQ ID NO 418
<211> LENGTH: 371
<212> TYPE: DNA
<213> ORGANISM: Artificial Sequence
<220> FEATURE:
<223> OTHER INFORMATION: Description of Artificial Sequence: Synthetic
      Affymetrix ID 3106645 polynucleotide

<400> SEQUENCE: 418
tgggtggttg cctatcattt gcaaactgct tacttgtaca acaaatgctt cttccaggat     60
ctactgtcct ggggacttga atccaccttt ctcaaatata aaaactctaa atatggcctt    120
ttaagttttt tctgctctga tatcttgcct ctaagcttat attgccatct ttggaaatac    180
tatttgtaga atctagtgct cacatgatct gaagtgtcaa agttatttta caaatgctgg    240
gcttatggtt tagttttaca actgttctta gagctttaat ttcctgcaat ttttccttga    300
gttttgaatt gttttgcctt tcctcacccc tagaataaca tttggtgcct cgcagagtca    360
tccctattgt a                                                          371

<210> SEQ ID NO 419
<211> LENGTH: 91
<212> TYPE: DNA
<213> ORGANISM: Artificial Sequence
<220> FEATURE:
<223> OTHER INFORMATION: Description of Artificial Sequence: Synthetic
      Affymetrix ID 3111568 oligonucleotide

<400> SEQUENCE: 419
cctacactgt tagagtcagt gtggacgggg ttcctgttac ggaaaataac acctgcaaag     60
gtcacatcaa cagctgggaa tgtaccttca a                                    91

```
<210> SEQ ID NO 420
<211> LENGTH: 389
<212> TYPE: DNA
<213> ORGANISM: Artificial Sequence
<220> FEATURE:
<223> OTHER INFORMATION: Description of Artificial Sequence: Synthetic
      Affymetrix ID 3167240 polynucleotide

<400> SEQUENCE: 420

tgctgggcat gtgcatagct ctacacattg tcatggtatt atagactcac aataatttgt     60

cagagctttt cagaaccata atggacaact cttagcccag cccagctttt ccttaacgtt    120

tttggttagt ctgttttgta ttttccactg cctcaggtac ctttaagatt aaatagttgc    180

ctgccattgt tttcaacaaa gctgccaggg aaaatgtttt catattggcc aagctccaaa    240

tccaatcata tgtagacagc cttgcaagtg gagttttcta gggaaccatt agaaaagtaa    300

acttaatgac aattctctgg gagtaaggct ttggcgaaat gccagcccat tctatcctct    360

ccagggcctg tcagcttcct tggtttta                                       389


<210> SEQ ID NO 421
<211> LENGTH: 270
<212> TYPE: DNA
<213> ORGANISM: Artificial Sequence
<220> FEATURE:
<223> OTHER INFORMATION: Description of Artificial Sequence: Synthetic
      Affymetrix ID 3288804 polynucleotide

<400> SEQUENCE: 421

gctgctccca tcttgctgga atttcttggg cggcttctcc acctgtatct caagacagac     60

acccgggggc ctgtgtctgt ggccgctccc atcccggcag ccctggctgc tgctcgcccc    120

accctcgctt atctgtagat tcaaagcgat gttctcttct gtgctcttag aagtagggag    180

ttcagcagta acagccaggt gaagcgaacc tgctgggtga tttgtttgcg ctctgtttta    240

tggggcattc ctgcgagatg tgtcagcttc                                     270


<210> SEQ ID NO 422
<211> LENGTH: 74
<212> TYPE: DNA
<213> ORGANISM: Artificial Sequence
<220> FEATURE:
<223> OTHER INFORMATION: Description of Artificial Sequence: Synthetic
      Affymetrix ID 3367674 oligonucleotide

<400> SEQUENCE: 422

atggtggagg atggtagttt cgtcctgggg aaggagggat ttattcatat gcaacatcag     60

taatgccttt caga                                                       74


<210> SEQ ID NO 423
<211> LENGTH: 274
<212> TYPE: DNA
<213> ORGANISM: Artificial Sequence
<220> FEATURE:
<223> OTHER INFORMATION: Description of Artificial Sequence: Synthetic
      Affymetrix ID 3367737 polynucleotide

<400> SEQUENCE: 423

gagctaccca gtctacgcta ttttgttaat agcatctcaa acagcccaag gcaggtaggc     60

agggaatata atgggaagat gaattttata gagggaacaa gaggagaaat gggcgtattt    120

gtgaaggaga gagggaaaaa gtaggaggga atatatagca gatgtgtttg tgagatcata    180

actcttcctt gtcagttacg atgtcctgac cttgggcttg actttagcac cgggagcagg    240
```

tcagcatccc tagacttcag tcaacaggga gatg 274

<210> SEQ ID NO 424
<211> LENGTH: 486
<212> TYPE: DNA
<213> ORGANISM: Artificial Sequence
<220> FEATURE:
<223> OTHER INFORMATION: Description of Artificial Sequence: Synthetic
Affymetrix ID 3391632 polynucleotide

<400> SEQUENCE: 424
gctcaaatct agattctggg ctcaaaagga aatggtatgt atagatttta tttggctttc 60
tacacaaagg ggatgtgtgg ggtaataatg tgtgttcacc aagaccagcc ccaactatac 120
aatcttctct gcttcattca acaaagccta aggagtcctt caaaagaagg gtgagaacgc 180
ctgggagcag atccctttc acagatgcag gcaggtggcg gctaatcaga aagtggtcta 240
acccccaaag aaacacaaaa ataaccaaaa attcaaaagc aaaaccattc cagaatgaga 300
tggattttca cctgagtggg acccaggcaa aaactgcaga tcagaaaaga ggggaagagc 360
agctgtaaac aatcatgttt tgtaaagttg tcctgtgcta aagcaagcgt gggatgatcc 420
tacctacctc taggtggtat ttgttacctt aaaaaataaa aggcagctat tttacacgga 480
cattta 486

<210> SEQ ID NO 425
<211> LENGTH: 72
<212> TYPE: DNA
<213> ORGANISM: Artificial Sequence
<220> FEATURE:
<223> OTHER INFORMATION: Description of Artificial Sequence: Synthetic
Affymetrix ID 3467567 oligonucleotide

<400> SEQUENCE: 425
aaaaggggag tgcacttcat gaagcagctt tgtttggaaa ggtggatgtt gtacgagttc 60
tgttagaaac ag 72

<210> SEQ ID NO 426
<211> LENGTH: 221
<212> TYPE: DNA
<213> ORGANISM: Artificial Sequence
<220> FEATURE:
<223> OTHER INFORMATION: Description of Artificial Sequence: Synthetic
Affymetrix ID 3607272 polynucleotide

<400> SEQUENCE: 426
ccctcagcct aaaccagcat gaaatccctc tgtaacagcc cccttgagaa caggctggcc 60
tcaggataaa gcaatctctg atctactgcc ccaccctgtc actctcgttc atcccactta 120
cctacaccag gttctttcta gactggttta ctccttccta taaaagaaaa tcccttttttg 180 cctacccctt gagagtttgt agatttatgg cctgagtgtt c 221

<210> SEQ ID NO 427
<211> LENGTH: 84
<212> TYPE: DNA
<213> ORGANISM: Artificial Sequence
<220> FEATURE:
<223> OTHER INFORMATION: Description of Artificial Sequence: Synthetic
Affymetrix ID 3733864 oligonucleotide

<400> SEQUENCE: 427
gctgcactta gggtcaggat ttggagagtg tgacaccgaa ggcgagagtt cttccacggg 60
gggatcaact ggtgatactg aatc 84

<210> SEQ ID NO 428
<211> LENGTH: 154
<212> TYPE: DNA
<213> ORGANISM: Artificial Sequence
<220> FEATURE:
<223> OTHER INFORMATION: Description of Artificial Sequence: Synthetic
Affymetrix ID 3950868 polynucleotide

<400> SEQUENCE: 428
ctgctggacc taggcctggc cctccgcctg cctggagagg cctggccctg ggcaaacagc 60
cgccatcagg gttcacctcg gtgggggacc ccactcaccc ccttagggtc gccacccctc 120
acggcaactt gtgcctggcg tcaataaaga cctg 154

<210> SEQ ID NO 429
<211> LENGTH: 143
<212> TYPE: DNA
<213> ORGANISM: Artificial Sequence
<220> FEATURE:
<223> OTHER INFORMATION: Description of Artificial Sequence: Synthetic
Affymetrix ID 2530203 polynucleotide

<400> SEQUENCE: 429
cttggacagg acattctatg ttccaaatag agattgtgtg ttacaaagtg actgcaggac 60
caaaaatgag tagcaaattc atgaacctct tagatttttt taatttagga catgatgaga 120
ttactgccag tgactcaact ttt 143

<210> SEQ ID NO 430
<211> LENGTH: 116
<212> TYPE: DNA
<213> ORGANISM: Artificial Sequence
<220> FEATURE:
<223> OTHER INFORMATION: Description of Artificial Sequence: Synthetic
Affymetrix ID 2537604 polynucleotide

<400> SEQUENCE: 430
gtgaaggact taccacctgc aaatcaccgt cgaggtgaga cctgcgaagc ctccgatcag 60
cagagcagcc agcgacatgg agatccaagt cacccgaggg agcctcccgg agtctg 116

<210> SEQ ID NO 431
<211> LENGTH: 1136
<212> TYPE: DNA
<213> ORGANISM: Artificial Sequence
<220> FEATURE:
<223> OTHER INFORMATION: Description of Artificial Sequence: Synthetic
Affymetrix ID 2583274 polynucleotide

<400> SEQUENCE: 431
tcttaggcat gtgctggtat ccacagttaa ttccctgcta aatgccatgt ttatcaccct 60
aattaataga atggagggga ctccaaagct ggaactgaag tccaaattgt ttgtacagta 120
atatgtttaa tgttcatttt ctctgtatga atgtgattgg taactaggat atgtatattt 180
taatagaatt tttaacaaaa cttcttagaa aattaaaata ggcatattac taggtgacat 240
gtctactttt taatttttaa gagcatccgg ccaaatgcaa aattagtacc tcaaagtaaa 300
aattgaactg taaactctat cagcattgtt tcaaaatagt catttttagc actggggaaa 360
aataaacaat aagacatgct tactttttaa tttttatttt tttgagactg agtctctctc 420
tgttgcccag gctggagtac aatggcgtga tctcggctca ctgcaaatct ccgcctccca 480
ggttcaagcg attctcctgc ctcagcctcc tgagtagctg ggattacagg caactgccac 540
catgcccggc taatttttgt atttttagta gagatggggt ttcaccatgt tggccaggct 600
ggtctcgaac tcgtgaccgc aggtgatcct cccgcctcgg cctcccaaag tgctgggatt 660
acaggcatga gccaccgcgc ctggcctctg cttacttttt atatagcaaa atgattcctc 720
ttggcaagat gtttcttata ttattccaaa gttatttcat accattatta tgtaaatatg 780
aagagttttt ttctgtttat aattgtttat aaaacaatga cttttaaaga tttagtgctt 840
aacattttcc caagtgtggg aacattattt ttagattgag taggtacctt gtagcagtgt 900
gctttgcatt ttctgatgta ttacatgact gtttcttttg taaagagaat caactaggta 960
tttaagactg ataattttac aatttatatg cttcacatag catgtcaact tttgactaag 1020
aattttgttt tactttttta acatgtgtta aacagagaaa gggtccatga aggaaagtgt 1080
atgagttgca tttgtaaaaa tgagactttt tcagtggaac tctaaacctt gtgatg 1136

<210> SEQ ID NO 432
<211> LENGTH: 139
<212> TYPE: DNA
<213> ORGANISM: Artificial Sequence
<220> FEATURE:
<223> OTHER INFORMATION: Description of Artificial Sequence: Synthetic
      Affymetrix ID 2586064 polynucleotide

<400> SEQUENCE: 432
ttgtgtatta cactgtgcga ggggagggct ctaggtttgg tgctatcaaa cgtgcctaca 60
tccccaactt tgaatccggc cgcaataatc ttgtgcagga agttgacctg aaactgaaat 120
acgtaatgca gccagatgg 139

<210> SEQ ID NO 433
<211> LENGTH: 93
<212> TYPE: DNA
<213> ORGANISM: Artificial Sequence
<220> FEATURE:
<223> OTHER INFORMATION: Description of Artificial Sequence: Synthetic
      Affymetrix ID 2586130 oligonucleotide

<400> SEQUENCE: 433
acagactgct ctacttcatg gactcctatc ttgattacat ggacttttgt gattataatg 60
gacaccatcg gagacaggtg atagccagtg att 93

<210> SEQ ID NO 434
<211> LENGTH: 73
<212> TYPE: DNA
<213> ORGANISM: Artificial Sequence
<220> FEATURE:
<223> OTHER INFORMATION: Description of Artificial Sequence: Synthetic
      Affymetrix ID 2669720 oligonucleotide

<400> SEQUENCE: 434
gtgcctgctt cacagcaatt cagggttcag ggctgcggcc ccaaagtcca ggccgtttgc 60
tggccatgtg cag 73

<210> SEQ ID NO 435
<211> LENGTH: 279
<212> TYPE: DNA
<213> ORGANISM: Artificial Sequence
<220> FEATURE:
<223> OTHER INFORMATION: Description of Artificial Sequence: Synthetic
      Affymetrix ID 2721309 polynucleotide

<400> SEQUENCE: 435

```
tttaagcgtg tcttcatgga actgctgcca tttgaaatgg tttgcccttg cgcattctgg     60

tcaggtgccc ccagtcctca catgtaccca cacatacttc ccctaaacca agcacacaca    120

ccacacacat acatacacac acacatacat gcacacacgc acactccatc accaagagac    180

tccaggaaaa gcaaagctga cacccatgaa taaacatgtg cttactggat atcattctgt    240

ctcttgcctc ttcagcagct gtgttcatgt aaaccattg                           279


<210> SEQ ID NO 436
<211> LENGTH: 72
<212> TYPE: DNA
<213> ORGANISM: Artificial Sequence
<220> FEATURE:
<223> OTHER INFORMATION: Description of Artificial Sequence: Synthetic
      Affymetrix ID 2730768 oligonucleotide

<400> SEQUENCE: 436

caccatacca tttacatcgg agtccatgtg ccgaagagtt acaggagaag gagacgtcac     60

aagagaaaga ca                                                          72


<210> SEQ ID NO 437
<211> LENGTH: 71
<212> TYPE: DNA
<213> ORGANISM: Artificial Sequence
<220> FEATURE:
<223> OTHER INFORMATION: Description of Artificial Sequence: Synthetic
      Affymetrix ID 2754766 oligonucleotide

<400> SEQUENCE: 437

tctggaagtg ctggcgttgc aggctcgttt tttgttttaa gagagaggtt tgcaagctaa     60

agtttctgga t                                                           71


<210> SEQ ID NO 438
<211> LENGTH: 165
<212> TYPE: DNA
<213> ORGANISM: Artificial Sequence
<220> FEATURE:
<223> OTHER INFORMATION: Description of Artificial Sequence: Synthetic
      Affymetrix ID 2763561 polynucleotide

<400> SEQUENCE: 438

tcctattatg tgttcaagga ccacatgtgt tctctatttt gcctttaaat ttttgtgaac     60

caattttaaa tacattctcc tttttgccct ggattgttga catgagtgga atacttggtt    120

tcttttctta cttatcaaaa gacagcacta cagatatcat attga                    165


<210> SEQ ID NO 439
<211> LENGTH: 70
<212> TYPE: DNA
<213> ORGANISM: Artificial Sequence
<220> FEATURE:
<223> OTHER INFORMATION: Description of Artificial Sequence: Synthetic
      Affymetrix ID 2797078 oligonucleotide

<400> SEQUENCE: 439

acacaagaaa atttcggtct gagccaagga gtatttttga atatgaacct ggcaagtcat     60

caattcttca                                                             70


<210> SEQ ID NO 440
<211> LENGTH: 55
<212> TYPE: DNA
<213> ORGANISM: Artificial Sequence
<220> FEATURE:
<223> OTHER INFORMATION: Description of Artificial Sequence: Synthetic
```

Affymetrix ID 3046300 oligonucleotide

<400> SEQUENCE: 440
gtgtgtttcc tactcaatgt taatttcaaa ctcacaaata cggagggatt acctt 55

<210> SEQ ID NO 441
<211> LENGTH: 74
<212> TYPE: DNA
<213> ORGANISM: Artificial Sequence
<220> FEATURE:
<223> OTHER INFORMATION: Description of Artificial Sequence: Synthetic
Affymetrix ID 3111652 oligonucleotide

<400> SEQUENCE: 441
ataaatagag ggaccaatac agttttacag aataatgtag tggctggatt tggaagagca 60
ggataccgca ttga 74

<210> SEQ ID NO 442
<211> LENGTH: 77
<212> TYPE: DNA
<213> ORGANISM: Artificial Sequence
<220> FEATURE:
<223> OTHER INFORMATION: Description of Artificial Sequence: Synthetic
Affymetrix ID 3111655 oligonucleotide

<400> SEQUENCE: 442
ataatgtgac cctggttgac aatggaatgg ccatttttcc aatgatttac atgccagctg 60
ctatatcaca caaaatt 77

<210> SEQ ID NO 443
<211> LENGTH: 31
<212> TYPE: DNA
<213> ORGANISM: Artificial Sequence
<220> FEATURE:
<223> OTHER INFORMATION: Description of Artificial Sequence: Synthetic
Affymetrix ID 3158784 oligonucleotide

<400> SEQUENCE: 443
cgaggcctac cacgcgggca tgtgcagccg g 31

<210> SEQ ID NO 444
<211> LENGTH: 53
<212> TYPE: DNA
<213> ORGANISM: Artificial Sequence
<220> FEATURE:
<223> OTHER INFORMATION: Description of Artificial Sequence: Synthetic
Affymetrix ID 3210770 oligonucleotide

<400> SEQUENCE: 444
tatatatttg gccagagatt actcttgtca ctgtccacaa aggtgtaact tga 53

<210> SEQ ID NO 445
<211> LENGTH: 164
<212> TYPE: DNA
<213> ORGANISM: Artificial Sequence
<220> FEATURE:
<223> OTHER INFORMATION: Description of Artificial Sequence: Synthetic
Affymetrix ID 3325106 polynucleotide

<400> SEQUENCE: 445
ggcctgacag ggaccagaaa atatggcttt ggtgttgctg tttattagca atgctgagac 60
cagttgtaat aggagccgag cagtgtgtgg gtgataaagt gtggggtgtc aagaagcggc 120
agcaaccaga aattagactg acaagagcca gcactcgctg gata 164

<210> SEQ ID NO 446
<211> LENGTH: 89
<212> TYPE: DNA
<213> ORGANISM: Artificial Sequence
<220> FEATURE:
<223> OTHER INFORMATION: Description of Artificial Sequence: Synthetic Affymetrix ID 3367705 oligonucleotide

<400> SEQUENCE: 446
ctctagaaat cactcttagt tacagagacc gtcgcttcaa ggctgcagtc aaagtagttg 60
gtgtcaagtt tgagattggt cggaagcta 89

<210> SEQ ID NO 447
<211> LENGTH: 362
<212> TYPE: DNA
<213> ORGANISM: Artificial Sequence
<220> FEATURE:
<223> OTHER INFORMATION: Description of Artificial Sequence: Synthetic Affymetrix ID 3367739 polynucleotide

<400> SEQUENCE: 447
aggcctggtg ctcattctct atgagaccct tccaatgtct aacatgagtc tttcatagta 60
ggactaaacc tctttgaaaa ctattgtata gtcaagatag aaaggaggtt agagctctgt 120
tgactgtttt taccactcct ggaagaattg aactcggggc atgtccaagt cacaagctct 180 tttttagga attgttttac atgagcattt aaaaaaaaat agtaggacac cccaaataca 240 cacaccccc caccctggaa tttacaaacg ctaaccaaac aaaagggtct ttccattgac 300
tgcctggata ttagtgtaaa tactaggatg ttgctttgca agtatattct ggagagcgag 360
tc 362

<210> SEQ ID NO 448
<211> LENGTH: 518
<212> TYPE: DNA
<213> ORGANISM: Artificial Sequence
<220> FEATURE:
<223> OTHER INFORMATION: Description of Artificial Sequence: Synthetic Affymetrix ID 3436258 polynucleotide

<400> SEQUENCE: 448
ctgcctcagt gaataaccgg gtatatcagt catttcctat ttttaccaat gtgtctttag 60
gatatattct agaattatta ctaggacaaa ggatagatgc aaacataatt tttgtagata 120
tatgaccatt tttgccgaaa ttttggggac ctaattgaat tttgtaattg taacactttc 180
acctataagc agtccagttt attttacatt ttaacattac atctcctcaa acacccatgc 240
atgttctctt tgtatggaac atattaaaag tgttacttta agaagaccta ttgatttcat 300
ttagttaatt ttaaagtatc atagcgtata gagtaaaaga aatgaaaaga ttgctaaaac 360
atagtcctaa accttaaaag atttcagagt gaatattttg agatttattt tcttctttta 420
tctcctcctt attctatttg tggtgtattt tgtcccctgt aggctatcaa agactggaaa 480
taaggcacta agaaatgtac ctttatctgc tccaccag 518

<210> SEQ ID NO 449
<211> LENGTH: 626
<212> TYPE: DNA
<213> ORGANISM: Artificial Sequence
<220> FEATURE:
<223> OTHER INFORMATION: Description of Artificial Sequence: Synthetic Affymetrix ID 3459733 polynucleotide

<400> SEQUENCE: 449
gatagcactg tgagaacccg gaagcgataa cttcactcct cttcattctt ctgccttttg 60
aaattctcag cccttaggct ccttgtattg ataggcctaa aaacatgttt ccaaatgctt 120
tatagagatt ataaacctag ggactcccta ggttttcaaa ttcttctttc taaaaataac 180
aaatatgtct cttaaagggt actgtccaat ataagccata actaaattaa ttaattcatt 240
atttgagtta gagtagcatc tcagtaaccc agcactcgaa gactgtcagt ccttttaaca 300
actctttgat agttcaaaaa ctaaagcttt ttggtttgga actaagatga acccattttt 360
ttctaaatcc atttccaaag taagaacctc agaacctata gatcttgctt caaaatgttg 420
atatgtaccc ccaagcaaaa caattcaatt tgaatgttat ttctgagaac agctcacaaa 480
aaaaagtgca tatcacccta cccagttgta ttttctcctt ttaaatgtat tgggagatga 540
gacagtagaa aatgggctgg ggaaacatga gatctgggtg ctagttctgc actaggcaaa 600
tacatggtct tattctctgc ggttta 626

<210> SEQ ID NO 450
<211> LENGTH: 57
<212> TYPE: DNA
<213> ORGANISM: Artificial Sequence
<220> FEATURE:
<223> OTHER INFORMATION: Description of Artificial Sequence: Synthetic
Affymetrix ID 3625103 oligonucleotide

<400> SEQUENCE: 450
tcttggtggt atcagtagct ggtgagctca aagtatggga tctttcctca tctatca 57

<210> SEQ ID NO 451
<211> LENGTH: 265
<212> TYPE: DNA
<213> ORGANISM: Artificial Sequence
<220> FEATURE:
<223> OTHER INFORMATION: Description of Artificial Sequence: Synthetic
Affymetrix ID 3727624 polynucleotide

<400> SEQUENCE: 451
gcttgtgatg acgaatcctg ctctaaaata cacaaggagc tttcttgttt cttattaggc 60
ctcagaaaga agtcagttaa cgtcacccaa aagcacaaaa tggattttag tcaaatattt 120
attggatgat acagtgtttt ttaggaaaag catctgccac aaaaatgttc acttcgaaat 180
tctgagttcc tggaatggca cgttgctgcc agtgccccag acagttcttt tctaccctgc 240
gggcccgcac gttttatgag gttga 265

<210> SEQ ID NO 452
<211> LENGTH: 326
<212> TYPE: DNA
<213> ORGANISM: Artificial Sequence
<220> FEATURE:
<223> OTHER INFORMATION: Description of Artificial Sequence: Synthetic
Affymetrix ID 2602031 polynucleotide

<400> SEQUENCE: 452
agcttctgct ccgaatgtgt gtgcaaacat tattttcctc acttcctcag caattgctgt 60
ctttgcttct tttcctcatt tctcaggtaa aacctgagac tcggtgaaag gaatagaggt 120
atgatgaggc gtgggctctg ttgaaacatc tcggcttgtt taaaattttt cattgtctgt 180
taagaggaga acacttgtga agcactgagc tcaggagctc tacttgttgg aagcctgtct 240
gctttacctg tagtccagtg acctttttctg cctgcccttt ctcttgcata gcctcttagt 300
tctggcttgc tcgttttcta gtacta 326

<210> SEQ ID NO 453
<211> LENGTH: 1186
<212> TYPE: DNA
<213> ORGANISM: Artificial Sequence
<220> FEATURE:
<223> OTHER INFORMATION: Description of Artificial Sequence: Synthetic
      Affymetrix ID 2727646 polynucleotide

<400> SEQUENCE: 453
ggcctcccta gccagcactt gtatatacgc atctataaat tgtccgtgtt catacatttg 60
aggggaaaac accataaggt ttcgtttctg tatacaaccc tggcattatg tccactgtgt 120
atagaagtag attaagagcc atataagttt gaaggaaaca gttaatacca ttttttaagg 180
aaacaatata accacaaagc acagtttgaa caaaatctcc tcttttagct gatgaactta 240
ttctgtagat tctgtggaac aagcctatca gcttcagaat ggcattgtac tcaatggatt 300
tgatgctgtt tgacaaagtt actgattcac tgcatggctc ccacaggagt gggaaaacac 360
tgccatctta gtttggattc ttatgtagca ggaaataaag tataggttta gcctccttcg 420
caggcatgtc ctggacaccg ggccagtatc tatatatgtg tatgtacgtt tgtatgtgtg 480
tagacaaata tttggagggg tatttttgcc ctgagtccaa gagggtcctt tagtacctga 540
aaagtaactt ggctttcatt attagtactg ctcttgtttc ttttcacata gctgtctaga 600
gtagcttacc agaagcttcc atagtggtgc agaggaagtg gaaggcatca gtccctatgt 660
atttgcagtt cacctgcact taaggcactc tgttatttag actcatctta ctgtacctgt 720
tccttagacc ttccataatg ctactgtctc actgaaacat ttaaatttta ccctttagac 780
tgtagcctgg atattattct tgtagtttac ctctttaaaa acaaaacaaa acaaaacaaa 840
aaactcccct tcctcactgc ccaatataaa aggcaaatgt gtacatggca gagtttgtgt 900
gttgtcttga aagattcagg tatgttgcct ttatggtttc cccettctac atttcttaga 960 ctacatttag agaactgtgg ccgttatctg gaagtaacca tttgcactgg agttctatgc 1020
tctcgcacct ttccaaagtt aacagatttt ggggttgtgt tgtcacccaa gagattgttg 1080
tttgccatac tttgtctgaa aaattccttt gtgtttctat tgacttcaat gatagtaaga 1140
aaagtggttg ttagttatag atgtctaggt acttcagggg cacttc 1186

<210> SEQ ID NO 454
<211> LENGTH: 121
<212> TYPE: DNA
<213> ORGANISM: Artificial Sequence
<220> FEATURE:
<223> OTHER INFORMATION: Description of Artificial Sequence: Synthetic
      Affymetrix ID 2763563 polynucleotide

<400> SEQUENCE: 454
ccacaggttc catagaacta atatcctgtc tctctctctc tctctctctc tctctttttt 60
ttttcttttt ccttttgcca tggaatctgg gtgggagagg atactgcggg caccagaatg 120
c 121

<210> SEQ ID NO 455
<211> LENGTH: 521
<212> TYPE: DNA
<213> ORGANISM: Artificial Sequence
<220> FEATURE:
<223> OTHER INFORMATION: Description of Artificial Sequence: Synthetic
      Affymetrix ID 2807301 polynucleotide

<400> SEQUENCE: 455

-continued

```
aacatgattt taggtacagc acatcacaac tgtttattca ccttaaaaaa atgtctgtag     60

tggtaacatt tcaagaaatg aaaaagggaa cagtttggga tccgcagttt ctccctatct    120

tctttcagct acatttacaa gcatttgacc aaacaaaaat tagtaaacag ttactagtat    180

ttataaaaaa cttaaaatat ttaacatata atactcactt taaaaaaaca ttcattctac    240

aaaccttata aaagacagaa acttatatct gttcacagta tgtgtatttt gtaaacagta    300

attcactata atgcaatttt gaaagtaaaa aaaggtaatt tcctagtgtt ataaggacct    360

tgacttatgg ccagctaatg aaagagaaga aaacctaaca tccttattag gaaagttaag    420

tattttgaaa tgatttattt tacctttcaa catactttta agatggtact atcttaaatc    480

taggatgtct atctatccag gccaatcttt tgcaagcaat t                        521
```

<210> SEQ ID NO 456
<211> LENGTH: 283
<212> TYPE: DNA
<213> ORGANISM: Artificial Sequence
<220> FEATURE:
<223> OTHER INFORMATION: Description of Artificial Sequence: Synthetic
Affymetrix ID 2877074 polynucleotide

<400> SEQUENCE: 456

```
ggctgactct cgttagatcc atttctatca gtgtgtttaa agccaaaagg aaagtaaaat     60

acacatggct ttcttctgac ttgagttgtg tgattatggt cttttactca agcttaaatg    120

tttttatttt tttgtcttcc gagttcatgt tgcccaaatg tcctgaggtg gttccaaata    180

ccaatcccac acttcttgac cattgtcctg tggacaataa cttggaataa atgtgaaact    240

gaagtctgag tgcccatcag agagtgtccc aatccaacca gtc                      283
```

<210> SEQ ID NO 457
<211> LENGTH: 42
<212> TYPE: DNA
<213> ORGANISM: Artificial Sequence
<220> FEATURE:
<223> OTHER INFORMATION: Description of Artificial Sequence: Synthetic
Affymetrix ID 2949242 oligonucleotide

<400> SEQUENCE: 457

```
gccctctaca cggtcctctt aatagtgctg gtcatgatga gc                        42
```

<210> SEQ ID NO 458
<211> LENGTH: 2552
<212> TYPE: DNA
<213> ORGANISM: Artificial Sequence
<220> FEATURE:
<223> OTHER INFORMATION: Description of Artificial Sequence: Synthetic
Affymetrix ID 3086827 polynucleotide

<400> SEQUENCE: 458

```
gccaaggcct tgcttctact taaagttttc agaaaactga gtgacagtgg agagaaacaa     60

gaagttttac aaggacttta ctaaattata agcaaacttg cttcaaaata agttgacatg    120

tgataataag gttttcaatg tagcccagga ggtttttaaa ggcactgtta ggctgagcat    180

ggtggctcat gcctgtaatc ccagcacttt gggaggccaa ggcagaagga tcacttgaac    240

ccaggagttc aagaatagcc tgggcaacat agcaagaccc catctctata aaaattagca    300

agatgtggtg gtgcatgcct gtcatccaag ctactcaaga gactgaggca ggaggatcac    360

gtgagcccag gaattcaagg ctgcagtgaa ctatgattgc atcactgcac tgcagcctgg    420

gcaacatagc aagactctgt ctcaaaataa taataataat aataataaag gcgttgttag    480
```

-continued

```
cttgtaagga gtggagtatg taggtagtag gagttatatg caagtaccca agtggtattc    540
ttccaatctt attagaagca tgaatattca agattgatat tactattgct tattagcaag    600
attgttatca atcatgctta ttagaaggat gaatatccaa gaccaagatt gactaatgat    660
gagtctgcat caagaactag gcatttcttc tgagttgacg gactctttag gaaaggagaa    720
tctaagtgaa gcactgattt tagctctgag aacaaacaaa ttaaggtaca gcatagttag    780
ccttggtaga ggtatgactt ggatttgctg tatcctttaa aatagtatct gggcatttat    840
tttattgaag gtgactacat tttattagtt atattaggaa tttaggtaga atcaacttct    900
actgattaca ggttgaattt ctgtcacttt gtagagaaac gaatagactg gacactgtgt    960
ggtcactgtt tagatttgcc catgggtctc tttaaatcta tgtcatggat cctgagacac   1020
aaatataatt aagacaggtc tagagacagg agaagcagaa ataagttgac ccaggagtac   1080
agtctcaagt agttcattaa tgagaaaatt gacatctgac aagagtcttt ttactttatg   1140
ctggatgaaa atccaaatct tgttttattt tttccactaa aagtgactaa aataataacg   1200
aatttcattt gttcttgggt tctttttttcc tttaatgatt gtgctataac ttaaaataat   1260
gatgttactt ttgaacaaac ttaaagaaat atttttaaag cgtatctgaa aacgattgat   1320
gtttataact ctcttttggc ttcaaaataa gattgtgtta tcaccatttt ggtagatgag   1380
gttgtctggt gaaaatgatg catatgagtt gtactgttca gtgtacatcc tgcagtagtg   1440
gatgattgaa aacatatata agtggagtat aaattaaaaa ttaatttggt ttcttctatt   1500
tctttttttt tttttttttt ttgagacaga gtctcgctct gtcgcccagg ctggagtgca   1560
ctggcgcgat ctcggctcac tgtaagctcc gcctcccggg ttcacgccat cctcctgcct   1620
cagcctccca agtagctggg actactggca cccaccacga cgcccggctg ttttttttgta   1680
tttttaggag agacggggtt tcaccgtgtt agccaggatg gtctcgatct cctgacgtcg   1740
tgatccaccc gcctcggccc cccacagtgc tgggattaca ggcgtgagcc accgcgcccg   1800
gcctgttcct tttatttctt aattcaggac actaaaccat gactgcaagg gatttccttg   1860
gtaaaaagaa aagattctca gagtcaaaat ggtcttacaa ctcgggcttg acggcctttg   1920
aattatgaat ggattgttcc tctctctgaa gcctattgtc acatgggttt ttaatcctgg   1980
ccttgctgct agaaatctgt gcttgaagtc ctctctttct gctgctagcc taccagttaa   2040
aagtcaagac ttggtggaac tcagtttacc agactcttta gcctttgagc taaactgtct   2100
gagcaacctc ttagatgtgc acacaccact ttgtatgaaa gggttctcta gaacggttct   2160
ttggagagaa atattttcat gtacgtttga caggggtgta aataaagcat gctgactaat   2220
aagtctttta ctcttcatct aatgaacata agaatctatg catccagata ttattttgta   2280
tacaaatatt taatttggtg attgataatc tctctttggg gtagtcacat ggaaagctct   2340
tttaaattta acttccgcct ttggattttt tttaaaaagc cattgaagag caaaactaat   2400
gtaaacgtct tgatcattta aaaagcttgc ttgtcctcga aaggaaacac aggtcatcag   2460
tgagtataaa cgtagacagt tgatttgtga atgctgtcgg cctcaacttg cttgatgata   2520
gattctactg acctagctgg agtaatctga tc                                 2552
```

<210> SEQ ID NO 459
<211> LENGTH: 487
<212> TYPE: DNA
<213> ORGANISM: Artificial Sequence
<220> FEATURE:
<223> OTHER INFORMATION: Description of Artificial Sequence: Synthetic
      Affymetrix ID 3106631 polynucleotide

<400> SEQUENCE: 459
ctggagagtg gaactaggca tattctgtta taagaagtat aaattttact aaaactttga 60
ctgttagaaa aacatatgtg ctggggcaag gaaataggaa acaaaataca gcttcctgct 120
gttgatatat ctgttacaca aagtgattca gaacattagt gccagtgctt caccttcttc 180
ttcataagcc tgaggcacta aaggaatgca aaacactggg cttatgagag ccagtctcca 240
tcctttgtta ttctaatttt tcatgtgtgt agtgagaata aaccatttcc atggtaggat 300
cttccaataa tcaagttcgc ttttcaagag agttataaat atcttcaggt gaaatcagat 360
aattgacatt taaggcaatt ataagaaaat atatgatata catatttaat ttcatgcaac 420
aaatactttt caaacaaatg accgtgaata cgtttagtta agagggcatt tagcttcatg 480
atgttca 487

<210> SEQ ID NO 460
<211> LENGTH: 333
<212> TYPE: DNA
<213> ORGANISM: Artificial Sequence
<220> FEATURE:
<223> OTHER INFORMATION: Description of Artificial Sequence: Synthetic
Affymetrix ID 3108620 polynucleotide

<400> SEQUENCE: 460
cggattacaa tgaacgcagt gcagagcccc aaagctcagg ctattgttaa atcaataatg 60
ttgtgaagta aaacaatcag tactgagaaa cctggtttgc cacagaacaa agacaagaag 120
tatacactaa cttgtataaa tttatctagg aaaaaaatcc ttcagaattc taagatgaat 180
ttaccaggtg agaatgaata agctatgcaa ggtattttgt aatatactgt ggacacaact 240
tgcttctgcc tcatcctgcc ttagtgtgca atctcatttg actatacgat aaagtttgca 300
cagtcttact tctgtagaac actggccata gga 333

<210> SEQ ID NO 461
<211> LENGTH: 118
<212> TYPE: DNA
<213> ORGANISM: Artificial Sequence
<220> FEATURE:
<223> OTHER INFORMATION: Description of Artificial Sequence: Synthetic
Affymetrix ID 3111624 polynucleotide

<400> SEQUENCE: 461
tcctgtgacc tggactcgct tggctcatac tgcaaaggca ggggaaagaa ttttaatttt 60
acaagaagca gtaacatgga aaccaggaga taacattgta attgcaagca caggacac 118

<210> SEQ ID NO 462
<211> LENGTH: 395
<212> TYPE: DNA
<213> ORGANISM: Artificial Sequence
<220> FEATURE:
<223> OTHER INFORMATION: Description of Artificial Sequence: Synthetic
Affymetrix ID 3145950 polynucleotide

<400> SEQUENCE: 462
ctatggccag tgttctacag aagtaagact gtgcaaactt tatcgtatag tcaaatgaga 60
ttgcacacta aggcaggatg aggcagaagc aagttgtgtc cacagtatat tacaaaatac 120
cttgcatagc ttattcattc tcacctggta aattcatctt agaattctga aggatttttt 180
tcctagataa atttatacaa gttagtgtat acttcttgtc tttgttctgt ggcaaaccag 240
gtttctcagt actgattgtt ttacttcaca acattattga tttaacaata gcctgagctt 300
tggggctctg cactgcgttc attgtaatcc gtgatacaat gactacaaat gtgtcgcgat 360
ttctaatctt catctgtatc tcaggcgatt ttcca 395

<210> SEQ ID NO 463
<211> LENGTH: 1054
<212> TYPE: DNA
<213> ORGANISM: Artificial Sequence
<220> FEATURE:
<223> OTHER INFORMATION: Description of Artificial Sequence: Synthetic
Affymetrix ID 3154270 polynucleotide

<400> SEQUENCE: 463
ccctgtgaca gactgagtgt gcttcttctg ctacaaattc cttttgttct ttggcaagga 60
tgccccagag agcactccat aaacccgatg ggaagtgggg cctgtcagag gtgtgacgtg 120
ctgtcgaaaa cctggtggtg gattggctct gaggccaggg gtggcttagc cctgccggag 180
gccagtggca cctcaccccc ttgaccacat catctccccc cagggcacag gagaagcact 240
ggggttttca gcctgagtaa gactgtgcag aatttcctca atctctaaga tggctgagta 300
cagcagaatc aagtctttct catgataaca tgggctaggg agaagccttc caagagacgg 360
aagctacatc gtaatgtgcc tggaaagatg gggatcctg agagtcagac attttataca 420
gagattttca tgcaagagaa aaaagaaacg ggtttattta acttttattc tttttgtgcg 480
tgagcttcta gagtgaaaga gagattgtct tcattctttg tctgcattct ctttgccctc 540
tttatctttg ttttctcttc cctcccttcc tgtgtcttct actttttgtg ctattttcac 600
ctcctcctct tcctccttct ccctctcact tttgcttttc ctcctcgccc tctttcattc 660
ctcctctgct ccctccctcc tttccttcct tctttcattg tttcttttat ctttcttcct 720
agagatctat ttagtccacc tgttccattg taaatgcaca actgggggga tcagcgctgt 780
atgcagcccc attctcacac cctgtgaggt taatggattg ggcatttgcg ggaaaccctg 840
gaaggctgcg gcttctgcag gcactcactt gttgcttcat ttctttcatt ctgcagttga 900
agaaaggaaa gctcagagac gttcttgata atttactatc ggggtaaagc taaaattcaa 960
acccaagctt ggttgatact ggatcttaaa cctctctctc tgcccatgcc tggctaagtg 1020
cagagtatac cagggcacgc ttacatttct caaa 1054

<210> SEQ ID NO 464
<211> LENGTH: 83
<212> TYPE: DNA
<213> ORGANISM: Artificial Sequence
<220> FEATURE:
<223> OTHER INFORMATION: Description of Artificial Sequence: Synthetic
Affymetrix ID 3154288 oligonucleotide

<400> SEQUENCE: 464
tgatgcacga tgctctctaa actgggtcat tctccacttg gagggctcag ggcacggttg 60
actttccccg tctgtctcct ata 83

<210> SEQ ID NO 465
<211> LENGTH: 26
<212> TYPE: DNA
<213> ORGANISM: Artificial Sequence
<220> FEATURE:
<223> OTHER INFORMATION: Description of Artificial Sequence: Synthetic
Affymetrix ID 3154291 oligonucleotide

<400> SEQUENCE: 465
aaaggatggg atttgcgctt cacttt 26

<210> SEQ ID NO 466
<211> LENGTH: 132
<212> TYPE: DNA
<213> ORGANISM: Artificial Sequence
<220> FEATURE:
<223> OTHER INFORMATION: Description of Artificial Sequence: Synthetic
Affymetrix ID 3297658 polynucleotide

<400> SEQUENCE: 466
gggagcatca atactaccag gaggaaaaca ctcctacact tgtctgtcag gttccagggg 60
tcaaagactc tggcataagg atggccaaca ggcgactatg cccagtgggc ccagcacatg 120
cccatctgtt gt 132

<210> SEQ ID NO 467
<211> LENGTH: 137
<212> TYPE: DNA
<213> ORGANISM: Artificial Sequence
<220> FEATURE:
<223> OTHER INFORMATION: Description of Artificial Sequence: Synthetic
Affymetrix ID 3327191 polynucleotide

<400> SEQUENCE: 467
taagaacttc acatgagctc tactctcttc aatgtttaag tgtacaatac agtcttgtta 60
cctatatgca cagtgttgtg cagcagatct ctggaatgta ttcatgtata actgaaacta 120
tacccacgga acagcaa 137

<210> SEQ ID NO 468
<211> LENGTH: 289
<212> TYPE: DNA
<213> ORGANISM: Artificial Sequence
<220> FEATURE:
<223> OTHER INFORMATION: Description of Artificial Sequence: Synthetic
Affymetrix ID 3346638 polynucleotide

<400> SEQUENCE: 468
gggctttaag tcagccatgg acatactgaa gcaagaggaa tgaagggaaa aaagaaaagg 60
ggggaaaaaa agaagaagaa tggggccaag gaggatttaa gactaccatt ataggttaca 120
agttgaattc tttttaatat tcttcaagca atgacagtaa agattcaaat aacttttaaa 180
ttacctttga tttctaaacc aagtttcttg gaatgtgaaa gtcgccaaga ctgggccctg 240
cagggcctgg gttgggctac tactgcctat ggagattctg agggtatta 289

<210> SEQ ID NO 469
<211> LENGTH: 235
<212> TYPE: DNA
<213> ORGANISM: Artificial Sequence
<220> FEATURE:
<223> OTHER INFORMATION: Description of Artificial Sequence: Synthetic
Affymetrix ID 3349403 polynucleotide

<400> SEQUENCE: 469
aacatcggcc ttctgttcac ttaggcagca tttatagaaa caaaagaaga aagaaacaac 60
ctactgtctg gagtcataac acaactttcc tggattggaa accaagtggg ggaaaaaata 120
cagaaacttt aagggggatg ggaggggggg gagaagggaa aagccagccc tttgtataga 180
aattttgctt ttttttccct cattctactt tagaactgca agcttgtgca ctgtg 235

<210> SEQ ID NO 470
<211> LENGTH: 800
<212> TYPE: DNA

<213> ORGANISM: Artificial Sequence
<220> FEATURE:
<223> OTHER INFORMATION: Description of Artificial Sequence: Synthetic
Affymetrix ID 3349416 polynucleotide

<400> SEQUENCE: 470
cagcgctgtg gtagtcttat tgtaaaacca cagggcttag tggaaatttt tgtcgtatca 60
ccatagatac caaaatctaa tttgattact cttgtgaata gttgctaact ataatctgat 120
attgactgtt acttttcatc ggctggaagt agtctgctaa ttgagctgga ggcaagccag 180
ggaaatcttt caaaggagta gttttatata cagcagtttt aataagcaat tcaatgaaac 240
cttttataaa aacaacaaag gcaagaaggg tctggacgct ctgagcgtgc ttgacacatc 300
tatgactgaa cgcaggacaa tgccggatca tgtcggtccc tcagacctgg ctcggcaagg 360
ttaaataaga agagcttaat ttattcagca accgtgagta tccttatttg cttaacaact 420
ctgtcaaaag caaccctcta tgtccctgga gttgaataaa tgagcaaggt gcctcttgcg 480
tcatcaaatt atgcacgtct atagtactgt gaggagggca gtttgctgct tgatttttca 540
atcacaatta aagtaatatc agataccttt actgggaaga gagtttttttc aaagaggcag 600 ccatatcttt gcctgttatc acctaggagc tcccaaaaca cagtgaatgt tgttttttttt 660 tttctttttc ttgagggaag acaaattcca tagggcaaat tgttagacca gttatttgtg 720
cttgtttagt ttaacaagtc tctgctcctg gccatgtggt ggggtgtgct atatttgttg 780
agcttttcct acgtgccata 800

<210> SEQ ID NO 471
<211> LENGTH: 527
<212> TYPE: DNA
<213> ORGANISM: Artificial Sequence
<220> FEATURE:
<223> OTHER INFORMATION: Description of Artificial Sequence: Synthetic
Affymetrix ID 3391634 polynucleotide

<400> SEQUENCE: 471
ctgagtccac tgaacagcct ggtgaccaga agagcctgcc cctcactgct gggccctccc 60
ggtctcagac acccaggctc tcacattcta ctgtgtgctc taagatctct cttcatgttc 120
ctctattctg agggcctgtg catttgaacc agagatctgt gcaggcccta gaatcaaagg 180
ggccagggct gtgtgttctg ggatcctcca tttccatccc caggagctga gaaaatgcaa 240
cataacccca cattgagcaa atgacaagac cattattctt cacagtttga aattataatc 300
tagcatcgcc actgatcaga ctgcagaagt gtcagaacgt tggggagagt ggcccacaga 360
atggacccag aggcagcctt gccaccctaa cctcttgctg ctttgtacct taggagagga 420
gcgcatgcgg agtactgatt tctgtttact tagcatcatc ttcatcatca tcatcatcat 480
ctgtatttca ttttctttgt taaaaggctt cgattccgtt tgagtga 527

<210> SEQ ID NO 472
<211> LENGTH: 62
<212> TYPE: DNA
<213> ORGANISM: Artificial Sequence
<220> FEATURE:
<223> OTHER INFORMATION: Description of Artificial Sequence: Synthetic
Affymetrix ID 3729896 oligonucleotide

<400> SEQUENCE: 472
aagccgtgga aacgttgagt tcacaaacag gacttcccgt gcaactgtcc agccagacct 60
gg 62

<210> SEQ ID NO 473
<211> LENGTH: 275
<212> TYPE: DNA
<213> ORGANISM: Artificial Sequence
<220> FEATURE:
<223> OTHER INFORMATION: Description of Artificial Sequence: Synthetic
      Affymetrix ID 3875993 polynucleotide

<400> SEQUENCE: 473
ttagtgctgg gcatgtagct tcttctgttc ccaagtgcat tcacaagact ccttttaatc     60
aaaagctggt tttcaaaaaa acataagaag tatttaaaaa cttcatttct gggctagaga    120
agccatcgta atcatcatta tcatcaaaaa ttcatatttc ggtggtggct gaaaagacag    180
atgtctccat ccacaggatg tcaatgaaag taggagctac tgacatgata atgtagcatt    240
agcctccaag gcctcatgat tcagggtgta attgc                               275

<210> SEQ ID NO 474
<211> LENGTH: 39
<212> TYPE: DNA
<213> ORGANISM: Artificial Sequence
<220> FEATURE:
<223> OTHER INFORMATION: Description of Artificial Sequence: Synthetic
      Affymetrix ID 2466573 oligonucleotide

<400> SEQUENCE: 474
atgaaatata agcccgacca ttccgaaact gccaactaa                            39

<210> SEQ ID NO 475
<211> LENGTH: 86
<212> TYPE: DNA
<213> ORGANISM: Artificial Sequence
<220> FEATURE:
<223> OTHER INFORMATION: Description of Artificial Sequence: Synthetic
      Affymetrix ID 2516646 oligonucleotide

<400> SEQUENCE: 475
cagttcatag acgtaaattg tgctgggcat agctccaagt ggaataagct gagagcaaga     60
aagctataca tattaggatg taattc                                          86

<210> SEQ ID NO 476
<211> LENGTH: 105
<212> TYPE: DNA
<213> ORGANISM: Artificial Sequence
<220> FEATURE:
<223> OTHER INFORMATION: Description of Artificial Sequence: Synthetic
      Affymetrix ID 2537578 polynucleotide

<400> SEQUENCE: 476
tctcgagcag tgaaacaatg gaacaattta atttaaaatt aaggactagc agaaactccc     60
gctatcattg ttggtactta gtactatctc agttagacca aagtc                    105

<210> SEQ ID NO 477
<211> LENGTH: 105
<212> TYPE: DNA
<213> ORGANISM: Artificial Sequence
<220> FEATURE:
<223> OTHER INFORMATION: Description of Artificial Sequence: Synthetic
      Affymetrix ID 2578956 polynucleotide

<400> SEQUENCE: 477
gtgacaatat gtgccgagta aataatgggg gctgtagtac actttgcttg gctatcccag     60
gaggccgggt gtgtgcttgt gccgataatc aacttttgga tgaaa                    105

<210> SEQ ID NO 478
<211> LENGTH: 74
<212> TYPE: DNA
<213> ORGANISM: Artificial Sequence
<220> FEATURE:
<223> OTHER INFORMATION: Description of Artificial Sequence: Synthetic
Affymetrix ID 2630524 oligonucleotide

<400> SEQUENCE: 478
caggctatgg gcatgtgctt ctcatggcaa cgtcagaaac gcaagataac aagcccaacc 60
aaacggtgct ttga 74

<210> SEQ ID NO 479
<211> LENGTH: 154
<212> TYPE: DNA
<213> ORGANISM: Artificial Sequence
<220> FEATURE:
<223> OTHER INFORMATION: Description of Artificial Sequence: Synthetic
Affymetrix ID 2730784 polynucleotide

<400> SEQUENCE: 479
ccatcagatt gagacaggcc tattgaaacc tgaacttaag gataaggtga cctatacttt 60
gctccggaag caccggcatc aaaccaagaa atccaacctt cggtccctgg ctgacattgg 120
gaagacagtc tccagtgcaa gtaggatgtt tacc 154

<210> SEQ ID NO 480
<211> LENGTH: 29
<212> TYPE: DNA
<213> ORGANISM: Artificial Sequence
<220> FEATURE:
<223> OTHER INFORMATION: Description of Artificial Sequence: Synthetic
Affymetrix ID 2730818 oligonucleotide

<400> SEQUENCE: 480
cctttccttc agtcactcgg tatgccaag 29

<210> SEQ ID NO 481
<211> LENGTH: 602
<212> TYPE: DNA
<213> ORGANISM: Artificial Sequence
<220> FEATURE:
<223> OTHER INFORMATION: Description of Artificial Sequence: Synthetic
Affymetrix ID 2797069 polynucleotide

<400> SEQUENCE: 481
gtacagcgta gtccagattc atttctgtac caaatggtca aatgtgctca gacatttcct 60
atgtggtttg taggtcattc attaagattt ctttacatct aattcattac aagttcaaaa 120
tcttgaggta gtttctgtga tggaatattc agacaattat tacagctgta tagaagattt 180
gtatttgttt acagtctatt tggtctagtt caagcagaag agcaccttga cattgagtcc 240
tgtttgctga gcaaacatca ggcacctgga gagtgcgggc ttctgtcttc attatctcct 300
cgaggcctcc tgatgtcccg ccaagaagaa gaaaatgggg actggagggg ttaagtaatg 360
tgcacaaaat agtaaatggc agagtaagaa gttaaacgca gagcctgtta aagaaaaatg 420
aaaatctctg ggcagttctc actataatat actgccagag taatcccact acaaaataca 480
gtcacgtgtt gcttaaggat gtggacgggt tctgagaaat gtgtcatcag gtggacttgc 540
cattgtgcaa acatcgcaga gtacttacac aaacccagat gctagagcct gctacacgcc 600
ta 602

<210> SEQ ID NO 482
<211> LENGTH: 119
<212> TYPE: DNA
<213> ORGANISM: Artificial Sequence
<220> FEATURE:
<223> OTHER INFORMATION: Description of Artificial Sequence: Synthetic
Affymetrix ID 2854108 polynucleotide

<400> SEQUENCE: 482
tagaacaagt tgttgggatg ggaaagggga ttctcctcac ctggcattac gaccccaaca 60
tgacttgcga ctacgtcatt aagtggtgta actcgtctcg gtcggaacca tgccttatg 119

<210> SEQ ID NO 483
<211> LENGTH: 73
<212> TYPE: DNA
<213> ORGANISM: Artificial Sequence
<220> FEATURE:
<223> OTHER INFORMATION: Description of Artificial Sequence: Synthetic
Affymetrix ID 2854129 oligonucleotide

<400> SEQUENCE: 483
ctaacaattt gcaagtgtgg aactgttctt ggaaagcacc ctctggaaca ggccgtggta 60
ctgattatga agt 73

<210> SEQ ID NO 484
<211> LENGTH: 109
<212> TYPE: DNA
<213> ORGANISM: Artificial Sequence
<220> FEATURE:
<223> OTHER INFORMATION: Description of Artificial Sequence: Synthetic
Affymetrix ID 3018618 polynucleotide

<400> SEQUENCE: 484
tggtggcttg cagattggat tcatagtgag gtacttggca gatcctttgg ttggtggctt 60
cacaacagct gctgccttcc aagtgctggt ctcacagcta aagattgtc 109

<210> SEQ ID NO 485
<211> LENGTH: 185
<212> TYPE: DNA
<213> ORGANISM: Artificial Sequence
<220> FEATURE:
<223> OTHER INFORMATION: Description of Artificial Sequence: Synthetic
Affymetrix ID 3046325 polynucleotide

<400> SEQUENCE: 485
taggagccac tcattcgctg cgatgcaaga tgaccttaaa ccttggtgga aaaaaaaaaa 60
agccctaagt gtcaccttgc aaatgtttag aaataaacca aataacaaga tttcctgagg 120
ccttacccgc tatttgactt accagctact tgaaagaagc aggttgattg attgccctgc 180
ttaca 185

<210> SEQ ID NO 486
<211> LENGTH: 851
<212> TYPE: DNA
<213> ORGANISM: Artificial Sequence
<220> FEATURE:
<223> OTHER INFORMATION: Description of Artificial Sequence: Synthetic
Affymetrix ID 3088273 polynucleotide

<400> SEQUENCE: 486
agcggtccct acttctgagg agaaaatgtg gtttctgact tttaggtaca tcacgatatc 60
accagtctga atgagtttcc ttttctgtaa agcagaaagt gtcattttct tttcctccag 120
tgttcagttg ctcctcttcg aaaatactct tcagagaaag tatctgtacg tctgtattag 180

-continued

```
tacaaaccat tccttcccta tgtctcaatg cctgacattc agtgcctgac agaatcagca    240

tttggcatgt ccttggatat ggcatcaatt tgatgctttg aactgaaagt tctcataatg    300

catctcaaag tatcttctta aaaaatataa aaatgtaggc caacttgtgc tctcttgtaa    360

ggcttgcaaa gtggtaatta aataagcaga ctataactca caagggaaaa aaagtgcatt    420

tttaaataaa agaaaaaaac ggagacagtt aaaaggacaa ccaaaaagat aagcagatta    480

tttttggtta atcttgggga aaatatgaca cgatatttat ggtttctttt cttttctggt    540

ccattttatt ttacttaatg tactcactag tatcataata agcctatctc ctctcctgcc    600

ttctgatatt ttagcattcc tagaaactag agccctgctg ataggctcat tcatatgagg    660

agaaatatgc ttgcctttca tgctaatgaa ttttttacaa aactgctctt aaatcatgaa    720

tatttcaatg agcacacaaa acaacaggtc tcagtgtgtt gtaaacacca tcaaaacctc    780

cacaccatta ggcttataat ctcacaagca ttctgccttt gtcagacact tcacagggtg    840

caactgggtt a                                                          851
```

<210> SEQ ID NO 487
<211> LENGTH: 43
<212> TYPE: DNA
<213> ORGANISM: Artificial Sequence
<220> FEATURE:
<223> OTHER INFORMATION: Description of Artificial Sequence: Synthetic Affymetrix ID 3116649 oligonucleotide

<400> SEQUENCE: 487

```
tgtgggtatg tttggagccg caaaaacatg agatgtttgc ttg                       43
```

<210> SEQ ID NO 488
<211> LENGTH: 62
<212> TYPE: DNA
<213> ORGANISM: Artificial Sequence
<220> FEATURE:
<223> OTHER INFORMATION: Description of Artificial Sequence: Synthetic Affymetrix ID 3116701 oligonucleotide

<400> SEQUENCE: 488

```
atgtgaatca aagcaacttg ggatagactc tcccttgtct cacaaggcct tttcagtctg     60

ca                                                                    62
```

<210> SEQ ID NO 489
<211> LENGTH: 52
<212> TYPE: DNA
<213> ORGANISM: Artificial Sequence
<220> FEATURE:
<223> OTHER INFORMATION: Description of Artificial Sequence: Synthetic Affymetrix ID 3132624 oligonucleotide

<400> SEQUENCE: 489

```
catctgcagt gtctccctaa actcaataga acagtatcat gcccatctga aa             52
```

<210> SEQ ID NO 490
<211> LENGTH: 90
<212> TYPE: DNA
<213> ORGANISM: Artificial Sequence
<220> FEATURE:
<223> OTHER INFORMATION: Description of Artificial Sequence: Synthetic Affymetrix ID 3354954 oligonucleotide

<400> SEQUENCE: 490

```
tttatgctaa aacaatcaca cagaattcta gatgagaagg aacatgaata ggcttgacca     60
```

-continued

```
atttcgtgat cactgagcac agtaaagatc                                     90


<210> SEQ ID NO 491
<211> LENGTH: 136
<212> TYPE: DNA
<213> ORGANISM: Artificial Sequence
<220> FEATURE:
<223> OTHER INFORMATION: Description of Artificial Sequence: Synthetic
      Affymetrix ID 3574068 polynucleotide

<400> SEQUENCE: 491

cacttcctgg aataacgttg ctttggattt aacaacagtt gggcaaagga ggtcggtata     60

cagatacagg acaagaagag tggtgtcaaa gggaggctaa atcattggtt ctggcttcat    120

ctaaggaatt cttatg                                                   136


<210> SEQ ID NO 492
<211> LENGTH: 222
<212> TYPE: DNA
<213> ORGANISM: Artificial Sequence
<220> FEATURE:
<223> OTHER INFORMATION: Description of Artificial Sequence: Synthetic
      Affymetrix ID 4023363 polynucleotide

<400> SEQUENCE: 492

tcaggtaagc ggtaggtgga aatccagatt tcctcttgag gaaaagtcct aggaatcaca     60

acagaaggga ctttgcagtc ctcattaaca catggacaaa gagcagacaa ctactacgtt    120

acaagggatt caactagtca ctgttgtgaa atgtcatatc catgttgatg acagccctgg    180

cgcctgctca actccccctc tagagttttg cggttacttc cg                      222


<210> SEQ ID NO 493
<211> LENGTH: 287
<212> TYPE: DNA
<213> ORGANISM: Artificial Sequence
<220> FEATURE:
<223> OTHER INFORMATION: Description of Artificial Sequence: Synthetic
      Affymetrix ID 2337202 polynucleotide

<400> SEQUENCE: 493

ggtcatattt atcttgggcc attgattaca ttttccaaac tgctattttt ggaaggcacc     60

tcagcttgag aagcacaata ataaattgga tggatggagg aagagatgga tgggaaagag    120

cctggagctt agaatcagaa aggcctgggt ttgaatcttt gctctgccac ttaccagact    180

taggcaggtc ttttaacttc tataatatag ttcctgcatt aataaaataa aagtaatact    240

acctacctca ttctcataag agttaaacgg tgttctgcaa gtcaagt                 287


<210> SEQ ID NO 494
<211> LENGTH: 80
<212> TYPE: DNA
<213> ORGANISM: Artificial Sequence
<220> FEATURE:
<223> OTHER INFORMATION: Description of Artificial Sequence: Synthetic
      Affymetrix ID 2350547 oligonucleotide

<400> SEQUENCE: 494

cagatctttt tttatagagt acccaaaccc tcctttctgc ttgcctcaaa cctgccaaat     60

atacccacac tttgtttgta                                                80


<210> SEQ ID NO 495
<211> LENGTH: 818
<212> TYPE: DNA
<213> ORGANISM: Artificial Sequence
```

<220> FEATURE:
<223> OTHER INFORMATION: Description of Artificial Sequence: Synthetic
Affymetrix ID 2400663 polynucleotide

<400> SEQUENCE: 495
cacccatctg ggctgtctct gcagggcaga gccgtccaga cctgggatca gggaagctgc 60
tggcatcgtc cccaccccca gcctgggggt ctgggctggg gcagggattg ctcagtggaa 120
gcaggactgg gggtctggct tgccccctcc ctgggcctcc atcaccccctg agcatccctc 180 tggactcaga gggaacaagg tgggagagag agtttgagac agctccgtgt ggagagctta 240
gcccctggag gcagcacaag gaggatgtga tatgtggggg agtgagcact gggttgggag 300
ccgggtcctg gtttccaatt tgggttctgc tgtgtgactc tgggcaagtc actctccctc 360
tctgggcatg tctgctacaa atggacaaga ttatttcaga ggtcactgaa gactgtgatt 420
acatgcacct gccttagaag gtaggatttt cttcccaggg acctcctatc accctaccct 480
gcttcttgag gtccctggag ccccaggtgg gctgaggggc agggagccgg ctgtgcccag 540
tatgcctcct ggaccctcca gttctgccac aggtctgccg atgccctgtc cactgcctac 600
acatgacaga caagtaaccc cctcatgggg gatggggacc tacctggctc ctcagccagc 660
acccagctta acccctgcca tcccatgctg ggccctccag gccaagagtc tcagctggcc 720
gagagtccag gccttgcctc ccccgaccgc catggagggg gcagcccggc acagctgctg 780
ggagcccttg tgtgtctggt cacacttttt aggcgtca 818

<210> SEQ ID NO 496
<211> LENGTH: 258
<212> TYPE: DNA
<213> ORGANISM: Artificial Sequence
<220> FEATURE:
<223> OTHER INFORMATION: Description of Artificial Sequence: Synthetic
Affymetrix ID 2608614 polynucleotide

<400> SEQUENCE: 496
agctcattct gagggcacaa aattctgttt tgaaaaatga gttctgctag tatcctgctg 60
tgatcatttg gtcataaatc agacttggtt ccagaacatg agttacattt gaaaactgat 120
aaaacactga gaatacgcaa aggaaactgg cctaagatct ggcacatagt gggcactcca 180
taaatgtttg ttgaataagt aaatgattgc atgaagttta tttacagttt ttatccaaga 240
ttgtagggga tctcatca 258

<210> SEQ ID NO 497
<211> LENGTH: 226
<212> TYPE: DNA
<213> ORGANISM: Artificial Sequence
<220> FEATURE:
<223> OTHER INFORMATION: Description of Artificial Sequence: Synthetic
Affymetrix ID 2721315 polynucleotide

<400> SEQUENCE: 497
actactaagc gaccaatttt gctgaagatt ttaagaggag atgacaattg tagacattat 60
atgttgcact gcatttcaag cccagaatat ctctagagaa aaaacaaatc tccctcaatc 120
tcctctttat gttattctcc aggaaggttc caaactttac cttctagcct cattcagcat 180
ctttcaagtc ctcatctcct tgctttccaa agctctaaat cacttc 226

<210> SEQ ID NO 498
<211> LENGTH: 330
<212> TYPE: DNA
<213> ORGANISM: Artificial Sequence
<220> FEATURE:
<223> OTHER INFORMATION: Description of Artificial Sequence: Synthetic
      Affymetrix ID 2754774 polynucleotide

<400> SEQUENCE: 498
tcagagagaa catcctacta ttagacatag gaaaatgcct agaaatcttg agatattttt     60
ccttctttat gccagtatta tatttggttt acacctcaga agtaatagtg aaattggtag    120
agacaaaata ttctagtaac caatttgcta ttttctgttg aatttaaaaa tttaattcaa    180
tttatatttg attcaatagt tgcaatagta ttaattgaga ttttaatgtc cataaaatac    240
tatttttctc caattattat ttagatcatt atagatgcat aattgttcgt gaaatggctt    300
tgctggagct ggtttttagg gtaactgaca                                     330

<210> SEQ ID NO 499
<211> LENGTH: 149
<212> TYPE: DNA
<213> ORGANISM: Artificial Sequence
<220> FEATURE:
<223> OTHER INFORMATION: Description of Artificial Sequence: Synthetic
      Affymetrix ID 2980485 polynucleotide

<400> SEQUENCE: 499
cggaggagga tatcgtgtaa agatctgggc catgctgact gccaagggtg gctgtataag     60
aaaaaggaaa agggaagttt cctaagcaac aaatggaaaa agttctgggt gatactgaag    120
gggtcgtcac tgtactggta tagcaatca                                      149

<210> SEQ ID NO 500
<211> LENGTH: 1054
<212> TYPE: DNA
<213> ORGANISM: Artificial Sequence
<220> FEATURE:
<223> OTHER INFORMATION: Description of Artificial Sequence: Synthetic
      Affymetrix ID 3010582 polynucleotide

<400> SEQUENCE: 500
tgccctggcg aagttaatgt tgttcagaaa gggtaaatgt ttggacactt gcaattgctc     60
atggatgaat ttatatgttt tagtcataga aaaattgtac cctttgatag aagcacattt    120
tctttccaaa gctggttatt aaccacagaa ttatagcagg tattcataac ttaagtttga    180
aaatcaatag cgtctgcaaa tggattaaca gattagagaa tcaacagcat cggaaaatag    240
gttaatgcat attgcttcta acaagtgcat gaagaaatag aagaagctat gtagctttca    300
gttctgacag aaaagggtga aggagggtat catttcaaga aaaaaaatag ctatcacgca    360
atggttatct ctgaaaatat ttgtattaag atgtgtatac atggccaggc atggtggctc    420
atgcctgtaa tcccagcact ttgggaggca ggtggatcac gaggtcagga gatcaagacc    480
atcctggcca acatggtgaa acctcatctc tactaaaaat acaaaaatga gcggggtgtg    540
gtggcccatg cctgtagtcc cagctgctcg ggagactgaa tctcttgagc ctgggaagca    600
gaggttgcag tgaactgaga tcgcgtcact gcactccagc ctggtgacag agcgagattc    660
catctcaaaa aaaaaaaaca gtatgcacgt acaaatttct taacctgtta tcaatgtctg    720
agctacataa ttatctttct agttggagtt tgttttaggt gtgtaccaac tgacatttca    780
gtttttctgt ttgaagtcca atgtattagt gactctgtgg ctgctctctt cacctgcccc    840
ttgtggcctg tctacaattc taaatggatt ttgaactcaa tgtcgtcgct tctggtttcc    900
tgcatatacc aatagcatta cctatgactt ttttttcct gagctatttt cactgagctg    960
agctaatgaa ctaaaactga gttatgttta atatttgtat caaatacata aaaggaatac   1020
tgctttttcc ttttgtggct caaaggtagc tgca 1054

<210> SEQ ID NO 501
<211> LENGTH: 420
<212> TYPE: DNA
<213> ORGANISM: Artificial Sequence
<220> FEATURE:
<223> OTHER INFORMATION: Description of Artificial Sequence: Synthetic
Affymetrix ID 3046247 polynucleotide

<400> SEQUENCE: 501
cagattaccc tgcttgctgc tagcagaaac ccaaacccac tgcagtctcc catcacattg 60
accattcatt tgtcagcagt gcccctgggt gggaatcagg ctgacagcct tccaaaacct 120
cccctcctgt ccctgcttcc cccacacccc tgcctcaagg gacatctgtg atgcactgga 180
aggtgaccta aacatttggc cagaacccta attctgatac ttctggttct gtgacccccca 240 ttaattccct tactttccaa acctccaatt cctcacctgt gaatgaggaa ggtgcacctg 300
ggctgcagca ttgctgtgaa gatgaagcaa gtgcttgagg ctctgtgaga tcctgctgtg 360
tggggtctgc tgtccagatc atgaagaact cttgcccctc aggaacttgt atgtagatgc 420

<210> SEQ ID NO 502
<211> LENGTH: 61
<212> TYPE: DNA
<213> ORGANISM: Artificial Sequence
<220> FEATURE:
<223> OTHER INFORMATION: Description of Artificial Sequence: Synthetic
Affymetrix ID 3067230 oligonucleotide

<400> SEQUENCE: 502
ctcagtccct gaagtagctg gcattacagg cctgtgccac tatgtcgagc caataatggc 60
a 61

<210> SEQ ID NO 503
<211> LENGTH: 59
<212> TYPE: DNA
<213> ORGANISM: Artificial Sequence
<220> FEATURE:
<223> OTHER INFORMATION: Description of Artificial Sequence: Synthetic
Affymetrix ID 3106600 oligonucleotide

<400> SEQUENCE: 503
ttgtaaacca cagacgaatt ggagcttggc attgaaagga ggtgttctgc aatgatttt 59

<210> SEQ ID NO 504
<211> LENGTH: 66
<212> TYPE: DNA
<213> ORGANISM: Artificial Sequence
<220> FEATURE:
<223> OTHER INFORMATION: Description of Artificial Sequence: Synthetic
Affymetrix ID 3106632 oligonucleotide

<400> SEQUENCE: 504
tgtgtccttg caagcattat tgttgtggga ctgaagggaa tgctaataca gttccgagat 60
ttaaaa 66

<210> SEQ ID NO 505
<211> LENGTH: 395
<212> TYPE: DNA
<213> ORGANISM: Artificial Sequence
<220> FEATURE:
<223> OTHER INFORMATION: Description of Artificial Sequence: Synthetic
Affymetrix ID 3106648 polynucleotide

<400> SEQUENCE: 505
agtaaattct agtgcctgcc aagtgatgga ttataatggt ctctagcaaa tgtgtggtaa 60
acattcatat ggccattaat tttaacatta aatcgtaggt agggcaatgt agtaaaatga 120
aagagaatta agaaaggttt tgaattctta taacatatcc agccatttca attttgattg 180
aaatgaacta caaagaatag tgtttgtccc tatggtagcc tcagtctctt tatcactaac 240
ttggattgaa atgagtgagg ccaactcaca ttcccatcaa acactcttcc aaggaaaagc 300
agaagtaata attggaggta aagtttcctt agagaaaata attttattct gctttgtcca 360
attaaattat tccaatggcg gatggtaata ttcac 395

<210> SEQ ID NO 506
<211> LENGTH: 68
<212> TYPE: DNA
<213> ORGANISM: Artificial Sequence
<220> FEATURE:
<223> OTHER INFORMATION: Description of Artificial Sequence: Synthetic
Affymetrix ID 3111639 oligonucleotide

<400> SEQUENCE: 506
ttctttttgg caatcatcac gagaaaataa ttatactgta cctcacccag gggcaaatgt 60
gattatac 68

<210> SEQ ID NO 507
<211> LENGTH: 379
<212> TYPE: DNA
<213> ORGANISM: Artificial Sequence
<220> FEATURE:
<223> OTHER INFORMATION: Description of Artificial Sequence: Synthetic
Affymetrix ID 3116823 polynucleotide

<400> SEQUENCE: 507
tctccacttt tcgaaggacc acagcccagt ttaatagact tgcagctcag catctcatag 60
caaaccacac aatgacaatt taaagactat ggggtgcatt ttttcctaaa gtcaagggca 120
ccactttaaa cacaggcctc agctctgcat ccgcttgttc tcgctgaggc tcccccaacc 180
ctttagagcc cctcacttgc ctctacctcc caccagctcc gtgacttgga caagccacct 240
aacttctctg agcctcattt cctcagtttt caaaagcaaa taacaatcac aatcctatag 300
gattgttctg aggattgcag aaaaataact ttttatgcat tgctcctccc cagccactcg 360
ggatggtgga tatcacctc 379

<210> SEQ ID NO 508
<211> LENGTH: 46
<212> TYPE: DNA
<213> ORGANISM: Artificial Sequence
<220> FEATURE:
<223> OTHER INFORMATION: Description of Artificial Sequence: Synthetic
Affymetrix ID 3154280 oligonucleotide

<400> SEQUENCE: 508
gccagacaca aaggtcggct ccttcatgat cagagagagt gagacc 46

<210> SEQ ID NO 509
<211> LENGTH: 250
<212> TYPE: DNA
<213> ORGANISM: Artificial Sequence
<220> FEATURE:
<223> OTHER INFORMATION: Description of Artificial Sequence: Synthetic
Affymetrix ID 3154296 polynucleotide

<400> SEQUENCE: 509
gtgccgtaat agctgcacct gtgtcaacat tctgggtcgg ccaccaaaga actctgtgac 60
tctgtacaag tcactttgcc ccttcgagta ttttccttgt aaaaagaaga ccagtttctc 120
tgtatgtttg aaagaagttt acatgtacta tctaggagat aataggtact aaataggagc 180
tattggtatc atttctaaat cagacaatta aaatatatcc aatccctttt acatttccta 240
ggcagaaagc 250

<210> SEQ ID NO 510
<211> LENGTH: 26
<212> TYPE: DNA
<213> ORGANISM: Artificial Sequence
<220> FEATURE:
<223> OTHER INFORMATION: Description of Artificial Sequence: Synthetic
Affymetrix ID 3205888 oligonucleotide

<400> SEQUENCE: 510
ctctttacgg agaaacagcg gatgaa 26

<210> SEQ ID NO 511
<211> LENGTH: 1102
<212> TYPE: DNA
<213> ORGANISM: Artificial Sequence
<220> FEATURE:
<223> OTHER INFORMATION: Description of Artificial Sequence: Synthetic
Affymetrix ID 3349404 polynucleotide

<400> SEQUENCE: 511
tgcgctcctc tcctaaggta caaagcagca agaggttagg gtggcaaggc tgcctctggg 60
tccattctgt gggccactct ccccaacgtt ctgacacttc tgcagtctga tcagtggcga 120
tgctagatta taatttcaaa ctgtgaagaa taatggtctt gtcatttgct caatgtgggg 180
ttatgttgca ttttctcagc tcctggggat ggaaatggag gatcccagaa cacacagccc 240
tggccccttt gattctaggg cctgcacaga tctctggttc aaatgcacag gccctcagaa 300
tagaggaaca tgaagagaga tcttagagca cacagtagaa tgtgagagcc tgggtgtctg 360
agaccgggag ggcccagcag tgaggggcag gctcttctgg tcaccaggct gttcagtgga 420
ctcagttctt catcttgtaa tgtcgatggc tttgccacac caggccaagc ccatgccata 480
ccttgtcaag actgtcaaag tggttgtggt taggtcaaac tggttttggt tctgatggtt 540
aggaagaaac aggtcagccc tcagatcacc tggcccggga cagctgaccc cctagaaccc 600
tggctctgcc attagctagg acctaagact ctgcccacat tttggtctgt tctctcccat 660
tacacatagg tttgtctcag catgcaagag tttttccttt aaaaaaaaaa aaaaaaaaaa 720
aaaaaaagca atgctttctc taaaatcaaa gagggagtca ttttattcca agatgtttta 780
tcttttatgt taagagatca aagcttataa ttttcttttt taatttttga aggagggatc 840
aactccagtt tccaatgtct atgtgtctat gtgtgtatgt gccatacata tgtattcaca 900
tgaagaccgg catggccaag ttctgctgga ggagcactca agtgtgacga gcagggccac 960
tggaccctgc agggctgtgg tgtatatagt gcagctttgg aggtggaact ctattttcac 1020
acttttctat ggagccttcc gagtcccagg ttttcacttg aggctgtctg tctggatggc 1080
ggttttcaga cctccattaa ca 1102

<210> SEQ ID NO 512
<211> LENGTH: 249
<212> TYPE: DNA
<213> ORGANISM: Artificial Sequence
<220> FEATURE:
<223> OTHER INFORMATION: Description of Artificial Sequence: Synthetic
Affymetrix ID 3367703 polynucleotide

<400> SEQUENCE: 512
aggcccatga gagacgagcg aattttcagg gtattgagtg ccttgctaca ttcacactgt 60
atgtgccgtt caagattact attgaaggga aaatcacaag gtattggttt ttaaggaggg 120
tattcgtatt taaggctatt tgctgtagga attaccttct acagagtttg aactctgttc 180
tgaaaagtct gagagaaata gaaacagttc ataggaaatt ttgaagtttg gctagcctgt 240
aaaccacag 249

<210> SEQ ID NO 513
<211> LENGTH: 39
<212> TYPE: DNA
<213> ORGANISM: Artificial Sequence
<220> FEATURE:
<223> OTHER INFORMATION: Description of Artificial Sequence: Synthetic
Affymetrix ID 3625069 oligonucleotide

<400> SEQUENCE: 513
gcaatacaag ctgttctctt ggcggaagtt caacaacac 39

<210> SEQ ID NO 514
<211> LENGTH: 29
<212> TYPE: DNA
<213> ORGANISM: Artificial Sequence
<220> FEATURE:
<223> OTHER INFORMATION: Description of Artificial Sequence: Synthetic
Affymetrix ID 3662208 oligonucleotide

<400> SEQUENCE: 514
gctgtgtttg caaaggggcg tcagagaag 29

<210> SEQ ID NO 515
<211> LENGTH: 37
<212> TYPE: DNA
<213> ORGANISM: Artificial Sequence
<220> FEATURE:
<223> OTHER INFORMATION: Description of Artificial Sequence: Synthetic
Affymetrix ID 2466600 oligonucleotide

<400> SEQUENCE: 515
cccaggccac acaagactca cggctctccc tggtctc 37

<210> SEQ ID NO 516
<211> LENGTH: 385
<212> TYPE: DNA
<213> ORGANISM: Artificial Sequence
<220> FEATURE:
<223> OTHER INFORMATION: Description of Artificial Sequence: Synthetic
Affymetrix ID 2583396 polynucleotide

<400> SEQUENCE: 516
cttacgtaag acaaagccga tgttgggatt tgcctgaatg caggttaggc gtaagggagg 60
ggtgggaaat tagatgagaa acatgggctt caagcatgtg tggaggactt tgaggattca 120
tgtttaaata aaagattgat aggattccag agctacaata atgatggtgg tgatattgtt 180
tggatattta ctagatatct ggctctgcac tttacataat atctcattta cacttaaagt 240
tcacctggcc taacccccttt attaaaaatg aaatgtaaac tcagagcatt aaatagtttc 300
ctaagtgtct cacagctgtc catcaccagt accaagagta gaaatcaagt ttcctgcata 360
gaattcacta acacaagctg gcctc 385

<210> SEQ ID NO 517
<211> LENGTH: 84
<212> TYPE: DNA
<213> ORGANISM: Artificial Sequence
<220> FEATURE:
<223> OTHER INFORMATION: Description of Artificial Sequence: Synthetic
Affymetrix ID 2608612 oligonucleotide

<400> SEQUENCE: 517
ggggcttcca atctagttat cgacctcatc atgaacgcat ccagtgaccg agtgttccat 60
gaaagcattc tcctggccat tgcc 84

<210> SEQ ID NO 518
<211> LENGTH: 67
<212> TYPE: DNA
<213> ORGANISM: Artificial Sequence
<220> FEATURE:
<223> OTHER INFORMATION: Description of Artificial Sequence: Synthetic
Affymetrix ID 2638546 oligonucleotide

<400> SEQUENCE: 518
tcaagaaccc tatgctgtcg tggtacttct ggagaaagat ctcattgtag ttgatctgac 60
acaaagc 67

<210> SEQ ID NO 519
<211> LENGTH: 157
<212> TYPE: DNA
<213> ORGANISM: Artificial Sequence
<220> FEATURE:
<223> OTHER INFORMATION: Description of Artificial Sequence: Synthetic
Affymetrix ID 2721641 polynucleotide

<400> SEQUENCE: 519
gaggtctcac cttcgccttt gctgaagtct ccccgcagcc ctctccaccc agaggtctcc 60
ctataccgag acccaccatc cttccatcct gaggaccgcc ccaaccctcg gagcccccca 120
ctcagtaggt ctgaaggcct ccatttgtac cgaaaca 157

<210> SEQ ID NO 520
<211> LENGTH: 566
<212> TYPE: DNA
<213> ORGANISM: Artificial Sequence
<220> FEATURE:
<223> OTHER INFORMATION: Description of Artificial Sequence: Synthetic
Affymetrix ID 2797132 polynucleotide

<400> SEQUENCE: 520
gtgttattgc cttgacctag agttaatctg tatttttgaa ggaaaatacg ttgccttttt 60
tcacaagcac tttataactc acttctccct aattcagatt gcttttctta atcatttgaa 120
gttaatgata caattatcac atagtagcct tacaaatagc cataatatta aatcataatt 180
tatgtaaagt aaacatccaa attccaaaac atctgaacat gggaacaggc tgattgaagt 240
ttttgtgggt cataggacct tggcaattgt ttgtgagcct gatgccgaca tttctcaaca 300
gtaatcaaag cacagaacaa caaccatcca catgaaaaat aactcaaatt gtcattgtac 360
ttcccatgct attgtcattt agcaagttat ggcatgactg attcagccag taagaaaaat 420
gtgatgagaa tattggctag gagtacagtc tgcttagatc ttttagtttt ttttccttca 480
aaagccaata gacttttact ctttaaaata ggagctatgc aaaaacgtaa tatttggaat 540
gccaagctgc ctccatgatt gagata 566

<210> SEQ ID NO 521
<211> LENGTH: 29
<212> TYPE: DNA
<213> ORGANISM: Artificial Sequence
<220> FEATURE:
<223> OTHER INFORMATION: Description of Artificial Sequence: Synthetic
Affymetrix ID 2819847 oligonucleotide

<400> SEQUENCE: 521
tgctggagag attctgacct ttgctgaag 29

<210> SEQ ID NO 522
<211> LENGTH: 32
<212> TYPE: DNA
<213> ORGANISM: Artificial Sequence
<220> FEATURE:
<223> OTHER INFORMATION: Description of Artificial Sequence: Synthetic
Affymetrix ID 2997617 oligonucleotide

<400> SEQUENCE: 522
agataaatga aacgatatgc tggttctttg aa 32

<210> SEQ ID NO 523
<211> LENGTH: 30
<212> TYPE: DNA
<213> ORGANISM: Artificial Sequence
<220> FEATURE:
<223> OTHER INFORMATION: Description of Artificial Sequence: Synthetic
Affymetrix ID 2997653 oligonucleotide

<400> SEQUENCE: 523
atgaatgtgc gggaacaagc gtctaaagga 30

<210> SEQ ID NO 524
<211> LENGTH: 157
<212> TYPE: DNA
<213> ORGANISM: Artificial Sequence
<220> FEATURE:
<223> OTHER INFORMATION: Description of Artificial Sequence: Synthetic
Affymetrix ID 3018633 polynucleotide

<400> SEQUENCE: 524
ctggaggaac ttgatatccc aaccaaggaa atagagattc aagtggattg gaactctgag 60
cttccagtca aagtgaacgt tcccaaagtg ccaatccata gccttgtgct tgactgtgga 120
gctatatctt tcctggacgt tgttggagtg agatcac 157

<210> SEQ ID NO 525
<211> LENGTH: 139
<212> TYPE: DNA
<213> ORGANISM: Artificial Sequence
<220> FEATURE:
<223> OTHER INFORMATION: Description of Artificial Sequence: Synthetic
Affymetrix ID 3018640 polynucleotide

<400> SEQUENCE: 525
ttcgggaggt ctctatgagc aaggaataca agacaaaact tcctcaatgc attgactatt 60
tcttcagact caaaacactc attctttttt ctattaagcc attgaaagag aagcactaag 120
actgcttcta ggctttatt 139

<210> SEQ ID NO 526
<211> LENGTH: 191
<212> TYPE: DNA
<213> ORGANISM: Artificial Sequence
<220> FEATURE:

<223> OTHER INFORMATION: Description of Artificial Sequence: Synthetic
      Affymetrix ID 3055435 polynucleotide

<400> SEQUENCE: 526
cagtgatcat tggtagctgc taaaaccatt aattaagtga aagattgatg gggagcttta     60
taatgaatca atcaggctga caacacctga acctgctgtt gaatcctaac atcagaaaca    120
gtgagataac cagacattat gtatctccca atgtcagcac taggaagttc atagcagagc    180
ttaaagtgtt c                                                         191

<210> SEQ ID NO 527
<211> LENGTH: 120
<212> TYPE: DNA
<213> ORGANISM: Artificial Sequence
<220> FEATURE:
<223> OTHER INFORMATION: Description of Artificial Sequence: Synthetic
      Affymetrix ID 3116653 polynucleotide

<400> SEQUENCE: 527
gtgtcctgaa ggaagctatt cccaagatga ggaatgcatt ccttgtcctg ttggattcta     60
ccaagaacag gcagggagct tggcctgtgt cccatgtcct gtgggcagaa cgaccatttc    120

<210> SEQ ID NO 528
<211> LENGTH: 170
<212> TYPE: DNA
<213> ORGANISM: Artificial Sequence
<220> FEATURE:
<223> OTHER INFORMATION: Description of Artificial Sequence: Synthetic
      Affymetrix ID 3116797 polynucleotide

<400> SEQUENCE: 528
tagcttcctg agatactgta aggttggcat cgttattgcc atgtcagatg gtggagtagg     60
gcttagagac agataaggtt gcccaagacc aaacagataa tacatgtgct agccagattt    120
tggtcaaaat tgattttgaa ttttatcaag ttagtgtaca aacacagttg               170

<210> SEQ ID NO 529
<211> LENGTH: 158
<212> TYPE: DNA
<213> ORGANISM: Artificial Sequence
<220> FEATURE:
<223> OTHER INFORMATION: Description of Artificial Sequence: Synthetic
      Affymetrix ID 3154254 polynucleotide

<400> SEQUENCE: 529
gcatgtgctc aaggggccac tcatcaaaca agtatgaatt gggcttcagc tgctatcagg     60
cactatgcta ggtaaggcag aaagcaagag agatcctacc tagtcctagg gacacacaac    120
ctcagagaca aatgcagaag gcagttacca agcaatta                            158

<210> SEQ ID NO 530
<211> LENGTH: 455
<212> TYPE: DNA
<213> ORGANISM: Artificial Sequence
<220> FEATURE:
<223> OTHER INFORMATION: Description of Artificial Sequence: Synthetic
      Affymetrix ID 3154273 polynucleotide

<400> SEQUENCE: 530
aggtctgaat tctcccaggc tgataagatg gggagcatcc actgagataa agcaagcatc     60
atgtggtgtg gtggctggaa gagtgtagga tactgccaga gagagaaagt tgagttatac    120
tgtgaaaggc ccaaatgtca gctcaggaat cggaacttta ccctacagaa aagggagaaa    180

-continued

```
ttgtgaacgg ttggctaaat gctacatttc caaaaaccca ctcaggaagc tctgtttcta    240

tcccagatcc actcactgtt agctaggcag cctgaggttg gctgtttgtg tctcactttc    300

ttcatctatg ccaggcagac actagtagtt ccccctccca aggacaccgt gaggatccac    360

agagttagtt catggaaagt ggggagggtg cctggcccat aatcgtgagc tcccattaaa    420

tgccagccac ttttacccag cggaacattg ccatc                               455


<210> SEQ ID NO 531
<211> LENGTH: 88
<212> TYPE: DNA
<213> ORGANISM: Artificial Sequence
<220> FEATURE:
<223> OTHER INFORMATION: Description of Artificial Sequence: Synthetic
      Affymetrix ID 3154290 oligonucleotide

<400> SEQUENCE: 531

gccaaccctt ctgtggtgca ctatgagttt atagcttttg cgagcctggt cattgtcttc     60

ggaatattac tatgcattag cttgagca                                        88


<210> SEQ ID NO 532
<211> LENGTH: 381
<212> TYPE: DNA
<213> ORGANISM: Artificial Sequence
<220> FEATURE:
<223> OTHER INFORMATION: Description of Artificial Sequence: Synthetic
      Affymetrix ID 3334195 polynucleotide

<400> SEQUENCE: 532

ttcctccgca gaaagcaaag tttggggagg gctgacgatt ttgtagaaca caacagtgac     60

aatttttttt aaaagaatag aaggcaggag ggggaattcg acattgttga agacataatt    120

tataccaagt tatgccagtt ggggagggaa ggactaaaaa taatattgca ggcagggctg    180

ggttgggttt tttttttttc ccccctgaac tggaaggata ctacctgtac aacatctgtg    240

gacacctcat gctctgttca aggccatcac aaaggaaccg ccagggagaa gcagccggct    300

ctcaaagctc ccacgcagct ctcccgccac tggccactcg ctggcgaccc gatggaaggt    360

tttcaggctc ctcacaaagg a                                              381


<210> SEQ ID NO 533
<211> LENGTH: 75
<212> TYPE: DNA
<213> ORGANISM: Artificial Sequence
<220> FEATURE:
<223> OTHER INFORMATION: Description of Artificial Sequence: Synthetic
      Affymetrix ID 3349400 oligonucleotide

<400> SEQUENCE: 533

agaaacgaag ccagcgccag ccgaagtcaa gacggtcccc aatgacgcca cacagacaaa     60

ggagaacgag agcaa                                                      75


<210> SEQ ID NO 534
<211> LENGTH: 242
<212> TYPE: DNA
<213> ORGANISM: Artificial Sequence
<220> FEATURE:
<223> OTHER INFORMATION: Description of Artificial Sequence: Synthetic
      Affymetrix ID 3367740 polynucleotide

<400> SEQUENCE: 534

agcgaatttg cctgagactc ctgacccccta gttcaatttg ctttacattg tattgcttgc     60

ctccattctg aaatatttct ttaaaatttc tgtagttttt ttttttttc ccacacctca    120
```

ccccactagc cctttacatt cagctgggaa ataggcctaa ttgggactaa ttgtccagct 180
actgctagat ccattgtctt gcctgttgct agtgaaacgt gtgctgcatg ctacaggact 240
ca 242

<210> SEQ ID NO 535
<211> LENGTH: 354
<212> TYPE: DNA
<213> ORGANISM: Artificial Sequence
<220> FEATURE:
<223> OTHER INFORMATION: Description of Artificial Sequence: Synthetic
Affymetrix ID 3396798 polynucleotide

<400> SEQUENCE: 535
tcagtttctt gagcagcctt gtatgtagtg cacatatgag tggtttcaca caacatgaga 60
gagtgtgtgt gcattttata acaatacctt tttttgtttt ttttacctaa atagtggtag 120
cattctttac cataaatttt ttacttaaca tcttgggata tcttctcata tggtacataa 180
aaagtatttt cattcctttt taaaaagttg ctgcttagtg gtccattgtg tagttgtaac 240
aatttgacta gtaccttatt gatggttgtt tttaatcttt tgctattaca aatagttcta 300
taatgaatgc ccttctacaa agattatttt gcgcctgtgt gagtatttgt aaaa 354

<210> SEQ ID NO 536
<211> LENGTH: 37
<212> TYPE: DNA
<213> ORGANISM: Artificial Sequence
<220> FEATURE:
<223> OTHER INFORMATION: Description of Artificial Sequence: Synthetic
Affymetrix ID 3396802 oligonucleotide

<400> SEQUENCE: 536
agctgaggtg cgctataaaa tccggggaaa atggctg 37

<210> SEQ ID NO 537
<211> LENGTH: 32
<212> TYPE: DNA
<213> ORGANISM: Artificial Sequence
<220> FEATURE:
<223> OTHER INFORMATION: Description of Artificial Sequence: Synthetic
Affymetrix ID 3505965 oligonucleotide

<400> SEQUENCE: 537
gtgacaatgc tcgatcccag gttttgagag ag 32

<210> SEQ ID NO 538
<211> LENGTH: 131
<212> TYPE: DNA
<213> ORGANISM: Artificial Sequence
<220> FEATURE:
<223> OTHER INFORMATION: Description of Artificial Sequence: Synthetic
Affymetrix ID 3921469 polynucleotide

<400> SEQUENCE: 538
tgctctgcat agctagacca tcttattaat aatactctga aaaaaatgat ttcaaggcat 60
ggaagttctc tgtgatacaa caatagtatt tcttcaaatg cgccttatgc tacttatctc 120
agaaacaggt t 131

<210> SEQ ID NO 539
<211> LENGTH: 156
<212> TYPE: DNA
<213> ORGANISM: Artificial Sequence
<220> FEATURE:

<223> OTHER INFORMATION: Description of Artificial Sequence: Synthetic
      Affymetrix ID 2578977 polynucleotide

<400> SEQUENCE: 539
ctttactgac tacgggaatg tcgccaaagt ggagagatgt gacatggatg ggatgaaccg     60
aacaaggata attgattcaa agacagagca gccagctgca ctggcactag acctagtcaa    120
caaattggtt tactgggtag atctttactt ggacta                              156

<210> SEQ ID NO 540
<211> LENGTH: 125
<212> TYPE: DNA
<213> ORGANISM: Artificial Sequence
<220> FEATURE:
<223> OTHER INFORMATION: Description of Artificial Sequence: Synthetic
      Affymetrix ID 2586145 polynucleotide

<400> SEQUENCE: 540
ttcacgattg tactgggtag atgcctattt tgataaaatt gagcacagca cctttgatgg     60
tttagacaga agaagactgg gccatataga gcagatgaca catccgtttg gacttgccat    120
ctttg                                                                125

<210> SEQ ID NO 541
<211> LENGTH: 158
<212> TYPE: DNA
<213> ORGANISM: Artificial Sequence
<220> FEATURE:
<223> OTHER INFORMATION: Description of Artificial Sequence: Synthetic
      Affymetrix ID 2754758 polynucleotide

<400> SEQUENCE: 541
taagagctca ttgttcatga tgctgatcat tacattttaa tataaaatag cgatgcaact     60
ttacaacaca atagttttcc cctgtagcct agctcagcct cttgtattgt catgattatt    120
accgaaggct tttatttact tactgtttgc acttctaa                            158

<210> SEQ ID NO 542
<211> LENGTH: 223
<212> TYPE: DNA
<213> ORGANISM: Artificial Sequence
<220> FEATURE:
<223> OTHER INFORMATION: Description of Artificial Sequence: Synthetic
      Affymetrix ID 2797082 polynucleotide

<400> SEQUENCE: 542
agtctattcc tagtaccagt ctgaattatt actagttctg aaataattga caaagattta     60
ctgtaatcag ggcttaggta cagaataaat ttgtaattaa taaattaatg gaaattagta    120
cattaatatt aataaattaa gaaactacct tctaatgtat gcattatgaa tatgcttatt    180
gataataatt tctatgcaat cattggctat tttgaggggg aca                      223

<210> SEQ ID NO 543
<211> LENGTH: 27
<212> TYPE: DNA
<213> ORGANISM: Artificial Sequence
<220> FEATURE:
<223> OTHER INFORMATION: Description of Artificial Sequence: Synthetic
      Affymetrix ID 2797113 oligonucleotide

<400> SEQUENCE: 543
ttagaagcgt tcgaccaaac ctacaag                                         27

<210> SEQ ID NO 544

<211> LENGTH: 780
<212> TYPE: DNA
<213> ORGANISM: Artificial Sequence
<220> FEATURE:
<223> OTHER INFORMATION: Description of Artificial Sequence: Synthetic
Affymetrix ID 3046383 polynucleotide

<400> SEQUENCE: 544
tgcactgcat ttctaggcca cataatcttt agcctaacat ttgcatatta atgcataatt 60
gtaaaacatt atgtaaatta tacatggtgg tgaatatatt atcaaatcaa atggccttta 120
ggggtaatta caggatgctg ctatgtcaac taggatgctg caggttgaat gctgaacact 180
tctcatagga tgaaatataa cccagccagg gtttatctgt gtccaaagtc acgagttgcc 240
tttcagtgtg accctccatt tttgttaaat gaagcacatt tggggtcaca gaatattagg 300
aatgaaaagg ataaaatcct gaatgaaaaa tattaaaatg tggaaacctt ttaggttggc 360
aattaatcta aatatcggag tcatagagaa aaccccatga gtattgatgc cattcggtgt 420
atttatttca gtataatttg tttattgttc ttttttattt ttaaataatc catgctcgtt 480
ataaaaggca gcagacagca tagtctcctt agggtacccc attgctaaat gacttgattc 540
ttttattggc tgcttacgtg tcccctcctt gaagaccact ggttgattta tcactcttct 600
ccactagtcc acctcaatgt ctgttttgta tatggtggcc acaaaagcat tgtggacgga 660
aaaaaggacg ggtgggagtg agggaggaaa gagattgggt cagtaagtgc taccaccatg 720
ggattgaatt ctgggggcaa ctctagtcac tttgttccac tattcgttag gcctgctgta 780

<210> SEQ ID NO 545
<211> LENGTH: 121
<212> TYPE: DNA
<213> ORGANISM: Artificial Sequence
<220> FEATURE:
<223> OTHER INFORMATION: Description of Artificial Sequence: Synthetic
Affymetrix ID 3074988 polynucleotide

<400> SEQUENCE: 545
ggctacactg atgaacctgt ttctaagatc ctgtgtcaag tggaagatgg gacagttgta 60
cagctagatc gctggaacct ccatgtggaa agaaaccccg acttgcctcc agaagaactt 120
g 121

<210> SEQ ID NO 546
<211> LENGTH: 71
<212> TYPE: DNA
<213> ORGANISM: Artificial Sequence
<220> FEATURE:
<223> OTHER INFORMATION: Description of Artificial Sequence: Synthetic
Affymetrix ID 3106623 oligonucleotide

<400> SEQUENCE: 546
tcatttgctt gttattgcac caatatggaa aacacatatg gattagaagt agttggtcat 60
attccacaag g 71

<210> SEQ ID NO 547
<211> LENGTH: 95
<212> TYPE: DNA
<213> ORGANISM: Artificial Sequence
<220> FEATURE:
<223> OTHER INFORMATION: Description of Artificial Sequence: Synthetic
Affymetrix ID 3290006 oligonucleotide

<400> SEQUENCE: 547
ataccaaatg ctctgaggga catgcatagg acactgacaa gtttggctac accaagaaaa 60
caaggtaata aagtctataa caggggcatg tgcaa 95

<210> SEQ ID NO 548
<211> LENGTH: 405
<212> TYPE: DNA
<213> ORGANISM: Artificial Sequence
<220> FEATURE:
<223> OTHER INFORMATION: Description of Artificial Sequence: Synthetic
Affymetrix ID 3353815 polynucleotide

<400> SEQUENCE: 548
gcagtgagca tcagtaaacc caacaaagaa cagattcagg gtggatccag ttaaaacagt 60
ttcacaattt tctccaataa cagtttgcaa ccattcttga aggctgcaga cttggcagac 120
ttggcaaggt ggaacaggag aaatacaaag tatggagctg atatggtttg gctgtgtccc 180
cacacaaagt cttatcttgg attgtaatcc ccataatctc cacatgtcaa gggagagccc 240
aagtggaggt aattgaatca tgggggtggt ttcccccatg ctgttgtcac gatagtgagt 300
tctcaggaga tccgatggtt ttataagtgt ttggtagttc ctcctgcgtt cattctcctt 360
cctgctgcct tgtgaagaag gtgccttgct gctgccatta ttgta 405

<210> SEQ ID NO 549
<211> LENGTH: 384
<212> TYPE: DNA
<213> ORGANISM: Artificial Sequence
<220> FEATURE:
<223> OTHER INFORMATION: Description of Artificial Sequence: Synthetic
Affymetrix ID 3354952 polynucleotide

<400> SEQUENCE: 549
ttcggctacc ctcaaagctc tcaggactgg ggctagggtt taaggaaggc ttatttaaat 60
atgggaaata aaatacaaaa gggccacacc cgatgcaaaa gactttgctg gctttctggt 120
cagacaagcc tagagatgtg tattttctta gggcagtaaa acaaaacgtt ttcacaagga 180
ggctaaattt ctatcctgaa gttcataaac atgtggcgct cggttaatgg taaaaataga 240
caatgtgtga ggcgggaccg ctcctcctca tcctcccaag ctcctctcct acccacctcc 300
cttccctcca aggaaacgca aagttgcccc gaggaggtgg gcctgcctcc acatcgcccc 360
cagggtcagg tatgttctca gcgt 384

<210> SEQ ID NO 550
<211> LENGTH: 388
<212> TYPE: DNA
<213> ORGANISM: Artificial Sequence
<220> FEATURE:
<223> OTHER INFORMATION: Description of Artificial Sequence: Synthetic
Affymetrix ID 3367691 polynucleotide

<400> SEQUENCE: 550
tttaattaag gtagtgcagg ggctggttcc atattaaaca tggtgatggg gatttaagat 60
aataatgcta ccatcagtac atctaaaatt gtttaatgtt ttactgcaaa tattttttag 120
ctagaagaaa ttaaacaagt ggggaagatt ctcagaaacc aacacagccc aaaatgtgca 180
gataaagaac caaaaaataa cgtagaaagg agcaagatta taataaatat ttttaatgag 240
ttaatttatt tcctcttttt aagtcttaac ttgtaacatt atttgaaatc acagtaaatg 300
tacattttat ttcttgtttc agccctgagg tgagtttatt tggaatgttt gttttaaatg 360
gatttagcca tcatggaatt aggtcatc 388

<210> SEQ ID NO 551
<211> LENGTH: 57
<212> TYPE: DNA
<213> ORGANISM: Artificial Sequence
<220> FEATURE:
<223> OTHER INFORMATION: Description of Artificial Sequence: Synthetic
Affymetrix ID 3548942 oligonucleotide

<400> SEQUENCE: 551
ggctccttac agcacatgcc ctggatgctt ctggaaccaa tgccaacctt gatccct 57

<210> SEQ ID NO 552
<211> LENGTH: 92
<212> TYPE: DNA
<213> ORGANISM: Artificial Sequence
<220> FEATURE:
<223> OTHER INFORMATION: Description of Artificial Sequence: Synthetic
Affymetrix ID 3692981 oligonucleotide

<400> SEQUENCE: 552
gctggttcct gggacggatg cagcacaaag gggcttttca gggcctcctg ttgaacgaag 60
tgttctgttc ccatcgaagc tttgaaagac gt 92

<210> SEQ ID NO 553
<211> LENGTH: 231
<212> TYPE: DNA
<213> ORGANISM: Artificial Sequence
<220> FEATURE:
<223> OTHER INFORMATION: Description of Artificial Sequence: Synthetic
Affymetrix ID 2797090 polynucleotide

<400> SEQUENCE: 553
cattgaattc ccacatgcat tgcgaataaa gcagtgatgt gttcgttttt tgaaatagat 60
gtgtgttaac accgggagat tggaagctgt gatttgggag ttgggaggtg agatgattgg 120
agtgaagaga gttaatgtca tggaaaggaa aagctgtctg aagaaaaata cacattttaa 180
tgtccctctt cagccgtgcc tgctgagagc tctcctggga tgataagtga a 231

<210> SEQ ID NO 554
<211> LENGTH: 26
<212> TYPE: DNA
<213> ORGANISM: Artificial Sequence
<220> FEATURE:
<223> OTHER INFORMATION: Description of Artificial Sequence: Synthetic
Affymetrix ID 2797115 oligonucleotide

<400> SEQUENCE: 554
ggcgtgattc tcagtcacca gactca 26

<210> SEQ ID NO 555
<211> LENGTH: 149
<212> TYPE: DNA
<213> ORGANISM: Artificial Sequence
<220> FEATURE:
<223> OTHER INFORMATION: Description of Artificial Sequence: Synthetic
Affymetrix ID 2854124 polynucleotide

<400> SEQUENCE: 555
ctccagagat cttgaatttg tctgctgatt tctcaacctc tacattatac ctaaagtgga 60
acgacagggg ttcagttttt ccacaccgct caaatgttat ctgggaaatt aaagttctac 120
gtaaagagag tatggagctc gtaaaatta 149

<210> SEQ ID NO 556
<211> LENGTH: 56

<212> TYPE: DNA
<213> ORGANISM: Artificial Sequence
<220> FEATURE:
<223> OTHER INFORMATION: Description of Artificial Sequence: Synthetic
Affymetrix ID 2932274 oligonucleotide

<400> SEQUENCE: 556
atggcccaga tctttacacg atatcctcct ccgactcatc gtgagaaaac ctgcaa 56

<210> SEQ ID NO 557
<211> LENGTH: 173
<212> TYPE: DNA
<213> ORGANISM: Artificial Sequence
<220> FEATURE:
<223> OTHER INFORMATION: Description of Artificial Sequence: Synthetic
Affymetrix ID 3018617 polynucleotide

<400> SEQUENCE: 557
accttttcca gtggtgagtt taatggtggg atctgttgtt ctgagcatgg cccccgacga 60
acactttctc gtatccagca gcaatggaac tgtattaaat actactatga tagacactgc 120
agctagagat acagctagag tcctgattgc cagtgccctg actctgctgg ttg 173

<210> SEQ ID NO 558
<211> LENGTH: 87
<212> TYPE: DNA
<213> ORGANISM: Artificial Sequence
<220> FEATURE:
<223> OTHER INFORMATION: Description of Artificial Sequence: Synthetic
Affymetrix ID 3095521 oligonucleotide

<400> SEQUENCE: 558
agtcttccag agttttcggg agctaattaa ttatgtgatt tcctctcctc tgagaactgt 60
tttgctggcg tgtcaccaag ttgtcac 87

<210> SEQ ID NO 559
<211> LENGTH: 88
<212> TYPE: DNA
<213> ORGANISM: Artificial Sequence
<220> FEATURE:
<223> OTHER INFORMATION: Description of Artificial Sequence: Synthetic
Affymetrix ID 3106633 oligonucleotide

<400> SEQUENCE: 559
atgtatttac aatatgcttt gctgccaatg tgggactgct gtttggtgtt gtttgtacca 60
tagctatagt gataggacgc ttcccaag 88

<210> SEQ ID NO 560
<211> LENGTH: 72
<212> TYPE: DNA
<213> ORGANISM: Artificial Sequence
<220> FEATURE:
<223> OTHER INFORMATION: Description of Artificial Sequence: Synthetic
Affymetrix ID 3154267 oligonucleotide

<400> SEQUENCE: 560
ccgagggaac agagaacccg cttggggtag acgagtccct tttcagctat ggccttcgag 60
agagcattgc ct 72

<210> SEQ ID NO 561
<211> LENGTH: 160
<212> TYPE: DNA
<213> ORGANISM: Artificial Sequence
<220> FEATURE:
<223> OTHER INFORMATION: Description of Artificial Sequence: Synthetic Affymetrix ID 3175792 polynucleotide

<400> SEQUENCE: 561
gcgttcaaaa ctggagggat ggataagcaa agatctggga gtaagaatgt gaagggacaa 60
tactggaagg tattaggttc agccctacca ggaaattaca tggaaaagaa acgctggggc 120
caattaagga gaactttgca tgctatggaa tctgggctca 160

<210> SEQ ID NO 562
<211> LENGTH: 340
<212> TYPE: DNA
<213> ORGANISM: Artificial Sequence
<220> FEATURE:
<223> OTHER INFORMATION: Description of Artificial Sequence: Synthetic
Affymetrix ID 3349402 polynucleotide

<400> SEQUENCE: 562
gtaggatcat cccacgcttg ctttagcaca ggacaacttt acaaaacatg attgtttaca 60
gctgctcttc ccctcttttc tgatctgcag tttttgcctg ggtcccactc aggtgaaaat 120
ccatctcatt ctggaatggt tttgcttttg aatttttggt tatttttgtg tttctttggg 180
ggttagacca ctttctgatt agccgccacc tgcctgcatc tgtgaaaagg gatctgctcc 240
caggcgttct cacccttctt ttgaaggact ccttaggctt tgttgaatga agcagagaag 300
attgtatagt tggggctggt cttggtgaac acacattatt 340

<210> SEQ ID NO 563
<211> LENGTH: 511
<212> TYPE: DNA
<213> ORGANISM: Artificial Sequence
<220> FEATURE:
<223> OTHER INFORMATION: Description of Artificial Sequence: Synthetic
Affymetrix ID 3573880 polynucleotide

<400> SEQUENCE: 563
gtttctccca taggctgtgt ttacatggag ctatcggttt agccttttaa gcttcattag 60
cttgtctatt attgaaatag tttccaagaa attttagata ttatcataac atctgggtct 120
actcaaacac ttattgtttg aaagacttat gtcttggacc tatcaaaaac tgactttatt 180
tattgcttag tgaaaatact agtgggatca acaatgattt tcttgaatgg gcatgaatgg 240
agatgcccgc acagtaatgt agaaatgttt catacagcta ttaaaatgta actgacctcc 300
ttagaggcag attagtaact gttcctactt tgtatagcta agtgacagtc acttaactta 360
catgactttc ttttttcaca ttgggtctct ggtcctgtgt cttcacctca tttatagcac 420
gtctccttga tttttggtag tatcaacttc ccagtgatct gttcagttaa gttcttctcc 480
cgttaaccag gaagtgctta ttctctcatc a 511

<210> SEQ ID NO 564
<211> LENGTH: 68
<212> TYPE: DNA
<213> ORGANISM: Artificial Sequence
<220> FEATURE:
<223> OTHER INFORMATION: Description of Artificial Sequence: Synthetic
Affymetrix ID 3787197 oligonucleotide

<400> SEQUENCE: 564
ttttttattg atggttgaat gttccttttt cactgtatcc tgttcttgca agatgtcatg 60
ctttcttt 68

<210> SEQ ID NO 565

```
<211> LENGTH: 130
<212> TYPE: DNA
<213> ORGANISM: Artificial Sequence
<220> FEATURE:
<223> OTHER INFORMATION: Description of Artificial Sequence: Synthetic
      Affymetrix ID 2586065 polynucleotide

<400> SEQUENCE: 565

gctctccttt gttgctactg cctgacaatg tccgaattcg aaaatataat ctctcatctg     60

agaggttctc agagtatctt caagatgagg aatatatcca agctgttgat tatgattggg    120

atcccaagga                                                           130


<210> SEQ ID NO 566
<211> LENGTH: 234
<212> TYPE: DNA
<213> ORGANISM: Artificial Sequence
<220> FEATURE:
<223> OTHER INFORMATION: Description of Artificial Sequence: Synthetic
      Affymetrix ID 2740186 polynucleotide

<400> SEQUENCE: 566

agccctgtca gcagagtcag ttttaacaac tgagaagagt ggcatgaaat ttagtacctg     60

ctttggacat gagcataccc attctcttgc tagttttgtt tttgcctgaa aattcactcc    120

aagtgtgagg tgtaccagta actcaatcac gtatagacat ttttttttta actgaaaatc    180

tccttttcca gaaggtttat taatacgctt tgaaacttag aatgccgaac tgcc          234


<210> SEQ ID NO 567
<211> LENGTH: 171
<212> TYPE: DNA
<213> ORGANISM: Artificial Sequence
<220> FEATURE:
<223> OTHER INFORMATION: Description of Artificial Sequence: Synthetic
      Affymetrix ID 2797137 polynucleotide

<400> SEQUENCE: 567

gtaaagaggg atacaagttc tcactttggg ccatggtttc aggcttttca gcttgagggt     60

ggggttttgc tggggaatca cccttttctg cctagaattt ctctggcttc tgttcatatc    120

agtaggatct gctccaacat gaggatagta ggaggagtta tgagtcaaat a             171


<210> SEQ ID NO 568
<211> LENGTH: 30
<212> TYPE: DNA
<213> ORGANISM: Artificial Sequence
<220> FEATURE:
<223> OTHER INFORMATION: Description of Artificial Sequence: Synthetic
      Affymetrix ID 3106642 oligonucleotide

<400> SEQUENCE: 568

gtttacatgg actgtaaagg caggagtgtg                                      30


<210> SEQ ID NO 569
<211> LENGTH: 267
<212> TYPE: DNA
<213> ORGANISM: Artificial Sequence
<220> FEATURE:
<223> OTHER INFORMATION: Description of Artificial Sequence: Synthetic
      Affymetrix ID 3667319 polynucleotide

<400> SEQUENCE: 569

ccagggagaa cactgcttag cacttttcct gttgccctca ctgaagaaat tgcctttggt     60

gaattattca tagtgcacac gactgtgctg agtgctgtcc gtccacagtc ctttcttacc    120
```

aatctgcaaa aaatctcctt ggagagtagc gagtttctta gagagagtcc attcccagtc 180
ctctgctctg aggtgtgtcc tgggctttac tttctcctgt aggcatgtgc tgctttaata 240
gagcatctct ggactttcgg gcaaatc 267

<210> SEQ ID NO 570
<211> LENGTH: 100
<212> TYPE: DNA
<213> ORGANISM: Artificial Sequence
<220> FEATURE:
<223> OTHER INFORMATION: Description of Artificial Sequence: Synthetic
Affymetrix ID 3018619 polynucleotide

<400> SEQUENCE: 570
tgctggattg ctcaccattg tcgtctgtat ggcagttaag gaattaaatg atcggtttag 60
acacaaaatc ccagtcccta ttcctataga agtaattgtg 100

<210> SEQ ID NO 571
<211> LENGTH: 543
<212> TYPE: DNA
<213> ORGANISM: Artificial Sequence
<220> FEATURE:
<223> OTHER INFORMATION: Description of Artificial Sequence: Synthetic
Affymetrix ID 3085944 polynucleotide

<400> SEQUENCE: 571
tcttgaactc ggtcaggcat cgtcaagcct gcccaggccc tccaggcctc tttgatagct 60
actgagcccc tgaaggcatc aagacatgac cacgcatggc agtgtcggtg gagagtttgc 120
gttttacacc cagcgatgct tggggatggc agagagatgg atggataatg agtacaactg 180
caaacagcac tgtacacatg tggtgagcca ggaggctggg acggaggtta ggccaatgtt 240
gctgctgact catagaccca cagagagcag ggacttcaca aagctgaatt aatgtggtta 300
gttgtgttca ctgtgcaaag taaggaagcc agtcaacact ggacgatgtt tagaaaacat 360
cgctgtcccc ctccacttct catcttgggt cacctcctca tcccataata aagttctctt 420
aggataaacc gagcaaaata gctcagacat ttaacttatc cccaaacatg tgtcttgatc 480
ttagtttcca cccagagaat gaagaaagca agcaagcact gggttaccca agcaactaaa 540
tca 543

<210> SEQ ID NO 572
<211> LENGTH: 151
<212> TYPE: DNA
<213> ORGANISM: Artificial Sequence
<220> FEATURE:
<223> OTHER INFORMATION: Description of Artificial Sequence: Synthetic
Affymetrix ID 3130325 polynucleotide

<400> SEQUENCE: 572
cgggcagcca acaggaacaa gtatccatta gattatcatg gagctgaaaa gttcctacca 60
cctagtgaca tcatgccatc gtaacatcac aatgcaaagc atcacccatg tgtttgtggt 120
ggtaatggtg taaacaaact caccttgctg c 151

<210> SEQ ID NO 573
<211> LENGTH: 288
<212> TYPE: DNA
<213> ORGANISM: Artificial Sequence
<220> FEATURE:
<223> OTHER INFORMATION: Description of Artificial Sequence: Synthetic
Affymetrix ID 3349327 polynucleotide

<400> SEQUENCE: 573
ttacattcag tgctacagca ggatgtgatc actcaactat ttagcttatg tatatcgttt 60
atttttatta tttgggcatt gattttctct accatttgtt tccacatgaa gtcttttttt 120
tttaacaaaa tctaatttct cataacaagc agaaatgctt ttaaggaatt attcttttc 180 gtcctgtcaa gttgcaggaa acatcaaata ttgactgtaa actgttatca atttcatatg 240
tgacaaggtc tgccatctct tcatgtacac atattttcac ggccctta 288

<210> SEQ ID NO 574
<211> LENGTH: 79
<212> TYPE: DNA
<213> ORGANISM: Artificial Sequence
<220> FEATURE:
<223> OTHER INFORMATION: Description of Artificial Sequence: Synthetic
Affymetrix ID 2586075 oligonucleotide

<400> SEQUENCE: 574
agtgcacaga gagcgagttt cgatgtgtca atcagcagtg cattccctcg cgatggatct 60
gtgaccatta caacgactg 79

<210> SEQ ID NO 575
<211> LENGTH: 49
<212> TYPE: DNA
<213> ORGANISM: Artificial Sequence
<220> FEATURE:
<223> OTHER INFORMATION: Description of Artificial Sequence: Synthetic
Affymetrix ID 2649002 oligonucleotide

<400> SEQUENCE: 575
gtatttgacc acctgctacg tggaagatat tatgctagac acaagttag 49

<210> SEQ ID NO 576
<211> LENGTH: 29
<212> TYPE: DNA
<213> ORGANISM: Artificial Sequence
<220> FEATURE:
<223> OTHER INFORMATION: Description of Artificial Sequence: Synthetic
Affymetrix ID 2781544 oligonucleotide

<400> SEQUENCE: 576
agtgcaggcc aaacctgtgg gaaagctcc 29

<210> SEQ ID NO 577
<211> LENGTH: 26
<212> TYPE: DNA
<213> ORGANISM: Artificial Sequence
<220> FEATURE:
<223> OTHER INFORMATION: Description of Artificial Sequence: Synthetic
Affymetrix ID 3106613 oligonucleotide

<400> SEQUENCE: 577
atctgtgcac ccagtgtttg gtttat 26

<210> SEQ ID NO 578
<211> LENGTH: 64
<212> TYPE: DNA
<213> ORGANISM: Artificial Sequence
<220> FEATURE:
<223> OTHER INFORMATION: Description of Artificial Sequence: Synthetic
Affymetrix ID 3108613 oligonucleotide

<400> SEQUENCE: 578
agactccgat ggaagacagg actctccagc aggggaactg ccaaaaacgg tccaacagcc 60
aaca 64

<210> SEQ ID NO 579
<211> LENGTH: 1000
<212> TYPE: DNA
<213> ORGANISM: Artificial Sequence
<220> FEATURE:
<223> OTHER INFORMATION: Description of Artificial Sequence: Synthetic
Affymetrix ID 2336909 polynucleotide

<400> SEQUENCE: 579
cctcaattct aggtgaccaa cgggagggct tctcaaggct tagctctccc tgagacccag 60
ctggctttta cccttgacct gtgtccctag ctgaatcact agctcagatt tttctgatct 120
aagcaaacaa ctcccagctg aggaatgcag gccacagcac ccaatcaaga caaattgtta 180
ttatcagaaa atgaagcaac acttgagctg ttcaggccag ttccctgttg aagaaacagt 240
tccctgttga agaaagtaga gcctgacact gctcccactt tggagaccac attccctgca 300
cacggtcttt gagagagcag ttgcactcta caggcacact tctgaggtac ggtatctctc 360
tccagccact ctgataccaa gtaattcaag ctggcattcc ttctattagg gaaattcatt 420
ttacccaatt tgcatttatg gaattgatca tttaagacac taaattagtt tttagaacca 480
attatgggaa gaattccagt tgttaggaag agatgaggag ttggaagagg agggattaga 540
aacaggagga ggcagtcatc ctctccttgc caaaagattt aaacctgtcc acattggtgg 600
tgatgatggg tgagtttcca tggtaacaca tccctaattt taccagggaa gaggagagta 660
ctcactttac catctttgaa tatatttcat agaaatctag ctctctgtac cctgaaatct 720
tccactagcc tcacttttca acagagtcat ctagaaggga gggttggctt cccaaaagca 780
taaccttgac caaaccaaac aataggcacc agcaatgctg tcattcagtt atgcagaagc 840
tcatttgtga aattctgttt ctctgatttc ttcgcaagtc tcttaatggt catttgtgtt 900
agattacatc aaactgatgg atagccattg gtattcatct attttaactc tgtgtcttta 960
catatttgtt tatgatggcc acagcctaaa gtacacacgg 1000

<210> SEQ ID NO 580
<211> LENGTH: 95
<212> TYPE: DNA
<213> ORGANISM: Artificial Sequence
<220> FEATURE:
<223> OTHER INFORMATION: Description of Artificial Sequence: Synthetic
Affymetrix ID 2797093 oligonucleotide

<400> SEQUENCE: 580
cccctgtacc gatcctcaga ggaagagaag agagtgacag tcatcaaagc cccgcattac 60
ccagggatcg ggcccgtgga tgaatccgga atccc 95

<210> SEQ ID NO 581
<211> LENGTH: 288
<212> TYPE: DNA
<213> ORGANISM: Artificial Sequence
<220> FEATURE:
<223> OTHER INFORMATION: Description of Artificial Sequence: Synthetic
Affymetrix ID 2797095 polynucleotide

<400> SEQUENCE: 581
ctaagatgac agctagtgga ccatatatga gaataataaa ataaagggtt aacttatatt 60
gcataaggta tgggttcata gaatgtaatg gatcagatgt gaaggcagag ttgattctcc 120
ttgcttagag taggactttg cacatgctgg tgttcaaaaa acattcgtcg ctaataaaaa 180
tactagtatc atggaggccc actcaagtcc tttttggaat taaatagaaa gtcaattagt 240

-continued

```
gtcaaatatc tcaccgtgtc ttaataagga ctagcttagc cgggcgcg                288


<210> SEQ ID NO 582
<211> LENGTH: 303
<212> TYPE: DNA
<213> ORGANISM: Artificial Sequence
<220> FEATURE:
<223> OTHER INFORMATION: Description of Artificial Sequence: Synthetic
      Affymetrix ID 3734511 polynucleotide

<400> SEQUENCE: 582

aaggatcggg atggccctgc ctcaaccaca agttccagcc tccatgccca cagcagccat     60

gaccagtaac tggctagccc cagggaaggg agagcctcag gagtctgacc cccacagcac    120

accctcctgg cagaactctg cgtgagaaga ggacagcaaa agcccagccc tcaccatgat    180

ttgaggctac tgaggtcact gatgaccatg gaagacatca tctgtcactg gggtcccatg    240

gccaggattt catggcagaa gccagaaaag cccaatcctg cctgccgctt aaccctgaca    300

gtg                                                                  303


<210> SEQ ID NO 583
<211> LENGTH: 29
<212> TYPE: DNA
<213> ORGANISM: Artificial Sequence
<220> FEATURE:
<223> OTHER INFORMATION: Description of Artificial Sequence: Synthetic
      Affymetrix ID 2608627 oligonucleotide

<400> SEQUENCE: 583

gtagctgaag ttgcatgtcg acgatggaa                                       29


<210> SEQ ID NO 584
<211> LENGTH: 295
<212> TYPE: DNA
<213> ORGANISM: Artificial Sequence
<220> FEATURE:
<223> OTHER INFORMATION: Description of Artificial Sequence: Synthetic
      Affymetrix ID 3763228 polynucleotide

<400> SEQUENCE: 584

cgggacattt tctccatcgc gatgcactca aattttttcc ccttaaaaaa agaaataaga     60

aagaaacaac cgccccctaa aatgttgctg agcttttcct ccgtcctttg ccaaaagtac    120

tcgctctcaa ggcggtggag aaaagggaag aaaaaaatta cttatatctt tataaataca    180

tctgcataaa aatatatatt aaaaaaaaac tttcgggttt ccagtgcaga cggtcccagg    240

agagcgcgcc aagtgcccgc gggctccccg gcgacgtgca ggatgctctc acctg         295
```